United States Patent
Bergnes et al.

(10) Patent No.: US 6,423,519 B1
(45) Date of Patent: Jul. 23, 2002

(54) COMPOSITIONS AND METHODS FOR INHIBITING FUNGAL GROWTH

(75) Inventors: Gustave Bergnes, Belmont; Vivian Berlin, Dunstable; Jon Come, Cambridge; Arthur Kluge, Lincoln; Krishna Murthi, Waltham; Kollol Pal, Needham, all of MA (US)

(73) Assignee: GPC Biotech Inc., Waltham, MA (US)

( * ) Notice: Subject to any disclaimer, the term of this patent is extended or adjusted under 35 U.S.C. 154(b) by 0 days.

(21) Appl. No.: 09/172,845

(22) Filed: Oct. 15, 1998

Related U.S. Application Data

(63) Continuation-in-part of application No. 09/115,846, filed on Jul. 15, 1998, now abandoned.

(51) Int. Cl.⁷ ............................ C12N 9/10; C12N 1/06; A61K 38/00
(52) U.S. Cl. .......................... 435/193; 435/259; 514/19
(58) Field of Search ................................ 435/193, 259; 514/19

(56) References Cited

U.S. PATENT DOCUMENTS

| | | | | |
|---|---|---|---|---|
| 4,427,582 A | * | 1/1984 | Gilvarg et al. | |
| 4,454,065 A | * | 6/1984 | Gilvarg et al. | |
| 4,863,898 A | * | 9/1989 | Ashmead et al. | 514/6 |
| 5,258,401 A | * | 11/1993 | Berger et al. | 514/452 |
| 5,270,332 A | * | 12/1993 | Chen et al. | 514/452 |
| 5,283,256 A | * | 2/1994 | Dufresne et al. | 514/452 |
| 5,294,533 A | * | 3/1994 | Lupski et al. | |
| 5,332,728 A | * | 7/1994 | Biller | 514/107 |
| 5,364,948 A | * | 11/1994 | Harris et al. | 554/36 |
| 5,369,125 A | * | 11/1994 | Berger et al. | 514/452 |
| 5,430,055 A | * | 7/1995 | Dabrah et al. | 514/468 |
| 5,447,717 A | * | 9/1995 | Biftu | 424/78.12 |
| 5,506,262 A | * | 4/1996 | Burk et al. | 514/452 |
| 5,523,430 A | | 6/1996 | Patel et al. | 554/40 |
| 5,532,359 A | * | 7/1996 | Marsters, Jr. et al. | 540/552 |
| 5,631,401 A | * | 5/1997 | Stein et al. | 562/451 |
| 5,827,838 A | | 10/1998 | Cohen et al. | 514/106 |

FOREIGN PATENT DOCUMENTS

| | | |
|---|---|---|
| EP | 0 128 249 A2 | 12/1984 |
| EP | 0 763 537 A3 | 3/1997 |
| WO | WO 91/16340 | 10/1991 |
| WO | WO 92/20336 | 11/1992 |
| WO | WO 94/18157 | 8/1994 |
| WO | WO 96/21456 | 7/1996 |
| WO | WO 97/30992 | 8/1997 |
| WO | WO 97/38129 | 10/1997 |
| WO | WO 97/38293 | 10/1997 |
| WO | WO 97/43437 | 11/1997 |
| WO | WO 98/02436 | 1/1998 |

OTHER PUBLICATIONS

Andruszkiewicz, R. et al., "Synthesis and Biological Properties of N3(4–Methoxyfumaroyl)–L–2,3–diaminopropanoic Acid Dipeptides, a Novel Group of Antimicrobial Agents", J. Med. Chem 30: 1715–1719 (1987).

DiDomenico, B., "Novel antifunal drugs", Curr. Opin. Microbiol. 2: 509–515 (1999).

Kingsbury, W. et al., "Transport of Antimicrobial Agents Using Peptide Carrier Systems: Anticandidal Activity of m–Fluorophenylalanine–Peptide Conjugates", J. Med. Chem. 26: 1725–1729 (1983).

Turner, W. W. and Rodriguez, M. J., "Recent Advances in the Medicinal Chemistry of Antifungal Agents", Curr. Pharm. Design. 2: 209–224 (1996).

Augeri et al., "Potent and Selective Non–Cysteine–Containing Inhibitors of Protein Farnesyltransferase", J. Med. Chem. 41 : 4288–4300 (1998).

Gootz, D. Thomas., "Discovery and Development of New Antimicrobial Agents", *Clinical Microbiology Reviews*, vol. 3, No. 1, pp. 13–31 (Jan. 1990).

Hector, F. Richard., Compounds Active against Cell Walls of Medically Important Fungi), *Clinical Microbiology reviews*, vol. 6, No. 1, pp. 1–21 (Jan. 1993).

* cited by examiner

*Primary Examiner*—Jon P. Weber
(74) *Attorney, Agent, or Firm*—Ropes & Gray; Matthew P. Vincent; David P. Halstead

(57) ABSTRACT

The present invention relates to compositions and methods for inhibiting fungal growth. In particular, the present invention relates to methods for use as anti-fungal agents of inhibitors, and compositions thereof, of fungal GGPTase. The inhibitors of fungal GGPTase may be peptides, peptidomimetics, or non-peptides.

39 Claims, 59 Drawing Sheets

Scheme 4

Scheme 7: General Templates
J₁ = 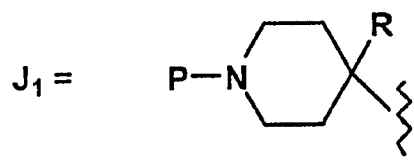
J₂ = 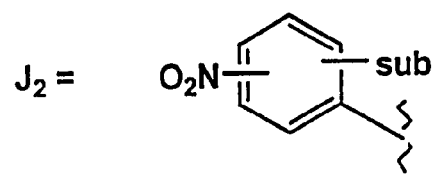
J₃ = 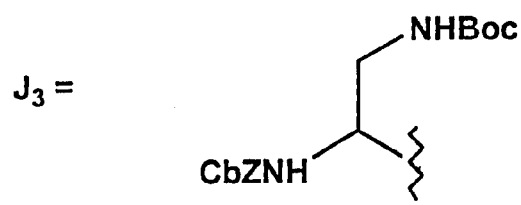
FIG. 7

Scheme 12
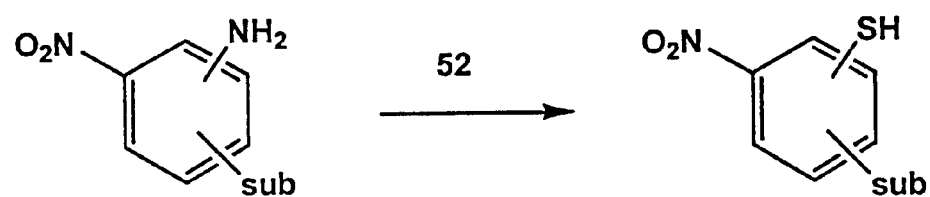
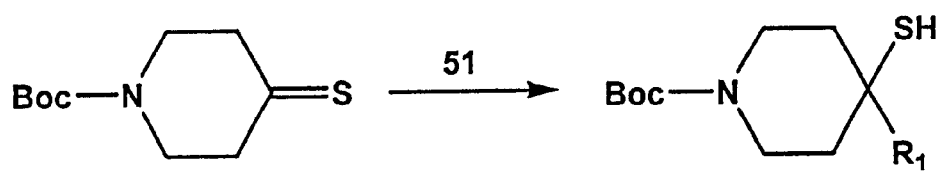
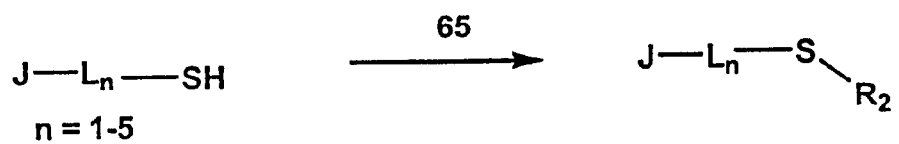
FIG. 12

Scheme 14b

Scheme 15
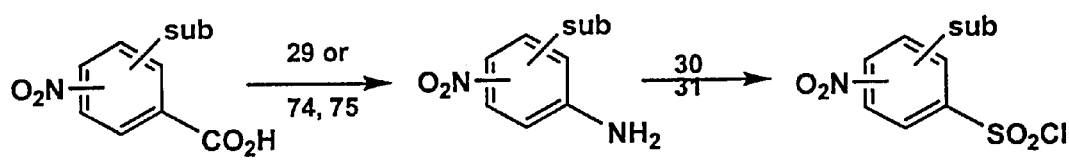
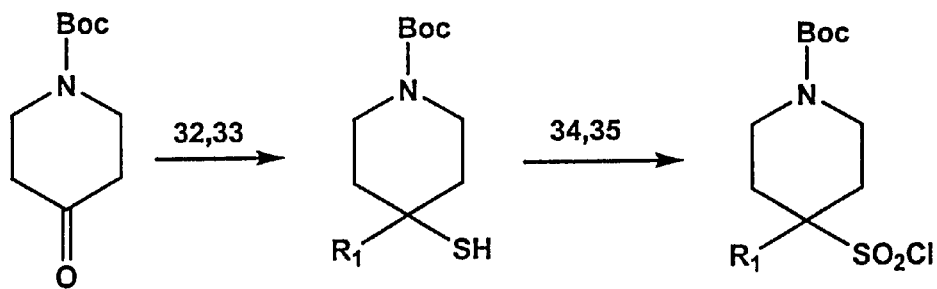
FIG. 15

Scheme 18: Definition of Templates
J-L$_n$ =
1 
2 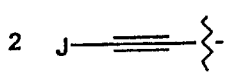
3 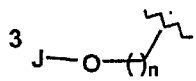
4 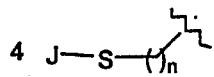
5 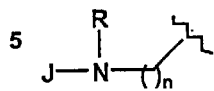
6 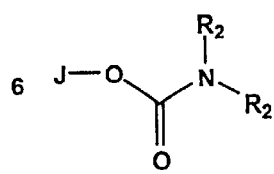
7 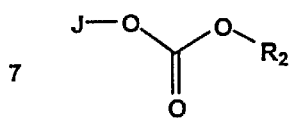
8 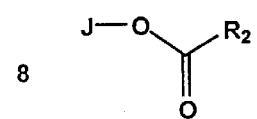
9 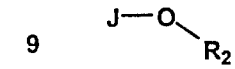
10 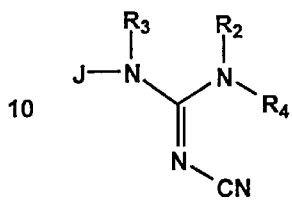
11 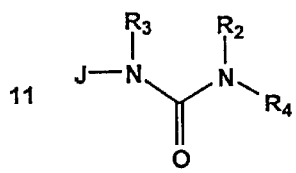
12 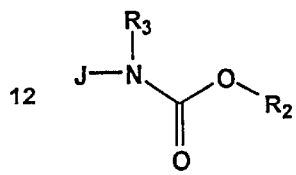
13 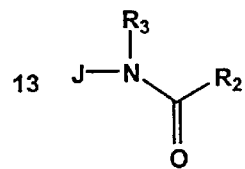
14 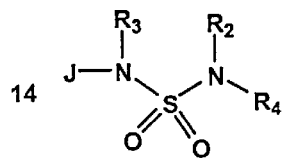
15 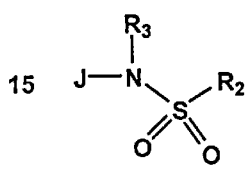
16 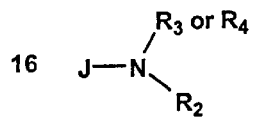
17 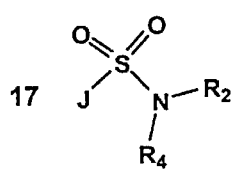
18 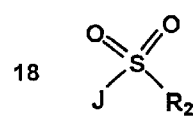
FIG. 18

Scheme 21

Scheme 22

Scheme 26

Scheme 36

Scheme 43 a) Leu Me ester, EDC, HOBt, Et$_3$N, CH$_2$Cl$_2$, b) (i) TFA/CH$_2$Cl$_2$, (ii) Boc-Valinal, KOAc, NaBH$_3$CN, MeOH, c) (i) TFA/CH$_2$Cl$_2$, (ii) S-Tr-N-Boc-cysteinal, KOAc, NaBH$_3$CN, MeOH, d) (i) LiOH, THF/MeOH, (ii) TFA, Et$_3$SiH, CH$_2$Cl$_2$, e) TFA, Et$_3$SiH, CH$_2$Cl$_2$ a) CH₃(OCH₃)NH, EDC, HOBt, Et₃N, CH₂Cl₂ b) LAH, Et₂O, c) Leu Me ester, NaBH₃CN, 10% AcOH/MeOH, d) SnCl₂, DMF e) S-Tr-N-Boc-cysteinal, NaBH₃CN, 10% AcOH/MeOH, f) LiOH, THF/MeOH, g) TFA, Et₃SiH, CH₂Cl₂

Scheme 46 a) (EtO)₂P(O)CH₂CO₂Et, n-BuLi, THF b) (i) PhB(OH)₂, Pd(PPh₃)₄, Na₂CO₃, DME, (ii) LiOH, THF/MeOH, c) Leu Me ester, EDC, HOBT, DIEA, CH₂Cl₂, d) SnCl₂, DMF e) S-Tr-N-Boc-cysteinal, NaBH₃CN, 10% AcOH/MeOH, f) LiOH, THF/MeOH, g) TFA, Et₃SiH, CH₂Cl₂

Scheme 47 a) pyBr3, THF, 10%HCl, b) PhB(OH)2, Pd(PPh3)4, Na2CO3, DME, c) Leu isocyanate, pyridine, d) SnCl2, DMF, e) S-Tr-N-Boc-cysteinal, NaBH3CN, 10% AcOH/MeOH, f) LiOH, THF, g) TFA, Et3SiH, CH2Cl2

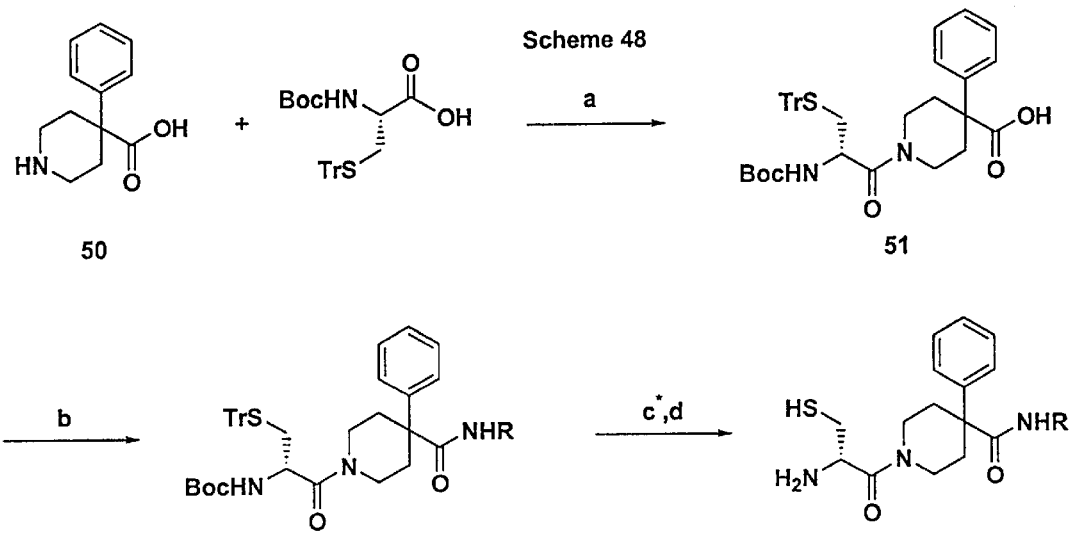

Scheme 48

| #: | NHR |
|---|---|
| 52a: | Leu-OMe |
| 52b: | NHCH₂(2-biphenyl) |
| 52c: | NH(isoamyl) |
| 52d: | NH(CH₂)₂(2-thiophene) |
| 52e: | NHCH₂(3-biphenyl) |
| 52f: | NH(CH₂)₃(1-morpholine) |
| 52g: | NH(CH₂)₂(1-pyrrolidine) |
| 52h: | NHCH₂(2-benzimidazole) |
| 52i: | Leu-NH₂ |
| 52j: | NH(CH₂)₃(1-imidazole) |
| 52k: | NHCH₂(4-pyridyl) |
| 52l: | NH(4-(1-ethoxycarbonyl)piperidine) |
| 52m: | NH(CH₂)₂(4-(SO₂NH₂)phenyl) |
| 52n: | NHCH₂(4-cyanocyclohexyl) |
| 52o: | Gly-NH(2-naphthyl) |
| 52p: | NHCH₂(3-(OCF₃)phenyl) |
| 52q: | NHCH₂(3-piperonyl) |
| 52r: | NHCH₂(2,4-difluorophenyl) |
| 52s: | NH-c-hexyl |
| 52t: | NHCH₂(2-THF) |
| 52u: | NHCH₂(2-(OMe)phenyl) |
| 52v: | NH(trans-phenylcyclopropyl) |
| 52w: | NHCH₂(1-naphthyl) |
| 52x: | NH(CH₂)₂S(CH₂)₂(2-Cl-6-F-phenyl) |
| 52y: | NHCH₂CHPh₂ |
| 52z: | NH(9-fluorenyl) |
| 52aa: | NH(CH₂)₄(4-phenyl) |

| #: | NHR |
|---|---|
| 53a: | Leu-OH |
| 53b: | NHCH₂(2-biphenyl) |
| 53c: | NH(isoamyl) |
| 53d: | NH(CH₂)₂(2-thiophene) |
| 53e: | NHCH₂(3-biphenyl) |
| 53f: | NH(CH₂)₃(1-morpholine) |
| 53g: | NH(CH₂)₂(1-pyrrolidine) |
| 53h: | NHCH₂(2-benzimidazole) |
| 53i: | Leu-NH₂ |
| 53j: | NH(CH₂)₃(1-imidazole) |
| 53k: | NHCH₂(4-pyridyl) |
| 53l: | NH(4-(1-ethoxycarbonyl)piperidine) |
| 53m: | NH(CH₂)₂(4-(SO₂NH₂)phenyl) |
| 53n: | NHCH₂(4-cyanocyclohexyl) |
| 53o: | Gly-NH(2-naphthyl) |
| 53p: | NHCH₂(3-(OCF₃)phenyl) |
| 53q: | NHCH₂(3-piperonyl) |
| 53r: | NHCH₂(2,4-difluorophenyl) |
| 53s: | NH-c-hexyl |
| 53t: | NHCH₂(2-THF) |
| 53u: | NHCH₂(2-(OMe)phenyl) |
| 53v: | NH(trans-phenylcyclopropyl) |
| 53w: | NHCH₂(1-naphthyl) |
| 53x: | NH(CH₂)₂S(CH₂)₂(2-Cl-6-F-phenyl) |
| 53y: | NHCH₂CHPh₂ |
| 53z: | NH(9-fluorenyl) |
| 53aa: | NH(CH₂)₄(4-phenyl) |
| 53bb: | NHCH₂(Ph) |

(a) EDC, HOBT, DIEA, CH₂Cl₂; (b) EDC, HOBT, DIEA, RNH₂, CH₂Cl₂; (c) LiOH, MeOH, THF, H₂O; (d) TFA, Et₃SiH, CH₂Cl₂. *Only with 52a.

FIG. 48 a) DPPA, Et₃N, Leu Me ester, toluene, 80°C, b) KHDMS, THF, c) TFA, CH₂Cl₂, d) S-Tr-N-Boc-cysteine, HBTU, HOBt, DIEA, CH₂Cl₂, e) TFA, Et₃SiH, CH₂Cl₂ a) DPPA, Et₃N, Leu Me ester, toluene, 80°C, b) DBU, CH₂Cl₂, c) SnCl₂, DMF, d) S-Tr-N-Boc-cysteinal, NaBH₃CN, CH₃CO₂H-MeOH, e) TFA, Et₃SiH, CH₂Cl₂

Scheme 55

96a = Ala-NH$_2$
96b = Ala-Ala-NH$_2$ a) CH$_2$Cl$_2$, diethylamine, rt., 15 hrs. b) i) Boc-Ala-OH or Boc-Ala-Ala-OH, DIEA, HOBT, EDC, CH$_2$Cl$_2$, rt., 15 hrs. ii) CH$_2$Cl$_2$, TFA, Et$_3$SiH, rt., 2 hrs.

a) H$_2$N-Ala-CO$_2$$^t$Bu or H$_2$N-Ala-Ala-CO$_2$$^t$Bu, DIEA, HOBT, EDC, CH$_2$Cl$_2$, rt., 15 hrs.
b) CH$_2$Cl$_2$, TFA, EtSiH, rt., 2 hrs.

COMPOSITIONS AND METHODS FOR INHIBITING FUNGAL GROWTH

REFERENCE TO RELATED APPLICATIONS

This application is a continuation-in-part of Ser. No. 09/115,846, filed Jul. 15, 1998, now abandoned the specification of which is incorporated by reference herewith.

BACKGROUND OF THE INVENTION

Fungal infections of humans range from superficial conditions, usually caused by dermatophytes or Candida species, that affect the skin (such as dermatophytoses) to deeply invasive and often lethal infections (such as *candidiasis* and *cryptococcosis*). Pathogenic fungi occur worldwide, although particular species may predominate in certain geographic areas.

In the past 20 years, the incidence of fungal infections has increased dramatically—along with the numbers of potentially invasive species. Indeed, fungal infections, once dismissed as a nuisance, have begun to spread so widely that they are becoming a major concern in hospitals and health departments. Fungal infections occur more frequently in people whose immune system is compromised or suppressed (e.g., because of organ transplantation, cancer chemotherapy, or the human immunodeficiency virus), who have been treated with broad-spectrum antibacterial agents, or who have been subject to invasive procedures (catheters and prosthetic devices, for example). Fungal infections are now important causes of morbidity and mortality of hospitalized patients: the frequency of invasive candidiasis has increased tenfold to become the fourth most common blood culture isolate (Pannuti et al. (1992) *Cancer* 69:2653). Invasive pulmonary *aspergillosis* is a leading cause of mortality in bone-marrow transplant recipients (Pannuti et al., supra), while *Pneumocystis carinii* pneumonia is the cause of death in many patients with acquired immunodeficiency syndrome in North America and Europe (Hughes (1991) *Pediatr Infect. Dis J.* 10:391). Many opportunistic fungal infections cannot be diagnosed by usual blood culture and must be treated empirically in severely immunocompromised patients (Walsh et al. (1991) *Rev. Infect. Dis.* 13:496).

The fungi responsible for life-threatening infections include Candida species (mainly *Candida albicans*, followed by *Candida tropicalis*), Aspergillus species, *Cryptococcus neoformans, Histoplasma capsulatum, Coccidioides immitis, Pneumocystis carinii* and some zygomycetes. Treatment of deeply invasive fungal infections has lagged behind bacterial chemotherapy.

There are numerous commentators who have speculated on this apparent neglect. See, for example, Georgopapadakou et al. (1994) *Science* 264:371. First, like mammalian cells, fungi are eukaryotes and thus agents that inhibit fungal protein, RNA, or DNA biosynthesis may do the same in the patient's own cells, producing toxic side effects. Second, life-threatening fungal infections were thought, until recently, to be too infrequent to warrant aggressive research by the pharmaceutical industry. Other factors have included:

(i) Lack of drugs. A drug known as Amphotericin B has become the mainstay of therapy for fungal infection despite side effects so severe that the drug is known as "amphoterrible" by patients. Only a few second-tier drugs exist.

(ii) Increasing resistance. Long-term treatment of oral candidiasis in AIDS patients has begun to breed species resistant to older anti-fungal drugs. Several other species of fungi have also begun to exhibit resistance.

(iii) A growing list of pathogens. Species of fungi that once posed no threat to humans are now being detected as a cause of disease in immune-deficient people. Even low-virulence baker's yeast, found in the human mouth, has been found to cause infection in susceptible burn patients.

(iv) Lagging research. Because pathogenic fungi are difficult to culture, and because many of them do not reproduce sexually, microbiological and genetic research into the disease-causing organisms has lagged far behind research into other organisms.

In the past decade, however, more antifungal drugs have become available. Nevertheless, there are still major weaknesses in their spectra, potency, safety, and pharmacokinetic properties, and accordingly it is desirable to improve the panel of anti-fungal agents available to the practitioner.

The Fungal Cell

The fungal cell wall is a structure that is both essential for the fungus and absent from mammalian cells, and consequently may be an ideal target for antifungal agents. Inhibitors of the biosynthesis of two important cell wall components, glucan and chitin, already exist. Polyoxins and the structurally related nikkomycins (both consist of a pyrimidine nucleoside linked to a peptide moiety) inhibit chitin synthase competitively, presumably acting as analogs of the substrate uridine diphosphate (UDP)-N-acetylglucosamine (chitin is an N-acetylglucosamine homopolymer), causing inhibition of septation and osmotic lysis. Unfortunately, the target of polyoxins and nikkomycins is in the inner leaflet of the plasma membrane; they are taken up by a dipeptide permease, and thus peptides in body fluids antagonize their transport.

In most fungi, glucans are the major components that strengthen the cell wall. The glucosyl units within these glucans are arranged as long coiling chains of $\beta$-(1,3)-linked residues, with occasional sidechains that involve $\beta$-(1,6) linkages. Three $\beta$-(1,3) chains running in parallel can associate to form a triple helix, and the aggregation of helices produces a network of water-insoluble fibrils. Even in the chitin-rich filamentous aspergilli, $\beta$-(1,3)-glucan is required to maintain the integrity and form of the cell wall (Kurtz et al. (1994) *Antimicrob Agents Chemother* 38:1408–1489), and, in *P. carinii*, it is important during the life cycle as a constituent of the cyst (ascus) wall (Nollstadt et al. (1994) *Antimicrob Agents Chemother* 38:2258–2265).

In a wide variety of fungi, $\beta$-(1,3)-glucan is produced by a synthase composed of at least two subunits (Tkacz, J. S. (1992) In: *Emerging Targets in Antibacterial and Antifungal Chemotherapy* Sutcliffe and Georgopapadakou, Eds., pp495–523, Chapman & Hall; and Kang et al. (1986) *PNAS* 83:5808–5812). One subunit is localized to the plasma membrane and is thought to be the catalytic subunit, while the second subunit binds GTP and associates with and activates the catalytic subunit (Mol et al. (1994) *J Biol Chem* 269:31267–31274).

Two groups of anti Candidal antibiotics known in the art interfere with the formation of $\beta$-(1,3)-glucan: the papulacandins and the echinocandins (Hector et al. (1993) *Clin Microbiol Rev* 6:1–21). However, many of the papulacandins are not active against a variety of Candida species, or other pathogenic fungi including Aspergillus. The echinocandins, in addition to suffering from narrow activity spectrum, are not in wide use because of lack of bioavailability and toxicity.

Protein Prenylation

Covalent modification by isoprenoid lipids (prenylation) contributes to membrane interactions and biological activities of a rapidly expanding group of proteins (see, for example, Maltese (1990) *FASEB J* 4:3319; and Glomset et al. (1990) *Trends Biochem Sci* 15:139). Either farnesyl (15-carbon) or geranylgeranyl (20-carbon) isoprenoids can be attached to specific proteins, with geranylgeranyl being the predominant isoprenoid found on proteins (Farnsworth et al. (1990) *Science* 247:320).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Schafer et al. (1992) *Annu. Rev. Genet.* 30:209–237). FPTase and GGPTase-I are α/β heterodimeric enzymes that share a common α subunit; the β subunits are distinct but share approximately 30% amino acid similarity (Brown et al. (1993). *Nature* 366:14–15; Zhang et al. (1994). *J. Biol. Chem.* 269:3175–3180). GGPTase II has different α and β subunits and complexes with a third component (REP, Rab Escort Protein) that presents the protein substrate to the α/β catalytic subunits. Each of these enzymes selectively uses farnesyl diphosphate or geranylgeranyl diphosphate as the isoprenoid donor and selectively recognizes the protein substrate. FPTase farnesylates CaaX-containing proteins that end with Ser, Met, Cys, Gln or Ala. GGPTase-I geranylgeranylates CaaX-containing proteins that end with Leu or Phe. For FPTase and GGPTase-I, CaaX tetrapeptides comprise the minimum region required for interaction of the protein substrate with the enzyme. GGPTase-II modifies XXCC and XCXC proteins; the interaction between GGPTase-II and its protein substrates is more complex, requiring protein sequences in addition to the C-terminal amino acids for recognition. The enzymological characterization of these three enzymes has demonstrated that it is possible to selectively inhibit one with little inhibitory effect on the others (Moores et al. (1991) *J. Biol. Chem.* 266:17438).

GGPTase I transfers the prenyl group from geranylgeranyl diphosphate to the sulphur atom in the Cys residue within the CAAX sequence. *S. cerevisiae* proteins such as the Ras superfamily proteins Rho1, Rho2, Rsr1/Bud1 and Cdc42 appear to be GGPTase substrates (Madaule et al. (1987) *PNAS* 84:779–783; Bender et al. (1989) *PNAS* 86:9976–9980; and Johnson et al. (1990) *J Cell Biol* 111:143–152).

The cell wall of many fungi, as set out above, is required to maintain cell shape and integrity. The main structural component responsible for the rigidity of the yeast cell wall is 1,3-β-linked glucan polymers with some branches through 1,6-β-linkages. The biochemistry of the yeast enzyme catalyzing the synthesis of 1,3-β-glucan chains has been studied extensively, but little was previously known at the molecular level about the genes encoding subunits of this enzyme. Only a pair of closely related proteins (Gsc1/Fks1 and Gsc2/Fks2) had previously been described as subunits of the 1,3-β-glucan synthase (GS) (Inoue et al. (1995) supra; and Douglas et al. (1994) *PNAS* 91:12907). GS activity in many fungal species, including *S. cerevisiae*, requires GTP or a non-hydrolyzable analog (e.g. GTPγS) as a cofactor, suggesting that a GTP-binding protein stimulates this enzyme (Mol et al. (1994) *J. Biol. Chem.* 269:31267).

SUMMARY OF THE INVENTION

The present invention relates to methods for treating or preventing fungal infections and infections involving other eukaryotic parasites of plants or animals, using compounds that specifically inhibit the biological activity of the enzyme geranylgeranylproteintransferase (GGPTase).

In certain embodiments, the subject GGPTase inhibitors can be used for the treatment of mycotic infections in animals; as additives in feed for livestock to promote weight gain; as disinfectant formulations; and as in agricultural applications to prevent or treat fungal infection of plants. In preferred embodiments, the practice of the subject method utilizes GGPTase inhibitors which are selective inhibitors of the fungal or parasites' GGPTase relative to human GGPTase or FPTase.

In certain preferred embodiments, the method can be used for treating a nosocomial fungal and skin/wound infection involving fungal organisms, including, among others, the species Aspergillus, Blastomyces, Candida, Coccidioides, Cryptococcus, Epidermophyton, Hendersonula, Histoplasma, Microsporum, Paecilomyces, Paracoccidioides, Pneumocystis, Trichophyton, and Trichosporium. In other preferred embodiments, the method can be used for treating an animal or plant parasites, such as infections involving liver flukes, nematodes or the like. According to the present invention, treatment of such infections comprises the administration of a pharmaceutical composition of the invention in a therapeutically effective amount to an individual in need of such treatment. The compositions may be administered parenterally by intramuscular, intravenous, intraocular, intraperitoneal, or subcutaneous routes; inhalation; orally, topically and intranasally.

In certain embodiments, the subject inhibitors include a permease tag. In certain embodiments, a permease tag may include a structure represented by the general formula

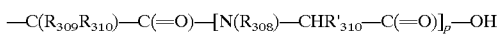

wherein $R_{308}$ represents H, lower alkyl, —$(CH_2)_n$aryl or —$(CH_2)_n$heteroaryl;

$R_{309}$ and $R_{310}$ represent H, lower alkyl, —$(CH_2)_n$aryl, —$(CH_2)_n$heteroaryl, or a sidechain of an amino acid;

$R'_{310}$ represents, individually for each occurrence, a natural or unnatural amino acid sidechain, such as a lower alkyl; and p is 1, 2 or 3.

In certain embodiments, a permease tag may include a structure represented by the general formula

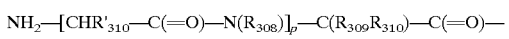

wherein $R_{308}$ represents H, lower alkyl, —$(CH_2)_n$aryl or —$(CH_2)_n$heteroaryl;

$R_{309}$ and $R_{310}$ represent H, lower alkyl, —$(CH_2)_n$aryl, —$(CH_2)_n$heteroaryl, or a sidechain of an amino acid;

$R'_{310}$ represents, individually for each occurrence, a natural or unnatural amino acid sidechain, such as a lower alkyl; and p is 1, 2 or 3.

BRIEF DESCRIPTION OF THE DRAWINGS

FIG. 1 depicts strategies for preparing substituted nitrobenzenes.

FIG. 7 shows general templates useful for compounds of the present invention.

FIG. 12 is a scheme for producing thiol and thioether derivatives.

FIGS. 15 and 16 illustrate techniques for generating sulfonic acid chlorides.

FIG. 18 defines various templates useful for compounds of the invention.

FIG. 48 is a scheme for the synthesis of phenylpiperidine compounds of the present invention, wherein the following conditions are used: (a) EDC, HOBt, DIEA, CH$_2$Cl$_2$, (b) EDC HOBt, DIEA, RNH$_2$, CH$_2$Cl$_2$, (c) LiOH, MeOH, THF, H$_2$O, (* only with 52a) (d) TFA, Et$_3$SiH, CH$_2$Cl$_2$.

FIG. 56 is a scheme for the synthesis of phenylpiperidine compounds of the present invention, wherein the following conditions are used: (a) $H_2N$-Ala-$CO_2{}^tBu$ or $H_2N$-Ala-Ala-$CO_2{}^tBu$, DIEA, HOBt, EDC, $CH_2Cl_2$, rt, 15 hrs., (b) $CH_2Cl_2$, TFA, $Et_3SiH$, rt, 2 hrs.

DETAILED DESCRIPTION OF THE INVENTION

Figure 1:
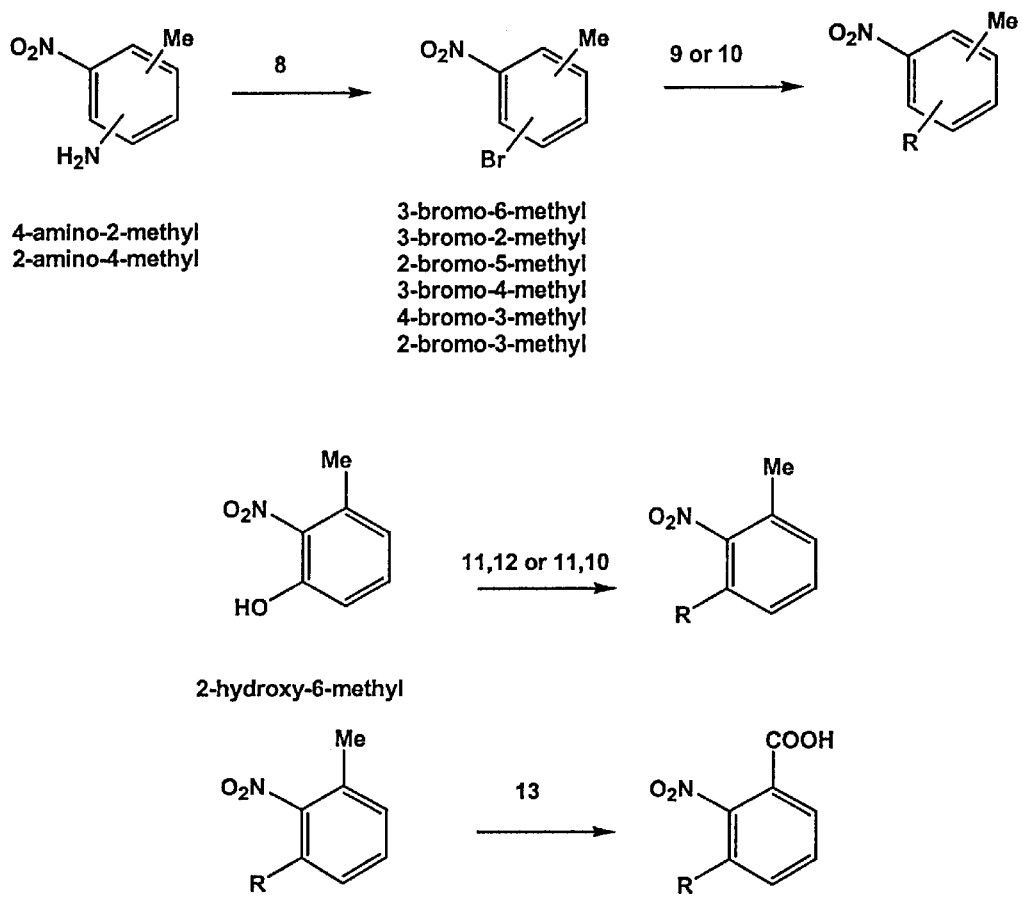
FIGS. 1–56 illustrate various reaction schemes for synthesizing prenyltransferase inhibitors useful in the methods and compositions of the present invention.
Figure 2:
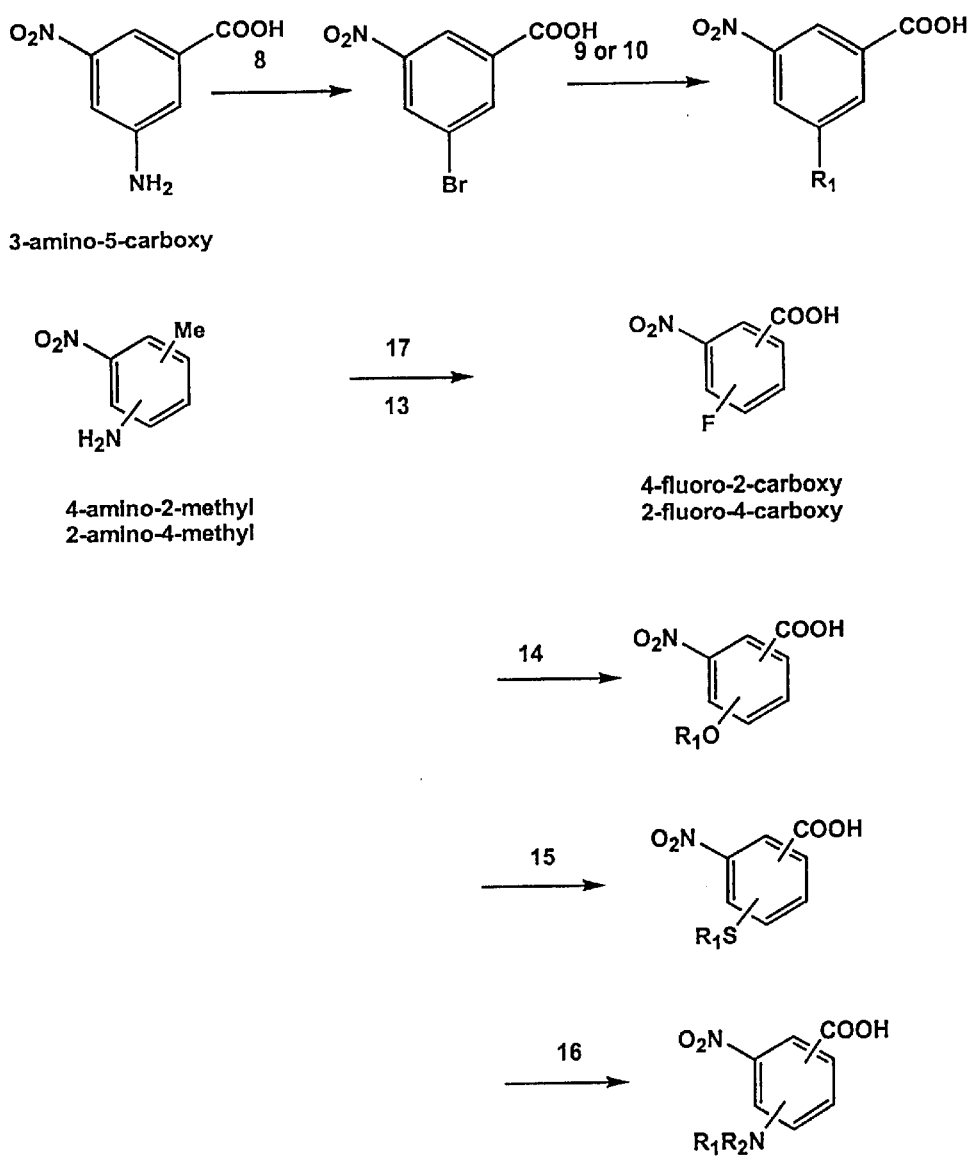
FIGS. 2–5 depict methods for preparing substituted nitrobenzoic acids.
Figure 3:
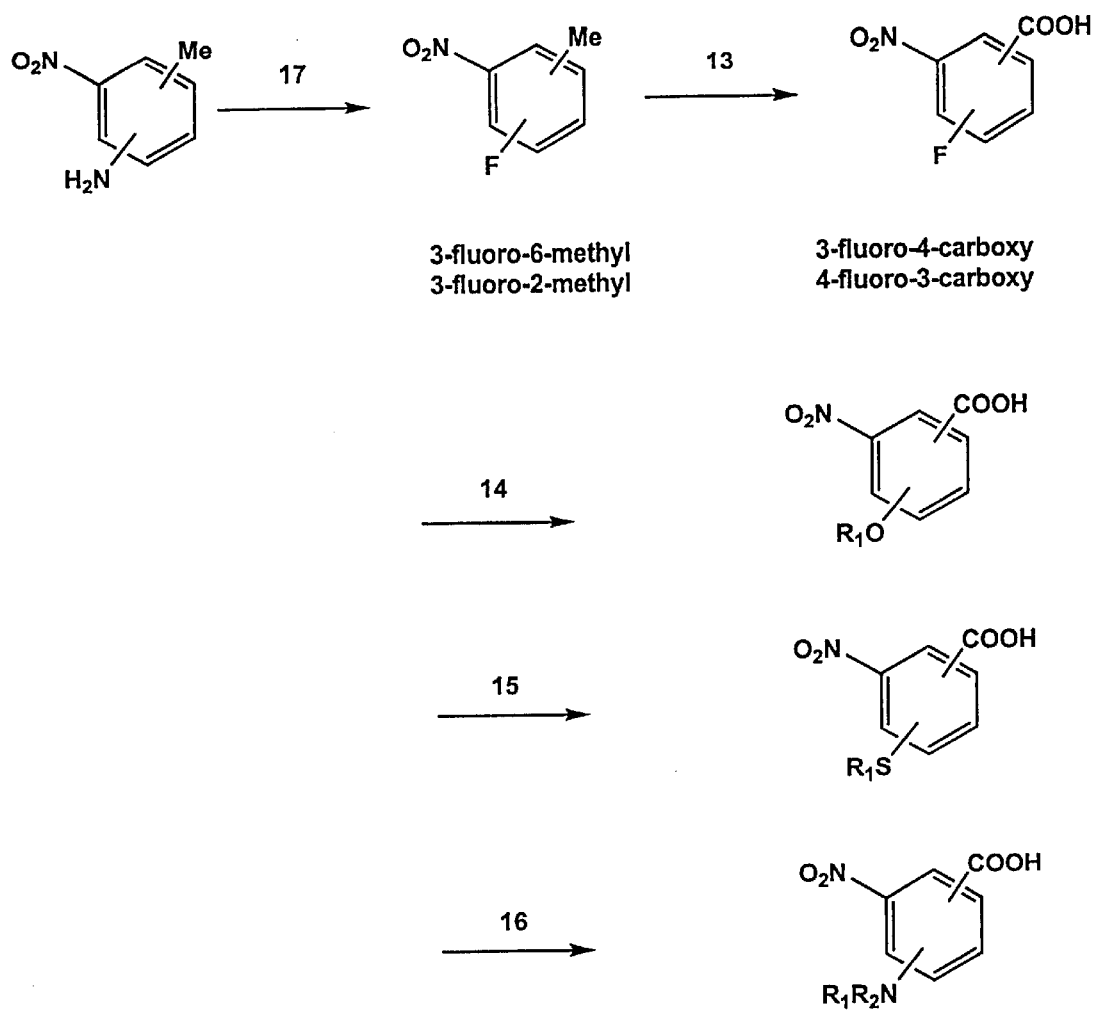
Figure 4:
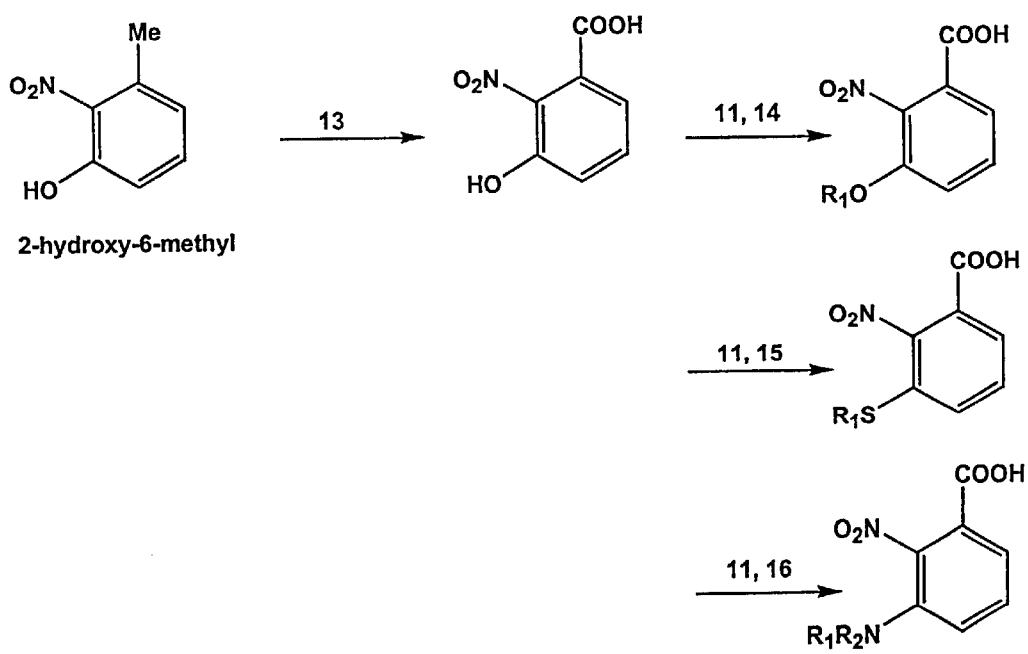
Figure 5:
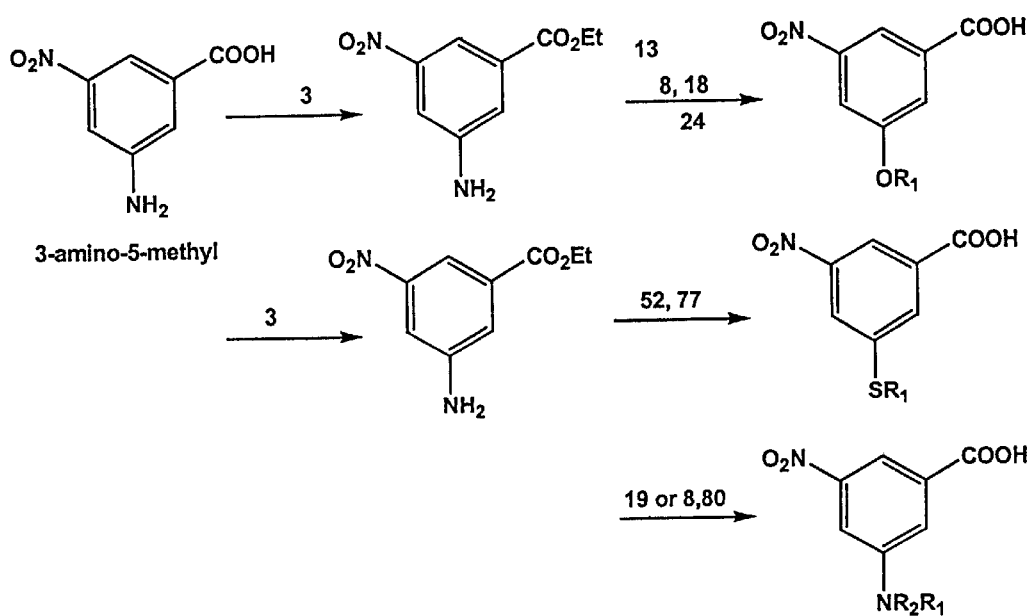
Figure 6:
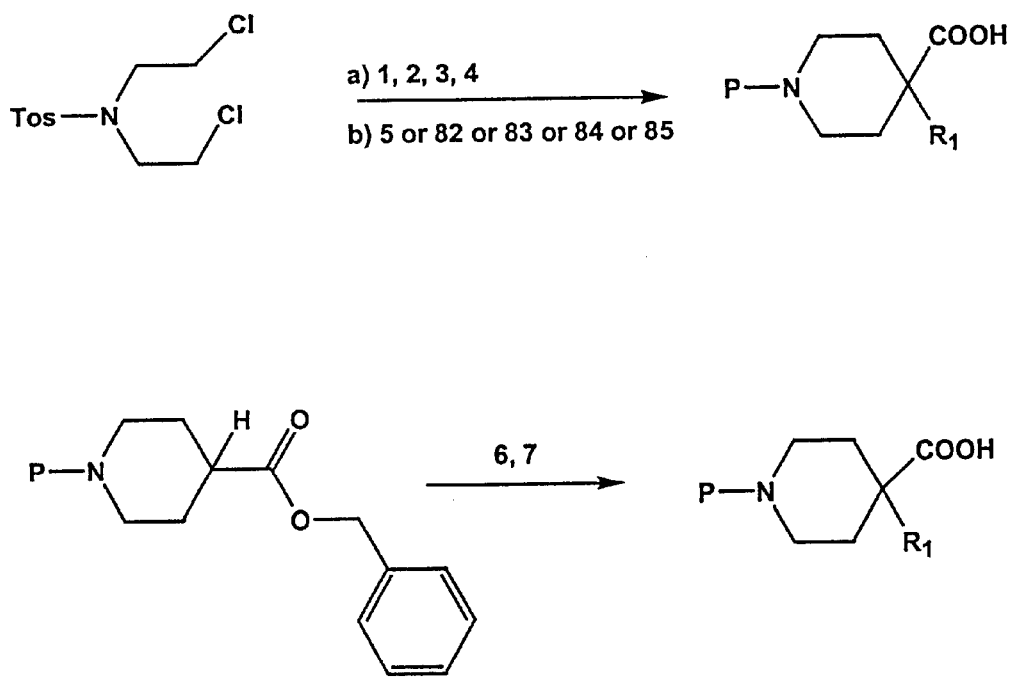
FIG. 6 provides methods for preparing 4-substituted piperidines.
Figure 8:
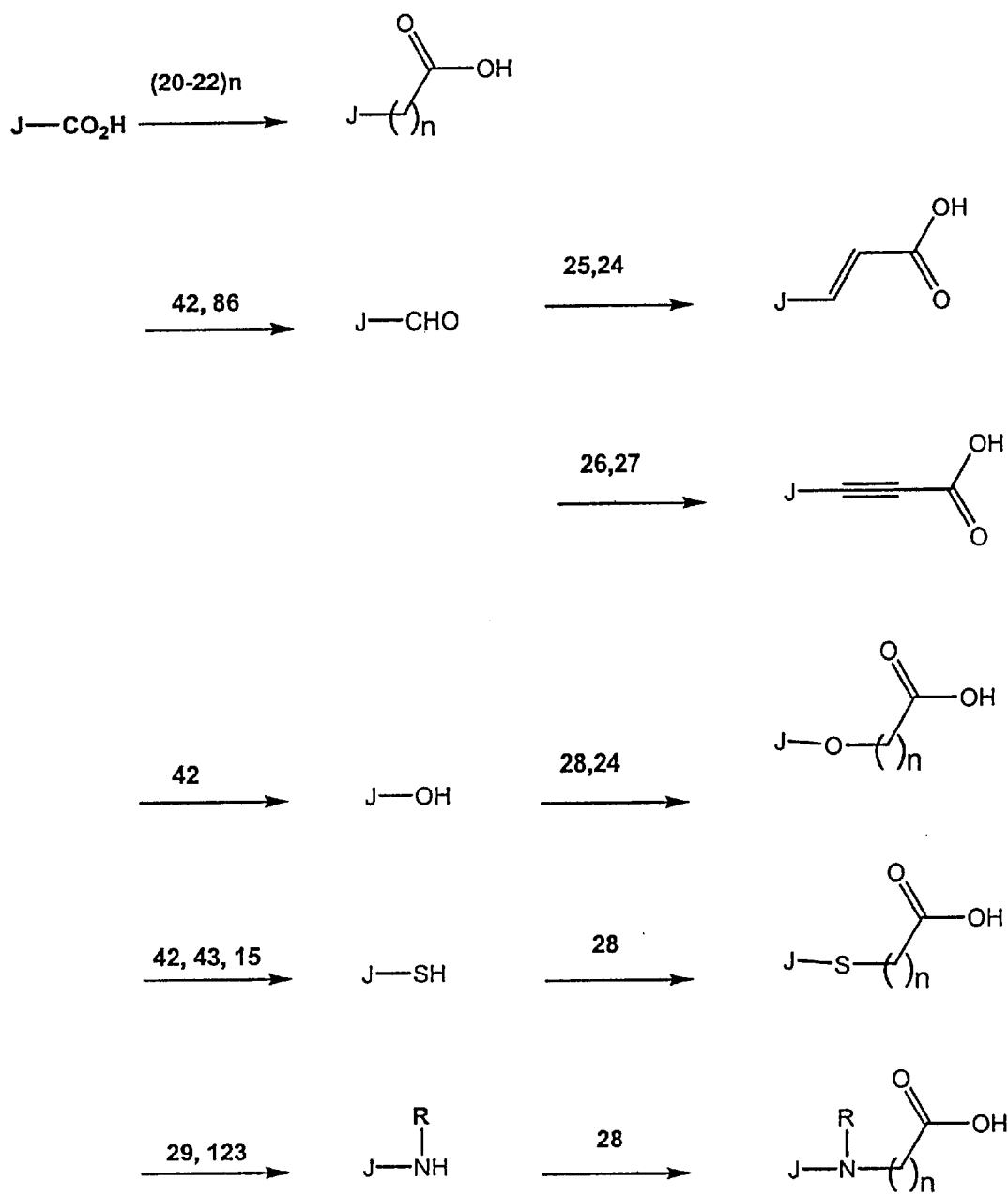
FIG. 8 illustrates methods for generating functionalized carboxylic acids.
Figure 9:
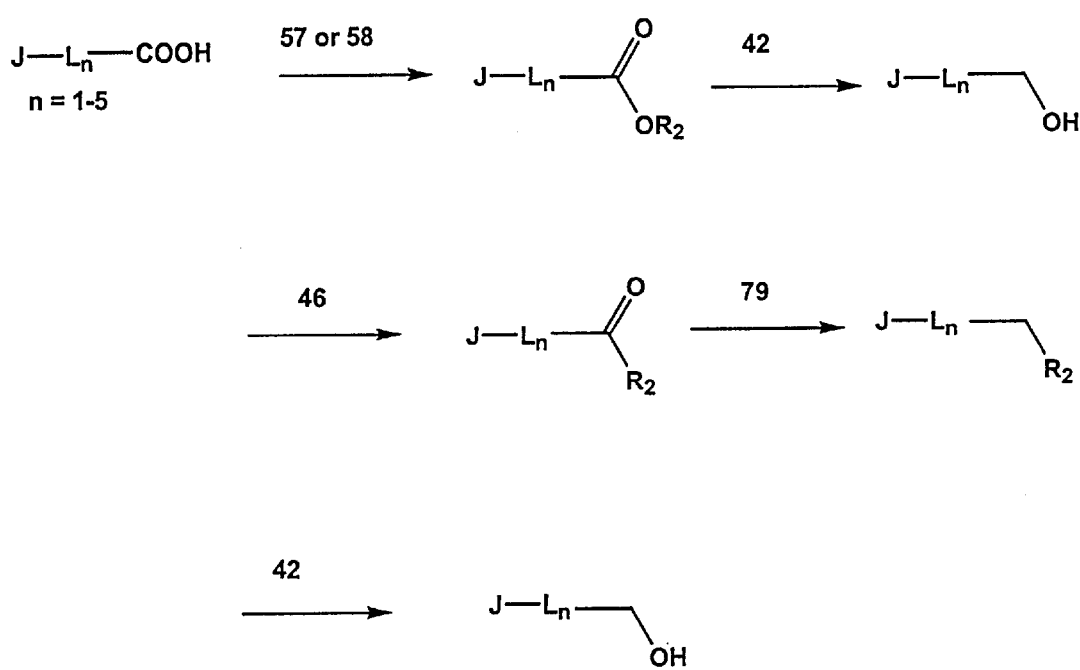
FIG. 9 illustrates reduction strategies for forming linkages.
Figure 10:
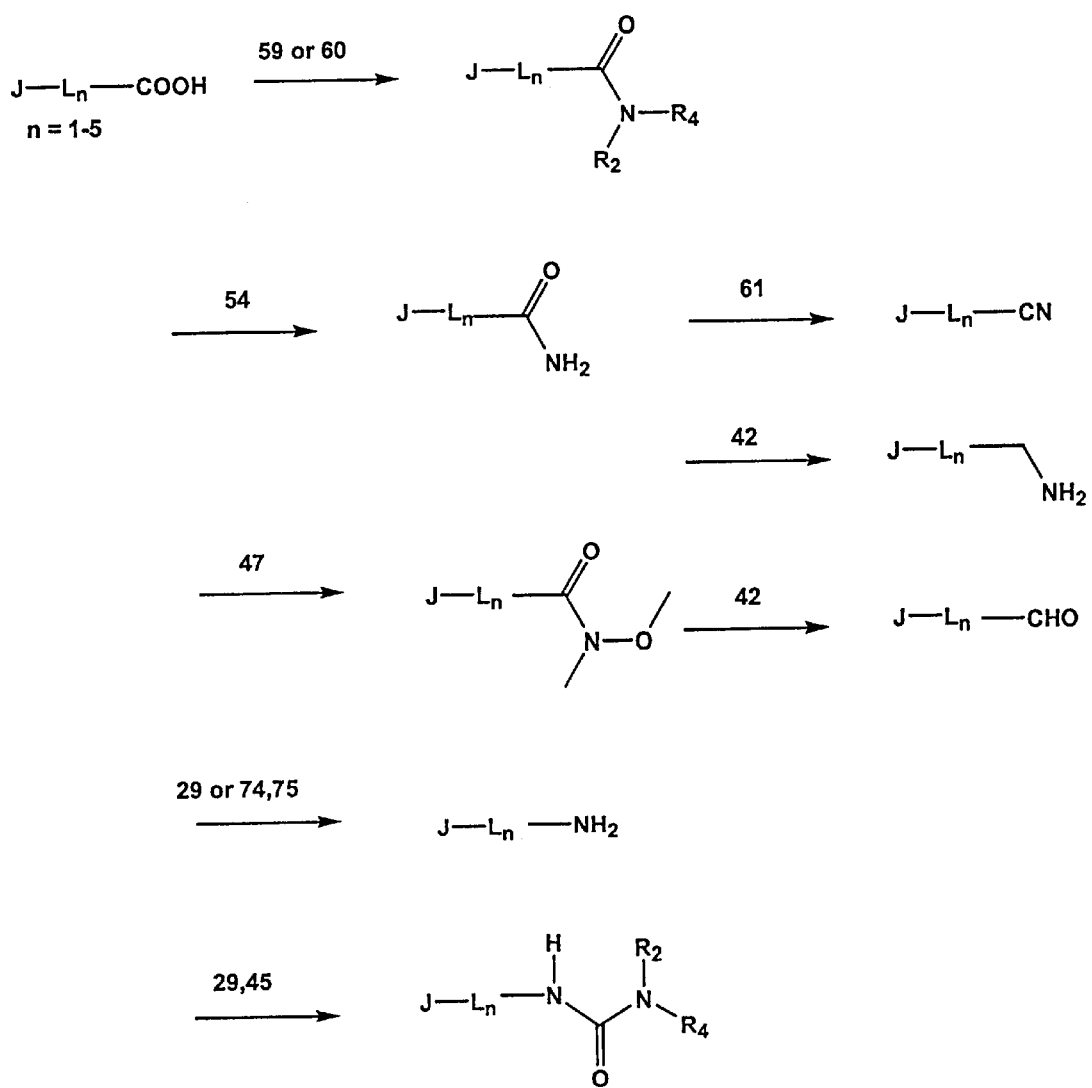
FIG. 10 depicts functional group transformations useful for generating prenyltransferase inhibitors.
Figure 11:
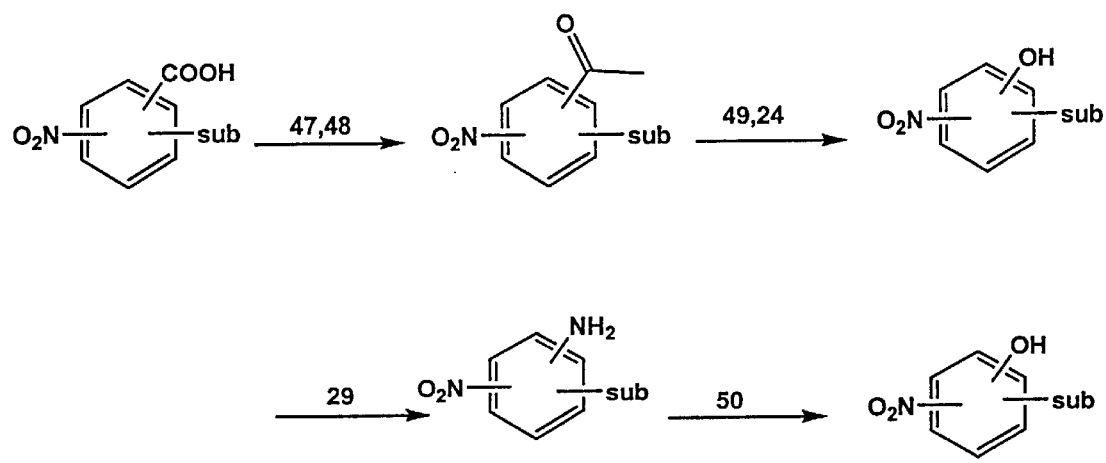
FIG. 11 illustrates methods for producing substituted nitrophenols.
Figure 13:
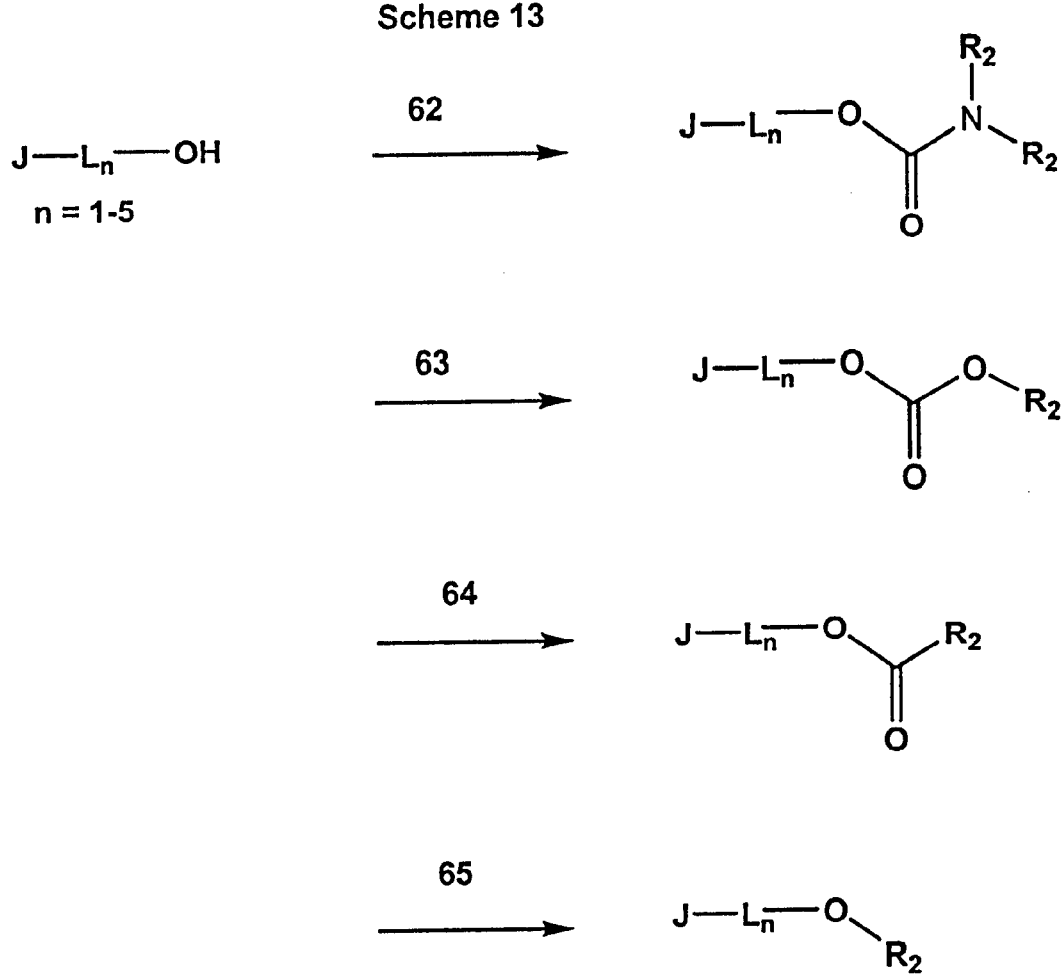
FIG. 13 depicts methods for functionalizing hydroxyl moieties.
Figure 14A:
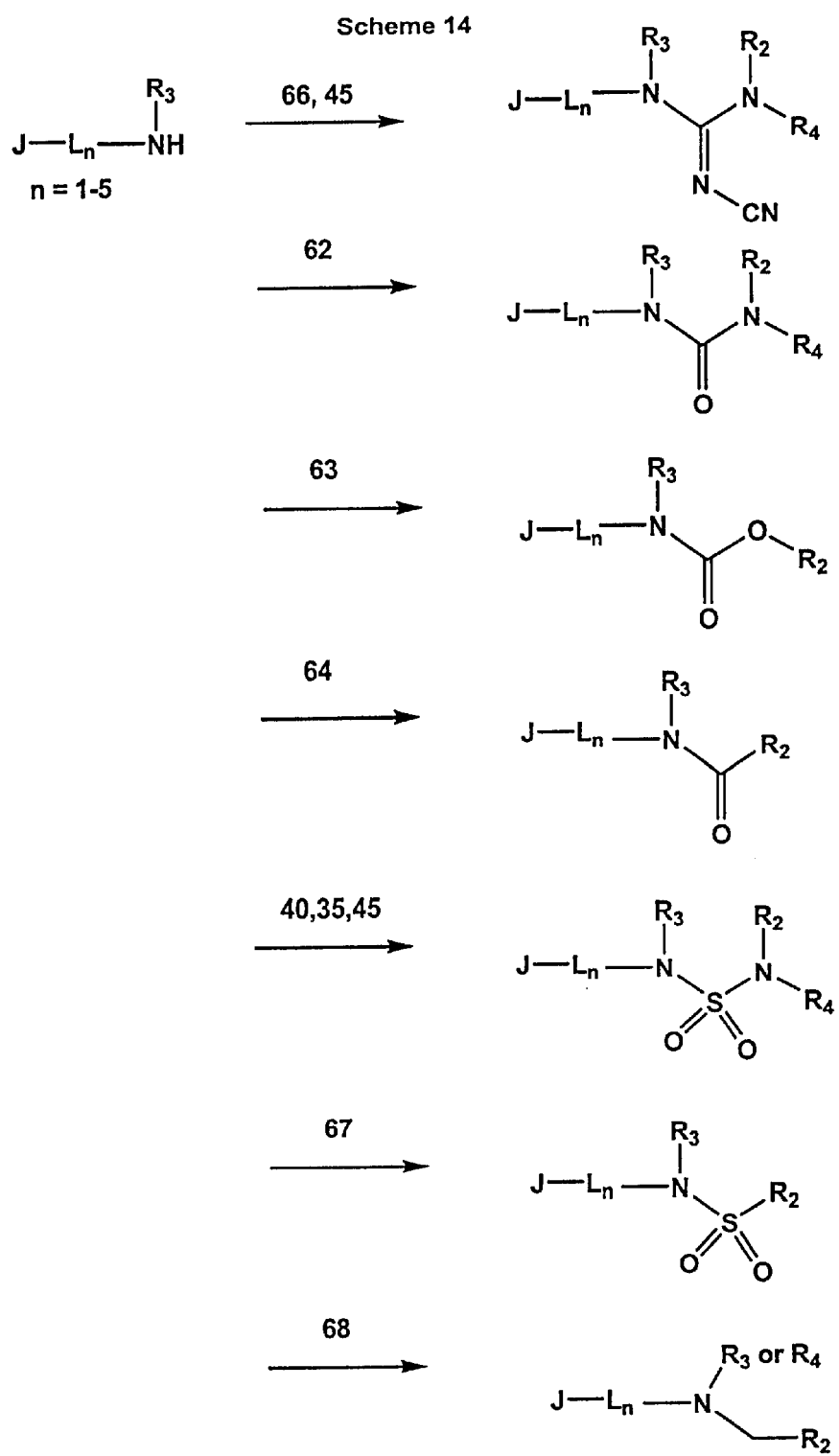
FIGS. 14 and 14B depict methods for functionalizing amine moieties.
Figure 14B:
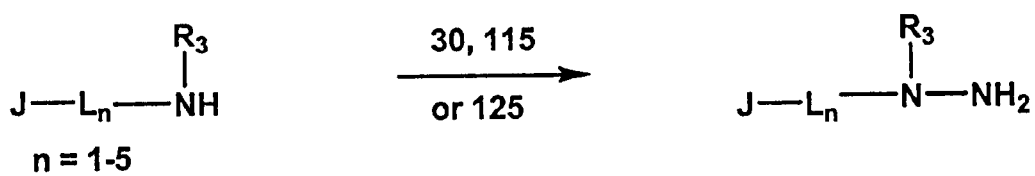
Figure 16:
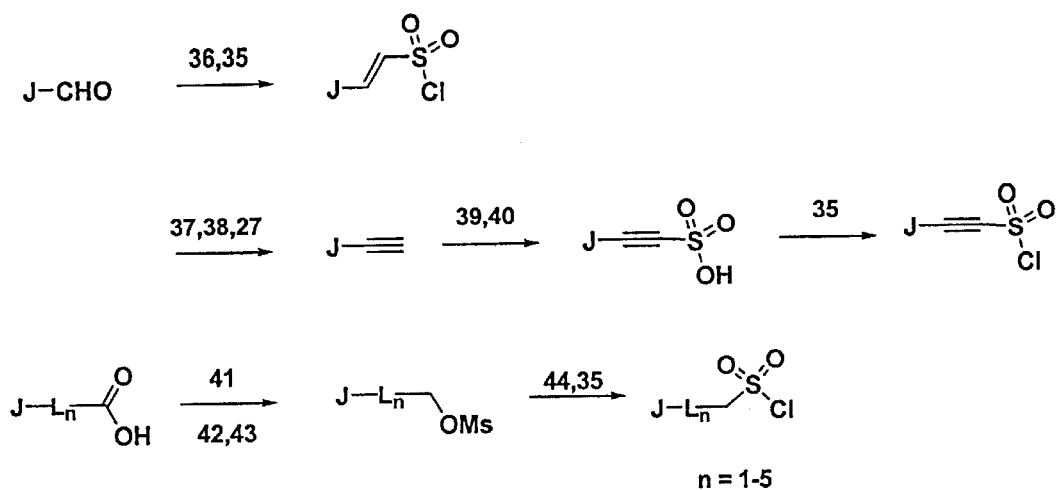
Figure 17:
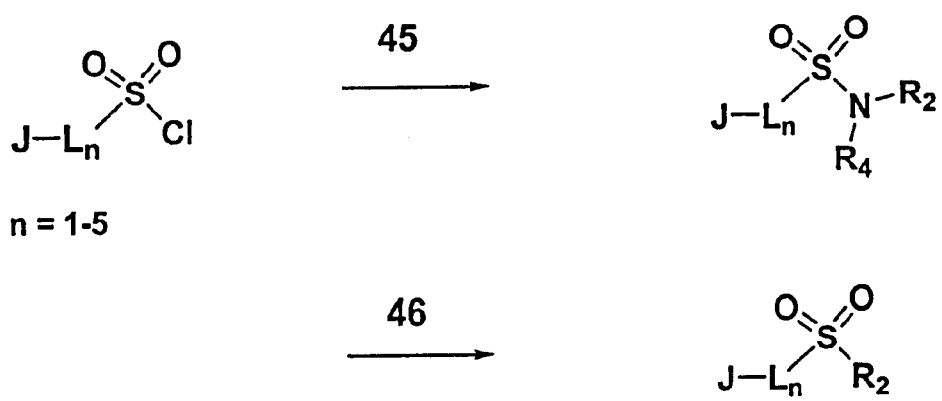
FIG. 17 depicts derivatization of sulfonic acid chlorides.
Figure 19:
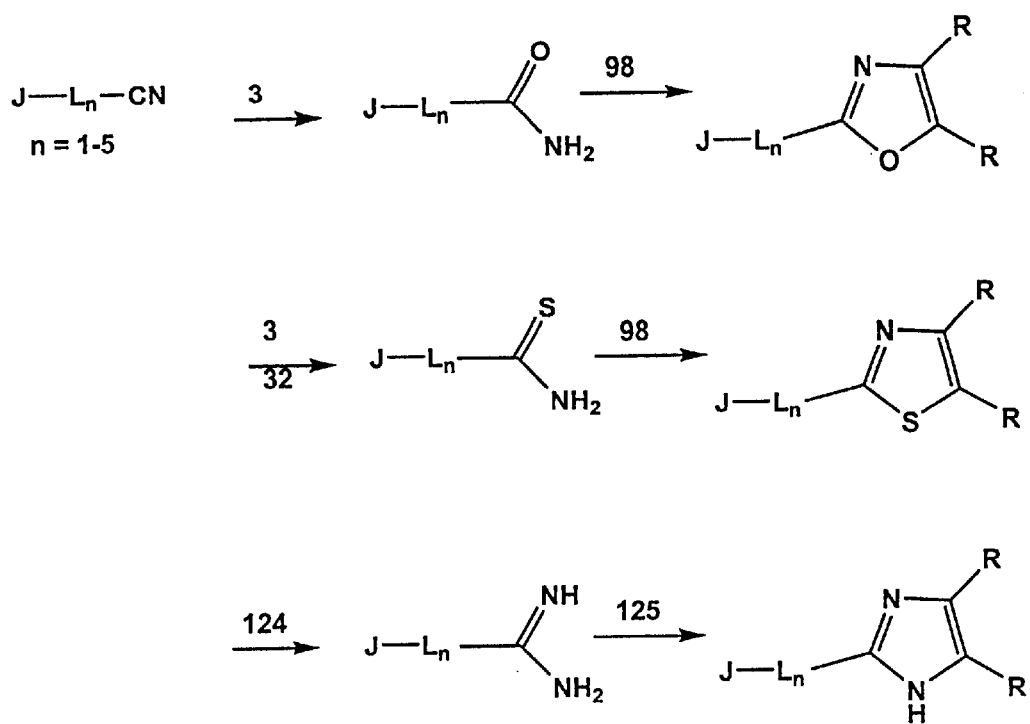
FIGS. 19–28 provide strategies for forming heterocyclic rings.
Figure 20:
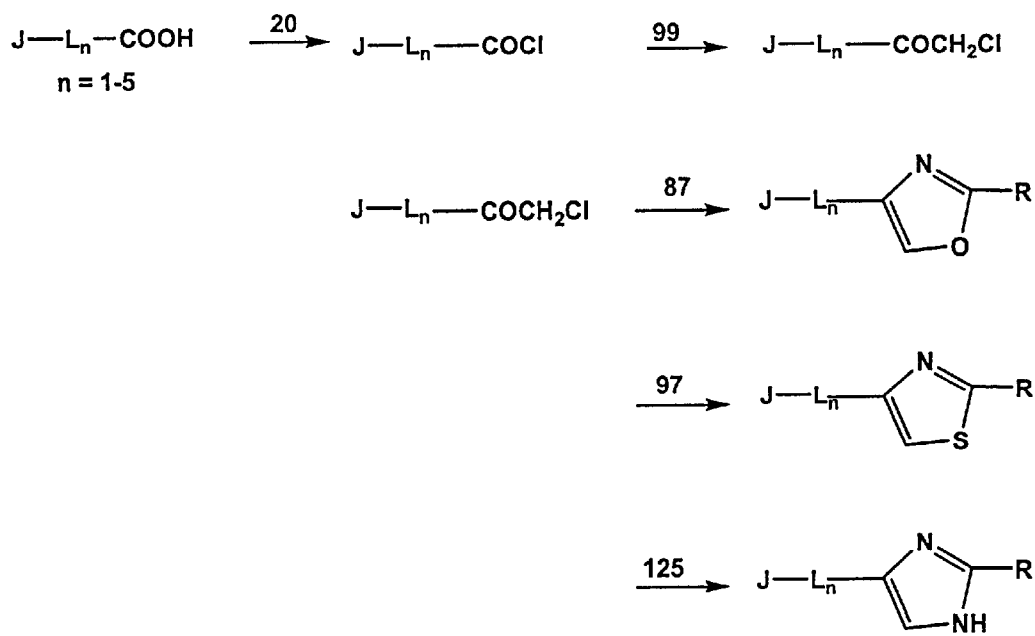
Figure 21:
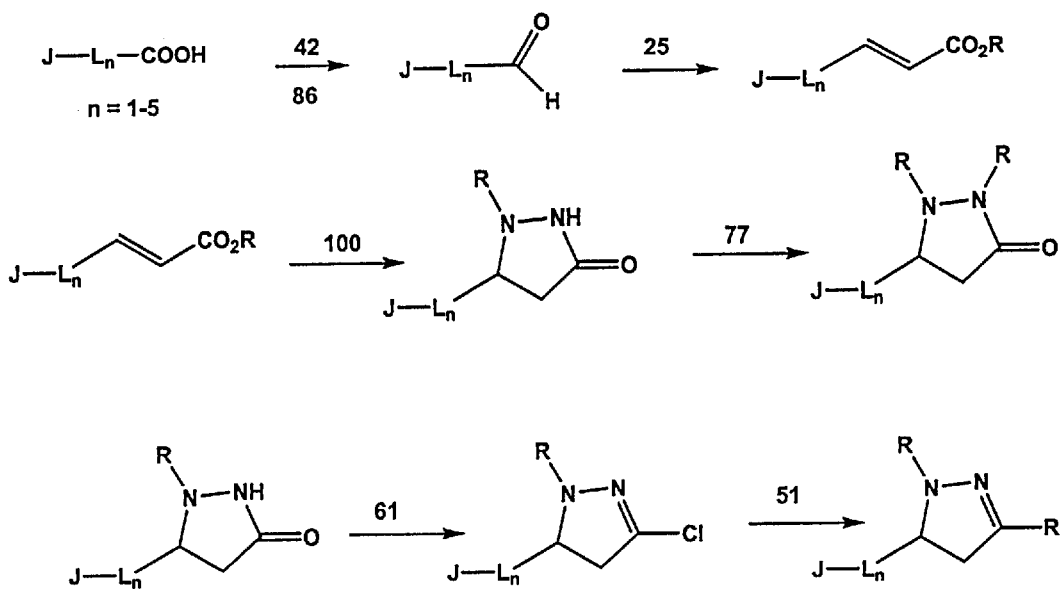
Figure 22:
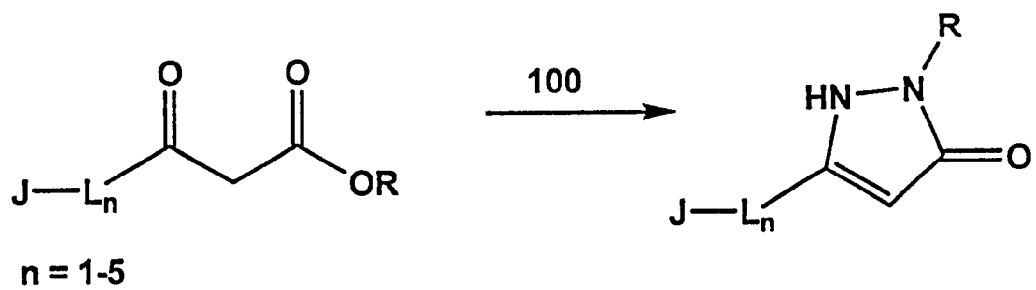
Figure 23:
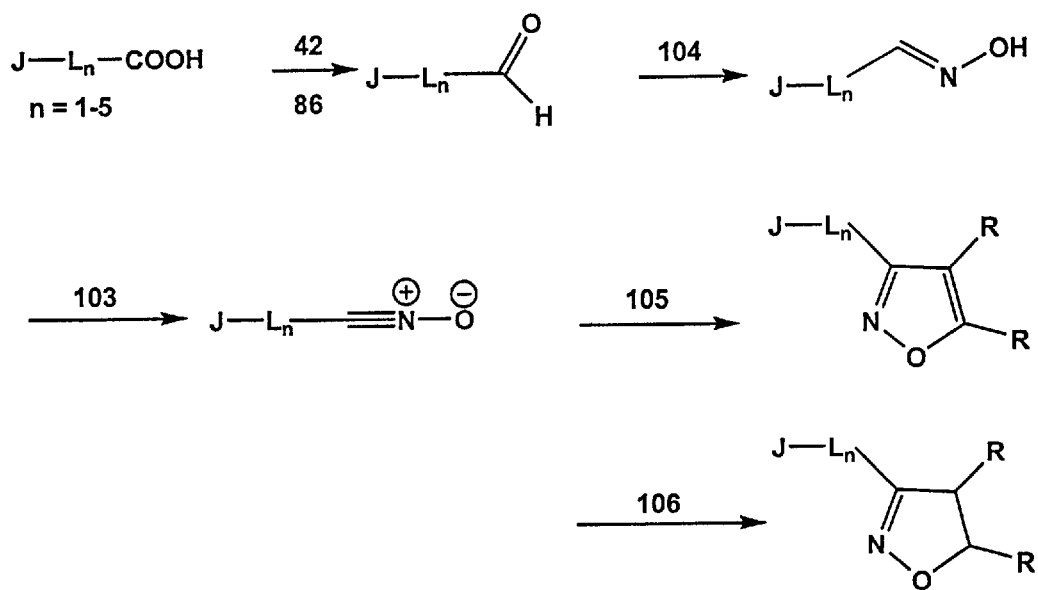
Figure 24:
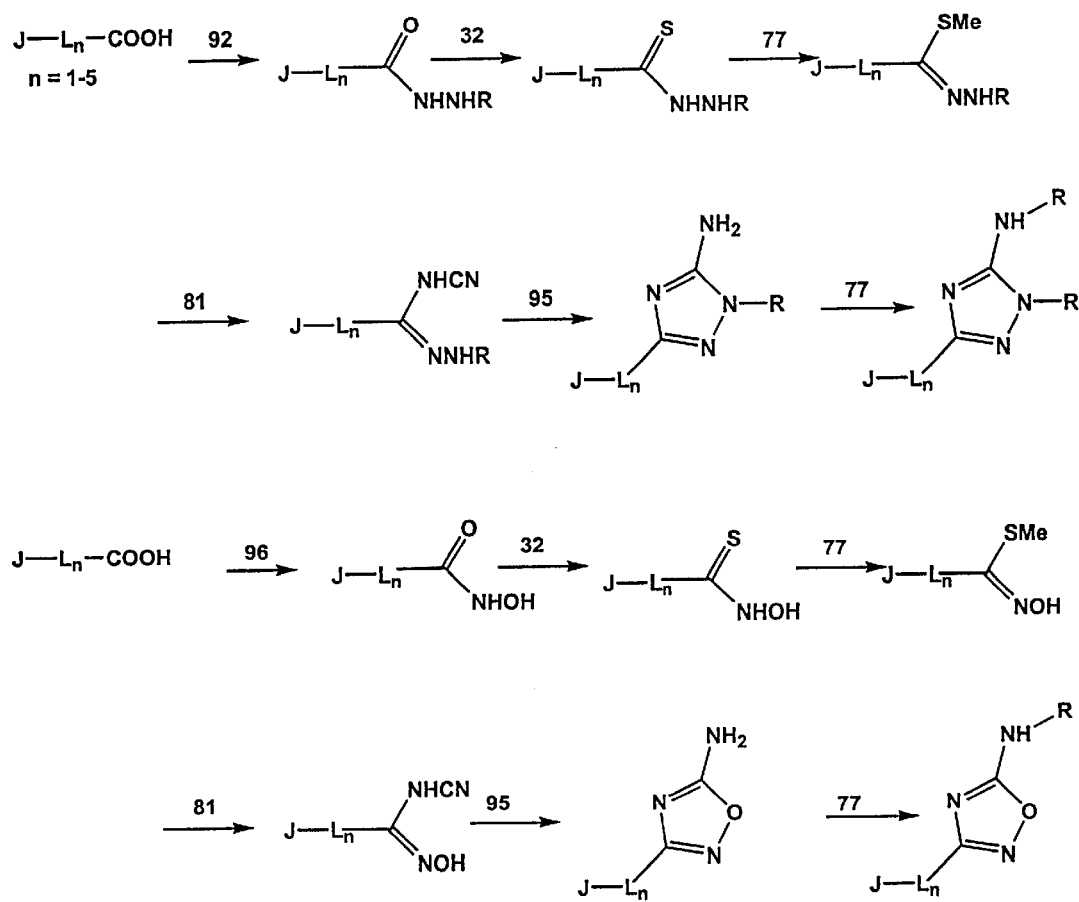
Figure 25:
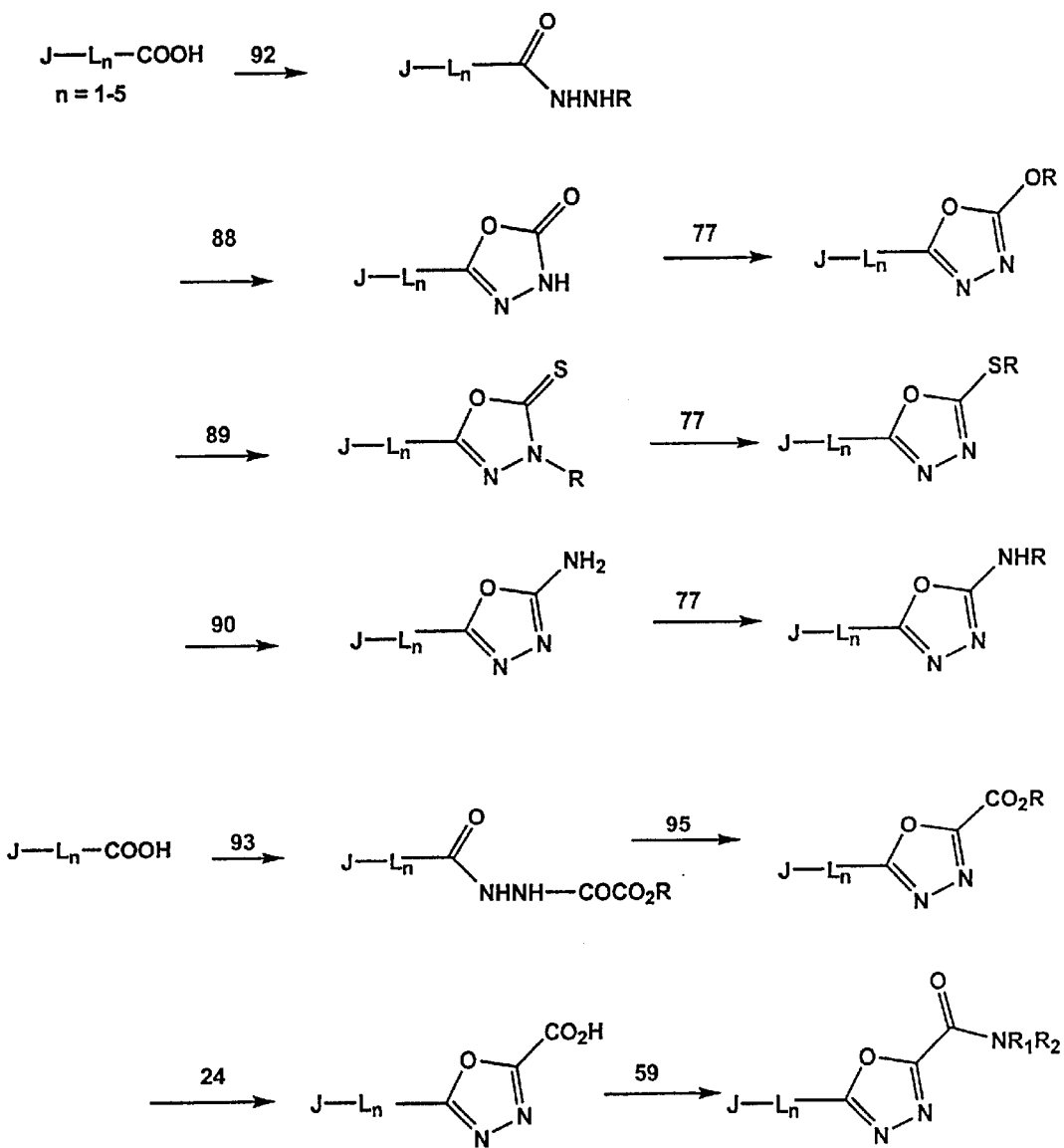
Figure 26:
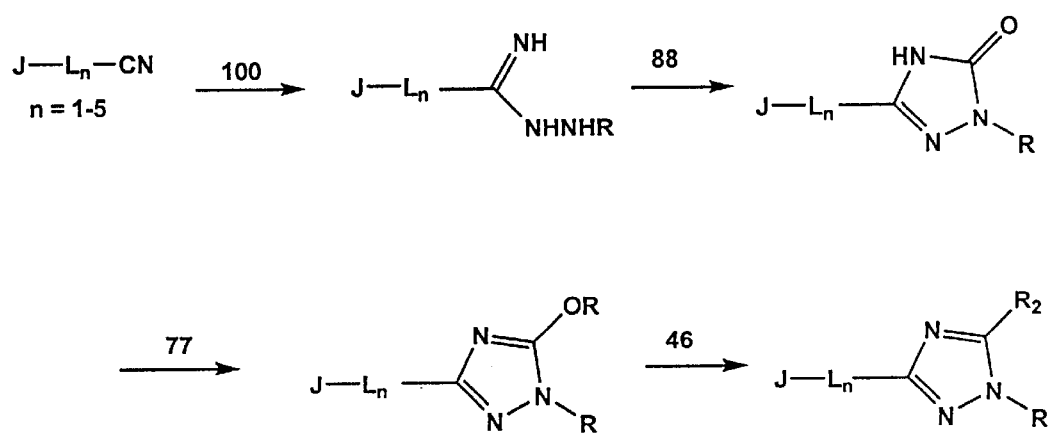
Figure 27:
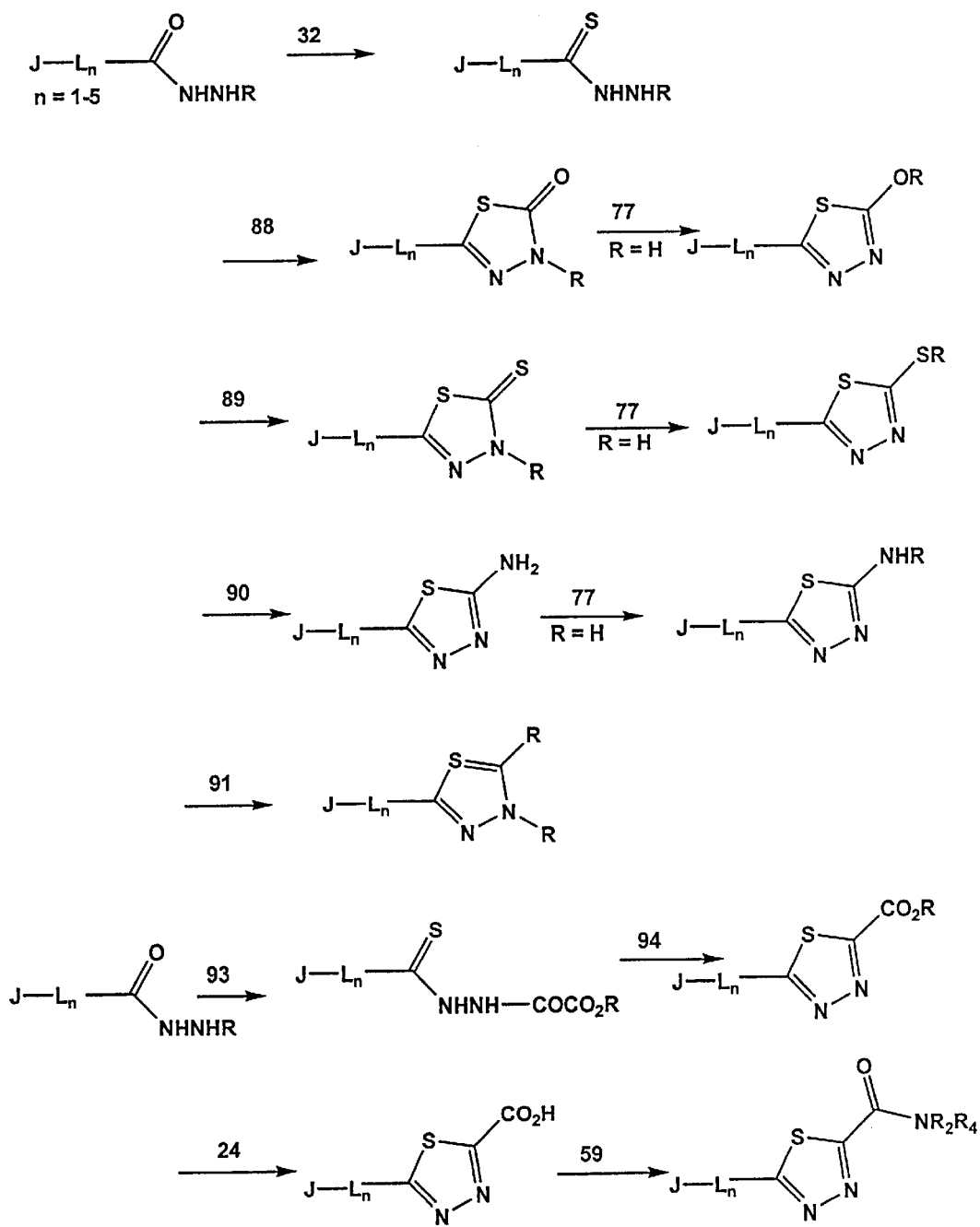
Figure 28:
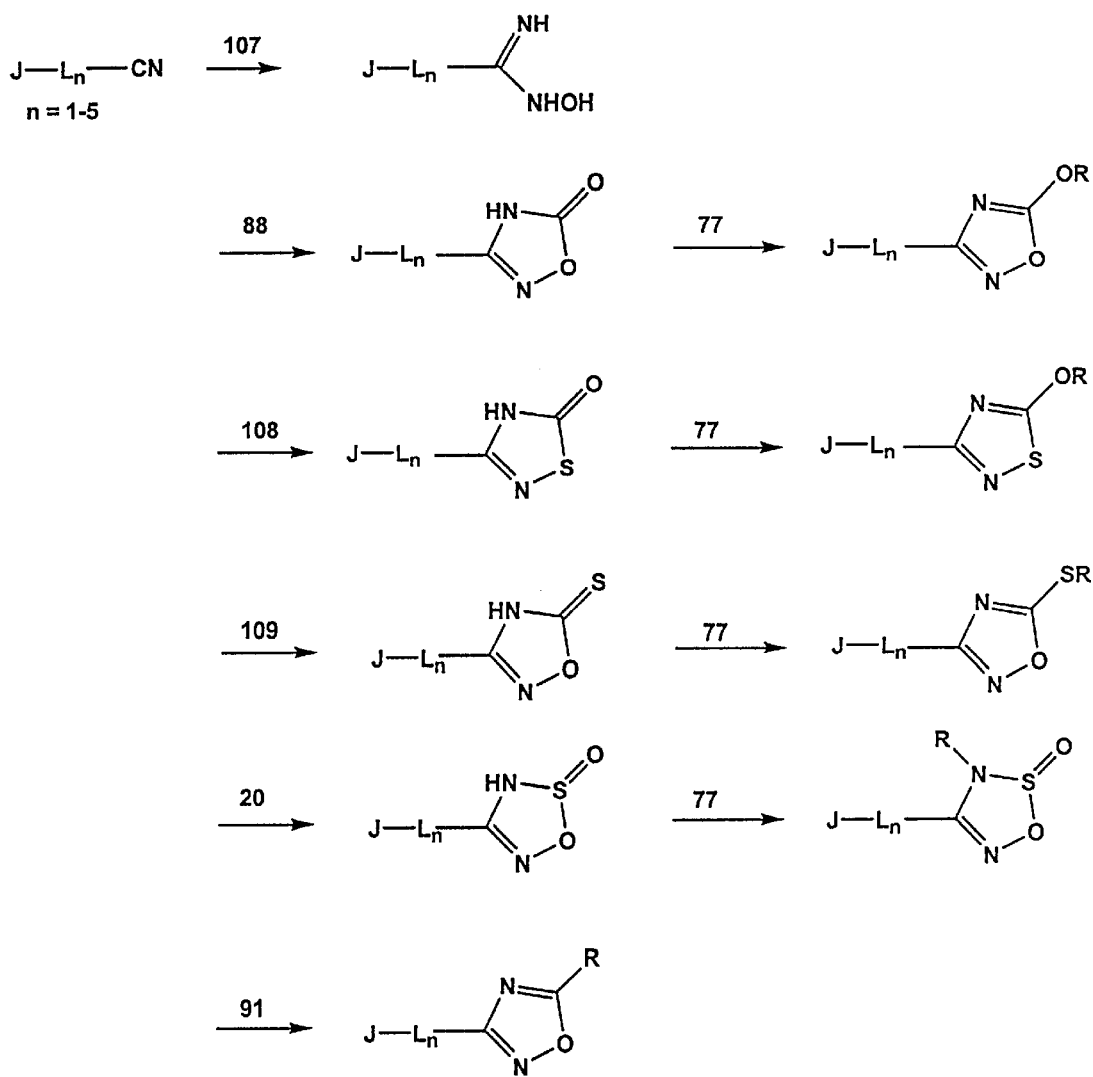
Figure 29:
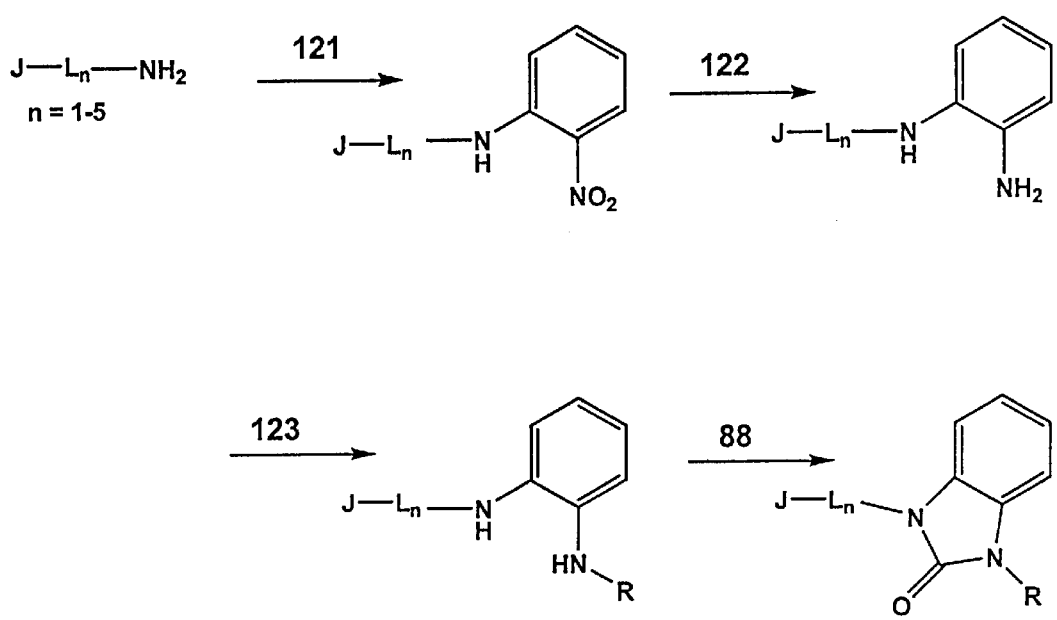
FIG. 29 depicts the synthesis of substituted benzimidazolidinones.
Figure 30:
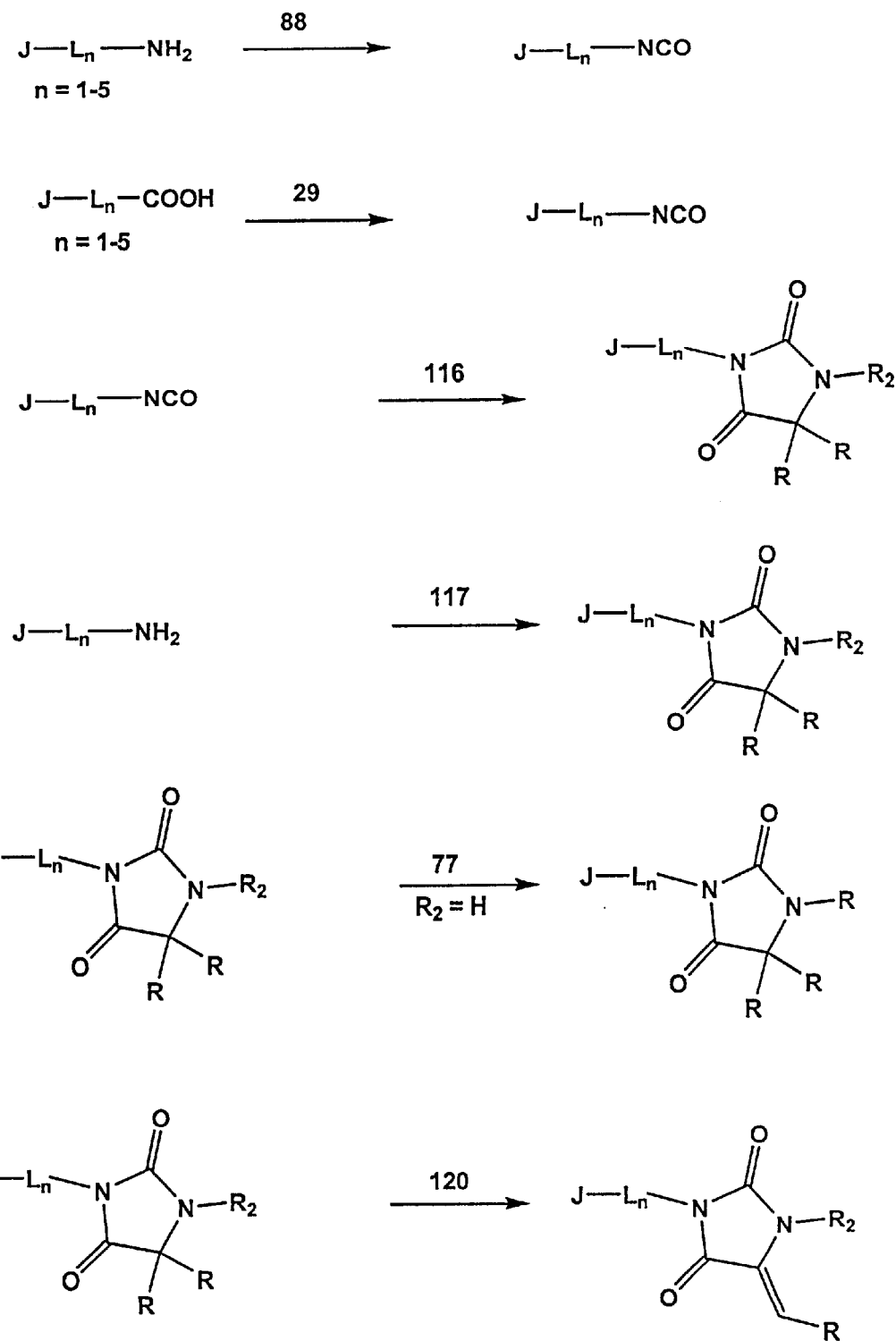
FIG. 30 is a synthetic scheme for substituted imidazolidinediones.
Figure 31:
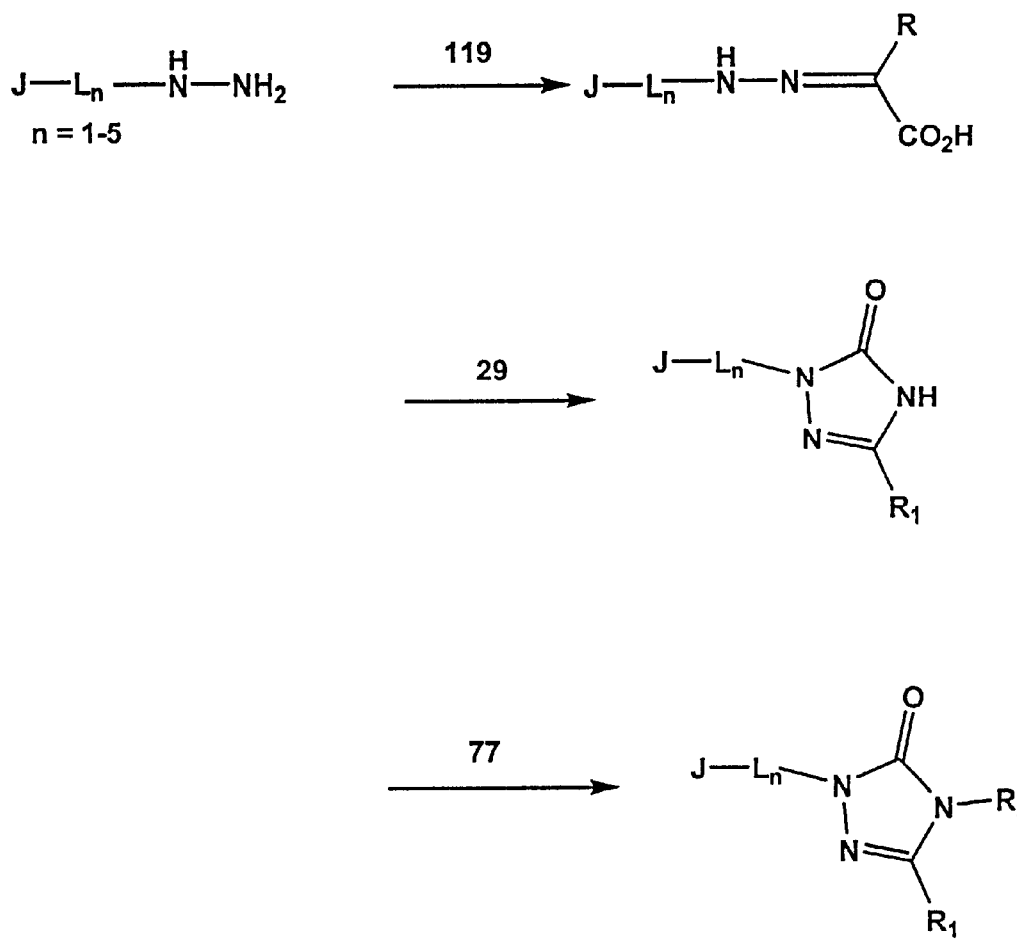
FIG. 31 shows techniques for forming substituted triazolones and hydrazine imines.
Figure 32:
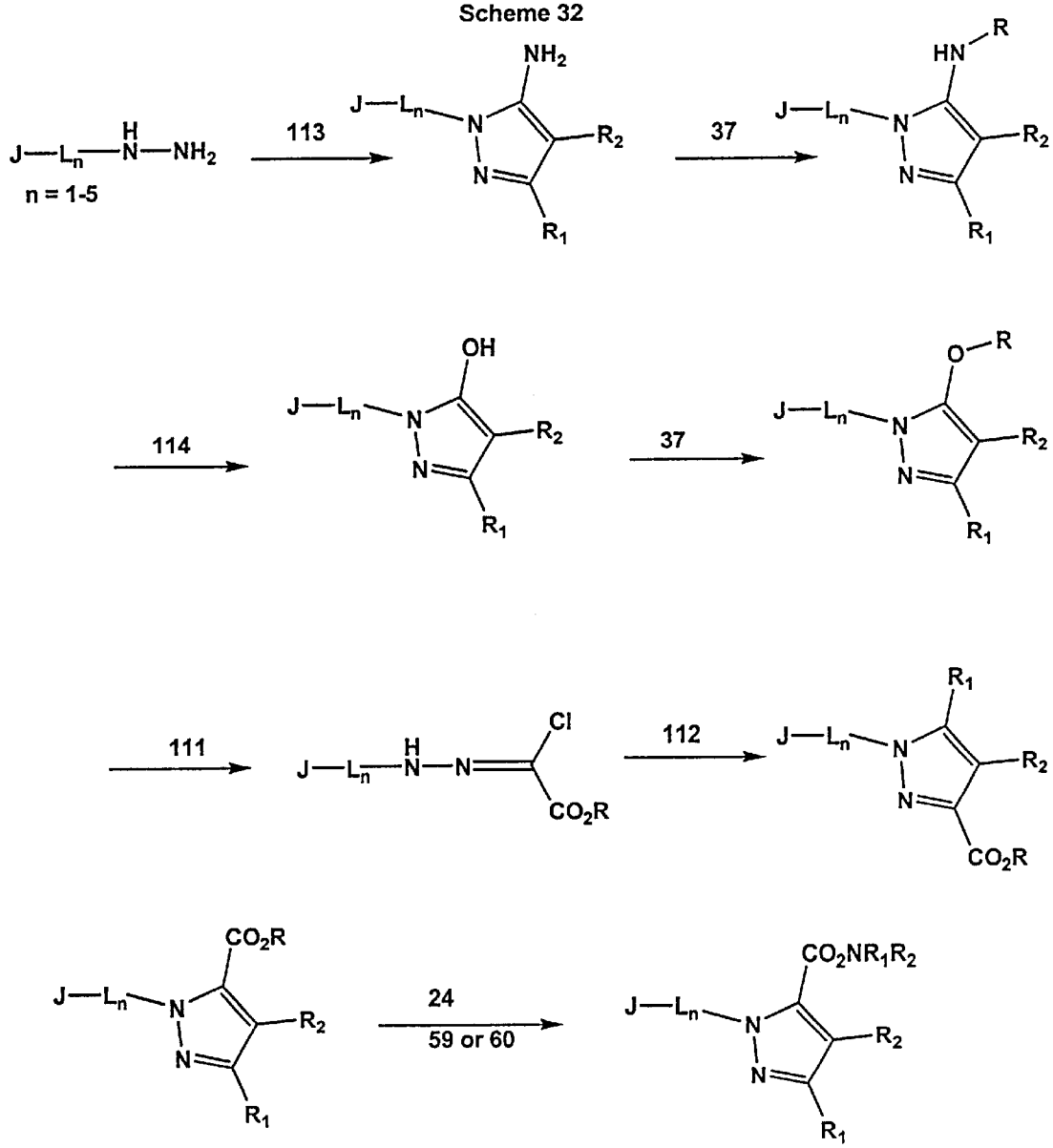
FIG. 32 depicts the synthesis of substituted pyrazoles.
Figure 33:
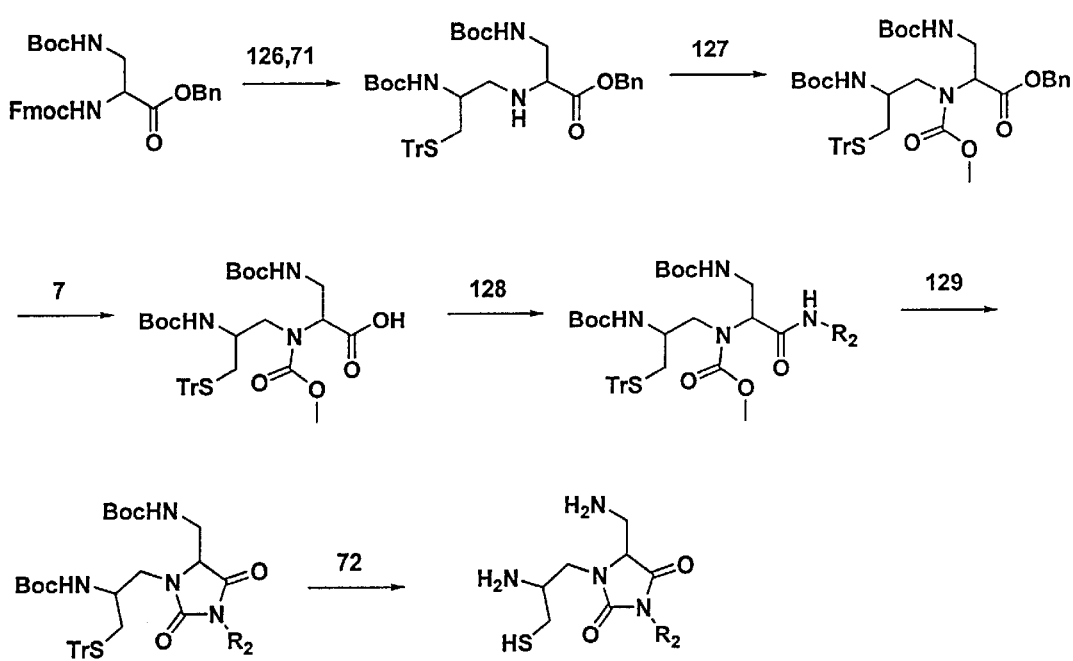
FIGS. 33 and 34 illustrate the preparation of substituted imidazolidinediones.
Figure 34:
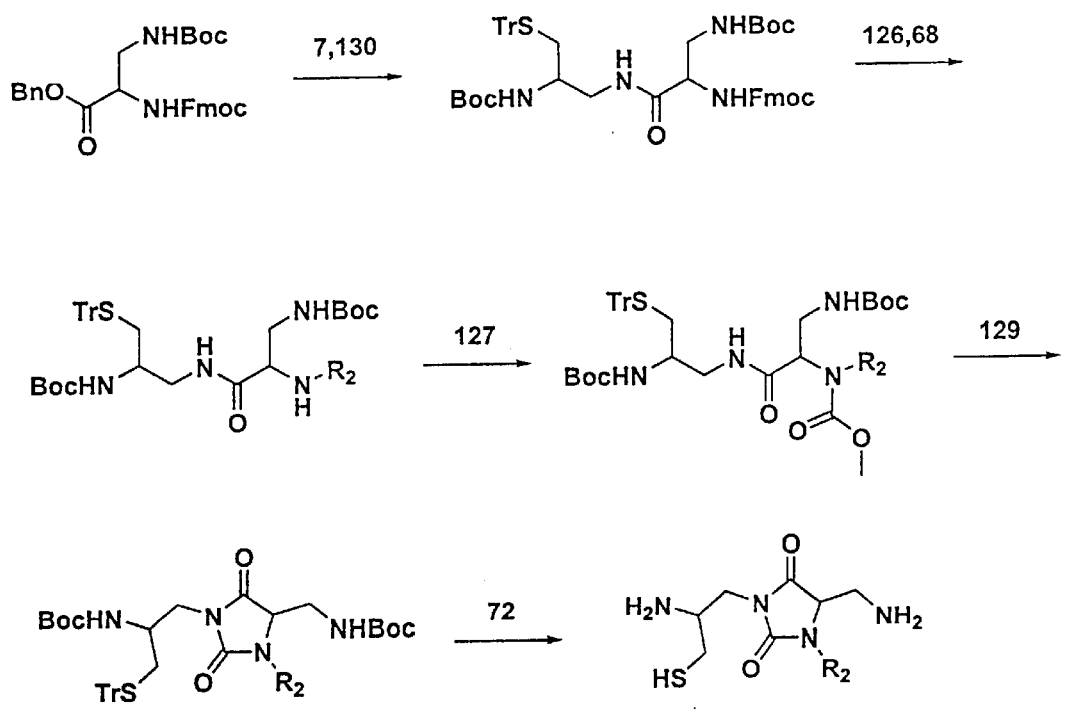
Figure 35:
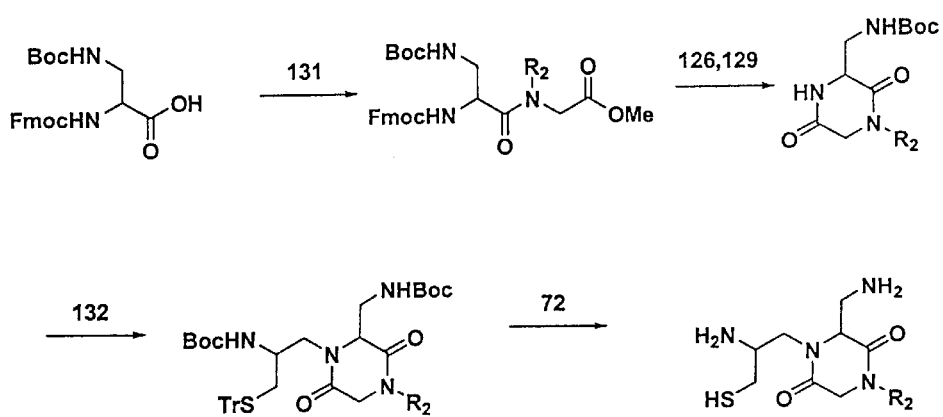
FIG. 35 depicts the formation of substituted piperazinediones.
Figure 36:
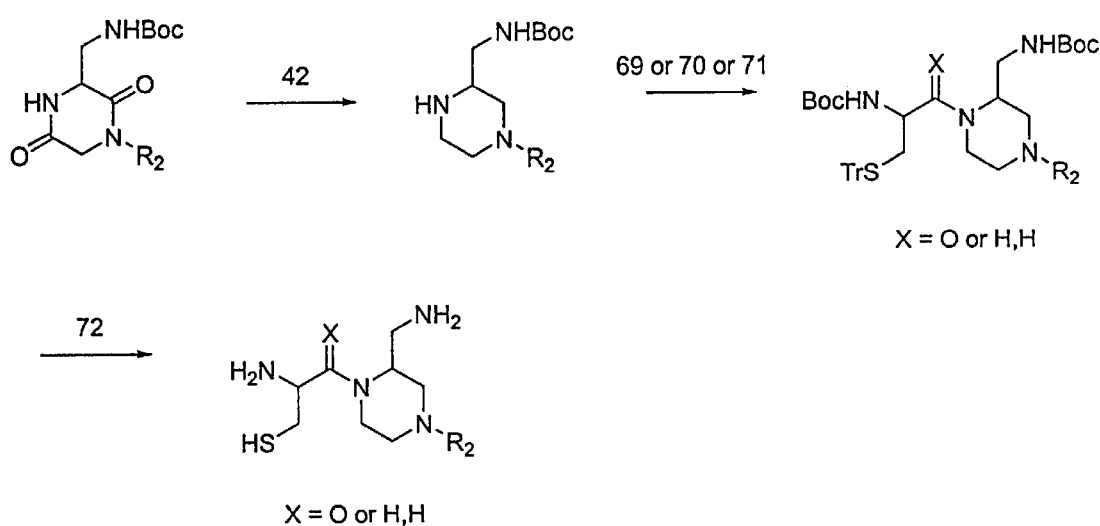
FIG. 36 is a scheme for forming substituted piperazines.
Figure 37:
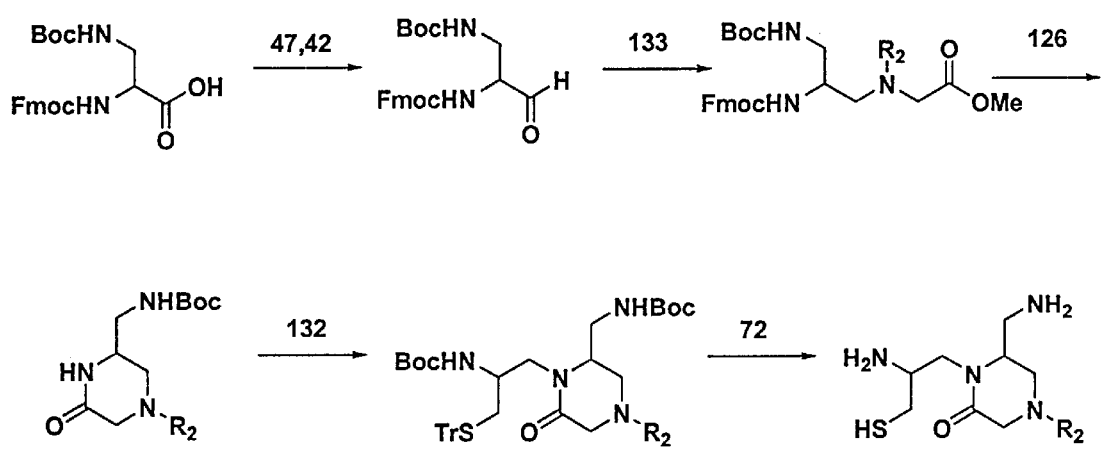
FIGS. 37 and 38 show methods for forming a substituted piperazinone.
Figure 38:
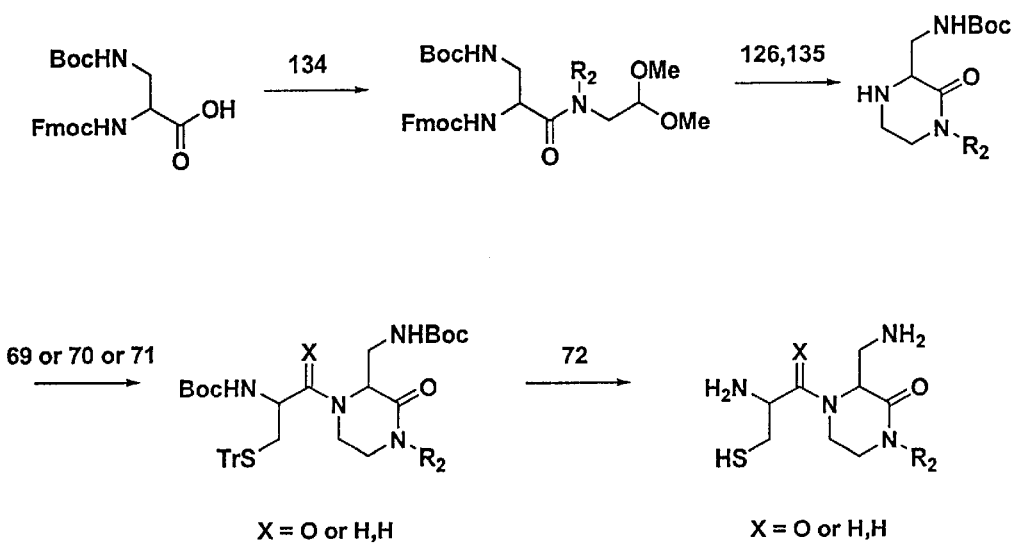
Figure 39:
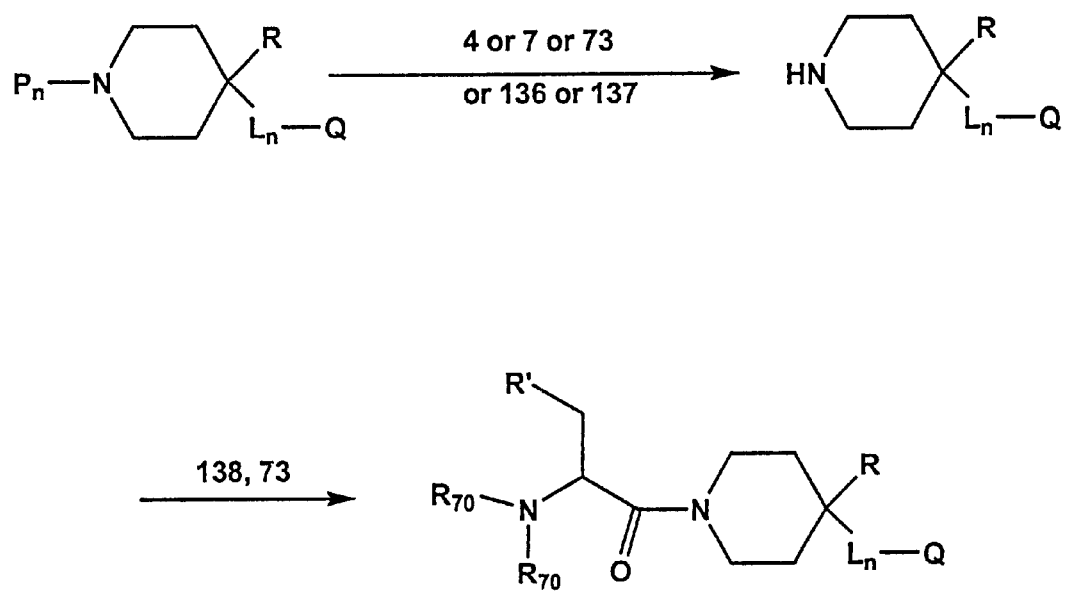
FIG. 39 illustrates a method for forming substituted piperines.
Figure 40:
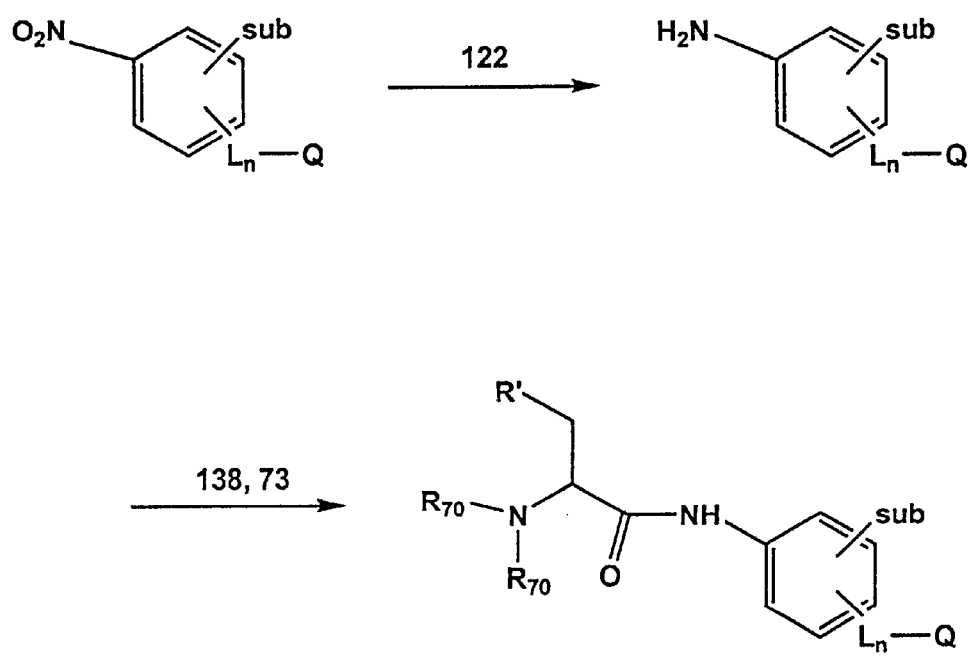
FIG. 40 shows the coupling of a cysteine residue to an aniline.
Figure 41:
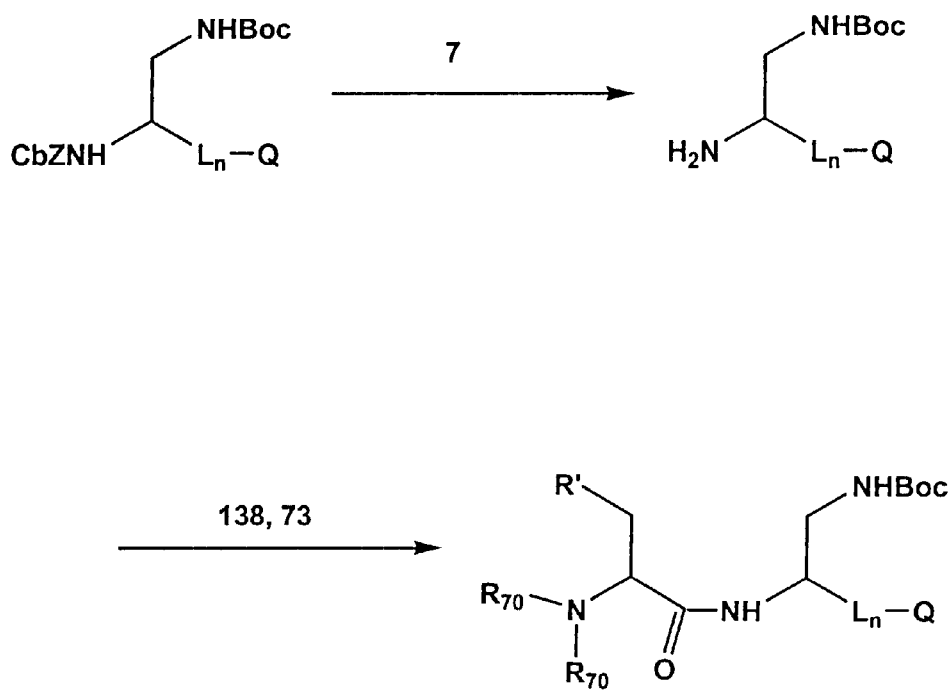
FIG. 41 shows the coupling of a cysteine residue to an amine.
Figure 42:
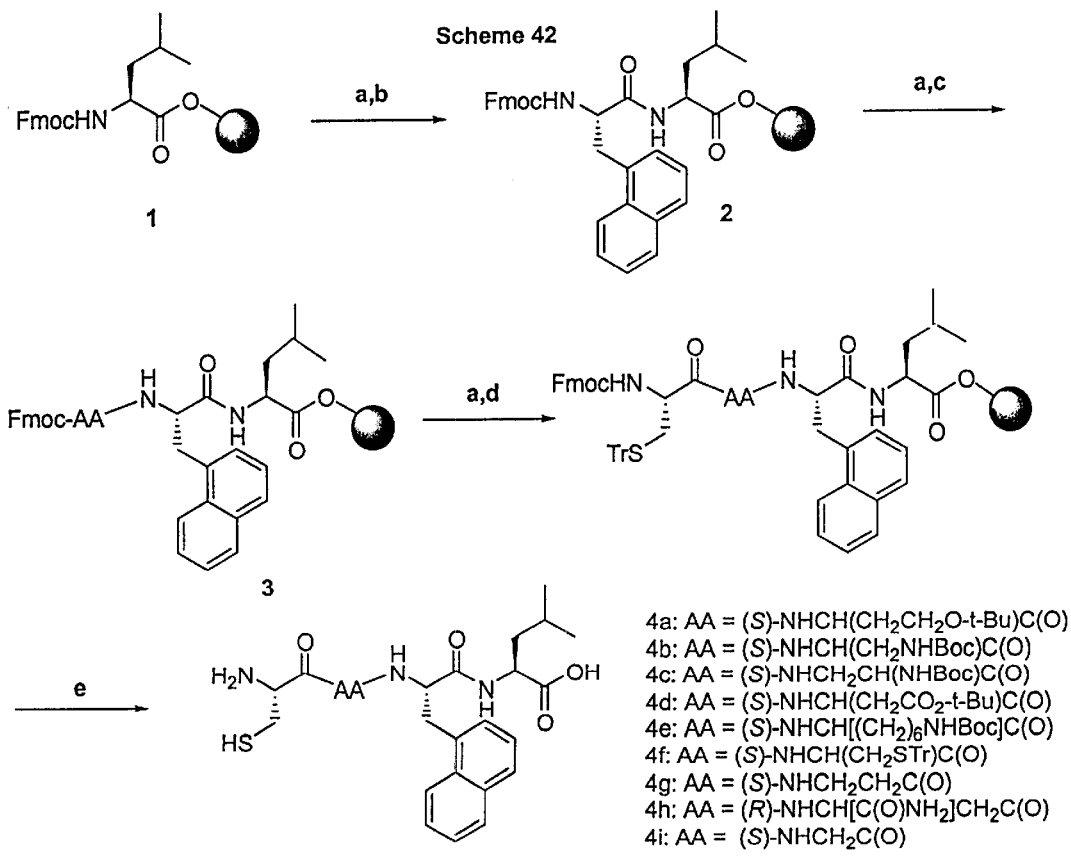
FIG. 42 is a scheme for the synthesis of naphthyl-containing inhibitors of the present invention, wherein the following conditions are used: (a) piperidine, DMF; (b) EDC, HOBt, DIEA, DMF, Fmoc-1-Nal-OH; (c) EDC, HOBt, DIEA, DMF, Fmoc-AA-OH; (d) EDC, HOBt, DIEA, Fmoc(Tr)Cys-OH; (e) TFA, Et$_3$SiH, CH$_2$Cl$_2$.
Figure 43:
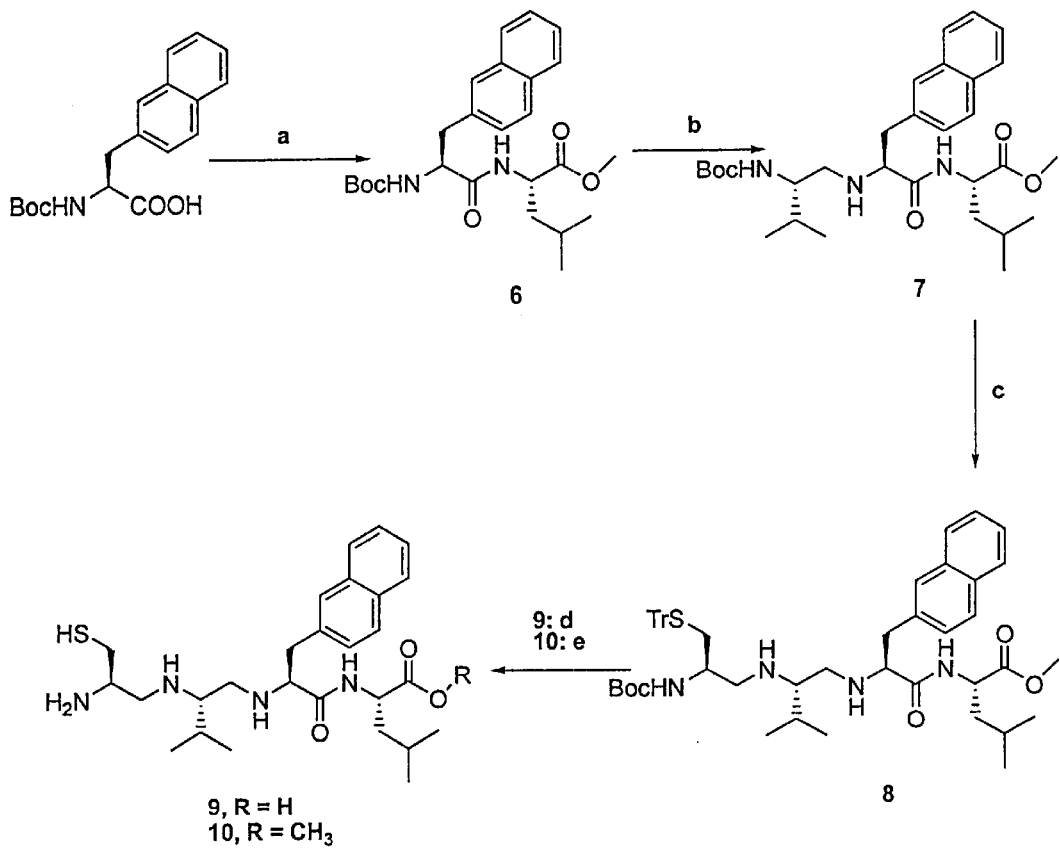
FIG. 43 is a scheme for the synthesis of naphthyl-containing inhibitors of the present invention, wherein the following conditions are used: (a) Leu Me ester, EDC, HOBt, Et$_3$N, CH$_2$Cl$_2$, (b) i) TFA/CH$_2$Cl$_2$, ii) Boc-Valinal, KOAc, NaBH$_3$CN, MeOH, (c) i) TFA/CH$_2$Cl$_2$, ii) S-Tr-N-Boc-cysteinal, KOAc, NaBH$_3$CN, MeOH, (d) i) LiOH, THF/MeOH, ii) TFA, Et$_3$SiH, CH$_2$Cl$_2$.
Figure 44:
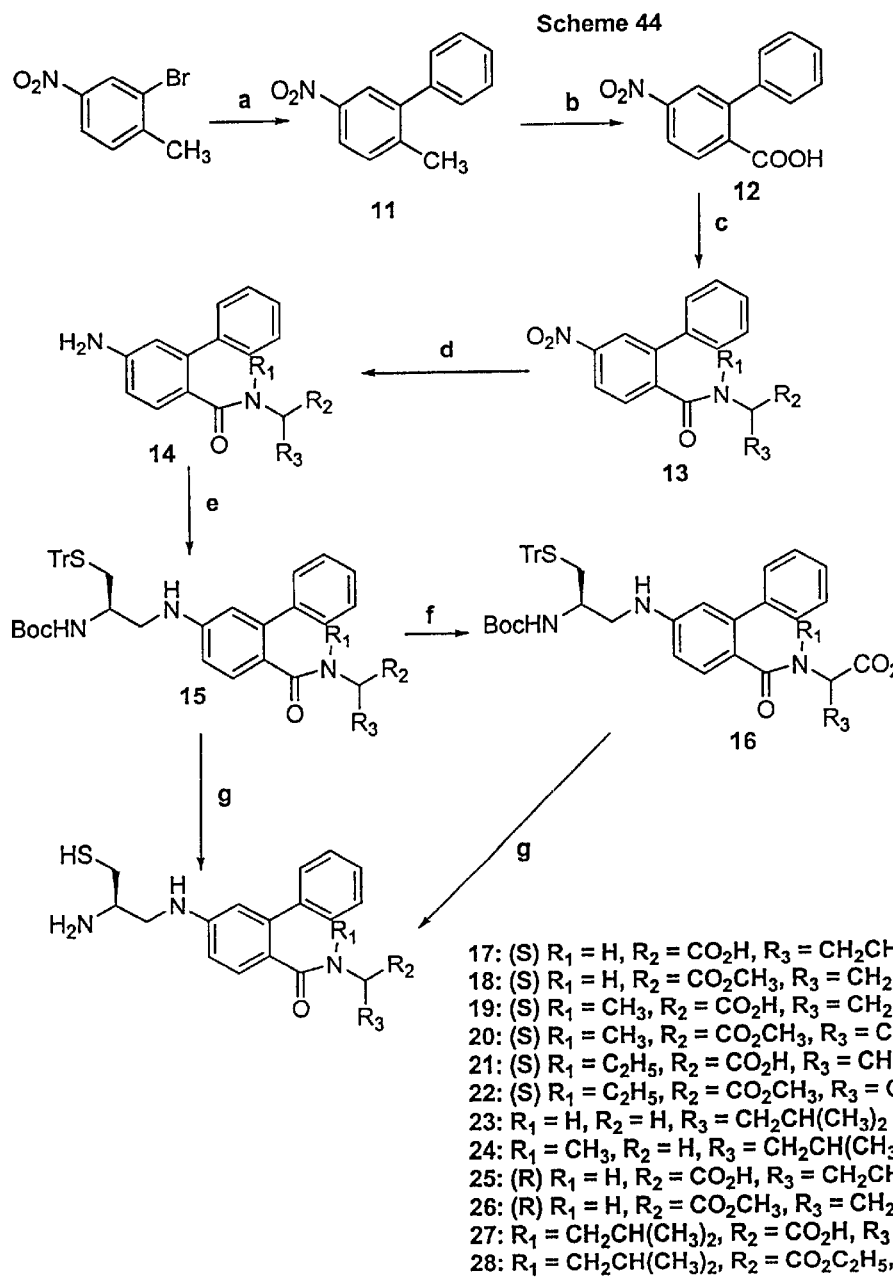
FIG. 44 is a scheme for the synthesis of biaryl-containing inhibitors of the present invention, wherein the following conditions are used: (a) PhB(OH)$_2$, Pd(PPh$_3$)$_4$, Na$_2$CO$_3$, DME, (b) KMnO$_4$, PY/H$_2$O, (c) (R$_1$R$_2$CH)R$_3$NH, EDC, HOBt, Et$_3$N, CH$_2$Cl$_2$, (d) SnCl$_2$, DMF, (e) S-Tr-N-Boc-cysteinal, NaBH$_3$CN, 10% AcOH/MeOH, (f) LiOH, THF/MeOH, (g) TFA, Et$_3$SiH, CH$_2$Cl$_2$.
Figure 45:
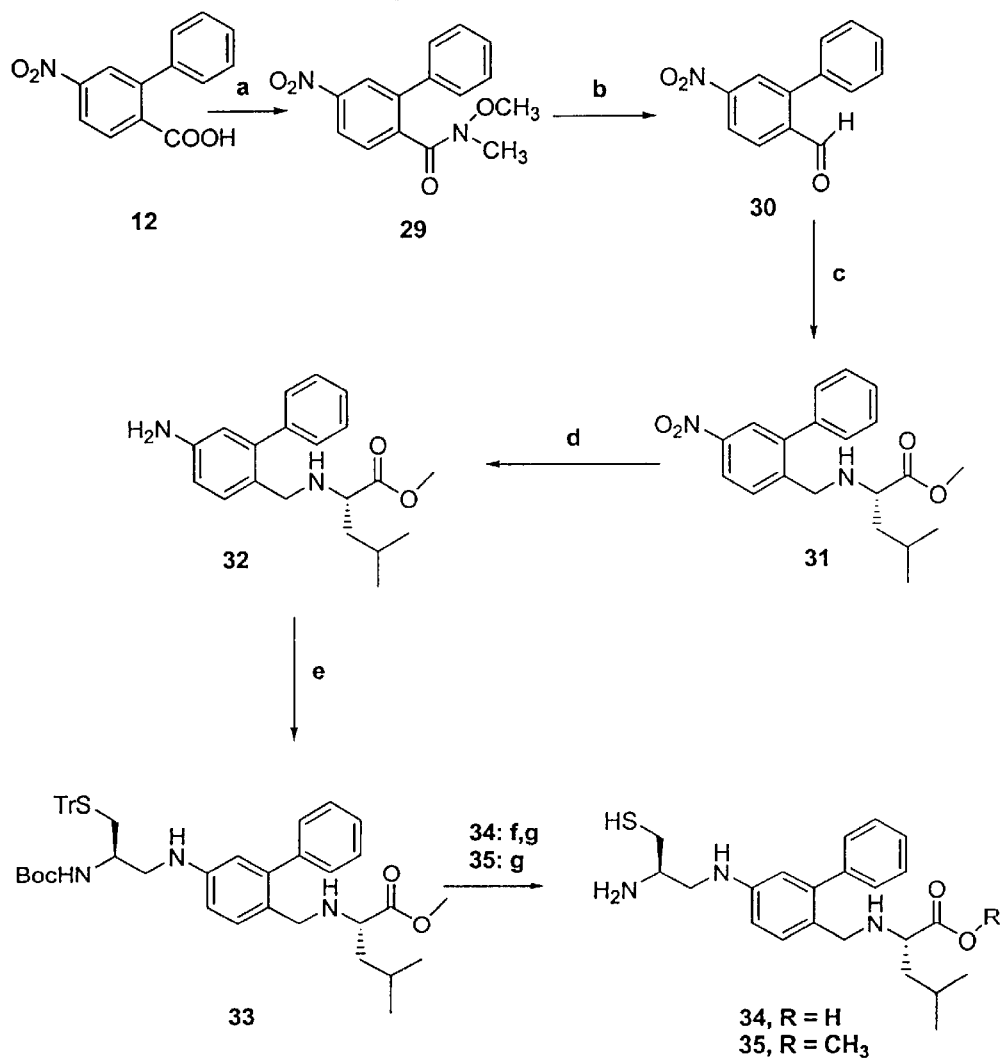
FIG. 45 is a scheme for the synthesis of biaryl-containing inhibitors of the present invention, wherein the following conditions are used: (a) CH$_3$(OCH$_3$)NH, EDC, HOBt, Et$_3$N, CH$_2$Cl$_2$, (b) LAH, Et$_2$O, (c) Leu Me ester, NaBH$_3$CN, 10% AcOH/MeOH, (d) SnCl$_2$, DMF, (e) S-Tr-N-Boc-cysteinal, NaBH$_3$CN, 10% AcOH/MeOH, (f) LiOH, THF/MeOH, (g) TFA, Et$_3$SiH, CH$_2$Cl$_2$.
Figure 46:
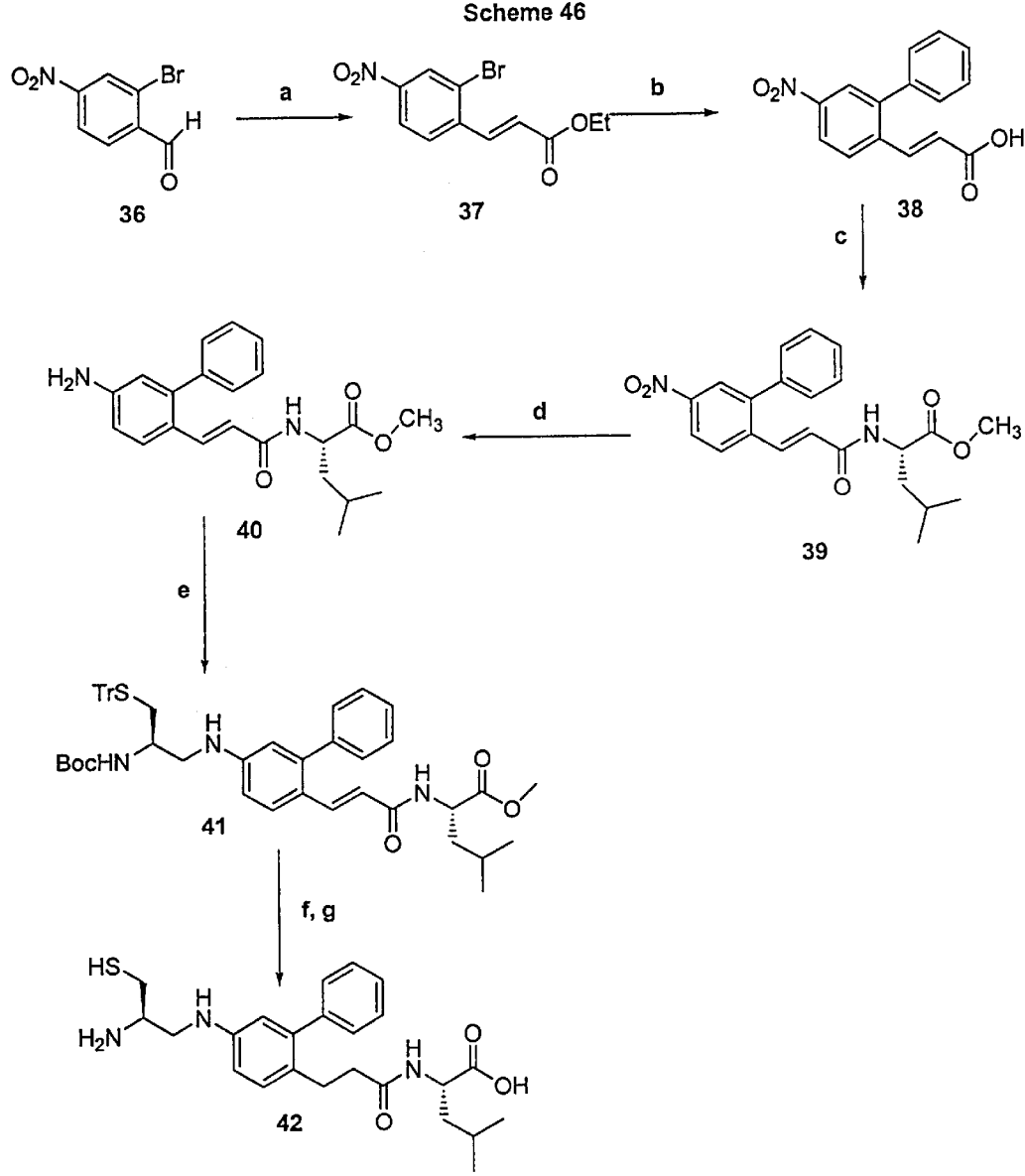
FIG. 46 is a scheme for the synthesis of biaryl-containing inhibitors of the present invention, wherein the following conditions are used: (EtO)$_2$P(O)CH$_2$CO$_2$Et, n-BuLi, THF, (b) i) PhB(OH)$_2$, Pd(PPh$_3$)$_4$, Na$_2$CO$_3$, DME, ii) LiOH, THF/MeOH, (c) Leu Me ester, EDC, HOBt, DIEA, CH$_2$Cl$_2$, (d) SnCl$_2$, DMF, (e) S-Tr-N-Boc-cysteinal, NaBH$_3$CN, 10% AcOH/MeOH, (f) LiOH, THF/MeOH, (g) TFA, Et$_3$SiH, CH$_2$Cl$_2$.
Figure 47:
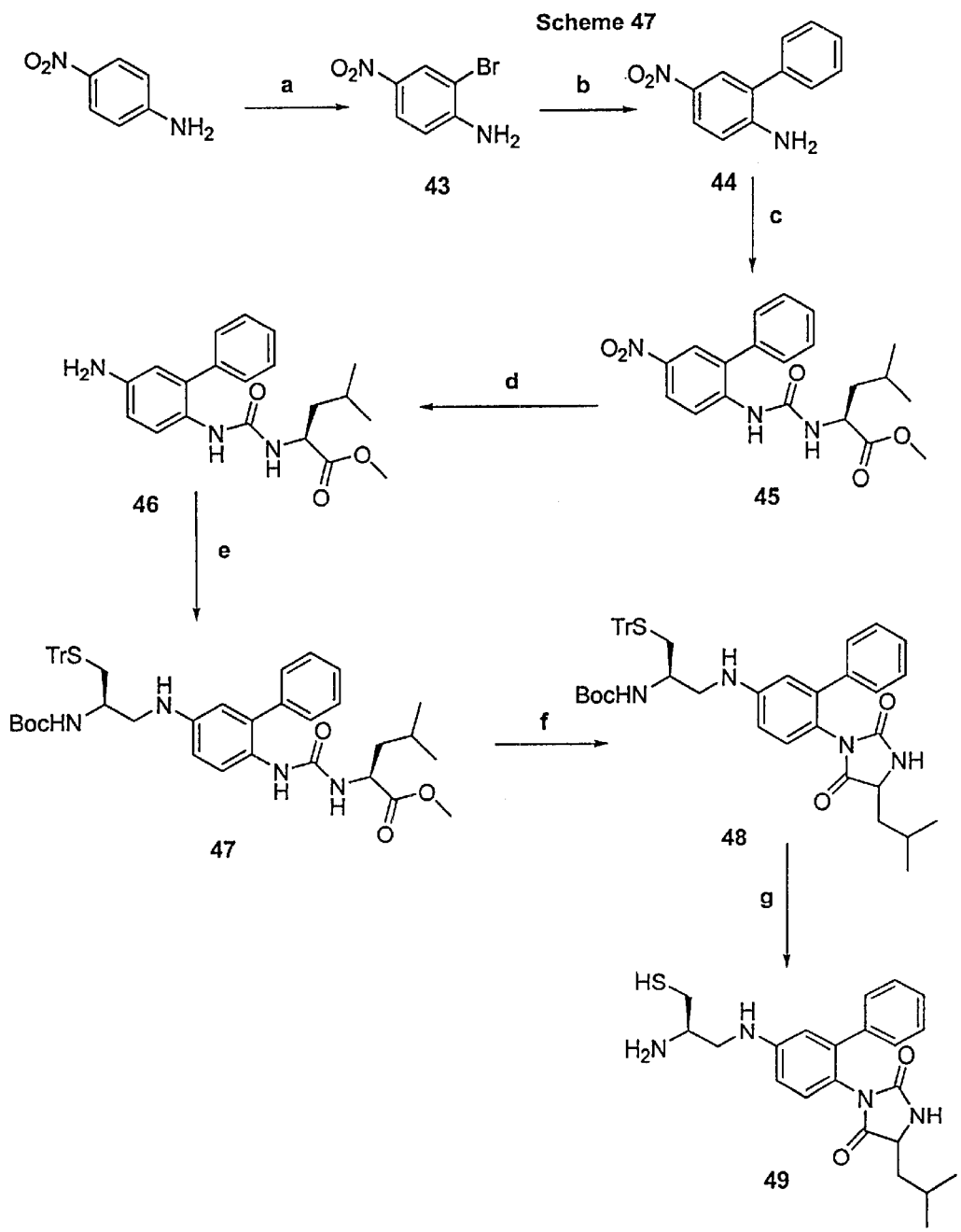
FIG. 47 is a scheme for the synthesis of biaryl-containing imidazolidinediones of the present invention, wherein the following conditions are used: (a) pyBr$_3$, THF, 10% HCl, (b) PhB(OH)$_2$, Pd(PPh$_3$)$_4$, Na$_2$CO$_3$, DME, (c) Leu isocyanate, pyridine, (d) SnCl$_2$, DMF, (e) S-Tr-N-Boc-cysteinal, NaBH$_3$CN, 10% AcOH/MeOH, (f) LiOH, THF, (g) TFA, Et$_3$SiH, CH$_2$Cl$_2$.
Figure 49:
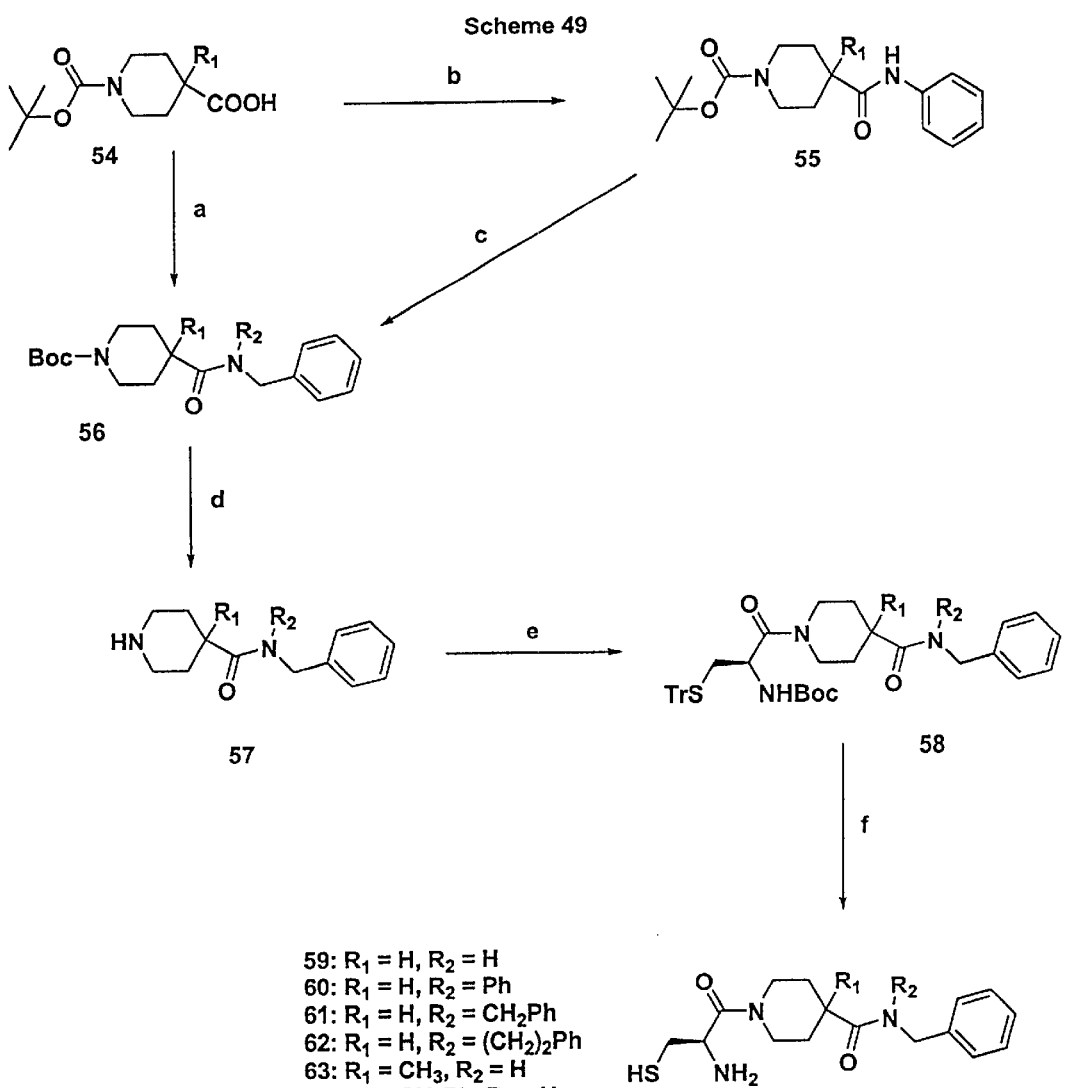
FIG. 49 is a scheme for the synthesis of phenylpiperidide compounds of the present invention, wherein the following conditions are used: (a) R$_2$(Bn)NH, HBTU, HOBt, DIEA, CH$_2$Cl$_2$, (b) aniline, EDC, HOBt, DIEA, CH$_2$Cl$_2$, (c) KHMDS, THF, BnBr, (d) TFA, CH$_2$Cl$_2$, (e) S-Tr-Boc-cysteine, HBTU, HOBt, DIEA, CH$_2$Cl$_2$, (f) TFA, Et$_3$SiH, CH$_2$Cl$_2$.
Figure 50:
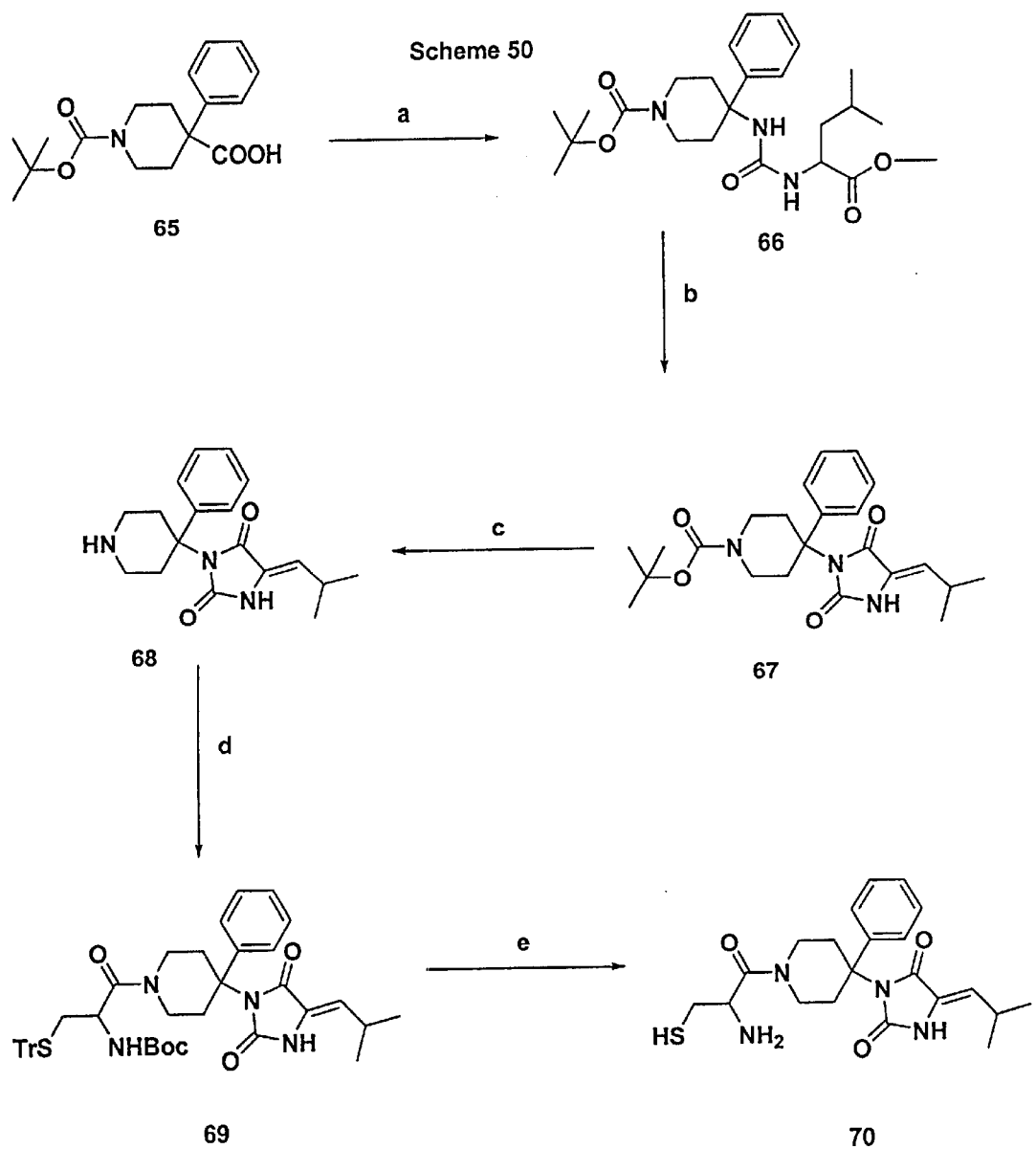
FIG. 50 is a scheme for the synthesis of phenylpiperidide compounds of the present invention, wherein the following conditions are used: (a) DPPA, Et$_3$N, Leu Me ester, toluene, 80° C., (b) KHMDS, THF, (c) TFA, CH$_2$Cl$_2$, (d) S-Tr-Boc-cysteine, HBTU, HOBt, DIEA, CH$_2$Cl$_2$, (e) TFA, Et$_3$SiH, CH$_2$Cl$_2$.
Figure 51:
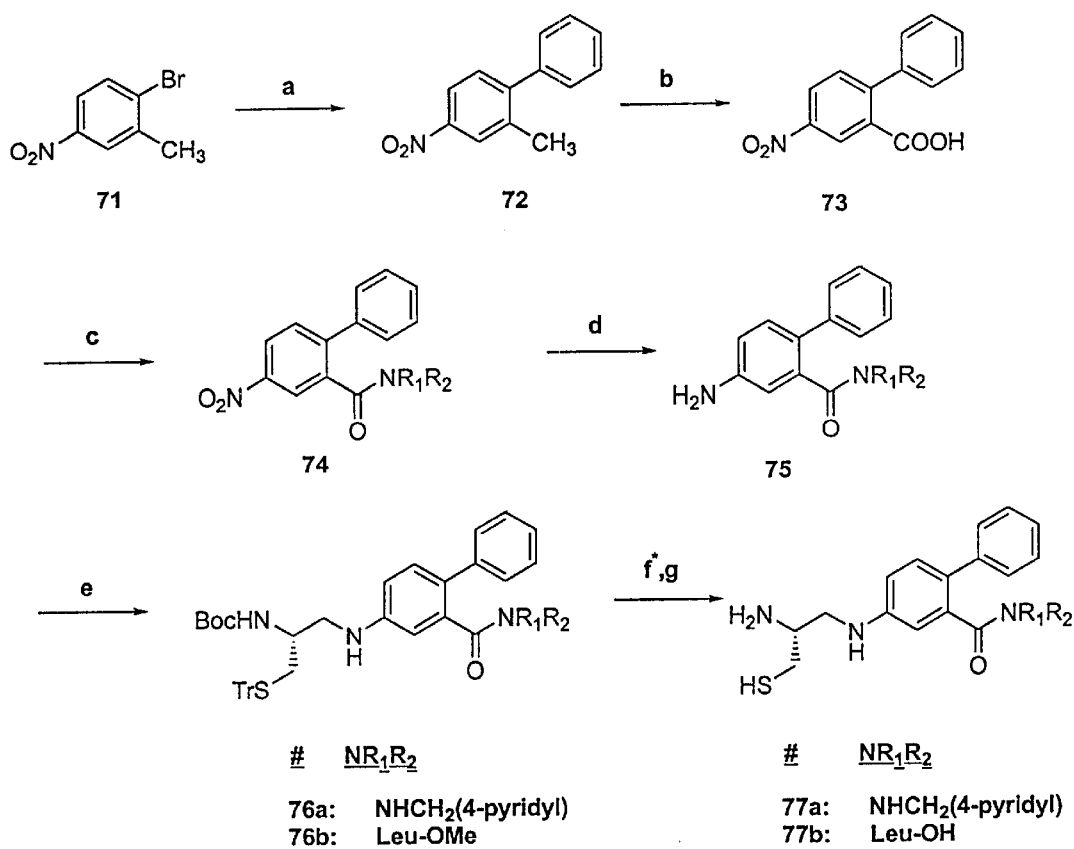
FIG. 51 is a scheme for the synthesis of biphenyl-containing compounds of the present invention, wherein the following conditions are used: (a) PhB(OH)$_2$, Pd(PPh$_3$)$_4$, Na$_2$CO$_3$, dioxane, (b) KMnO$_4$, py/H$_2$O, (c) HNR$_1$R$_2$, EDC, HOBt, Et$_3$N, CH$_2$Cl$_2$, (d) H$_2$, 10% Pd/C MeOH, (e) S-Tr-N-Boc-cysteinal, NaBH$_3$CN, 10% AcOH/MeOH, (f) LiOH, THF/MeOH, (* only for 77b), (g) TFA, Et$_3$SiH, CH$_2$Cl$_2$.
Figure 52:
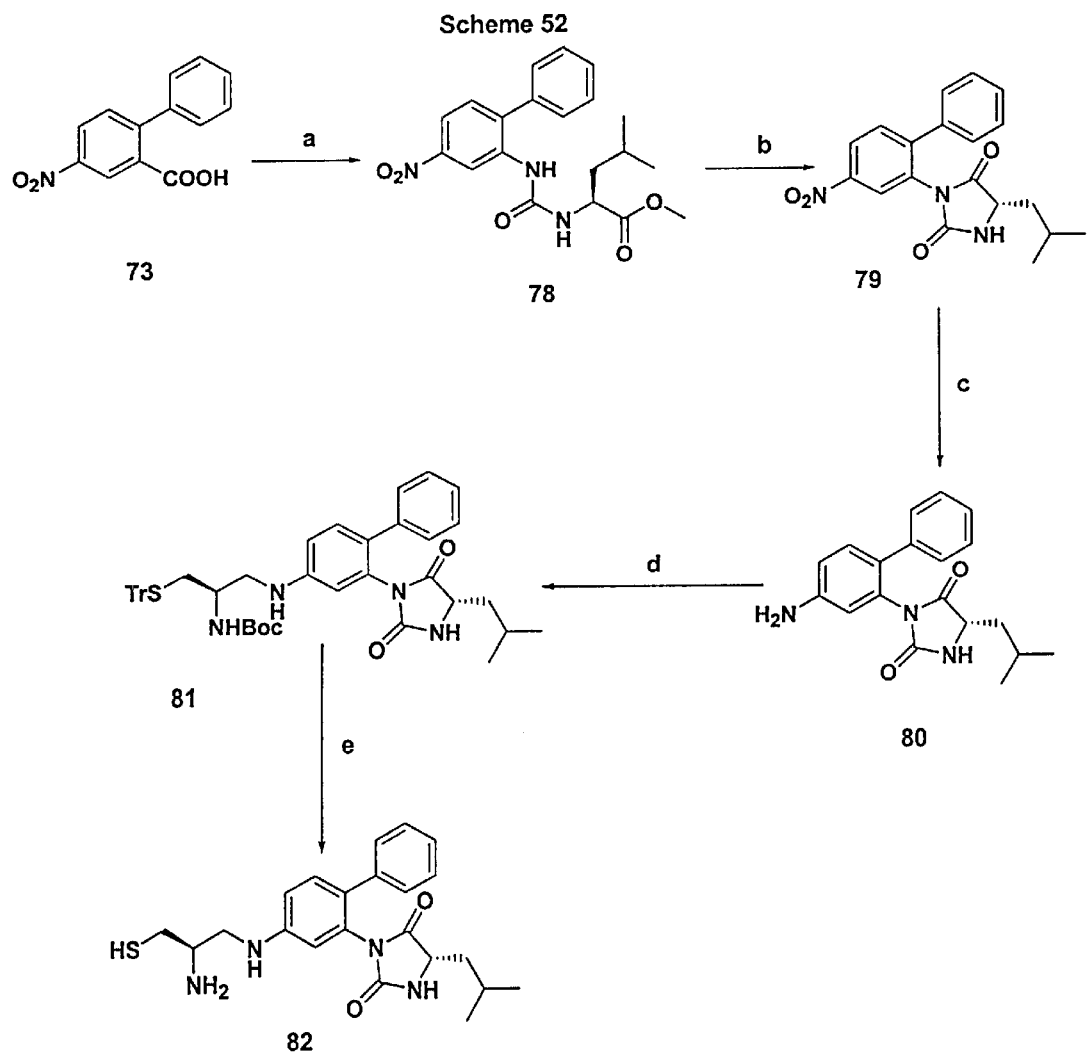
FIG. 52 is a scheme for the synthesis of biphenyl-containing compounds of the present invention, wherein the following conditions are used: (a) DPPA, Et$_3$N, Leu Me ester, toluene, 80° C., (b) DBU, CH$_2$Cl$_2$, (c) SnCl$_2$, DMF, (d) S-Tr-N-Boc-cysteinal, NaBH$_3$CN, AcOH-MeOH, (e) TFA, Et$_3$SiH, CH$_2$Cl$_2$.
Figure 53:
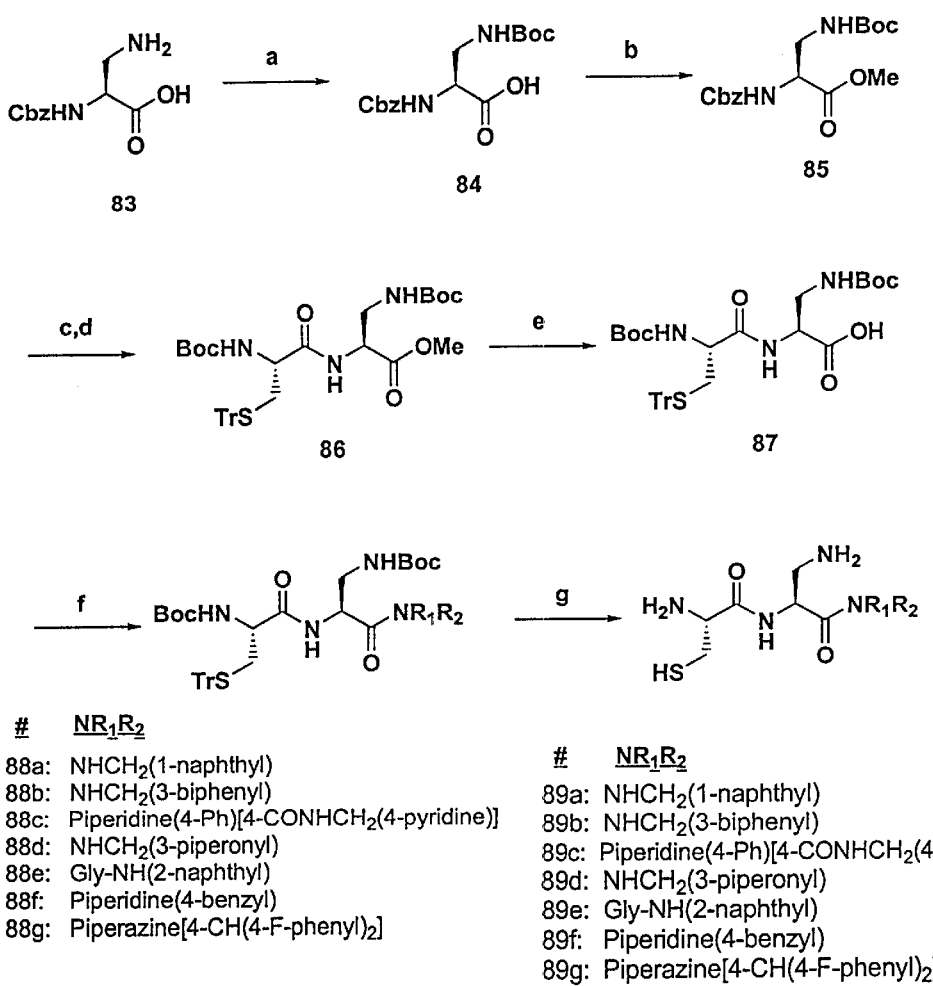
FIG. 53 is a scheme for the synthesis of peptidyl compounds of the present invention, wherein the following conditions are used: (a) (Boc)$_2$O, 2 M NaOH/H$_2$O, THF, (b) CsCO$_3$MeI, CH$_2$Cl$_2$, (c) H$_2$, 10% Pd/C, MeOH, (d) Boc(Tr)Cys-OH, EDC, HOBt, DIEA, CH$_2$Cl$_2$, (e) LiOH, H$_2$O, MeOH, THF, (f) HNR$_1$R$_2$, EDC or HBTU, HOBt, Et$_3$N, CH$_2$Cl$_2$, (R$_{304}$=H), (g) TFA, Et$_3$SiH, CH$_2$Cl$_2$.
Figure 54:
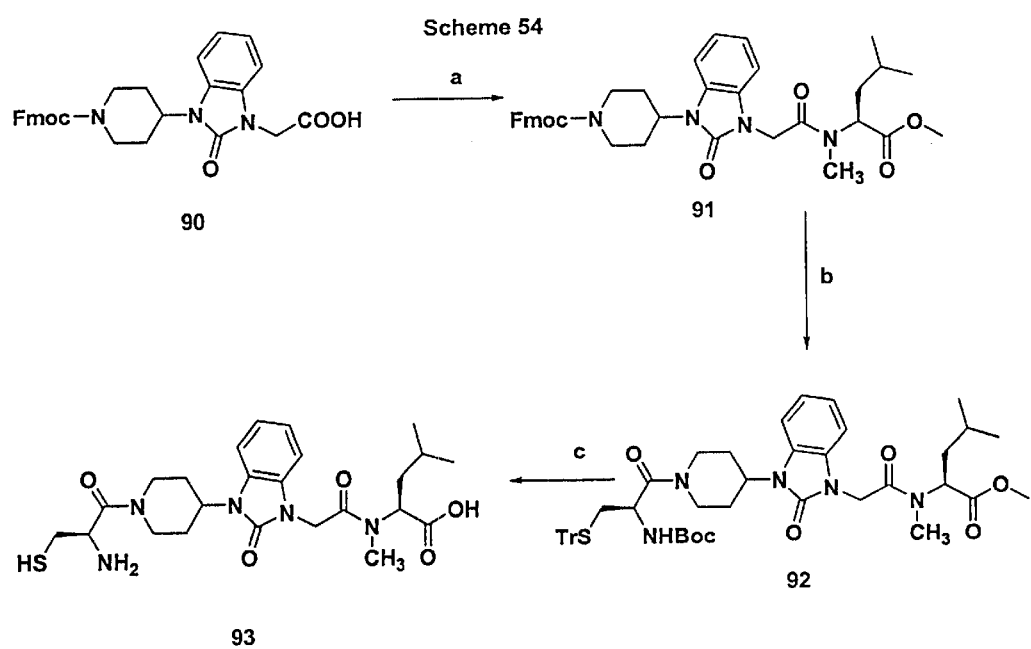
FIG. 54 is a scheme for the synthesis of benzimidazolone compounds of the present invention, wherein the following conditions are used: (a) N-Me leu Me ester, HBTU, HOBt, DIEA, $CH_2Cl_2$, (b) i) diethylamine/$CH_2Cl_2$, ii) S-Tr-Boc-cysteine, HBTU, HOBt, DIEA, $CH_2Cl_2$, (c) i) LiOH, THF/MeOH, ii) TFA, $Et_3SiH$, $CH_2Cl_2$.
Figure 55:
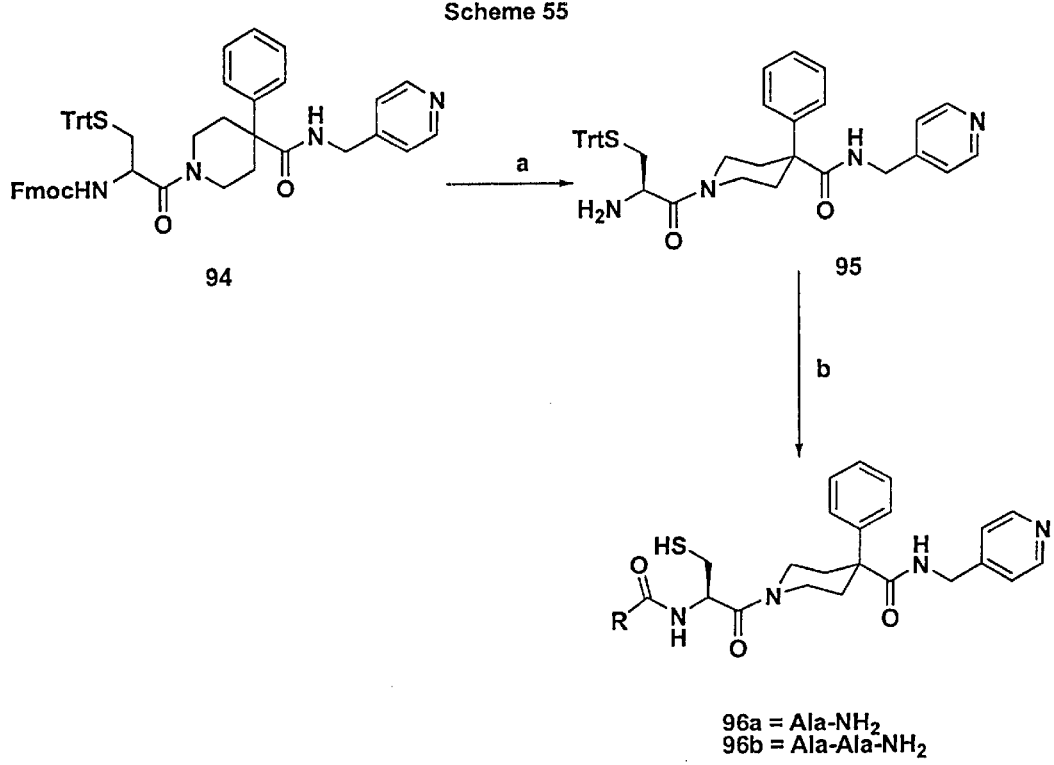
FIG. 55 is a scheme for the synthesis of phenylpiperidine compounds of the present invention, wherein the following conditions are used: (a) $CH_2Cl_2$, diethylamine, rt, 15 hrs, (b) i) Boc-Ala-OH or Boc-Ala-Ala-OH, DIEA, HOBt, EDC, $CH_2Cl_2$, rt, 15 hrs., ii) $CH_2Cl_2$, TFA, $Et_3SiH$, rt, 2 hrs.

In general, the mere knowledge that a particular protein/enzyme is critical to cell growth is not sufficient to render that protein a suitable target for generation of anti-fungal agents. Rather, a salient feature of effective anti-fungal agents is that the agent is cytotoxic to a fungal cell rather than only cytostatic.

The present invention relates to methods for preventing fungal infections using compounds that specifically inhibit the biological activity of fungal enzymes involved in cell wall integrity, hyphael formation, and other cellular functions critical to pathogenesis. In particular, it has been observed by us that prenylation of Rho1-like phosphatases by a geranylgeranylproteintransferase (GGPTase) activity can be critical to maintenance of cell wall integrity in yeast. As described in U.S. Ser. No. 08/631,319, prenylation of, inter alia, Rho1-like GTPase(s) is required for sufficient glucan synthase activity. It was demonstrated that the prenylation of Rho1 by GGPTase I is not only critical to cell growth, but inhibition of the prenylation reaction is a potential target for developing a cytotoxic agent for killing various fungi. Moreover, the relatively high divergence between fungal and human GGPTase subunits suggests that selectivity for the fungal GGPTase activity can be obtained to provide antifungal agents having desirable therapeutic indices.

The present invention demonstrates, for the first time, that small molecules which inhibit fungal geranylgeranylprotein-transferase bioactivity can cause cell death, rather than quiescence or sporulation, when contacted with various microbial organisms. For example, as illustrated in the appended examples, the use of GGPTase inhibitors as described herein can result in cell lysis and thereby should ensure destruction of the pathogen.

The use of, and need for anti-fungal agents is widespread and ranges from the treatment of mycotic infections in animals; to additives in feed for livestock to promote weight gain; to disinfectant formulations. Thus, as described in greater detail below, the present invention provides methods and compositions for inhibiting fungal growth using small molecule (e.g., less than about 1000 amu) inhibitors of fungal GGPTase. The GGPTase inhibitors can be, among others: peptidomimetics, such as those described below which mimic the geranylgeranyl substrate sequence of, for example, a Rho1-like phosphatase; acyclic terpenes such as a geranylgeranyl analog; or other small organic molecules which inhibit a target fungal GGPTase activity. In the practice of the instant method, the preferred inhibitors, whether peptoid or non-peptidyl, inhibit a targeted fungal GGPTase with a $K_i$ of 10 $\mu$M or less, more preferably 1 $\mu$M or less, and even more preferably with a $K_i$ less than 100 nM, 10 nM or even 1 nM. In treatment of humans or other animals, the subject method preferably employs GGPTase inhibitors which are selective for the fungal enzyme relative to the host animals' GGPTase enzyme(s), e.g., the $K_i$ for inhibition of the fungal enzyme is at least one order of magnitude less than the $K_i$ for inhibition of GGPTase from the human (or other animal), and even more preferably at least two, three or even four orders of magnitude less. That is, in preferred embodiments, the practice of the subject method in vivo in animals utilizes GGPTase inhibitors with therapeutic indexes of at least 10, and more preferably at least 100 or 1000.

The antifungal properties of the compounds of the present invention may be determined from a fungal lysis assay, as well as by other methods, including, inter alia, growth inhibition assays, fluorescence-based fungal viability assays, flow cytometry analyses, and other standard assays known to those skilled in the art.

The assays for growth inhibition of a microbial target can be used to derive an $ED_{50}$ value for the compound, that is, the concentration of compound required to kill 50% of the fungal sample being tested. Preferred antifungal agent pharmaceutical preparation, whether for topical, injection or oral delivery (or other route of administration), would provide a dose less than the $ED_{50}$ for modulation of FPTase and/or GGPTase activity in the host (mammal), more preferably at least 1 order of magnitude less, more preferably at least 2, 3 or 4 orders of magnitude less.

Alternatively, growth inhibition by an antifungal compound of the invention may also be characterized in terms of the minimum inhibitory concentration (MIC), which is the concentration of compound required to achieve inhibition of fungal cell growth. Such values are well known to those in the art as representative of the effectiveness of a particular antifungal agent against a particular organism or group of organisms. For instance, cytolysis of a fungal population by an antifungal compound can also be characterized, as described above by the minimum inhibitory concentration, which is the concentration required to reduce the viable fungal population by 99.9%. The value of $MIC_{50}$ can also be used, defined as the concentration of a compound required to reduce the viable fungal population by 50%. In preferred embodiments, the compounds of the present invention are selected for use based, inter alia, on having MIC values of less than 25 $\mu$g/mL, more preferably less than 7 $\mu$g/mL, and even more preferably less than 1 $\mu$g/mL against a desired fungal target, e.g., *Candida albicans*.

Another parameter useful in identifying and measuring the effectiveness of the antifungal compounds of the invention is the determination of the kinetics of the antifungal activity of a compound. Such a determination can be made by determining antifungal activity as a function of time. In a preferred embodiment, the compounds display kinetics which result in efficient lysis of a fungal cell. In a preferred embodiment, the compounds are fungicidal.

Furthermore, the preferred antifungal compounds of the invention display selective toxicity to target microorganisms and minimal toxicity to mammalian cells. Determination of the toxic dose (or "$LD_{50}$") can be carried out using protocols well known in the field of pharmacology. Ascertaining the effect of a compound of the invention on mammalian cells is preferably performed using tissue culture assays, e.g., the present compounds can be evaluated according to standard methods known to those skilled in that art (see for example Gootz, T. D. (1990) *Clin. Microbiol. Rev.* 3:13–31). For mammalian cells, such assay methods include, inter alia, trypan blue exclusion and MTT assays (Moore et al. (1994) *Compound Research* 7:265–269). Where a specific cell type may release a specific metabolite upon changes in membrane permeability, that specific metabolite may be assayed, e.g., the release of hemoglobin upon the lysis of red blood cells (Srinivas et al. (1992) *J. Biol. Chem.* 267:7121–7127). The compounds of the invention are preferably tested against primary cells, e.g., using human skin fibroblasts (HSF) or fetal equine kidney (FEK) cell cultures, or other primary cell cultures routinely used by those skilled in the art. Permanent cell lines may also be used, e.g., Jurkat cells. In preferred embodiments, the subject compounds are selected for use in animals, or animal cell/tissue culture based at least in part on having $LD_{50}$'s at least one order of magnitude greater than the MIC or $ED_{50}$ as the case may be, and even more preferably at least two, three and even four orders of magnitude greater. That is, in preferred embodiments where the subject compounds are to be administered to an animal, a suitable therapeutic index is preferably greater than 10, and more preferably greater than 100, 1000 or even 10,000.

The invention is also directed to methods for treating a microbial infection in a host using the compositions of the invention. The compounds provided in the subject methods exhibit broad antifungal activity against various fungi and can be used as agents for treatment and prophylaxis of fungal infectious diseases. For instance, the subject method can be used to treat or prevent nosocomial fungal and skin/wound infection involving fungal organisms, including, among others, the species Aspergillus, Blastomyces, Candida, Coccidioides, Cryptococcus, Epidermophyton, Hendersonula, Histoplasma, Microsporum, Paecilomyces, Paracoccidioides, Pneumocystis, Trichophyton, and Trichosporium. According to the present invention, treatment of such fungal infections comprises the administration of a pharmaceutical composition of the invention in a therapeutically effective amount to an individual in need of such treatment. The compositions may be administered parenterally by intramuscular, intravenous, intraocular, intraperitoneal, or subcutaneous routes; inhalation; orally, topically and intranasally.

The subject antifungal methods of the invention are also particularly useful in inhibiting unwanted fungal growth in tissue culture, especially those used for production of recombinant proteins or vectors for use in gene therapy.

The invention is also directed to pharmaceutical compositions containing one or more of the antimicrobial compounds of the invention as the active ingredient which may be administered to a host animal.

I. Definitions

Before further description of the preferred embodiments of the subject invention, certain terms employed in the specification, examples, and appended claims are collected here for convenience.

The terms "fungi" and "yeast" are used interchangeably herein and refer to the art recognized group of eukaryotic protists known as fungi. That is, unless clear from the context, "yeast" as used herein can encompass the two basic morphologic forms of yeast and mold and dimorphisms thereof.

As used herein, the term "antimicrobial" refers to the ability of the inhibitors of the invention to prevent, inhibit or destroy the growth of microbes such as bacteria, fungi, protozoa and viruses.

The term "prodrug" is intended to encompass compounds which, under physiological conditions, are converted into the antifungal agents of the present invention. A common method for making a prodrug is to select moieties which are hydrolyzed under physiological conditions to provide the desired biologically active drug. In other embodiments, the prodrug is converted by an enzymatic activity of the host animal or the target fungii.

The term "heteroatom" as used herein means an atom of any element other than carbon or hydrogen. Preferred heteroatoms are boron, nitrogen, oxygen, phosphorus, sulfur and selenium.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, alkylaminos, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" refers to both substituted and unsubstituted aromatic rings. The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocycle" refer to 4- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The phrase "fused ring" is art recognized and refers to a cyclic moiety which can comprise from 4 to 8 atoms in its ring structure, and can also be substituted or unsubstituted, (e.g., cycloalkyl, a cycloalkenyl, an aryl, or a heterocyclic ring) that shares a pair of carbon atoms with another ring. For example, in the structure described below

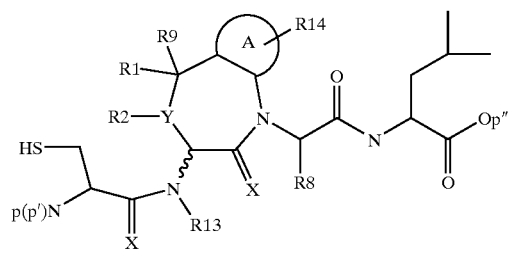

both A and the azepine together form a fused ring system. To illustrate, the fused ring system can be a benzodiazepine, a benzoazepine, a pyrrolodiazepine, a pyrroloazepine, a furanodiazepine, a furanoazepine, a thiophenodiazepine, a thiophenoazepine, an imidazolodiazepine, an imidazoloazepine, an oxazolodiazepine, an oxazoloazepine, a thiazolodiazepine, a thiazoloazepine, a pyrazolodiazepine, a pyrazoloazepine, a pyrazinodiazepine, a pyrazinoazepine, a pyridinodiazepine, a pyridinoazepine, a pyrimidinodiazepine, and a pyrimidinoazepine.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

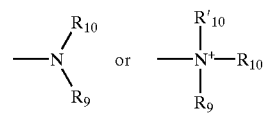

wherein $R_9$, $R_{10}$ and $R'_{10}$ each independently represent a hydrogen, an alkyl, an alkenyl, —$(CH_2)_m$—$R_{80}$, or $R_9$ and $R_{10}$ taken together with the N atom to which they are attached complete a heterocycle having from 4 to 8 atoms in the ring structure; $R_{80}$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_{80}$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

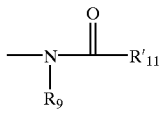

wherein $R_9$ is as defined above, and $R'_{11}$ represents a hydrogen, an alkyl, an alkenyl or —$(CH_2)_m$—$R_{80}$, where m and $R_{80}$ are as defined above.

The term "amido" is art recognized as an amino-substituted carbonyl and includes a moiety that can be represented by the general formula:

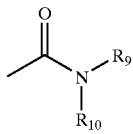

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_{80}$, wherein m and $R_{80}$ are defined above. Representative alkylthio groups include methylthio, ethylthio, and the like.

The term "carbonyl" is art recognized and includes such moieties as can be represented by the general formula:

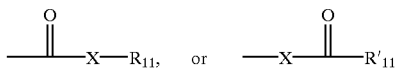

wherein X is a bond or represents an oxygen or a sulfur, and $R_{11}$ represents a hydrogen, an alkyl, an alkenyl, $(CH_2)_m$—$R_{80}$ or a pharmaceutically acceptable salt, $R'_{11}$ represents a hydrogen, an alkyl, an alkenyl or —$(CH_2)_m$—$R_{80}$, where m and $R_{80}$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_{80}$, where m and $R_{80}$ are described above.

The terms "sulfoxido", as used herein, refers to a moiety that can be represented by the general formula:

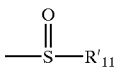

in which $R'_{11}$ is as defined above, but is not hydrogen.

A "sulfone", as used herein, refers to a moiety that can be represented by the general formula:

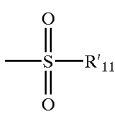

in which $R'_{11}$ is as defined above, but is not hydrogen.

The term "sulfonamido" is art recognized and includes a moiety that can be represented by the general formula:

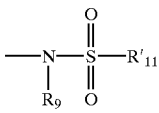

in which $R_9$ and $R'_{11}$ are as defined above.

The term "sulfamoyl" is art-recognized and includes a moiety that can be represented by the general formula:

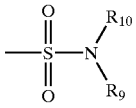

in which $R_9$ and $R_{10}$ are as defined above.

A "phosphoryl" can in general be represented by the formula:

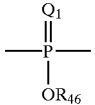

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

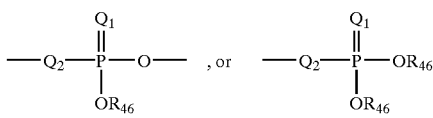

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidate" can be represented in the general formula:

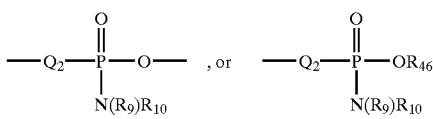

wherein $R_9$ and $R_{10}$ are as defined above, and $Q_2$ represents O, S or N.

A "phosphonamidate" can be represented in the general formula:

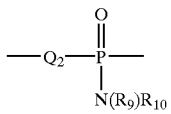

wherein $R_9$ and $R_{10}$ are as defined above, and $Q_2$ represents O, S.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivitization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to inhibit fungal cell growth), wherein one or more simple variations of substituents are made which do not adversely affect the efficacy of the compound in inhibiting fungal cell growth. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

By the terms "amino acid residue" and "peptide residue" is meant an amino acid or peptide molecule without the —OH of its carboxyl group (C-terminally linked) or the proton of its amino group (N-terminally linked). In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH(CH$_3$)—CH$_2$CH$_3$ (the side chain of isoleucine), —CH$_2$CH(CH$_3$)$_2$ (the side chain of leucine) or H-(the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

However, the term amino acid residue further includes analogs, derivatives and congeners of any specific amino acid referred to herein. For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject peptidomimetic can include an amino acid analog as for example, β-cyanoalanine, canavanine, djenkolic acid, norleucine, 3-phosphoserine, homoserine, dihydroxyphenylalanine, 5-hydroxytryptophan, 1-methylhistidine, or 3-methylhistidine. Other naturally occurring amino acid metabolites or precursors having side chains which are suitable herein will be recognized by those skilled in the art and are included in the scope of the present invention.

Also included are the D and L stereoisomers of such amino acids when the structure of the amino acid admits of stereoisomeric forms. The configuration of the amino acids and amino acid residues herein are designated by the appropriate symbols D, L or DL, furthermore when the configuration is not designated the amino acid or residue can have the configuration D, L or DL.

It will be noted that the structure of some of the compounds of this invention includes asymmetric carbon atoms. It is to be understood accordingly that the isomers arising from such asymmetry are included within the scope of this invention. Such isomers are obtained in substantially pure form by classical separation techniques and by sterically controlled synthesis and have arbitrarily been named, for example, as isomers #1 or #2. For the purposes of this application, unless expressly noted to the contrary, a named amino acid shall be construed to include both the D or L stereoisomers, preferably the L stereoisomer.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, carbonylbenzyloxy (Cbz); and aliphatic urethane protecting groups such as t-butyloxycarbonyl (Boc) or 9-Fluorenylmethoxycarbonyl (FMOC). Peptidomimetics of the present invention which have sidechain or azepine ring substituents which include amino groups—such as where R$_3$ is a lysine or arginine, or where R$_8$, R$_1$, R$_2$ or Y comprise a free amino group—can optionally comprise suitable N-terminal protecting groups attached to the sidechains.

The phrase "C-terminal protecting group" or "carboxyl-protecting group" as used herein refers to those groups intended to protect a carboxylic acid group, such as the C-terminus of an amino acid or peptide. Benzyl or other suitable esters or ethers are illustrative of C-terminal protecting groups known in the art.

As used herein, the definition of each expression, e.g. lower alkyl, m, n, p, etc., when it occurs more than once in any structure, is intended to be independent of its definition elsewhere in the same structure.

II. Compounds and Preparations Thereof

The present invention makes available a novel method for inhibiting fungal cell growth by selectively inhibiting the activity of fungal geranylgeranyl transferases.

In certain embodiments, the subject method can be practiced using a peptide or peptide-like inhibitor of the fungal GGPTase activity. For example, a peptidyl inhibitor of a fungal GGPTase may be represented in the general formula I

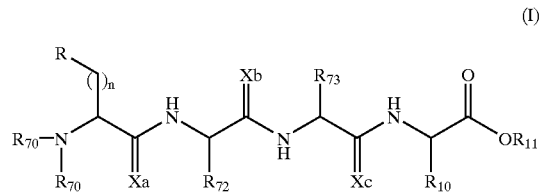

wherein

X$_a$, X$_b$ and X$_c$ each, independently, represent O or H$_2$;

R represents

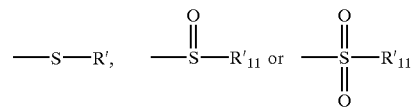

R' represents H, a lower alkyl, a lower alkenyl, an aryl,

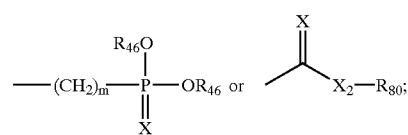

R$_7$ represents an aryl, a cycloalkyl, a cycloalkenyl, or a heterocycle;

R$_{10}$ represents a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and preferably is a sidechain of an alpha-amino acid residue or analog thereof, and even more preferably a straight chain, branched lower alkyl, aryl or arylalkyl;

$R_{11}$ represents H, a carboxy-terminal blocking group, or a pharmaceutically acceptable salt, or $R_{10}$ and $R_{11}$ taken together form a 5–7 membered lactone;

$R'_{11}$ represents an alkyl, an alkenyl or —$(CH_2)_m$—$R_7$;

$R_{46}$, independently for each occurrence, represents hydrogen, a lower alkyl or an aryl $R_{70}$, independently for each occurrence, represents H,

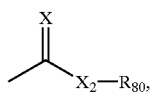

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or $R_{70}$ and R taken together, or $R_{70}$ and $R_{70}$ taken together, form a 4 to 8 membered heterocycle;

$R_{72}$ and $R_{73}$, independently for each occurrence, represents H, lower alkyl, aryl, heteroaryl, —$(CH_2)_m$— $R_7$ or the sidechain of an amino acid (e.g., a naturally occurring or unnatural amino acid);

$R_{80}$ represents an hydrogen, a lower alkyl, a lower alkenyl, a lower alkynyl, or —$(CH_2)_m$—$R_7$;

X represents, independently for each occurrence, O or S;

$X_2$ represents O or S; and m and n, independently for each occurrence, represent zero or an integer in the range of 1 to 4.

In a preferred embodiment, the subject inhibitor is represented in Formula I, wherein $X_a$, $X_b$ and $X_c$ each represent $H_2$ or O, more preferably O; R represents —S—R'; R' represents H or a lower alkyl, and more preferably H; $R_{72}$ represents a lower alkylamine, a lower alkylthiol or a lower alkyl, and more preferably $CH_2NH_2$, $CH_2SH$; $R_{73}$ represents —$(CH_2)_m$—$R_7$; m=1; $R_7$ represents aryl, and more preferably a C6–C12 aryl, and even more preferably 2-naphthyl; $R_{10}$ represents a lower alkyl, more preferably a branched C4–C6 lower alkyl, and even more preferably 2-methylpropyl; $R_{11}$, represents H or lower alkyl (e.g., methyl); $R_{70}$ for each occurrence is H.

In another preferred embodiment, the subject inhibitor is represented in Formula I, wherein $X_a$, $X_b$ and $X_c$ each represent $H_2$ or O, more preferably $X_a$ and $X_b$ are $H_2$ and $X_c$ is O; R represents —S—R'; R' represents H or a lower alkyl, and more preferably H; $R_{72}$ represents a lower alkylamine, a lower alkylthiol or a lower alkyl, and more preferably isopropyl; $R_{73}$ represents —$(CH_2)_m$—$R_7$; m=1; $R_7$ represents aryl, and more preferably a C6–C12 aryl, and even more preferably 2-naphthyl; $R_{10}$ represents a lower alkyl, and even more preferably a branched C4–C6 lower alkyl, and even more preferably 2-methylpropyl; $R_{11}$ represents H or lower alkyl (e.g., methyl); $R_{70}$ for each occurrence is H.

In one aspect of the invention, the subject GGPTase inhibitors are peptidomimetics of the general formula C-A-A-X, wherein each A is, independently, an aliphatic amino acid, e.g., glycine, alanine, valine, leucine, isoleucine or an analog thereof, or A-A can represent a dipeptide equivalent spacer, C represents a cysteine or isosteric/isoelectronic equivalent thereof, and X represents any amino acid, but is preferably a leucine or phenylalanine or isosteric/isoelectronic equivalent thereof. The principal objectives in generating a peptidomimetic for use in the subject method is to increase the bioavailability of the compound and/or decrease the hydrolyzability of the peptidomimetic relative to the equivalent peptide.

To further illustrate, one class of compounds which are contemplated for use in the subject method are peptidomimetic inhibitors generated by replacing the A-A-X of the C-A-A-X tetrapeptide with a non-amino acid component while retaining the desired GGPTase inhibitory activity. Likewise, the cysteine residue can be replaced with an isosteric/isoelectronic equivalent, e.g., such as replacement of the sulfhydryl group with a polar moiety such as a cyano, nitro, thiocarbamate, amino, carbamic, phosphate, thiophosphate, sulfoxide, carboximide, urea, sulfone, phosphorothioate, phosphorodithioate, thiourea, dithiocarbamate, phosphoramidodithioate, methylsulfonyl, phosphonate, sulfamide, phosphoramide, sulfonate, dithiocarbonate, hydroxyl, sulfate, sulfinate, sulfamate, phosphinate, carboxylate, hydroxymate, imidazole or other heterocyclic moieties. The sulfhydryl group can be functionalized, e.g., to form an 9-alkyl cysteine or the corresponding sulfoxide, sulfone, sulfonate or sulfate derivatives thereof (though more preferably a sulfoxide or sulfone).

In an exemplary embodiment, the A-A-Leu tripeptide is replaced with a substituted aryl or heteraryl group which corresponds essentially in size with the tripeptide. For instance, the subject method can be performed using a fungal GGPTase inhibitor that is represented in the general formula (II):

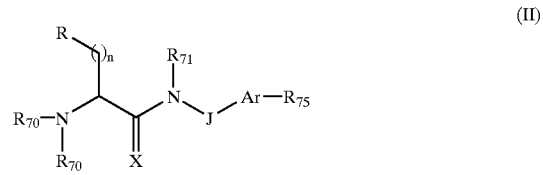

(II)

wherein

Ar represents an aryl group (e.g., substituted or unsubstituted);

J is absent (e.g., N and Ar are joined by a direct bond), or represents —$CH(R_{72})$—;

R represents

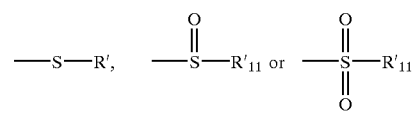

R' represents H, a lower alkyl, a lower alkenyl, an aryl,

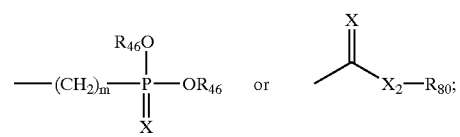

$R_7$ represents an aryl, a cycloalkyl, a cycloalkenyl, or a heterocycle;

$R_{10}$ represents a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and preferably is an alpha-carbon sidechain of an amino acid residue or analog thereof, and even more preferably a straight chain, branched lower alkyl, aryl or arylalkyl;

$R_{11}$ represents H, a carboxy-terminal blocking group, or a pharmaceutically acceptable salt, or $R_{10}$ and $R_{11}$ taken together form a 5–7 membered lactone;

$R'_{11}$ represents an alkyl, an alkenyl or —$(CH_2)_m$—$R_7$;

$R_{46}$, independently for each occurrence, represents hydrogen, a lower alkyl or an aryl;

$R_{70}$, independently for each occurrence, represents H,

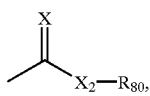

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or $R_{70}$ and R, or $R_{70}$ and $R_{70}$, taken together form a 4 to 8 membered heterocycle;

$R_{71}$ each independently represent H or lower alkyl;

$R_{72}$, independently for each occurrence, represents H, lower alkyl, aryl, heteroaryl or the sidechain of a naturally occurring amino acid;

$R_{75}$ represents

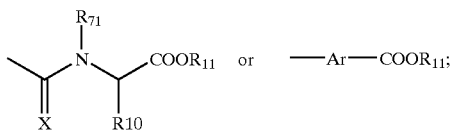

$R_{80}$ represents an hydrogen, a lower alkyl, a lower alkenyl, a lower alkynyl, or —$(CH_2)_m$—$R_7$;

X represents, independently for each occurrence, O, S or $H_2$ $X_2$ represents O or S; and m and n, independently for each occurrence, represent zero or an integer in the range of 1 to 4.

For instance, the peptidomimetic can have a structure represented by formula IIa or IIIb:

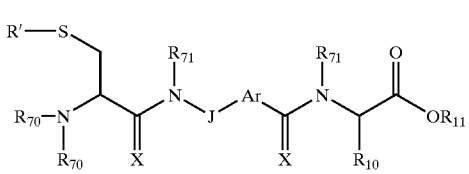

(IIIa)

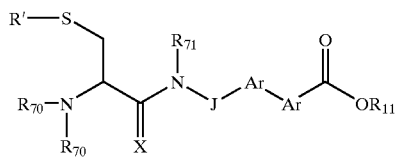

(IIIb)

wherein

Ar, J, R', $R_{70}$, $R_{71}$ and X are as defined above; and $R_{10}$ represents a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, or an alpha-carbon sidechain of an amino acid residue or analog thereof, and is preferably a straight chain, branched lower alkyl, aryl or arylalkyl;

$R_{11}$ represents H, a carboxy-terminal blocking group, or a pharmaceutically acceptable salt, or $R_{10}$ and $R_{11}$ taken together in formula IIIa form a 5–7 membered lactone.

In preferred embodiments, Ar, for each occurrence, refers to aryl group selected from the group consisting of 5-, 6- and 7-membered monocyclic or 10–14 membered bicyclic aromatic groups that may include from zero to four heteroatoms, as for example, benzene, pyrrole, furan, thiophene, imidazole, oxazole, thiazole, triazole, pyrazole, pyridine, pyrazine, pyridazine, pyrimidine, benzothiophene, quinoline, quinolone, and the like.

Exemplary compounds of this class can be found with the generic structures described in, inter alia, U.S. Pat. No. 5,705,686 and PCT publication WO96/21456, and the class includes compounds of the general formula IVb.

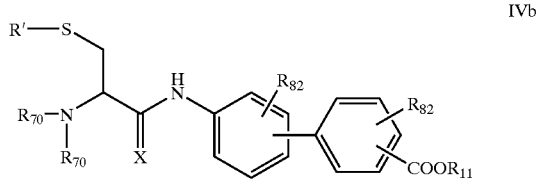

IVb wherein, X, R', $R_{11}$, and $R_{70}$ are as defined above in formula IIIb, and each $R_{82}$ is absent or represents one or more substitutions, each of which can independently be a lower alkyl, —$(CH)_2$—$R_7$ or $COOR_{11}$, ($R_7$ and $R_{11}$ being defined above). In a preferred embodiment, the core aryl structure is a para-phenyl benzamide or meta-phenyl benzamide.

In certain other preferred embodiments, the subject antifungal agent is a compound represented in the general formula:

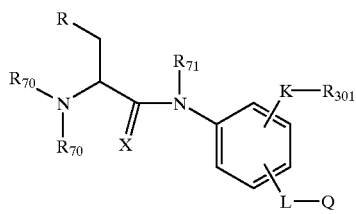

wherein,

R, $R_{70}$, and $R_{71}$ are as defined in formula II above, and $R_{301}$, independently for each occurrence, represents H, lower alkyl, —$(CH_2)_n$aryl (e.g., substituted or unsubstituted), —(CH$_2$)$_n$heteroaryl (e.g., substituted or unsubstituted), R$_{313}$ independently for each occurrence, represents H, lower alkyl, —(CH$_2$)$_n$aryl, —(CH$_2$)$_n$heteroaryl;

R$_{315}$, independently for each occurrence, represents H, lower alkyl, —(CH$_2$)$_n$aryl, —(CH$_2$)$_n$heteroaryl, —(CH$_2$)$_n$CO$_2$R$_{316}$, —(CH$_2$)$_n$CON(R$_{316}$)$_2$ or —(CH$_2$)$_n$COR$_{317}$;

R$_{316}$ independently for each occurrence, represents H, lower alkyl, —(CH$_2$)$_n$aryl, —(CH$_2$)$_n$heteroaryl;

R$_{317}$ represents a naturally occurring amino acid, dipeptide, or tripeptide connected through an amide linkage;

K represents —(CH$_2$)$_n$, —(CH$_2$)$_n$O, —(CH$_2$)$_n$S, —(CH$_2$)$_n$NR$_{313}$;

L represents (CH$_2$)$_n$, alkenyl, alkynyl, (CH$_2$)$_n$alkenyl, (CH$_2$)$_n$alkynyl, (CH$_2$)$_n$O(CH$_2$)$_p$, (CH$_2$)$_n$NR$_{313}$(CH$_2$)$_p$, (CH$_2$)$_n$S(CH$_2$)$_p$, (CH$_2$)$_n$alkenyl(CH$_2$)$_p$, (CH$_2$)$_n$alkynyl (CH$_2$)$_p$, O(CH$_2$)$_n$, NR$_{301}$(CH$_2$)$_n$, S(CH$_2$)$_n$;

Q represents one of the heterocyclic groups shown below;

X represents O or H$_2$; and p represents an integer from 0–3;

Q =

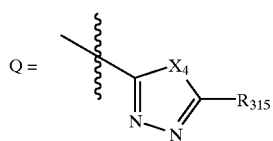

1

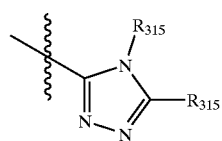

2

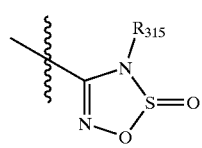

3

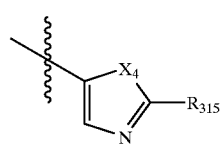

4

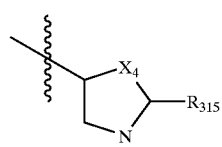

5

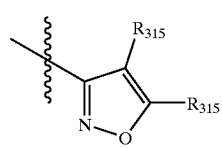

6

-continued

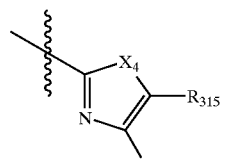

7

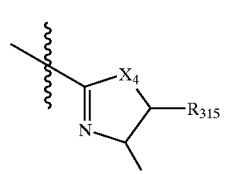

8

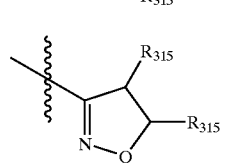

9

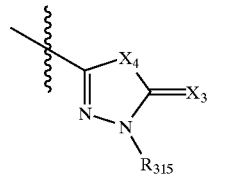

10

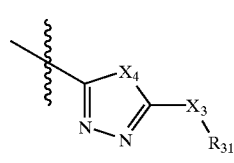

11

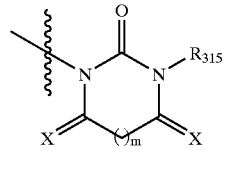

12

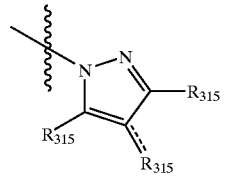

13

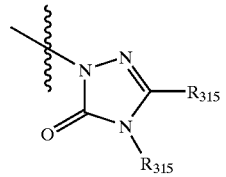

14

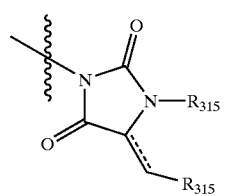

15 any two $R_{315}$, when occurring more than once in Q, can be taken together form a 5 to 8 membered cycloalkyl, aryl, or heteroaryl ring;

$X_3$ independently represents either N, O, or S;

$X_4$ independently represents either N, O, or S; and m represents 0 or an integer 1–3;

n, individually for each occurence, represents 0 or an integer from 1 to 5.

In certain other more preferred embodiments, the subject antifungal agent is a compound represented in the general formula:

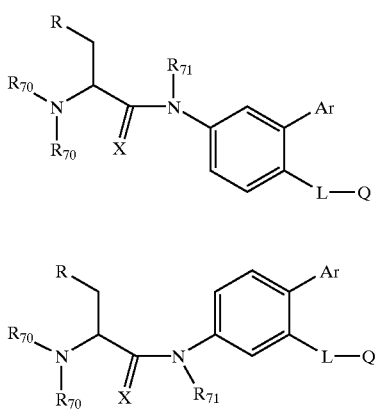

wherein,

R, $R_{70}$, and $R_{71}$ are as defined in formula II above, and

Ar represents an aryl or heteroaryl group (substituted or unsubstituted)

$R_{313}$ independently for each occurrence, represents H, lower alkyl, —(CH$_2$)$_n$aryl, —(CH$_2$)$_n$heteroaryl;

$R_{315}$, independently for each occurrence, represents H, lower alkyl, —(CH$_2$)$_n$aryl, —(CH$_2$)$_n$heteroaryl, —(CH$_2$)$_n$CO$_2$R$_{316}$, —(CH$_2$)$_n$CON(R$_{316}$)$_2$ or —(CH$_2$)$_n$COR$_{317}$;

$R_{316}$ independently for each occurrence, represents H, lower alkyl, —(CH$_2$)$_n$aryl, —(CH$_2$)$_n$heteroaryl;

$R_{317}$ represents a naturally occurring amino acid, dipeptide, or tripeptide connected through an amide linkage;

L represents (CH$_2$)$_n$, alkenyl, alkynyl, (CH$_2$)$_n$alkenyl, (CH$_2$)$_n$alkynyl, (CH$_2$)$_n$O(CH$_2$)$_p$, (CH$_2$)$_n$NR$_{313}$(CH$_2$)$_p$, (CH$_2$)$_n$S(CH$_2$)$_p$, (CH$_2$)$_n$alkenyl(CH$_2$)$_p$, (CH$_2$)$_n$alkynyl (CH$_2$)$_p$, O(CH$_2$)$_n$, NR$_{301}$(CH$_2$)$_n$, S(CH$_2$)$_n$;

Q represents one of the heterocyclic groups shown below;

X represents O or H$_2$;

p represents an integer from 0–3;

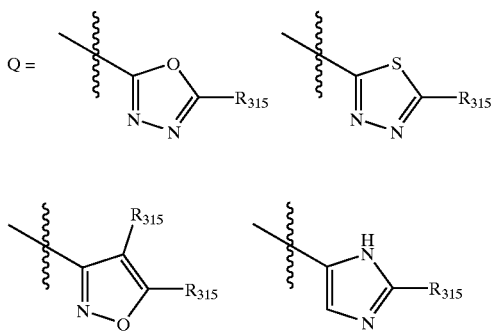

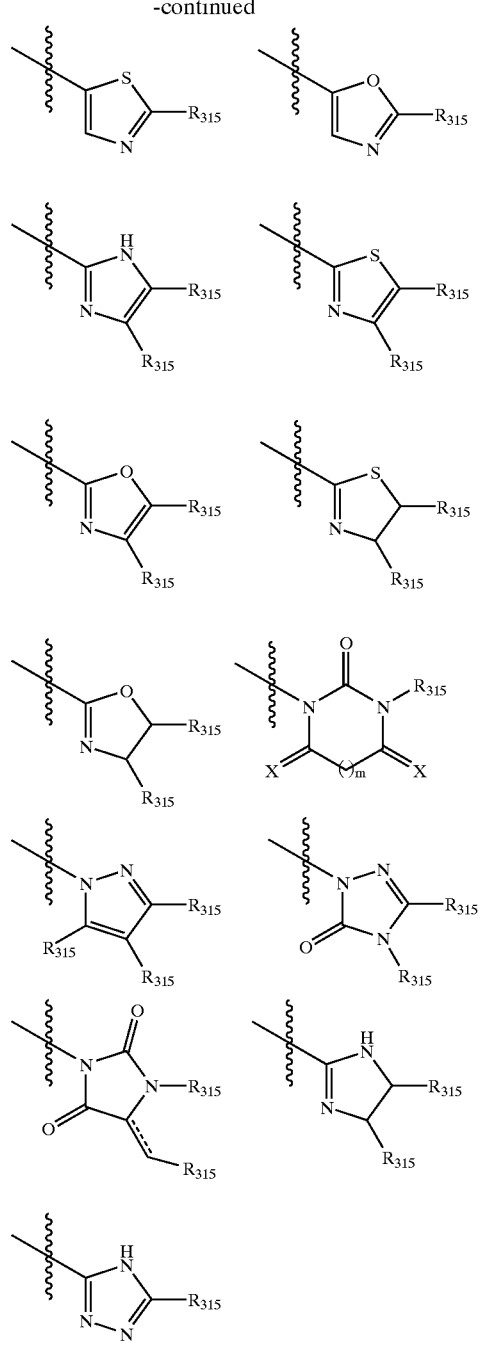

any two $R_{315}$, when occurring more than once in Q, can be taken together to form a 5 to 8 membered cycloalkyl, aryl, or heteroaryl ring;

X independently represents either O, or H$_2$;

m represents 0 or an integer from 1 to 3;

n, individually for each occurence, represents 0 or an integer from 1 to 5.

In a preferred embodiment, $R_{70}$ is H; R is —SH or —S-lower alkyl, more preferably —SH; X is H$_2$ or O, more preferably H$_2$; $R_{71}$ is H or lower alkyl, more preferably H; L is —(CH$_2$)$_n$— where n is 0, 1 or 2, more preferably 0 (e.g., L is a bond to Q); Q is

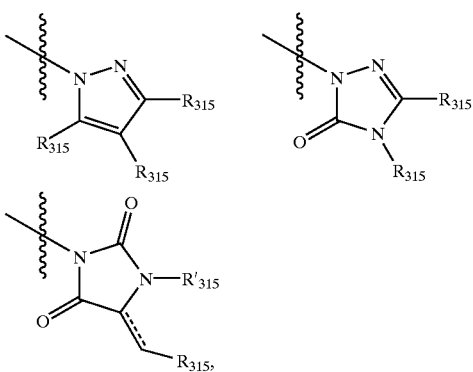

and more preferably

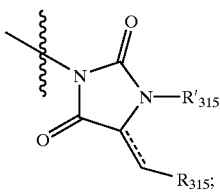

R'$_{315}$ is H or lower alkyl, more preferably H; R$_{315}$ is a branched lower alkyl; and Ar is phenyl.

In another embodiment, the subject method can be carried out using an inhibitor represented in the general formula:

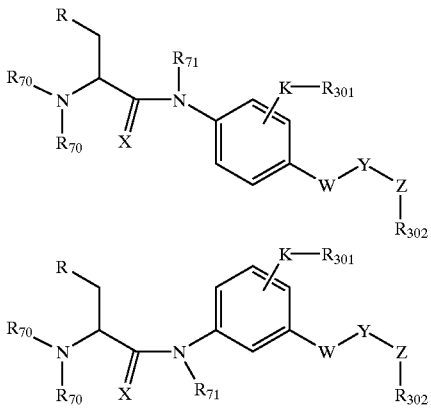

wherein,

R, R$_7$, R$_{70}$, R$_{71}$ and X are as defined in formula II above, and

K represents —(CH$_2$)$_n$, —(CH$_2$)$_n$O, —(CH$_2$)$_n$S, —(CH$_2$)$_n$NR$_{313}$;

R$_{301}$, independently for each occurrence, represents H, lower alkyl, —(CH$_2$)$_n$aryl (e.g., substituted or unsubstituted), —(CH$_2$)$_n$heteroaryl (e.g., substituted or unsubstituted), R$_{302}$, independently for each occurrence, represents H, lower alkyl, —(CH$_2$)$_n$aryl, —(CH$_2$)$_n$heteroaryl, —(CR$_{309}$R$_{310}$)$_n$CO$_2$R$_7$, —(CR$_{309}$R$_{310}$)$_n$CON(R$_{308}$)$_2$, —(CR$_{309}$R$_{310}$)$_n$COR$_{311}$;

R$_{303}$ and R$_{304}$, independently for each occurrence, represents H, lower alkyl, —(CH$_2$)$_n$aryl (e.g., substituted or unsubstituted), —(CH$_2$)$_n$heteroaryl (e.g., substituted or unsubstituted);

R$_{308}$ independently for each occurrence, represents H, lower alkyl, —(CH$_2$)$_n$aryl, —(CH$_2$)$_n$heteroaryl, or, taken together along with the N form a 4 to 8 membered heterocycle;

R$_{309}$ and R$_{310}$ represent independently for each occurrence, H, lower alkyl, —(CH$_2$)$_n$aryl (e.g., substituted or unsubstituted), —(CH$_2$)$_n$heteroaryl (e.g., substituted or unsubstituted), or a sidechain of a naturally occurring amino acid;

R$_{311}$ is a naturally occurring amino acid or dipeptide or tripeptide connected through an amide linkage;

R$_{313}$ independently for each occurrence, represents H, lower alkyl, —(CH$_2$)$_n$aryl, —(CH$_2$)$_n$heteroaryl;

W can be selected from (CH$_2$)$_n$, vinyl, acetylene, —O(CH$_2$)$_n$—, —N(R$_{303}$)(CH$_2$)$_n$—, —S(CH$_2$)$_n$—, —(CH$_2$)$_n$—O—, —(CH$_2$)$_n$—N(R$_{303}$)—, —(CH$_2$)$_n$—S—; n is an integer from 0–3;

Y can be selected from —C(=O)—, —S(O$_2$)—, —C(=NCN)— or a direct bond between W and Z;

Z can be selected from —N(R$_{304}$)—, —O—, —S— or a direct bond between Y and R$_{302}$ with the following provisions when W is (CH$_2$)$_n$ and Y is C=O, then Z is NR$_{304}$, O, or a direct bond between Y and R$_{302}$;

when W is (CH$_2$)$_n$ and Y is SO$_2$ then Z is NR$_{304}$ or a direct bond between Y and R$_{302}$;

when W is (CH$_2$)$_n$ and Y is direct bond between W and Z, then Z is NR$_{304}$, O, S or a direct bond between Y and R$_{302}$;

when W is vinyl or acetylene and Y is C=O, then Z is NR$_{304}$, O, or a direct bond between Y and R$_{302}$;

when W is vinyl or acetylene and Y is SO$_2$, then Z is NR$_{304}$ or a direct bond between Y and R$_{302}$;

when W is vinyl or acetylene and Y is direct bond between W and Z, then Z is direct bond between Y and R$_{302}$;

when W is O—(CH$_2$)$_n$ and Y is C=O, then Z is NR$_{304}$, O, or a direct bond between Y and R$_{302}$;

when W is O—(CH$_2$), and Y is SO$_2$, then Z is NR$_{304}$, or a direct bond between Y and R$_{302}$ if n is an integer from 1–3;

when W is O—(CH$_2$)$_n$ and Y is direct bond between W and Z, then Z is a direct bond between Y and R$_{302}$ if n is an integer from 0–1;

when W is O—(CH$_2$)$_n$ and Y is a direct bond between W and Z, then Z is NR$_{304}$, O, S, or a direct bond between Y and R$_{302}$ if n is an integer from 2–4;

when W is S—(CH$_2$)$_n$ and Y is C=O, then Z is NR$_{304}$, O, or a direct bond between Y and R$_{302}$ if n is an integer from 1–3;

when W is S—(CH$_2$)$_n$ and Y is SO$_2$, then Z is NR$_{304}$ or a direct bond between Y and R$_{302}$, if n is an integer from 1–3;

when W is S—(CH$_2$)$_n$ and Y is direct bond between W and Z, then Z is direct bond between Y and R$_{302}$, if n is an integer from 0–1;

when W is NR$_{303}$—(CH$_2$)$_n$ and Y is C=O, then Z is NR$_{304}$, O, or a direct bond between Y and R$_{302}$;

when W is NR$_{303}$—(CH$_2$)$_n$ and Y is SO$_2$, then Z is NR$_{304}$ or a direct bond between Y and R$_{302}$;

when W is NR$_{303}$—(CH$_2$)$_n$ and Y is direct bond between W and Z, if n is an integer from 0–1, then Z is direct bond between Y and R$_{302}$;

when W is NR$_{303}$—(CH$_2$)$_n$ and Y is direct bond between W and Z, if n is an integer from 2–4, then Z is NR$_{304}$, O, S or a direct bond between Y and R$_{302}$;

when W is $NR_{303}$—$(CH_2)_n$ and Y is C=NCN, then Z is $NR_{304}$ if n=0 when W is $(CH_2)_n$—O and Y is C=O, then Z is $NR_{304}$, O, or a direct bond between Y and $R_{302}$;

when W is $(CH_2)_n$—O and Y is direct bond between W and Z, then Z is direct bond between Y and $R_{302}$;

when W is $(CH_2)_n$—S and Y is direct bond between W and Z, then Z is direct bond between Y and $R_{302}$;

when W is $(CH_2)_nNR_{303}$ and Y is C=O, then Z is $NR_{304}$, O, or a direct bond between Y and $R_{302}$;

when W is $(CH_2)_nNR_{303}$ and Y is $SO_2$, then Z is $NR_{304}$ or a direct bond between Y and $R_{302}$;

when W is $(CH_2)_nNR_{303}$ and Y is direct bond between W and Z, then Z is direct bond between Y and $R_{302}$;

when W is $(CH_2)_nNR_{303}$ and Y is C=NCN, then Z is $NR_{304}$; and n, individually for each occurence, represents 0 or an integer from 1 to 5.

In a more preferred embodiment, the subject method can be carried out using an inhibitor represented in the general formula:

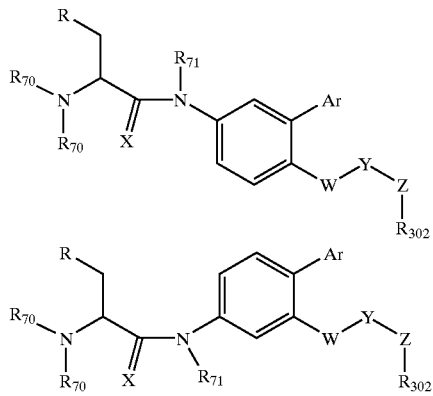

wherein,

R, $R_7$, $R_{70}$, $R_{71}$ and X are as defined in formula II above, and

Ar represents substituted aryl or heteroaryl;

$R_{302}$, independently for each occurrence, represents H, lower alkyl, —$(CH_2)_n$aryl, —$(CH_2)_n$heteroaryl, —$(CR_{309}R_{310})_nCO_2R_7$, —$(CR_{309}R_{310})_nCON(R_{308})_2$, —$(CR_{309}R_{310})_nCOR_{311}$;

$R_{303}$ and $R_{304}$, independently for each occurrence, represents H, lower alkyl, —$(CH_2)_n$aryl (e.g., substituted or unsubstituted), —$(CH_2)_n$heteroaryl (e.g., substituted or unsubstituted);

$R_{308}$ independently for each occurrence, represents H, lower alkyl, —$(CH_2)_n$aryl, —$(CH_2)_n$heteroaryl, or, taken together along with the N form a 4 to 8 membered heterocycle;

$R_{309}$ and $R_{310}$ represent independently for each occurrence, H, lower alkyl, —$(CH_2)_n$aryl (e.g., substituted or unsubstituted), —$(CH_2)_n$heteroaryl (e.g., substituted or unsubstituted), or a sidechain of a naturally occurring amino acid;

$R_{311}$ is a naturally occurring amino acid or dipeptide or tripeptide connected through an amide linkage;

W can be selected from $(CH_2)_n$, vinyl, acetylene, —$O(CH_2)_n$—, —$N(R_{303})(CH_2)_n$—, —$S(CH_2)_n$—, —$(CH_2)_n$—O—, —$(CH_2)_n$—$N(R_{303})$—, —$(CH_2)_n$—S—; n is an integer from 0–3;

Y can be selected from —C(=O)—, —$S(O_2)$—, —C(=NCN)— or a direct bond between W and Z;

Z can be selected from —$N(R_{304})$—, —O—, —S— or a direct bond between Y and $R_{302}$ with the following provisions when W is $(CH_2)_n$ and Y is C=O, then Z is $NR_{304}$, O, or a direct bond between Y and $R_{302}$;

when W is $(CH_2)_n$ and Y is $SO_2$ then Z is $NR_{304}$ or a direct bond between Y and $R_{302}$;

when W is $(CH_2)_n$ and Y is direct bond between W and Z, then Z is $NR_{304}$, O, S or a direct bond between Y and $R_{302}$;

when W is vinyl or acetylene and Y is C=O, then Z is $NR_{304}$, O, or a direct bond between Y and $R_{302}$;

when W is vinyl or acetylene and Y is $SO_2$, then Z is $NR_{304}$ or a direct bond between Y and $R_{302}$;

when W is vinyl or acetylene and Y is direct bond between W and Z, then Z is direct bond between Y and $R_{302}$;

when W is O—$(CH_2)_n$ and Y is C=O, then Z is $NR_{304}$, O, or a direct bond between Y and $R_{302}$;

when W is O—$(CH_2)_n$ and Y is $SO_2$, then Z is $NR_{304}$, or a direct bond between Y and $R_{302}$ if n is an integer from 1–3;

when W is O—$(CH_2)_n$ and Y is direct bond between W and Z, then Z is a direct bond between Y and $R_{302}$ if n is an integer from 0–1;

when W is O—$(CH_2)_n$ and Y is a direct bond between W and Z, then Z is $NR_{304}$, O, S, or a direct bond between Y and $R_{302}$ if n is an integer from 2–4;

when W is S—$(CH_2)_n$ and Y is C=O, then Z is $NR_{304}$, O, or a direct bond between Y and $R_{302}$ if n is an integer from 1–3;

when W is S—$(CH_2)_n$ and Y is $SO_2$, then Z is $NR_{304}$ or a direct bond between Y and $R_{302}$, if n is an integer from 1–3;

when W is S—$(CH_2)_n$ and Y is direct bond between W and Z, then Z is direct bond between Y and $R_{302}$, if n is an integer from 0–1;

when W is $NR_{303}$—$(CH_2)_n$ and Y is C=O, then Z is $NR_{304}$, O, or a direct bond between Y and $R_{302}$;

when W is $NR_{303}$—$(CH_2)_n$ and Y is $SO_2$, then Z is $NR_{304}$ or a direct bond between Y and $R_{302}$;

when W is $NR_{303}$—$(CH_2)_n$ and Y is direct bond between W and Z, if n is an integer from 0–1, then Z is direct bond between Y and $R_{302}$;

when W is $NR_{303}$—$(CH_2)_n$ and Y is direct bond between W and Z, if n is an integer from 2–4, then Z is $NR_{304}$, O, S or a direct bond between Y and $R_{302}$;

when W is $NR_{303}$—$(CH_2)_n$ and Y is C=NCN, then Z is $NR_{304}$ if n=0 when W is $(CH_2)_n$—O and Y is C=O, then Z is $NR_{304}$, O, or a direct bond between Y and $R_{302}$;

when W is $(CH_2)_n$—O and Y is direct bond between W and Z, then Z is direct bond between Y and $R_{302}$;

when W is $(CH_2)_n$—S and Y is direct bond between W and Z, then Z is direct bond between Y and $R_{302}$;

when W is $(CH_2)_nNR_{303}$ and Y is C=O, then Z is $NR_{304}$, O, or a direct bond between Y and $R_{302}$;

when W is $(CH_2)_nNR_{303}$ and Y is $SO_2$, then Z is $NR_{304}$ or a direct bond between Y and $R_{302}$;

when W is $(CH_2)_nNR_{303}$ and Y is direct bond between W and Z, then Z is direct bond between Y and $R_{302}$;

when W is $(CH_2)_n NR_{303}$ and Y is C=NCN, then Z is $NR_{304}$; and n, individually for each occurence, represents 0 or an integer from 1 to 5.

In certain preferred embodiments, $R_{70}$ is H; R is —SH or S-lower alkyl, and more preferably —SH; X is $H_2$ or O, and more preferably $H_2$; $R_{71}$ is H or lower alkyl, and more preferably H; W is —$(CH_2)_n$— where n is 0, 1 or 2, and more preferably 0 (e.g., W is a bond to Y); Y is —C(=O)—; Z is —$N(R_{304})$—; $R_{304}$ is H or lower alkyl, and more preferably H or $CH_3$; $R_{302}$ is —$CHR_{310}$—$CO_2R_7$; $R_7$ is H or methyl; $R_{310}$ is a branched lower alkyl; and Ar is benzene.

In certain other preferred embodiments, $R_{70}$ is H; R is —SH or S-lower alkyl, and more preferably —SH; X is $H_2$ or O, and more preferably $H_2$; $R_7$, is H or lower alkyl, and more preferably H; W is —$(CH_2)_n$— where n is 0, 1 or 2, and more preferably 0 (e.g., W is a bond to Y); Y is —C(=O)—; Z is —$N(R_{304})$—; $R_{304}$ is 4-pyridyl; $R_{302}$ is H; and Ar is benzene.

Another example of such peptidomimetics is described by Lerner et al. (1995) *J Biol Chem* 270:26770, as well as PCT publication WO96/21456, which each teach compounds represented in the general forumal IVa:

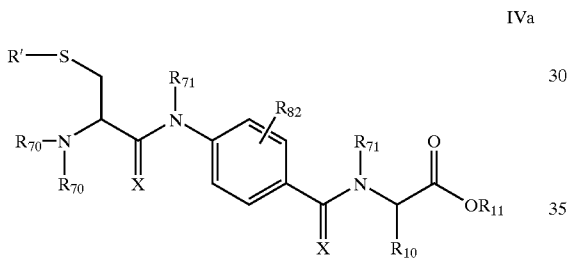

IVa wherein, R', $R_{10}$, $R_{11}$, $R_{70}$, $R_{71}$ and X are as defined above in formula IIIa, and $R_{82}$ is absent or represent one or more substitutions, each of which can independently be a lower alkyl, —$(CH)_2$—$R_7$ or $COOR_{11}$, ($R_7$ and $R_{11}$ being defined above).

With reference to the compounds of formula IIIa, the PCT publication WO96/21456 describes a number of other aryl groups. Thus, for example, a GGPTase inhibitor useful as an antifungal agent may represented in any one of the following generic formulas:

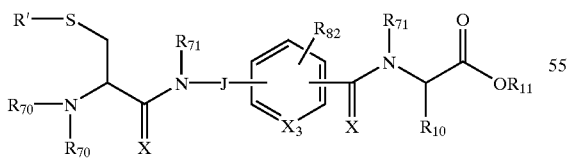

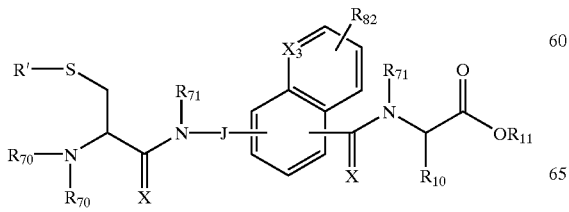

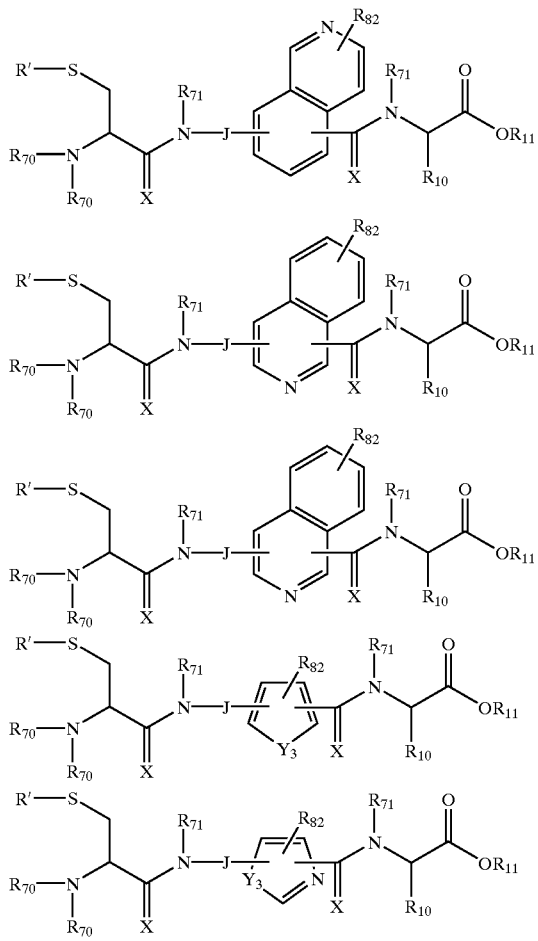

wherein R', $R_{10}$, $R_{11}$, $R_{70}$, $R_{71}$, $R_{82}$, J and X are as defined above, and $X_3$ represents C or N, and $Y_3$ represents O, S or NH.

Another class of preferred inhibitors is derived from a piperidine, and is represented in the general formula:

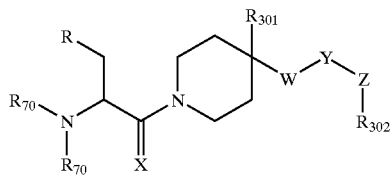

wherein,

R, $R_7$, $R_{70}$ and X are as defined in formula II above, and $R_{301}$ independently for each occurrence, represents H, lower alkyl, —$(CH_2)_n$aryl (e.g., substituted or unsubstituted), —$(CH_2)_n$heteroaryl (e.g., substituted or unsubstituted), $R_{302}$, independently for each occurrence, represents H, lower alkyl, —$(CH_2)_n$aryl, —$(CH_2)_n$heteroaryl, —$(CR_{309}R_{310})_n CO_2R_7$, —$(CR_{309}R_{310})_n C(=O)N(R_{308})_2$, —$C(R_{309}R_{310})$—C(=O)—[$N(R_{308})$—$CHR'_{310}$—C(=O)$]_p$—OH, —$(CR_{309}R_{310})_n COR_{311}$;

$R_{303}$ and $R_{304}$, independently for each occurrence, represents H, lower alkyl, —$(CH_2)_n$aryl (e.g., substituted or unsubstituted), —$(CH_2)_n$heteroaryl (e.g., substituted or unsubstituted);

$R_{308}$ independently for each occurrence, represents H, lower alkyl, —$(CH_2)_n$aryl, —$(CH_2)_n$heteroaryl, or, taken together along with the N form a 4 to 8 membered heterocycle;

$R_{309}$ and $R_{310}$ represent independently for each occurrence, H, lower alkyl, —$(CH_2)_n$aryl (e.g., substituted or unsubstituted), —$(CH_2)_n$heteroaryl (e.g., substituted or unsubstituted), or a sidechain of a naturally occurring amino acid;

$R'_{310}$ represents, individually for each occurrence, a natural or unnatural amino acid sidechain, such as a lower alkyl;

$R_{311}$ is an amino acid residue or dipeptide or tripeptide connected through an amide linkage;

W can be selected from $(CH_2)_n$, vinyl, acetylene, —$O(CH_2)_n$—, —$N(R_{303})(CH_2)_n$—, —$S(CH_2)_n$—, —$(CH_2)_n$—O—, —$(CH_2)_n$—$N(R_{303})$—, —$(CH_2)_n$—S—; n is an integer from 0–3;

Y can be selected from —C(=O)—, —$S(O_2)$—, —C(=NCN)— or a direct bond between W and Z;

Z can be selected from —$N(R_{304})$—, —O—, —S— or a direct bond between Y and $R_{302}$ with the following provisions when W is $(CH_2)_n$ and Y is C=O, then Z is $NR_{304}$, O, or a direct bond between Y and $R_{302}$;

when W is $(CH_2)_n$ and Y is $SO_2$ then Z is $NR_{304}$ or a direct bond between Y and $R_{302}$;

when W is $(CH_2)_n$ and Y is direct bond between W and Z, then Z is $NR_{304}$, O, S or a direct bond between Y and $R_{302}$;

when W is vinyl or acetylene and Y is C=O, then Z is $NR_{304}$, O, or a direct bond between Y and $R_{302}$;

when W is vinyl or acetylene and Y is $SO_2$, then Z is $NR_{304}$ or a direct bond between Y and $R_{302}$;

when W is vinyl or acetylene and Y is direct bond between W and Z, then Z is direct bond between Y and $R_{302}$;

when W is O—$(CH_2)_n$ and Y is C=O, then Z is $NR_{304}$, O, or a direct bond between Y and $R_{302}$ and $R_{301}$ is H;

when W is O—$(CH_2)_n$ and Y is $SO_2$, then Z is $NR_{304}$, or a direct bond between Y and $R_{302}$ if n is an integer from 1–3 and $R_{301}$ is H;

when W is O—$(CH_2)_n$ and Y is direct bond between W and Z, then Z is a direct bond between Y and $R_{302}$ if n is an integer from 0–1 and $R_{301}$ is H;

when W is O—$(CH_2)_n$ and Y is a direct bond between W and Z, then Z is $NR_{304}$, O, S, or a direct bond between Y and $R_{302}$ if n is an integer from 2–4 and $R_{301}$=H when W is S—$(CH_2)_n$ and Y is C=O, then Z is $NR_{304}$, O, or a direct bond between Y and $R_{302}$ if n is an integer from 1–3 and $R_{301}$ is H;

when W is S—$(CH_2)_n$ and Y is $SO_2$, then Z is $NR_{304}$ or a direct bond between Y and $R_{302}$ if n is an integer from 1–3 and $R_{301}$ is H;

when W is S—$(CH_2)_n$ and Y is direct bond between W and Z, then Z is direct bond between Y and $R_{302}$ if n is an integer from 0–1 and $R_{301}$ is H;

when W is $NR_{303}$—$(CH_2)_n$ and Y is C=O, then Z is $NR_{304}$, O, or a direct bond between Y and $R_{302}$;

when W is $NR_{303}$—$(CH_2)_n$ and Y is $SO_2$, then Z is $NR_{304}$ or a direct bond between Y and $R_{302}$;

when W is $NR_{303}$—$(CH_2)_n$ and Y is direct bond between W and Z, then Z is direct bond between Y and $R_{302}$ if n is an integer from 0–1;

when W is $NR_{303}$—$(CH_2)_n$ and Y is direct bond between W and Z, then Z is $NR_{304}$, O, S or a direct bond between Y and $R_{302}$ if n is an integer from 2–4;

when W is $NR_{303}$—$(CH_2)_n$ and Y is C=NCN, then Z is $NR_{304}$ if n=0 when W is $(CH_2)_n$—O and Y is C=O, then Z is $NR_{304}$, O, or a direct bond between Y and $R_{302}$;

when W is $(CH_2)_n$—O and Y is direct bond between W and Z, then Z is direct bond between Y and $R_{302}$;

when W is $(CH_2)_n$—S and Y is direct bond between W and Z, then Z is direct bond between Y and $R_{302}$;

when W is $(CH_2)_nNR_{303}$ and Y is C=O, then Z is $NR_{304}$, O, or a direct bond between Y and $R_{302}$;

when W is $(CH_2)_nNR_{303}$ and Y is $SO_2$, then Z is $NR_{304}$ or a direct bond between Y and $R_{302}$;

when W is $(CH_2)_nNR_{303}$ and Y is direct bond between W and Z, then Z is direct bond between Y and $R_{302}$;

when W is $(CH_2)_nNR_{303}$ and Y is C=NCN, then Z is $NR_{304}$; and p represents 1, 2 or 3.

n, individually for each occurence, represents 0 or an integer from 1 to 5.

In certain preferred embodiments, $R_{70}$ is H; R is —SH or —S-lower alkyl, more preferably —SH; X is $H_2$ or O, more preferably O; W is $CH_2)_n$— where n is 0, 1 or 2, more preferably 0; Y is —C(=O)—, Z is —$N(R_{304})$—; $R_{302}$ is H or aryl, such as benzyl; $R_{304}$ is aralkyl, e.g., 4-pyridylmethyl, trans-phenylcyclopropyl, phenylethyl or 9-fluorenyl; and $R_{301}$ is an aryl, more preferably a phenyl.

In other preferred embodiments, $R_{70}$ is H; R is —SH or —S-lower alkyl, more preferably —SH; X is $H_2$ or O, more preferably O; W is —$CH_2)_n$— where n is 0, 1 or 2, more preferably 0; Y is —C(=O)—, Z is —$N(R_{304})$—; $R_{302}$ is —$CH(R_{310})$—C(=O)—[NH—$CR'_{310}$—C(=O)]$_p$—OH or H; $R_{310}$ is a lower alkyl, preferably a branched lower alkyl; $R'_{310}$ is is lower alkyl, preferably a methyl; p is 1 or 2; $R_{304}$ is H, aralkyl, e.g., 4-pyridylmethyl, trans-phenylcyclopropyl, or 9-fluorenyl; and $R_{301}$ is an aryl, more preferably a phenyl.

Another preferred class of piperidine-derived inhibitors for use in the subject method are represented in the general formula:

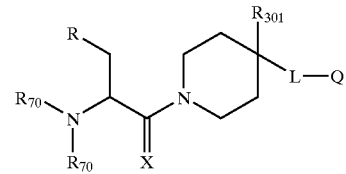

wherein,

R and $R_{70}$ are as defined in formula II above, and

L represents $(CH_2)_n$, alkenyl, alkynyl, $(CH_2)_n$alkenyl, $(CH_2)_n$alkynyl, $(CH_2)_nO(CH_2)_p$, $(CH_2)_nNR_{313}(CH_2)_p$, $(CH_2)_nS(CH_2)_p$, $(CH_2)_n$alkenyl$(CH_2)_p$, $(CH_2)_n$alkynyl$(CH_2)_p$, $O(CH_2)_n$, $NR_{301}(CH_2)_n$, $S(CH_2)_n$;

Q represents one of the heterocyclic groups shown below;

$R_{301}$, independently for each occurrence, represents H, lower alkyl, —$(CH_2)_n$aryl (e.g., substituted or unsubstituted), —$(CH_2)_n$heteroaryl (e.g., substituted or unsubstituted);

$R_{313}$ independently for each occurrence, represents H, lower alkyl, —$(CH_2)_n$aryl, —$(CH_2)_n$heteroaryl;

$R_{315}$, independently for each occurrence, represents H, lower alkyl, —$(CH_2)_n$aryl, —$(CH_2)_n$heteroaryl, —$(CH_2)_nCO_2R_{316}$, —$(CH_2)_nCON(R_{316})_2$ or —$(CH_2)_nCOR_{317}$;

$R_{316}$ independently for each occurrence, represents H, lower alkyl, —$(CH_2)_n$aryl, —$(CH_2)_n$heteroaryl;

$R_{317}$ represents a naturally occurring amino acid, dipeptide, or tripeptide connected through an amide linkage;

X represents O or $H_2$;

n represents an integer from 0–3;

p represents an integer from 0–3;

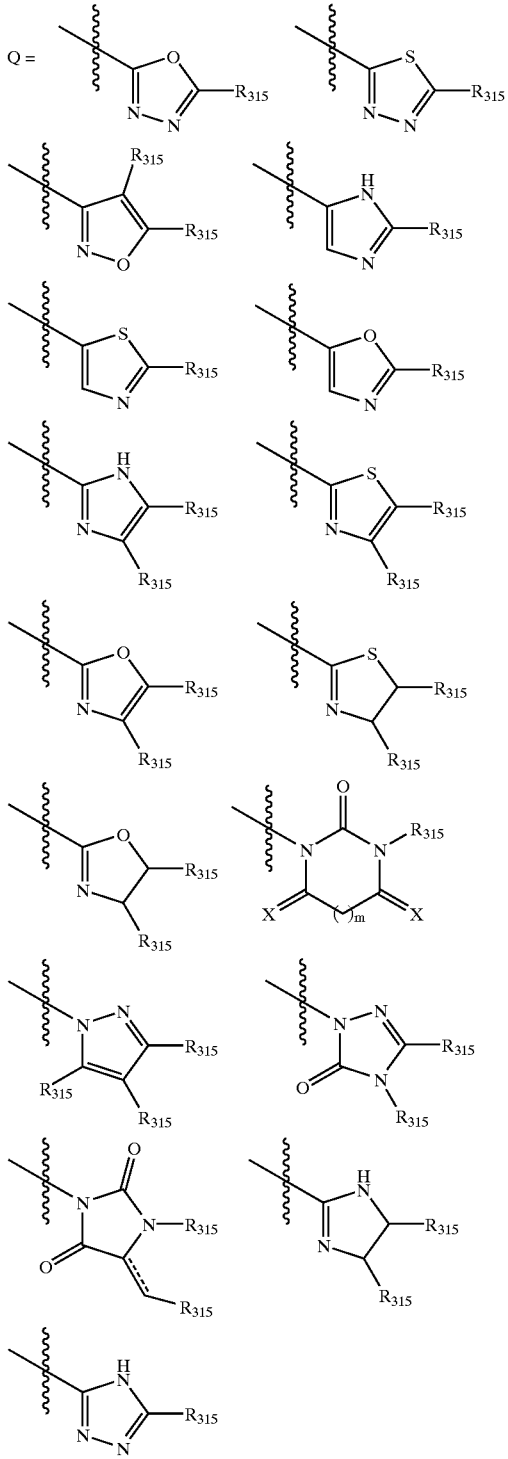

any two $R_{315}$, when occurring more than once in Q, can be taken together to form a 5 to 8 membered cycloalkyl, aryl, or heteroaryl ring;

X independently represents either O, or $H_2$;

m represents 0 or an integer from 1 to 3;

n, individually for each occurence, represents 0 or an integer from 1 to 5.

In a preferred embodiment, $R_{70}$ is H; R is —SH or —S-lower alkyl, more preferably —SH; X is $H_2$ or O, more preferably O; L is $CH_2)_n$— where n is 0, 1 or 2, more preferably 0 (e.g., L is a bond to Q); Q is

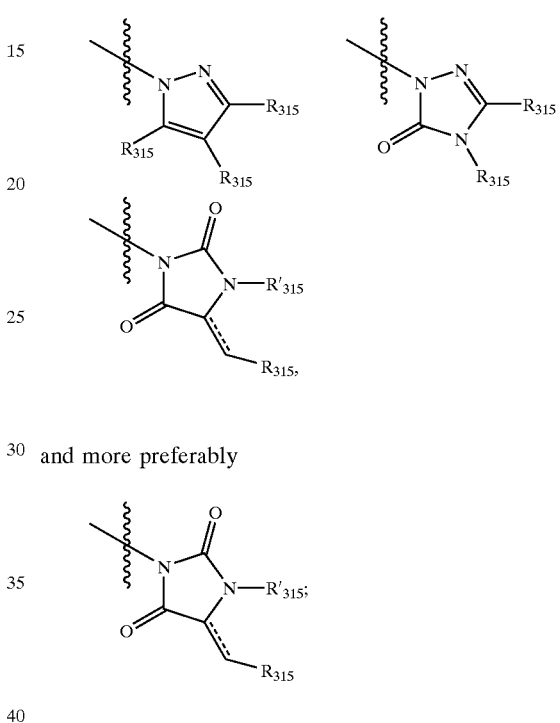

and more preferably

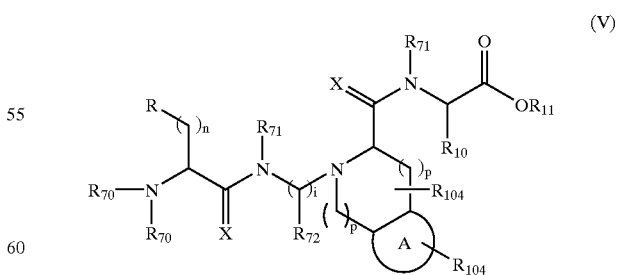

$R'_{315}$ is H or lower alkyl, more preferably H; $R_{315}$ is a branched lower alkyl; and $R_{301}$ is phenyl.

In yet another embodiment, the subject method can be practiced using a compound selected from the teachings of U.S. Pat. No. 5,624,936 and of Canadian Application 2,143,588, or analogs thereof. For instance, the method of the present invention can be carried out by treatment with a compound represented in the general formula (V):

(V)

wherein

R, $R_{10}$, $R_{11}$, $R_{70}$, $R_{71}$, $R_{72}$ and X are as defined above in formula I;

A represents a fused ring selected from a group consisting of a cycloalkyl, a cycloalkenyl, an aryl, and a heterocycle, wherein the fused ring A can comprise from 4 to 8 atoms in its ring structure;

$R_{104}$ is absent or represents one or more substitutions, each independently selected from lower alkyl, aryl, heterocycle, cycloalkyl, alkenyl, alkynyl, $R_{110}$—O, $R_{111}$—S(O)$_m$—, $R_{110}$C(O)NR$_{110}$—, CN, N$_3$, $(R_{110})_2$N—C(NR$_{110}$)—, $R_{110}$C(O)—, $R_{110}$OC(O)—, $(R_{110})_2$N— or $R_{111}$OC(O)NR$_{110}$—, lower alkyl unsubstituted or substituted by one or more aryl, heterocycle, cycloalkyl, alkenyl, alkynyl, $R_{110}$O—, $R_{111}$S(O)$_m$—, $R_{110}$C(O)NR$_{110}$—, CN, $(R_{110})_2$N—, or $R_{111}$OC(O)—NR$_{110}$—;

$R_{110}$ represents hydrogen, lower alkyl, benzyl or aryl;

$R_{111}$ is a lower alkyl or aryl;

i is 1, 2, or 3; and p is, independently for each occurrence, 0, 1 or 2.

m is an integer in the range of 0 to 2.

The teachings of Canadian Application 2,143,588 are also instructive for classes of compounds which are potential inhibitors of fungal GGPTases and which can be used in the present method. Thus, in another embodiment, the method of the present invention can be carried out by treatment with a compound represented in the general formula (VI):

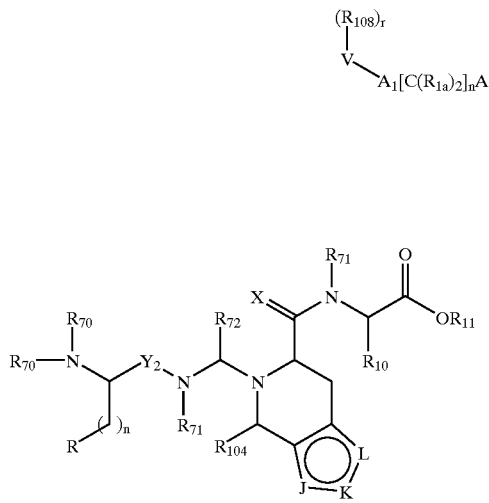

wherein,

R, $R_{10}$, $R_{11}$, $R_{70}$, $R_{71}$, $R_{72}$, $R_{104}$, X and n are as defined above in formula V;

$Y_2$ is —CH$_2$— or —C(O)—;

J, K and L are each independently N, NR$_{105}$, O, S or CR$_{106}$, with the proviso that only one of the three groups can be O or S, one or two of the three groups can be N or NR$_{105}$, and at least one must be a heteroatom to form a heteroaryl;

$R_{105}$ represents H, lower alkyl or phenylalkyl; and $R_{106}$ represents H or lower alkyl.

EP publication 618,221 teaches a similar class of compounds which are potential inhibitors of fungal GGPTases for use in the present method, e.g., which antifungal compounds may be represented in the general formula VII:

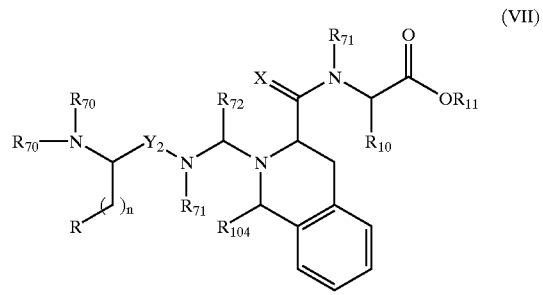

wherein,

R, $R_{10}$, $R_{11}$, $R_{70}$, $R_{71}$, $R_{72}$, $R_{104}$, X and n are as defined above in formula V, and $Y_2$ is —CH$_2$— or —C(O)—.

The teachings of U.S. Pat. No. 5,624,936 also provide guidance for the design of other analogs which can be used in the present method. To further illustrate, the method of the present invention can be carried out by treatment with a compound represented in the general formula (VIII) (for additional structures in this class of GGPTase inhibitors, see: PCT application WO 97/38664):

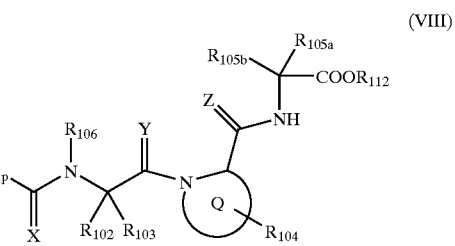

wherein, $R_{1a}$ and $R_{1b}$, independently for each occurrence, are selected from hydrogen, lower alkyl, aryl, heterocycle, cycloalkyl, alkenyl, alkynyl, $R_{110}$O—, $R_{111}$—S(O)$_m$—, $R_{110}$C(O)NR$_{110}$—, CN, NO$_2$, $(R_{110})_2$N—C(NR$_{110}$)—, $R_{110}$OC(O)—, $R_{110}$OC(O)—, N$_3$, $(R_{110})_2$N— or $R_{111}$OC(O)NR$_{110}$—, lower alkyl unsubstituted or substituted by one or more aryl, heterocycle, cycloalkyl, alkenyl, alkynyl, $R_{110}$O—, $R_{111}$S(O)$_m$—, $R_{110}$C(O)NR$_{110}$—, CN, $(R_{110})_2$N—, or $R_{111}$OC(O)—NR$_{110}$—;

$R_{102}$ and $R_{103}$ are independently selected from a side chain of a naturally occurring amino acid, or are a lower alkyl, lower alkenyl, cycloalkyl, aryl or heterocyclic group, or $R_{102}$ and $R_{103}$ taken together form a cycloalkyl, or $R_{102}$ along with the adjacent N form a heterocycle;

$R_{104}$ is absent or represents one or more substitutions to Q, each independently selected from lower alkyl, aryl, heterocycle, cycloalkyl, alkenyl, alkynyl, $R_{110}$O—, $R_{111}$—S(O)$_m$—, $R_{110}$C(O)NR$_{110}$—, CN, N$_3$, $(R_{110})_2$N—C(NR$_{110}$)—, $R_{110}$C(O)—, $R_{110}$OC(O)—, $(R_{110})_2$N— or $R_{111}$OC(O)NR$_{110}$—, lower alkyl unsubstituted or substituted by one or more aryl, heterocycle, cycloalkyl, alkenyl, alkynyl, $R_{110}O—$, $R_{111}S(O)_m—$, $R_{110}C(O)NR_{110}—$, CN, $(R_{110})_2N—$, or $R_{111}OC(O)—NR_{110}—$;

$R_{105a}$ and $R_{105b}$ are independently selected from a side chain of an amino acid, or otherwise a straight chain or branched lower alkyl, alkenyl, alkynyl, cycloalkyl, aryl or heterocycle;

$R_{106}$ represents hydrogen or a lower alkyl;

$R_{108}$ and $R_{109}$ represent, independently, hydrogen, alkyl, aryl, heterocycle, cycloalkyl, alkenyl, alkynyl, halogen, $R_{110}O—$, $R_{111}S(O)_m—$, $R_{110}C(O)NR_{110}—$, CN, $N_3$, $(R_{110})_2N—C(NR_{110})—$, $R_{110}C(O)—$, $R_{110}OC(O)—$, $(R_{110})_2N—$ or $R_{111}OC(O)NR\,O—$, lower alkyl unsubstituted or substituted by one or more aryl, heterocycle, cycloalkyl, alkenyl, alkynyl, $R_{110}O—$, $R_{111}S(O)_m—$, $R_{110}C(O)NR_{110}—$, CN, $(R_{110})_2N—$, or $R_{111}OC(O)—NR_{110}$;

$R_{110}$ represents hydrogen, lower alkyl, benzyl and aryl;

$R_{111}$ is a lower alkyl or aryl;

Q is a substituted or unsubstituted nitrogen-containing bicyclic ring system;

V represents hydrogen, lower alkyl, lower alkenyl, aryl or heterocycle;

W is a heterocycle;

X, Y and Z are independently O, S or $H_2$;

m is 0, 1 or 2;

n and p are, independently, 0, 1, 2, 3 or 4; and r is an integer in the range of 0–5.

U.S. Pat. No. 5,470,832 and PCT publication WO95/20396 provide insight into still other embodiments of compounds wherein the backbone of a peptide inhibitor is replaced with a non-hydrolyzable analog thereof. Accordingly, in certain embodiments of the subject method, the GGPTase inhibitor can be a compound represented in the general formula IX

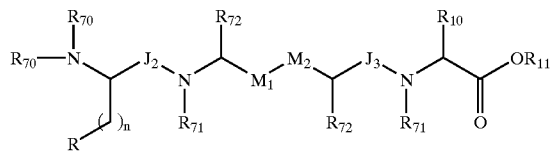

(IX)

wherein $M_1—M_2$ represents $—CH_2\,O—$ or $—CH=CH—$;

$J_2$ and $J_3$ each represent $—CH_2—$ or $—C(X)—$;

R represents

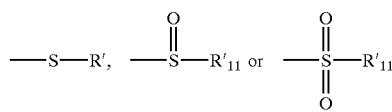

R' represents H, a lower alkyl, a lower alkenyl, an aryl,

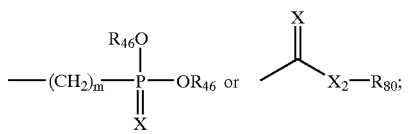

$R_7$ represents an aryl, a cycloalkyl, a cycloalkenyl, or a heterocycle;

$R_{11}$ represents H, a carboxy-terminal blocking group, or a pharmaceutically acceptable salt;

$R'_{11}$ represents an alkyl, an alkenyl or $—(CH_2)_m—R_7$ $R_{46}$, independently for each occurrence, represents hydrogen, a lower alkyl or an aryl $R_{70}$, independently for each occurrence, represents H,

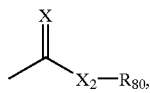

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or $R_{70}$ and R taken together form a 4 to 8 membered heterocycle;

$R_{71}$ represents H or a lower alkyl;

$R_{72}$, independently for each occurrence, represents H, lower alkyl, aryl, heteroaryl or the sidechain of a naturally occurring amino acid;

$R_{80}$ represents an hydrogen, a lower alkyl, a lower alkenyl, a lower alkynyl, or $—(CH_2)_m—R_7$;

X represents, independently for each occurrence, O or S;

$X_2$ represents O or S; and m and n, independently for each occurrence, represent zero or an integer in the range of 1 to 4 inclusive.

In other embodiments, the subject compounds may be selected from the generic structures described in U.S. Pat. No. 5,602,098, and may be represented in the general formula X:

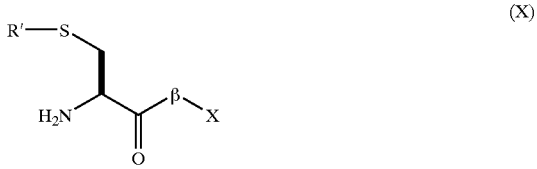

(X)

wherein R' is defined above; X is a leucine residue, or analog thereof, and β is a residue of ortho-, meta-, or para-aminobenzoic acid, or a residue of an aminoalkylbenzoic acid.

Inhibitors of fungal GGPTases may also be selected from amongst the class of compounds disclosed in the PCT publication WO95/25086, e.g., represented in the general formula (XI):

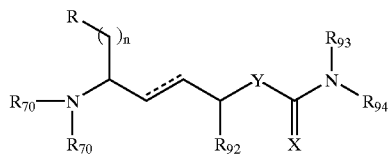

(XI)

wherein
R represents

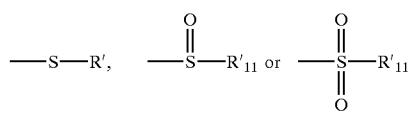

R' represents H, a lower alkyl, a lower alkenyl, an aryl,

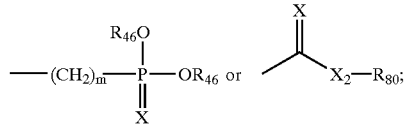

$R_7$ represents an aryl, a cycloalkyl, a cycloalkenyl, or a heterocycle;
$R'_{11}$ represents an alkyl, an alkenyl or $—(CH_2)_m—R_7$
$R_{46}$, independently for each occurrence, represents hydrogen, a lower alkyl or an aryl
$R_{70}$, independently for each occurrence, represents H,

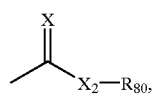

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or
$R_{70}$ and R taken together form a 4 to 8 membered heterocycle;
$R_{92}$ represents H, lower alkyl, aryl, heteroaryl or the sidechain of an amino acid;
$R_{80}$ represents an hydrogen, a lower alkyl, a lower alkenyl, a lower alkynyl, or $—(CH_2)_m—R_7$;
X represents, independently for each occurrence, O or S;
$X_2$ represents O or S; and
$R_{93}$ represents H, lower alkyl, aryl or heteroaryl;
$R_{94}$ represents a cycloalkyl, a heterocycle, an aryl,

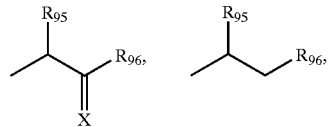

$—CH_2—R_{95}$, or any other amino-protecting group;
$R_{95}$ represents a lower alkyl, a heterocycle, an aryl, a lower alkoxyl, $—(CH_2)_n—A—(CH_2)_m—$lower alkyl (wherein A is O, S, SO or $SO_2$), or any other side chain of a naturally occurring amino acid;
$R_{96}$ represents H, $—NH_2$, $—NHOH$, heterocycle, aryl, $—N(R_{97})_2$, $—OR_{98}$, $—N(R_{97})OR_{98}$, $—NHOR_{98}$, or any other carboxyl-protecting group;
$R_{97}$, independently for each occurrence, represents a lower alkyl, a heterocycle, an alkyloxycarbonyl, an aryl or any other amino-protecting group;
$R_{98}$, independently for each occurrence, represents H, a lower alkyl, an acyloxyalkyl, alkyloxyalkyl, alkyloxycarbonyl or another hyrdoxyl- or carbonyl-protecting group;

Y is selected from the group consisting of

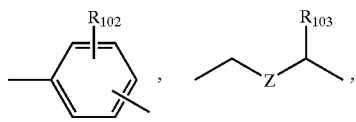

and

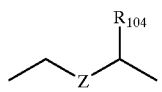

$AR_{102}$ is absent or represents one or more substitutions independently being a halogen, $—OH$, a lower alkyl, a lower alkenyl, a lower alkynyl, an alkoxyl, an acyloxyl, an acyl, an aryl, a heterocycle, an alkylsulfonyloxyl, a haloalkylsulfonyloxyl, an arylsulfonyloxyl, or an aryloxyl;

$R_{103}$ represents H, a lower alkyl, an aryl, or a heterocycle;

$R_{104}$ represents H, a lower alkyl, an aryl, or a heterocycle;

Z represents O, S, SO, $SO_2$ or an amine;

m and n, independently for each occurrence, represent zero or an integer in the range of 1 to 4 inclusive.

In another embodiment, the GGPTase inhibitor is an azepine-derived peptidomimetic represented by the general formula α-amino-N-[1-(2-Leu-2-oxoethyl)-1-azepin-3-yl]-Cys (Formula XII), wherein Cys represents a cysteine or a cysteine analog which is carboxy-terminally linked with a 3-amino moiety of an azepine, and Leu represents a leucine or leucine analog amino-terminally linked through a peptide bond with the 2-oxoethyl moiety of the azepine. The azepine core mimics a dipeptidyl amide backbone, and the Cys, azepine, and Leu moieties together form a peptidyl analog of the general formula Cys-Xaa-Xaa-Leu. In certain embodiments of the present invention, the Cys moiety can further include an additional amino acid residue or peptide, linked in a peptidyl bond to the N-terminus of the leucine in order to further extend the peptidomimetic at the amino terminus.

In an exemplary embodiment, the peptidyl-azepine is represented by Formula XIII (numerous examples of GGPTase inhibitors of this general structural class are described in U.S. Pat. No. 5,532,359):

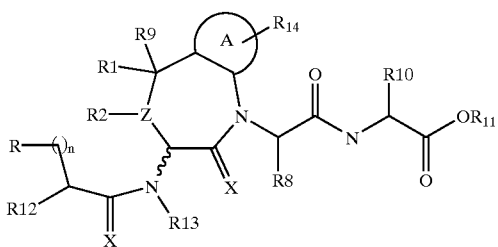

(XIII)

wherein

A represents a fused ring selected from a group consisting of a cycloalkyl, a cycloalkenyl, an aryl, and a heterocyclic ring, wherein the fused ring A can comprise from 4 to 8 atoms in its ring structure;

R represents

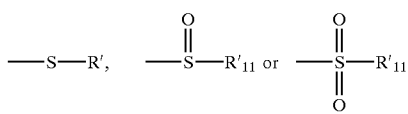

R' represents H, a lower alkyl, a lower alkenyl, an aryl,

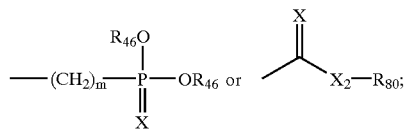

$R_1$, $R_2$, $R_8$ and $R_{10}$ each independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_7$;

$R_4$ and $R_5$ each independently represent hydrogen, lower alkyl, lower alkenyl, —$(CH_2)_m$—$R_7$, —C(O)-lower alkyl, —C(O)-lower alkenyl, —C(O)—$(CH_2)_m$—$R_7$, or a pharmaceutically acceptable salt forming ion, or $R_4$ and $R_5$ taken together with the N atom to which they are attached complete a heterocyclic ring having from 4 to 8 atoms in the ring structure;

$R_7$ represents an aryl, a cycloalkyl, a cycloalkenyl, or a heterocycle;

$R_9$ is a hydrogen or a lower alkyl;

$R_{11}$ represents H, a carboxy-terminal blocking group, or a pharmaceutically acceptable salt;

$R'_{11}$ represents an alkyl, an alkenyl or —$(CH_2)_m$—$R_7$;

$R_{12}$ represents N(—$R_4$)$R_5$;

$R_{13}$ represents hydrogen, or a lower alkyl;

$R_{14}$ is absent or represents one or more substitutions with halogens, lower alkyls, lower alkoxyls, lower alkylthiols, —$NO_2$, —$CF_3$, —CN, and —OH;

$R_{46}$, independently for each occurrence, represents hydrogen, a lower alkyl or an aryl;

$R_{80}$ represents an hydrogen, a lower alkyl, a lower alkenyl, a lower alkynyl, or —$(CH_2)_m$—$R_7$;

X and $X_2$, for each occurrence, represents O or S;

Z represents C or N; and n is zero or an integer in the range of 1 to 6 inclusive; and m is an integer in the range of 0 to 6 inclusive.

In preferred embodiments, the fused ring A is selected from a group consisting of benzene, pyrrole, furan, thiophene, imidazole, oxazole, thiazole, triazole, pyrazole, pyrrolidine, pyridine, pyrazine, pyridazine and pyrimidine, and the like. The fused ring A can be substituted, for example, by any of a halogen, a lower alkyl, a lower alkoxy, a lower alkylthio, —$NO_2$, —$CF_3$, —CN, and —OH. Though it will be understood that in some instances it may be undesirable to have a substituent, such as a halogen or a nitro group, in the 7 position (particularly wherein A is a benzene ring) as such substituents are generally required for sedative-hypnotic activity in other benzodiazepines, such as diazepam or nitrazepam.

Likewise, in preferred, yet optional, embodiments, $R_1$ is particularly selected from a group consisting of —$(CH_2)_m$—phenyl, —$(CH_2)_n$—S—$(CH_2)_m$—phenyl, —$(CH_2)_n$—O—$(CH_2)_m$—phenyl, —$(CH_2)_m$—pyridyl, —$(CH_2)_n$—S—$(CH_2)_m$—pyridyl, and —$(CH_2)_n$—O—$(CH_2)_m$—pyridyl. Additionally, each of the benzyl and pyridyl moieties can be substituted at one or more positions with a halogen, a lower alkyl, a lower alkoxy, a lower alkylthio, —$NO_2$, —$CF_3$, —CN, and —OH. The choice of $R_1$, as well as the other substituents of the azepine peptidomimetic, can effect the solubility, as well as membrane partioning of the subject peptidomimetics. For instance, as a result of their pyridyl-substituted nature, pyridyl containing $R_1$ substituents can exhibit a greater water solubility than the analogous phenyl-substituted azepines.

In an exemplary embodiment, the peptidomimetic of the present invention is a benzodiazepine represented by the general formula XIV (for specific examples of compounds of this formula, and representative synthetic schemes, see: inter alia U.S. Pat. No. 5,580,979):

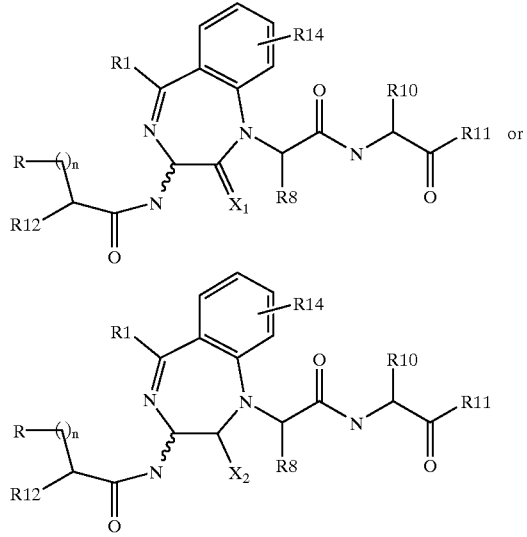

(XIV)

wherein

R, $R_1$, $R_9$, $R_{10}$, $R_{11}$, $R_{12}$, $R_{14}$ are as defined above in formula XIII;

$X_1$ represents O or S; and $X_2$ represents hydrogen, a lower alkyl, —$(CH_2)_m$—OH, —$(CH_2)_m$—O—lower alkyl, a carboxyl, an amide, a nitrosyl, a sulfhydryl, a sulfonyl, or a sulfonamide;

n is zero or an integer in the range of 1 to 6 inclusive; and m is an integer in the range of 1 to 6 inclusive.

For instance, the peptidomimetic can be a 5-phenyl substituted 1,4-diazepine represented by the general formula XV:

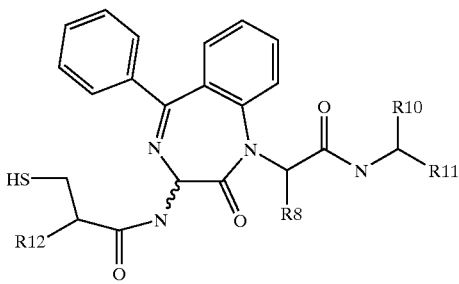

(XV)

wherein $R_8$, $R_{10}$, $R_{11}$, $R_{12}$ are as defined above in formula XIII.

Another class of azepine-derived mimetics from which a fungal GGPTase inhibitor can be selected are described in PCT publication WO97/30992, e.g., the inhibitor may be represented in one of the general formulas XVI, XVII, XVIII, XIX:

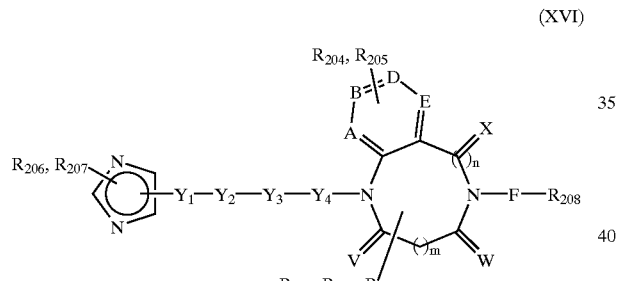

(XVI)

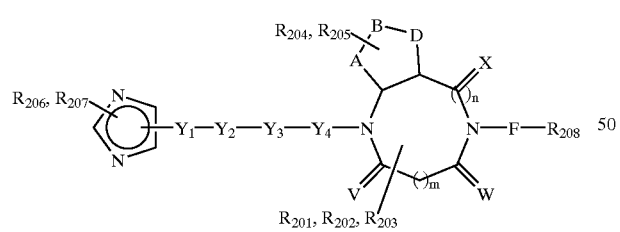

(XVII)

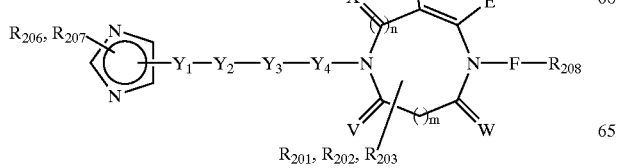

(XVIII)

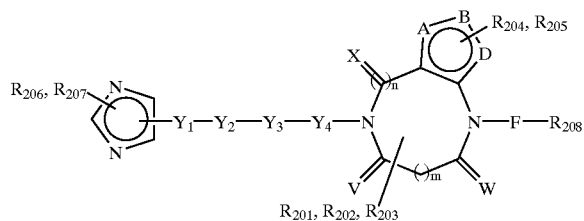

(XIX)

wherein m and n are, independently, 0 or 1;

p is 0, 1 or 2;

V, W and X are selected from the group consisting of O, $H_2$, $R_{201}$, $R_{202}$ or $R_{203}$;

F and $Y_4$ are selected from the group consisting of $CHR_{209}$, $SO_2$, $SO_3$, CO, $CO_2$, O, $NR_{210}$, $SO_2$, $SO_3$, CO, $CO_2$, O, $NR_{210}$, $SO_2NR_{211}$, $CONR_{212}$,

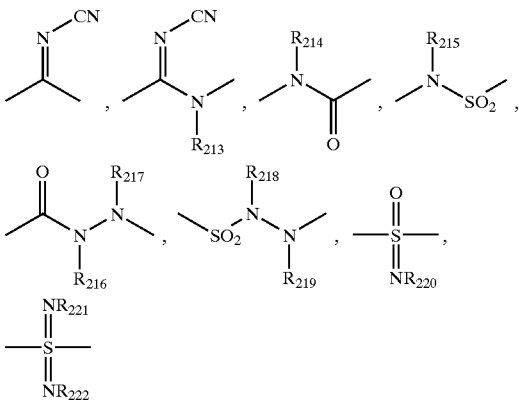

or F may be absent;

$R_{206}$, $R_{207}$, $R_{209}$, $R_{210}$, $R_{211}$, $R_{212}$, $R_{213}$, $R_{214}$, $R_{215}$, $R_{216}$, $R_{217}$, $R_{218}$, $R_{219}$, $R_{220}$, $R_{221}$, $R_{222}$, $R_{224}$, $R_{225}$, $R_{226}$, $R_{227}$, $R_{228}$, $R_{229}$, $R_{230}$, $R_{231}$, $R_{232}$, $R_{233}$, $R_{234}$, $R_{235}$, $R_{236}$, $R_{237}$, and $R_{238}$ are, independently, selected from the group consisting of H, lower alkyl or aryl;

$R_{204}$ and $R_{205}$ are selected from the group consisting of H, halogens, nitro, cyano, and U—$R_{223}$;

U is selected from the group consisting of S, O, $NR_{224}$, CO, SO, $SO_2$, $CO_2$, $NR_{25}CO_2$, $NR_{26}CNR_{27}$, $NR_{28}SO_2$, $NR_{29}SO_2NR_{30}$, $SO_2NR_{31}$, $NR_{32}CO$, $CCONR_{33}$, $PO_3R_{34}$, $PO_3R_{35}$ or U is absent;

$R_{201}$, $R_{202}$, $R_{203}$ are absent or, each independently, selected from the group consisting of alkyls, alkoxycarbonyl, alkenyl, alkynyl, aralkyl, cycloalkyl, aryl, heterocycle, cyano, carboxy and carbamyl, or cases where there are two substituents on a single nitrogen, selected from the group consisting of alkyl, aryl or aralkyl, or any two of the $R_{201}$, $R_{202}$ and $R_{203}$ taken together form a cycloalkyl or heterocycle;

$R_{208}$ and $R_{223}$ are selected from the group consisting of H, alkyls, alkenyls, alkynyls, aralkyls, cycloalkyls, aryls and heterocycles;

$Y_1$, $Y_2$, and $Y_3$ are, independently, absent or selected from the group consisting of —$CH_2$, —C(O)— and —CH($CH_2)_pQ$—;

Q is $NR_{236}$, $R_{237}$, $OR_{238}$ or CN; and

A, B, D and E are C, O, S or N, with the provisos that
(i) when m is zero, then V and W are not both oxygens; or
(ii) W and X together can be oxygen only if F is either absent, O, $NR_{210}$, $CHR_{209}$, —$N(R_{214})$—C(O)— or —$N(R_{215})$—$SO_2$— in formulas XVII and XVIII, and V and X together with can be oxygen only if F is O, $NR_{210}$, $CHR_{209}$, —$N(R_{214})$—C(O)— or —$N(R_{215})$—$SO_2$— in formulas XIX and XX: or
(iii) $R_{223}$ may be $H_2$ except when U is SO, $SO_2$, $NR_{225}CO_2$, or $NR_{228}SO_2$; or
(iv) $R_{208}$ may be H except when F is $SO_2$, $CO_2$,

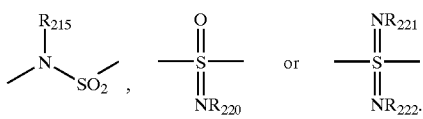

In another preferred embodimemt, the subject method makes use of inhibitors represent in the general formula

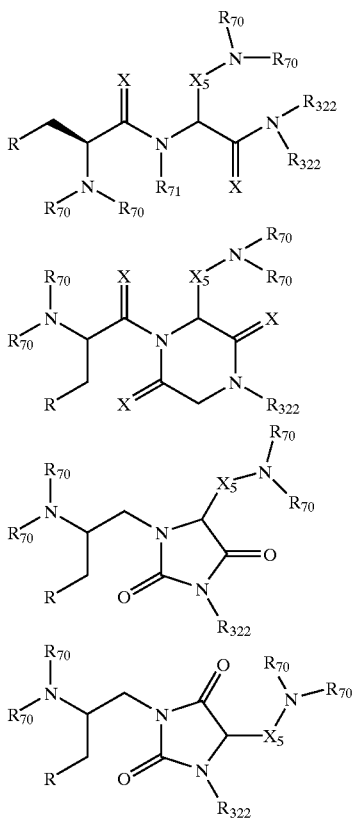

wherein

R, $R_7$, $R_{70}$, $R_{71}$ and X are as defined in formula II above, and $X_5$ represents $(CH_2)_n$ or $(CH_2)_nCO$ $R_{322}$, independently for each occurrence, represents H, lower alkyl, —$(CH_2)_n$aryl, —$(CH_2)_n$heteroaryl, —$(CR_{309}R_{310})_nCO_2R_7$, —$(CR_{309}R_{310})_nCON(R_{308})_2$, —$(CR_{309}R_{310})_nCOR_{311}$, or $R_{322}$ and $R_{322}$, taken together, form a 5–8 membered heterocycle (substituted or unsubstituted);

$R_{308}$ independently for each occurrence, represents H, lower alkyl, —$(CH_2)_n$aryl, —$(CH_2)_n$heteroaryl;

$R_{308}$ and $R_{308}$ taken together form a 4 to 8 membered heterocycle;

$R_{309}$ and $R_{310}$ represent independently for each occurrence, H, lower alkyl, —$(CH_2)_n$aryl (e.g., substituted or unsubstituted), —$(CH_2)_n$heteroaryl (e.g., substituted or unsubstituted), or a sidechain of a naturally occurring amino acid;

$R_{311}$ is a naturally occurring amino acid; and n is 0 or an integer from 1 to 5.

In certain preferred embodiments, the inhibitor is represented in the formula

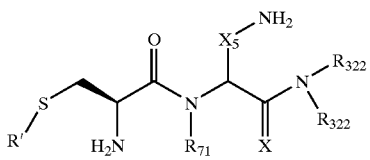

wherein: R' is H or lower alkyl, more preferably H; $R_7$, is H or lower alkyl, and more preferably H; $X_5$ is —$CH_2$—; one $R_{322}$ represents H and the other $R_{322}$ represents aralkyl or araheteroalkyl (more preferably —$CH_2$-aryl, and even more preferably —$CH_2$-3-biphenyl), or both $R_{322}$ and $R_{322}$ taken to together form an N-heterocycle or N-heteroaryl, more preferably a piperazine, and even more preferably piperazin-1-yl-[4-bis-parafluorophenylmethyl].

In still other embodiments, the subject compound is represented by one of the following formulas. First, the subject compounds may be retro N-alkyl oligoglycine peptoids (Simon et al. *Proc. Natl. Acad. Sci., USA* 1992, 89, 9367; Zuckermann et al. *J. Med. Chem.* 1994, 37, 2678), represented by Formula XX:

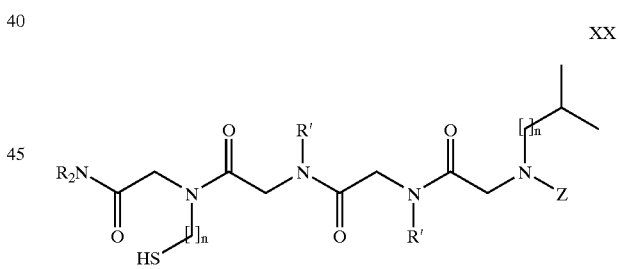

wherein

R represents, independently for each occurrence, H, Me, lower alkyl, aryl, aralkyl, heteroalkyl, or heteroaryl;

R' represents, independently for each occurrence, Me, lower alkyl, aryl, aralkyl, heteroalkyl, or heteroaryl;

Z represents H, Me, lower alkyl, aryl, aralkyl, heteroalkyl, heteroaryl, acyl, sulfonyl, —C(O)OR, or —C(O)N(R)$_2$; and n represents, independently for each occurrence, an integer in the range 1 to 3 inclusive.

Second, the subject compounds may be N-alkyl oligoglycine peptoids, represented by Formula XXI:

XXI

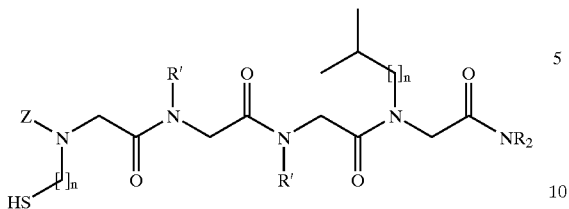

wherein
R represents, independently for each occurrence, H, Me, lower alkyl, aryl, aralkyl, heteroalkyl, or heteroaryl;
R' represents, independently for each occurrence, Me, lower alkyl, aryl, aralkyl, heteroalkyl, or heteroaryl;
Z represents H, Me, lower alkyl, aryl, aralkyl, heteroalkyl, heteroaryl, acyl, sulfonyl, —C(O)OR, or —C(O)N(R)$_2$; and
n represents, independently for each occurrence, an integer in the range 1 to 3 inclusive.

As noted above, certain peptidomimetics of the present invention may exist in particular geometric or stereoisomeric forms. The present invention contemplates all such compounds, including cis- and trans-isomers, R- and S-enantiomers, diastereomers, D-isomers, L-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts may be formed with an appropriate optically-active acid or base, followed by resolution of the diastereomers thus formed by fractional crystallization or chromatographic means well known in the art, and subsequent recovery of the pure enantiomers.

In certain embodiments, the GGPTase inhibitors of the subject method are non-peptide inhibitors of GGPTase. For example, the methods of the present invention can be carried out with antifungal analogs of prenyl diphosphates, particularly geranylgeranyl diphosphate. Such inhibitors include acyclic terpenes. Terpenes are organic compounds constructed of multiples of 2-methyl-1,3-butadiene. The inhibitors of the present invention can be analogs of monoterpenes (those containing two isoprene units, such as myrcenyl moieties), sesquiterpenes (those containing three such units, such as farnesyl moieties) or diterpenes (those containing four isoprene subunits, such as geranylgeranyl moieties).

In an illustrative embodiment, the terpene-derived GGPTase inhibitor is represented in the general formula (XXII):

XXII

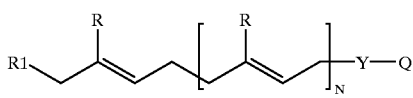

wherein
R, independently for each occurrence, represents a halogen or lower alkyl;
R$_2$ represents —H, —OH, —O-alkyl, —O-aryl, —O—C(O)—H, —O—C(O)-alkyl, or —O—C(O)-aryl;
Y represents a bond (i.e. is absent) or —S—, —O—, —(CH$_2$)$_m$—,

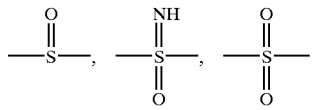

Q represents —C$_1$—C$_6$alkyl-R$_2$, —C(O)—R$_2$, —NH—(CH$_2$)$_n$—R$_2$, —NH—C(O)—(CH$_2$)$_n$—R$_2$, —C(O)—NH(CH$_2$)$_n$—R$_2$;
R$_2$ represents a hydrogen, a lower alkyl, or a phosphate or bisphosphate or analog thereof such as sulfate, sulfonate, sulfamoyl, sulfinyl, sulfoxyl, sulfinate, phosphoryl, phosphorothioate, phosphoramidite, phosphonamidite or boronate;
or Y and Q taken together represent

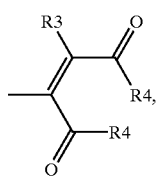

R$_3$ represents a hydrogen or lower alkyl, and R$_4$, independently for each occurrence, represents a hydrogen, lower alkyl, —OH, —O— lower alkyl, or a carboxyl blocking group;
m, independently for each occurrence, is an integer in range of 1 to 6 inclusive;
n, independently for each occurrence, is zero or an integer in range of 1 to 6 inclusive; and
N is an integer in the range of 1 to 3 inclusive (though preferably 2). For example, the art describes, in the context of inhibition of mammalian FPTases or GGPTases, a variety of analogs of isoprenyl diphosphates, e.g., wherein the biologically labile diphosphate moiety is replaced with a group that is a stable isostere. The various compounds described in the art, and certain equivalents that may be evident therefrom, can be tested for inhibition of fungal cell growth either directly, or by first assessing the compounds in such high throughput, cell-free assays as described herein.

For instance, Macchia et al. (1996) *J Med Chem* 39:1352 describes non-peptidic inhibitors of mammalian GGPTase activity. The compounds described by Macchia et al. include those which are represented in the general formula XXII (as above)

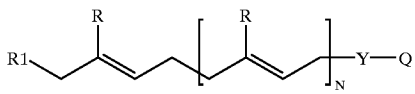

wherein
N=2;
each R represents a methyl;
R$_1$ represents hydrogen;

Y represents —O—;

Q represents C(O)—NH(CH$_2$)$_n$—R$_2$ or —NH—C(O)—(CH$_2$)$_n$—R$_2$; and

R$_2$ represents a sulfamoyl, phosphoryl or phosphorylalkyl.

The Balsamo PCT publication WO97/19091 describes other GGPTase inhibitors which may be useful in the subject method. For instance, the compounds described in this application are also represented in general formula XXII above, wherein Y represents —CH$_2$—X—A—, CH$_2$—CH$_2$, or —CH(OH)—;

X represents —ONH—, —O—NH—C(O)—, —OCH$_2$C(O)—, OCH$_2$P(O)(OH)—, —NHC(O)—, —NCH$_3$C(O)—, —O—SO$_2$—, or —NHSO$_2$—;

A represents —C(R')(R")—, —C(R')HCH$_2$—, NH when X=—OSO$_2$—, or —NHSO$_2$—;

B represents —OC(O)—, —O—, —ONHC(O)—, —NHC(O)—, or —NCH$_3$C(O)—; and

R', R" each independently represent H, CH$_3$, or CH$_2$CH$_3$;

The Rando PCT publication WO 94/01126 teaches yet another class of GGPTase inhibitors, including those represented in the general formula:

W—Y—CH$_2$—Q wherein

W represents farnesyl, geranylgeranyl, substituted farnesyl, or substituted geranylgeranyl;

Y represents —S—, —O—, —CH$_2$—, $$-\overset{O}{\underset{O}{\overset{\|}{S}}}-, \quad -\overset{NH}{\underset{O}{\overset{\|}{S}}}-, \quad -\overset{O}{\underset{O}{\overset{\|}{S}}}- \quad -\overset{T_1}{\underset{T_3}{\overset{|}{-}}}-T_2;$$

T$_1$ represents H, F, or —(CH$_2$)$_n$—X$_1$;

T$_2$ is —NHCOCH$_3$, —NH—(CH$_2$)$_n$—X$_1$, —NHC(O)—OC(CH$_3$)$_3$, or an oligopeptide of 20 or fewer amino acids, linked to the carbon via the N terminal nitrogen;

X$_1$ represents —SH, —COOH, CONH$_2$;

T$_3$ represents —C(O)—X$_2$, —CH(O), —C(O)—CF$_3$, —C(O)—CF$_2$—X$_2$, —CH(OH)—(CH$_2$)$_n$—C(O)—X$_2$, —CH$_2$—X$_2$, —CF$_2$—X$_2$, $$-\overset{O}{\underset{OH}{\overset{\|}{P}}}-X_2, \quad -\overset{X_2}{\underset{OH}{\overset{/}{B}}}, \quad -\overset{OH}{\underset{O}{\overset{|}{C}}}-X_2, \text{ or}$$

-continued $$-\overset{OH}{\underset{H}{\overset{|}{C}}}-CF_2-\overset{O}{\overset{\|}{C}}-X_2; \text{ and}$$

X$_2$ represents a peptide of 20 or fewer amino acids, linked to the carbon via the N terminal nitrogen.

In preferred embodiments, Q is a peptide or peptidyl moiety which resembles the substrate of a fungal GGPTase, e.g., a sequence from a fungal Rho1-like phosphatase which includes the GGPTase recognition sequence.

Hara et al. (1993) *PNAS* 90:2281 describes a generic class of non-peptidyl inhibitors of FPTase inhibitors which could be screened for activity (and selectivity) against fungal GGPTases. Thus, in another embodiment of the present method the antifungal agent may be represented in the general formula:

wherein

X is O or S;

R$_{301}$ represents;

and n is 0, 1 or 2.

GGPTase inhibitors which are useful in the method of the present invention may also be found in the compounds described in the PCT publication WO92/20336, e.g., which are similar to the structure:

In still other embodiments of the subject method, the inhibitor of the fungal GGPTase is a small organic molecule which is neither peptidyl or prenyl in nature. For example, U.S. Pat. No. 5,721,236 describes tricyclic carbamate compounds and the like as inhibitors of mammalian FPTase activities. It is contemplated herein that within the generic class of compounds disclosed in that patent there exist inhibitors selective for a fungal GGPTase, e.g., represented in the general formula:

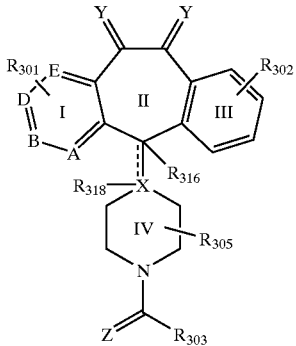

wherein,

A, B, D and E independently represent C or N or $NR_{309}$;

Y, independently for each occurrence, represents O or $H_2$;

X represents N or C;

Z represents O or S;

$R_{301}$ is absent, or represents one or more substitutions of the ring I, each independently selected from halogens, —$CF_3$, —$OR_{310}$, —$COR_{310}$, —$SR_{310}$, —$N(R_{310})_2$, —$NO_2$, —$C(O)R_{310}$, —$CO_2R_{310}$, —$OCOR_{310}$, benzotriazol-1-yloxy, CN, alkynyl, alkenyl or alkyl;

$R_{302}$ is absent, or represents one or more substitutions of the ring III, each independently selected from halogens, —$CF_3$, —$OR_{310}$, —$COR_{310}$, —$SR_{310}$, —$N(R_{310})_2$, —$NO_2$, —$C(O)R_{310}$, —$CO_2R_{310}$, —$OCOR_{310}$, benzotriazol-1-yloxy, CN, alkynyl, alkenyl or alkyl;

$R_{303}$ represents —$SR_{310}$, —$OR_{310}$, —$N(R_{310})_2$ or $CH_2)_mR_{310}$;

$R_{305}$ is absent, or represents one or more substitutions of the ring IV, each independently selected from halogens, —$CF_3$, alkyl, or aryl;

$R_{310}$, independently for each occurrence, represents H, alkyl, cycloalkyl, aryl or aralkyl;

$R_{316}$ and $R_{318}$ each independently represent H or F when the bond to X is a single bond and X is C, or $R_{318}$ is absent when X is N, or both $R_{316}$ and $R_{318}$ are absent when the bond to X is a double bond (and X is C);

m is 0 or an integer in the range 1 to 3; and n is an integer in the range1 to 3.

Another small molecule inhibitors of prenyltransferases are the quinolinone derivatives disclosed in PCT publication WO97/21701. Inhibitors suitable for use in the subject method may be selected from amongst these compounds, e.g., having a structure represented in the general formula:

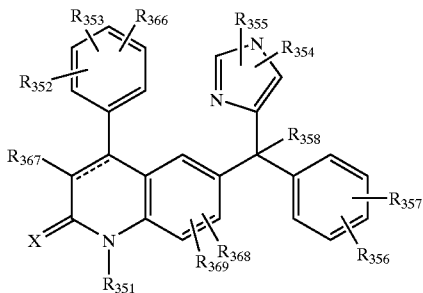

wherein

X is O or S;

$R_{351}$ is H, alkyl, aryl, —$(CH_2)_m$—$C(=O)$—$R_{359}$, —$(CH_2)_m$—$S(=O)$—$R_{359}$, —$(CH_2)_m$—$S(=O)_2$—$R_{359}$;

$R_{352}$, $R_{353}$ and $R_{366}$, independently represent H, halo, hydroxyl amino, cyano, alkyl, alkenyl, alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, or alkylsulfonylalkyl, or $R_{352}$ and $R_{353}$, when on adjacent positions, can be taken together to form a ring of 5 to 8 ring atoms;

$R_{354}$ and $R_{355}$ are each independently H, halo, hydroxyl amino, alkyl, alkenyl, alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, —$(CH_2)_m$—$C(=O)$—$R_{359}$, —$(CH_2)_m$—$S(=O)$—$R_{359}$, or $(CH_2)_m$—$S(=O)_2$—$R_{359}$;

$R_{356}$ and $R_{357}$ are each independently H, halo, cyano, alkyl, alkyloxy, aryl, aryloxy, alkylthio, alkylamino, or $R_{356}$ and $R_{357}$, when on adjacent positions, can be taken together to form a ring of 5 to 8 ring atoms $R_{358}$ is H, halo, hydroxyl amino, cyano, alkyl, alkenyl, alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, —O—$R_{360}$, —S—$R_{360}$, —$N(R_{361})_2$;

$R_{359}$, independently for each occurrence, represents hydroxyl, alkyl, alkyloxy, amino or alkylamino;

$R_{360}$, independently for each occurrence, represents hydrogen, alkyl, alkylcarbonyl, aryl, arylalkyl, alyyloxycarbonylalkyl, -alkyl-$OR_{361}$ or -alykyl—N$(R_{361})_2$;

$R_{361}$, independently for each occurrence, represents hydrogen, alkyl, aryl, or arylakyl;

$R_{367}$ is hydrogen, halo, cyano, alkyl, alkyloxycarbonyl, or aryl;

$R_{368}$ is hydrogen, halo, alkyl, or alkyloxy;

$R_{369}$ is hydrogen or alkyl; and m is integer from 1 to 5.

Yet another class of non-peptide small molecule inhibitors of prenyltransferases are represented in the general formula:

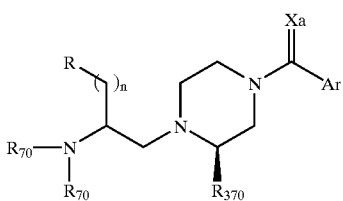

wherein
Ar represents an aryl group (e.g., substituted or unsubstituted);
$X_a$ represents, independently for each occurrence, O, S or $H_2$
R represents

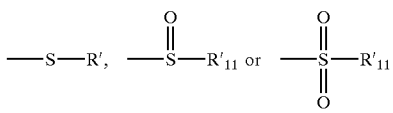

R' represents H, a lower alkyl, a lower alkenyl, an aryl,

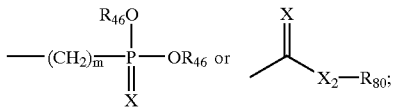

$R_7$ represents an aryl, a cycloalkyl, a cycloalkenyl, or a heterocycle;
$R'_{11}$ represents an alkyl, an alkenyl or —$(CH_2)_m$—$R_7$;
$R_{46}$, independently for each occurrence, represents hydrogen, a lower alkyl or an aryl;
$R_{70}$, independently for each occurrence, represents H,

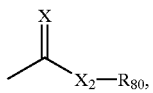

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or
$R_{70}$ and R, or $R_{70}$ and $R_{70}$, taken together form a 4 to 8 membered heterocycle;
$R_{80}$ represents an hydrogen, a lower alkyl, a lower alkenyl, a lower alkynyl, or —$(CH_2)_m$—$R_7$;
$R_{370}$ represents an hydrogen, a lower alkyl, a lower alkenyl, a lower alkynyl, —$(CH_2)_m$—O— lower alkyl, —$(CH_2)_m$—O—$R_7$, or —$(CH_2)_m$—$R_7$;
X represents, independently for each occurrence, O or S;
$X_2$ represents O or S; and
m and n, independently for each occurrence, represent zero or an integer in the range of 1 to 4.
In preferred embodiments, R is —SR'; R' is H or lower alkyl, preferably H; Ar is C6–C12 aryl; $R_{70}$ are each H; $R_{370}$ is $CH_2)_2$—O—$CH_3$; $X_a$ is O; n is 1.
Still another class of non-peptide small molecule inhibitors of prenyltransferases are the bisphosphonates disclosed in EP publication 537,008. Inhibitors suitable for use in the subject method may be selected from amongst these compounds, e.g., having a structure represented in the general formula:

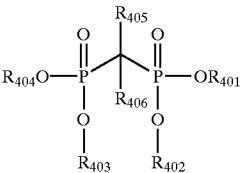

wherein $R_{401}$, $R_{402}$, $R_{403}$ and $R_{404}$ each independently represent H, alkyl, aryl, alkylaryl, arylalkyl, ammonium, alkali metal or a prodrug ester.
Another group of prenyl transferase inhibitors is disclosed in the PCT publication WO 96/17623. The inhibitors of this publication are represented, in part, by the following general structure.

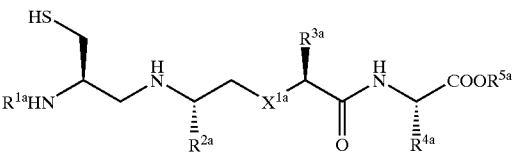

wherein
$X^{1a}$ represents —O—, $S(O)_m$, —$N(R^{3a})$—, —$(CH_2)_2$—, or —CHCH—;
m is an integer of 0 to 2;
$R^{1a}$ represents hydrogen, lower alkyl, aralkyl, acyl, lower alkylsulfonyl, aralkylsulfonyl, or arylsulfonyl;
$R^{2a}$ represents lower alkyl;
$R^{3a}$ represents lower alkyl, or aralkyl;
$R^{4a}$ represents mercapto lower alkyl, lower alkylthio lower alkyl, lower alkylsulfinyl lower alkyl, lower alkylsulfonyl lower alkyl, or hydroxy lower alkyl;
$R^{5a}$ represents hydrogen, or lower alkyl;
$R^{4a}$ and $R^{5a}$ may together form $C_2$ to $C_4$ alkylene.
The pharmaceutically acceptable salts of the subject GGPTase inhibitors include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.
The pharmaceutically acceptable salts of the present invention can be synthesized from the subject GGPTase inhibitor which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject GGPTase inhibitors are also readily prepared by conventional procedures such as treating an acid of the compound with an appropriate amount of a base such as an alkali or alkaline earth metal hydroxide (e.g. sodium, potassium, lithium, calcium or magnesium) or an organic base such as an amine, piperidine, pyrrolidine, benzylamine and the like, or a quaternary ammonium hydroxide such as tetramethylammonium hydroxide and the like.

Contemplated equivalents of the compounds described herein include compounds which otherwise correspond thereto, and which have the general properties thereof (e.g. the ability to inhibit a fungal GGPTase), wherein one or more simple variations of substituents are made which do not adversely affect the efficacy of the compound in inhibiting such enzymes.

As is apparent from the present disclosure, other non-hydrolyzable peptide analogs can be generated which incorporate the basic structure of CXXL. For illustrative purposes, peptide analogs of the present invention can be generated using, in addition to the benzodiazepines described above, substituted gamma lactam rings (Garvey et al. in *Peptides: Chemistry and Biology*, G. R. Marshall ed., ESCOM Publisher: Leiden, Netherlands, 1988, p123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29;295; and Ewenson et al. in *Peptides: Structure and Function* (Proceedings of the 9th Amnerican Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modified (Roark et al. in *Peptides: Chemistry and Biology*, G. R. Marshall ed., ESCOM Publisher: Leiden, Netherlands, 1988, p134). Also, see generally, Session III: Analytic and synthetic methods, in *Peptides: Chemistry and Biology*, G. R. Marshall ed., ESCOM Publisher: Leiden, Netherlands, 1988).

In an exemplary embodiment, the peptidomimetic can be derived as a retro-inverso analog of the peptide. To illustrate, certain of the subject peptides can be generated as the retro-inverso analog:

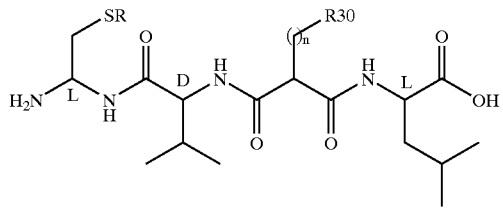

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the cysteine analog is synthesized by treating an S-protected (e.g. as the benzoyl) N-Boc-L-cysteine with ammonia under HOBT-DCC coupling conditions to yield N-Boc-L-cysteinylamide, and then effecting a Hofmann-type rearrangement with I,I-bis-(trifluoroacetoxy)iodobenzene (TIB), as described in Radhakrishna et al. (1979) *J. Org. Chem.* 44:1746. The product amine salt is then coupled to a side-chain protected (e.g., as the benzyl ester) N-Fmoc D-Val residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog. The pseudotripeptide is then coupled with L-Ile under standard conditions to give the protected tetrapeptide analog. The protecting groups are removed to release the final product, which is purified by HPLC.

In another illustrative embodiment, the peptidomimetic can be derived as a retro-enantio analog of the peptide, such as the exemplary retro-enantio peptide analog:

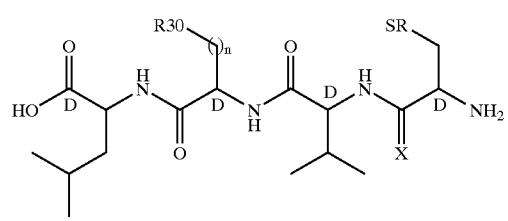

Retro-enantio analogs such as this can be synthesized using D-enantiomers of commercially available D-amino acids or other amino acid analogs and standard solid- or solution-phase peptide-synthesis techniques. The side-chains of the resulting peptide are coincident in space with the sidechains of the L-amino acid peptide, though the backbone amide is reversed, rendering that bond resistant to cleavage.

In still another illustrative embodiment, trans-olefin derivatives can be made with the subject peptide analogs. For example, an exemplary olefin analog is:

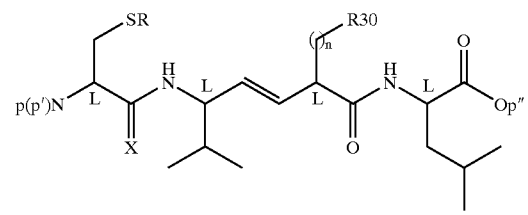

The trans-olefin analog of a cysteine-containing peptide can be synthesized according to the method of Y. K. Shue et al. (1987) *Tetrahedron Letters* 28:3225. The following example is illustrative:

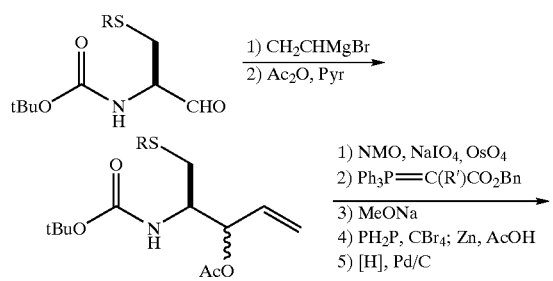

-continued

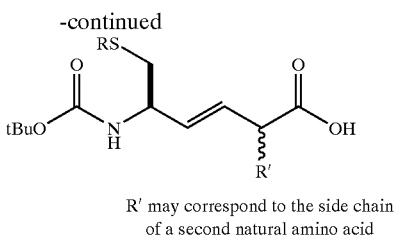

R' may correspond to the side chain of a second natural amino acid

Another relevant class of peptidomimetic derivatives is the phosphonates. The utility of phosphonic acids as peptide analogues derives, to a great extent, from the similarities between α-amino carboxylic acids and α-amino phosphonic acids. Significant progress has been reported recently in the synthesis of enantiomerically-pure α-amino phosphonic acids (see: Smith et al. *Org. Synth.* 1997, 75, 19–30; and references cited therein). In certain embodiments, the peptidomimetic will comprise a phosphonamide linkage in place of the natural amide linkage. Any amide linkage in a given peptide may be replaced with a phosphonamide linkage; the tetrapeptide analog below serves as an illustrative embodiment:

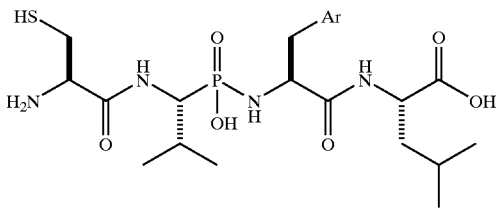

The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

In certain embodiments, the ability of fungal cells to transport ectopically added compounds, particularly peptide or peptide-like compounds, can be enhanced by conjugation of the compound with an amino acid residue or oligopeptide (preferably a dipeptide or tripeptide) which is itself taken-up by the fungal cell in a permease-mediated transport mechanism. Thus, another aspect of the invention features fungal prenyltransferase inhibitors which include a "permease tag", e.g., which comprises an amino acid residue, dipeptide or tripeptide which facilitates permease-mediated transport of the inhibitor into the fungal pathogen. Such compounds can have desirable pharmacokinetic properties due to, for example, increased bioavailability and/or increased selectivity. With regard to the latter, in preferred embodiments, the permease tag does not increase the cellular uptake of the inhibitor by mammalian cells to any greater degree than it does for cellular uptake by the fungal pathogen, though in the most preferred embodiments, the permease tag increases the uptake by fungal cells to a greater degree than for uptake by mammalian cells.

In another embodiments, the permease tag is removed from the inhibitor as a result of its permease-mediated transport into the fungal pathogen.

In other embodiments the amino acid or oligopeptide of the permease tag includes a free N-terminal amine, or a group hydrolyzable thereto under the conditions that the pathogen is contacted with the inhibitor.

As demonstrated in the appended examples, in one embodiment the permease tag facilitates permease-mediated transport by an alanine transporter of the fungal pathogen. For example, the inhibitor is derivatized at a free amine with L-alanine, or a dipeptide or tripeptide including L-alanine. In preferred embodiments, the L-alanine moiety is attached to the prenyltransferase inhibitor through an amide linkage through either an amine or carboxyl group of the inhibitor, and provides the complementary functionality in the permease tag. For instance, the L-alanine containing permease tag is provided by derivatization of a free amine on the inhibitor with a carboxyl group on an L-alanine containing oligopeptide, with the oligopeptide providing a free amine (or a group which is hydrolyzable thereto).

Other Candida permeases are known in the art, and appropriate permease tags can be generated for facilitating uptake of the subject inhibitors by other permease-mediated mechanisms. For instance, the permease tag can selected to increase uptake of the inhibitor by any one of the following Candida permeases:

| reference | permease |
|---|---|
| Mukherjee et al. (1998) Yeast 14:335–45 | Arginine permease |
| Matijekova et al. (1997) FEBS Lett 408:89–93 | *Candida albicans* CAN1 gene, encoding a high-affinity permease for arginine, lysine and histidine |
| Jethwaney et al. (1997) Microbiology 143:397 | Proline permease |
| Grobler et al. (1995) Yeast 11:1485 | mael gene, permease for malate and other C4 dicarboxylic acids |
| Sen Gupta et al. (1995) FEMS Microbiol Lett 126:93 | purine permease |
| Sychrova et al. (1993) Curr Genet 24:487 | lysine-permease |

Moreover, many more permeases have been identified in *S. cervesiae* through various genomic projects. Applicants contemplate that the subject permease tags can be selected to increase permease-mediated uptake by a mechanism relying on a Candida homolog of any one of the following *S. cerevisae* permeases:

| Cerevisae gene | transporter activity |
|---|---|
| AGP1 | asparagine and glutamine permease |
| DIP5 | dicarboxylic amino acid permease |
| MUP1 | high affinity methionine permease |
| TAT2 | high affinity tryptophan transport protein |
| GNP1 | high-affinity glutamine permease |
| ALP1 | high-affinity permease for basic amino acids |
| HIP1 | histidine permease |
| STP4 | involved in pre-tRNA splicing and in uptake of branched-chain amino acids |
| BAP2 | leucine permease, high-affinity (S1) |
| LYP1 | lysine-specific high-affinity permease |
| ARG11 | member of the mitochondrial carrier family (MCF) |
| PUT4 | proline and gamma-aminobutyrate permease |
| BAP3 | valine transporter |

Pharmaceutical Compositions In another aspect, the present invention provides pharmaceutically acceptable compositions which comprise a therapeutically-effective amount of one or more GGPTase inhibitors, such as described above, formulated together with one or more pharmaceutically acceptable carriers (additives) and/or diluents for use in the treatment of fungal infections. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The phrase "therapeutically-effective amount" as used herein means that amount of a compound, material, or composition comprising a GGPTase inhibitor according to the present invention which is effective for producing some desired therapeutic effect by inhibiting fungal cell wall biosynthesis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present GGPTase-inhibitors may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of GGPTase inhibitors. These salts can be prepared in situ during the final isolation and purification of the peptidomimetics of the invention, or by separately reacting a purified peptidomimetic of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a GGPTase inhibitor. These salts can likewise be prepared in situ during the final isolation and purification of the peptides or peptidomimetics, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the GGPTase inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a peptide or peptidomimetic of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A peptide or peptidomimetic of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active GGPTase inhibitor (s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a peptide or peptidomimetic of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active GGPTase inhibitor, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the peptidomimetic in the proper medium. Absorption enhancers can also be used to increase the flux of the drug across the skin. The rate of such flux can be controlled by either providing a rate controlling membrane or dispersing the peptidomimetic in a polymer matrix or gel.

Opthalmic formulations, eye ointments, powders, solutions and the like, are also contemplated as being within the scope of this invention.

Pharmaceutical compositions of this invention suitable for parenteral administration comprise one or more peptides or peptidomimetics of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsuled matrices of the subject peptides or peptidomimetics in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the GGPTase inhibitors useful in the subject method may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response, e.g., antimycotic activity, for a particular patient, composition, and mode of administration, without being toxic to the patient.

The selected dosage level will depend upon a variety of factors including the activity of the particular GGPTase inhibitor employed, or the ester, salt or amide thereof, the route of administration, the time of administration, the rate of excretion of the particular compound being employed, the duration of the treatment, other drugs, compounds and/or materials used in combination with the particular inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a potent GGPTase inhibitor, e.g., having an $EC_{50}$ in the range of 1 mM to sub-nanomolar, will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated antifungal effects, will range from about 0.0001 to about 1000 mg per kilogram of body weight per day, though preferably 0.5 to 300 mg per kilogram.

If desired, the effective daily dose of the active inhibitor may be administered as two, three, four, five, six or more sub-doses administered separately at appropriate intervals throughout the day, optionally, in unit dosage forms.

In a preferred embodiment, the antifungal agent is formulated for oral administration, as for example in the form of a solid tablet, pill, capsule, caplet or the like (collectively hereinafter "tablet") or an aqueous solution or suspension. In a preferred embodiment of the tablet form of the antifungal agent, the tablets are preferably formulated such that the amount of antifungal agent (or antifungal agents) provided in 20 tablets, if taken together, would provide a dose of at least the median effective dose ($ED_{50}$), e.g., the dose at which at least 50% of individuals exhibited the quantal effect of inhibition of fungal cell growth or protection (e.g., a statistically significant reduction in infection). More preferably, the tablets are formulated such that the total amount of antifungal agent (or antifungal agents) provided in 10, 5, 2 or 1 tablets would provide at least an $ED_{50}$ dose to a patient (human or non-human mammal). In other embodiments, the amount of antifungal agent (or antifungal agents) provided in 20, 10, 5 or 2 tablets taken in a 24 hour time period would provide a dosage regimen providing, on average, a mean plasma level of the antifungal agent(s) of at least the $ED_{50}$ concentration (the concentration for 50% of maximal effect of, e.g., inhibiting fungal cell growth), though preferably less than 100 times the $ED_{50}$, and even more preferably less than 10 or 5 times the $ED_{50}$. In preferred embodiments, a single dose of tablets (1–20 tablets) provides about 0.25 mg to 1250 mg of an antifungal agent(s).

Likewise, the antifungal agents can be formulated for parenteral administration, as for example, for subcutaneous, intramuscular or intravenous injection, e.g., the antifungal agent can be provided in a sterile solution or suspension (collectively hereinafter "injectable solution"). The injectable solution is preferably formulated such that the amount of antifungal agent (or antifungal agents) provided in a 200 cc bolus injection would provide a dose of at least the median effective dose, though preferably less than 100 times the $ED_{50}$, and even more preferably less than 10 or 5 times the $ED_{50}$. More preferably, the injectable solution is formulated such that the total amount of antifungal agent (or antifungal agents) provided in 100, 50, 25, 10, 5, 2.5, or 1 cc injections would provide an $ED_{50}$ dose to a patient, and preferably less than 100 times the $ED_{50}$, and even more preferably less than 10 or 5 times the $ED_{50}$. In other embodiments, the amount of antifungal agent (or antifungal agents) provided in a total volume of 100 cc, 50, 25, 5 or 2 cc to be injected at least twice in a 24 hour time period would provide a dosage regimen providing, on average, a mean plasma level of the antifungal agent(s) of at least the $ED_{50}$ concentration, though preferably less than 100 times the $ED_{50}$, and even more preferably less than 10 or 5 times the $ED_{50}$. In preferred embodiments, a single dose injection provides about 0.25 mg to 1250 mg of antifungal agent.

For continuous intravenous infusion, e.g., drip or push, the antifungal agent can be provided in a sterile dilute solution or suspension (collectively hereinafter "i.v. injectable solution"). The i.v. injectable solution is preferably formulated such that the amount of 0–86- I antifungal agent (or antifungal agents) provided in a 1 L solution would provide a dose, if administered over 15 minutes or less, of at least the median effective dose, though preferably less than 100 times the $ED_{50}$, and even more preferably less than 10 or 5 times the $ED_{50}$. More preferably, the i.v. injectable solution is formulated such that the total amount of antifungal agent (or antifungal agents) provided in IL solution administered over 60, 90, 120 or 240 minutes would provide an $ED_{50}$ dose to a patient, though preferably less than 100 times the $ED_{50}$, and even more preferably less than 10 or 5 times the $ED_{50}$. In preferred embodiments, a single i.v. "bag" provides about 0.25 mg to 5000 mg of antifungal agent per liter i.v. solution, more preferably 0.25 mg to 2500 mg, and even more preferably 0.25 mg to 1250 mg.

As discussed above, the preferred antifungal agent pharmaceutical preparation, whether for injection or oral delivery (or other route of administration), would provide a dose less than the $ED_{50}$ for modulation of FPTase and/or GGPTase activity in the host, more preferably at least 1 order of magnitude less, more preferably at least 2, 3 or 4 orders magnitude less.

An $ED_{50}$ dose, for a human, is based on a body weight of from 10 lbs to 250 lbs, though more preferably for an adult in the range of 100 to 250 lbs.

Potential antifungal agents can be assessed for $ED_{50}$ values for both antifungal activity, as well as activity arising from inhibition of mammalian FPTase or GGPTase activity in a host organism using any of a number of well known techniques in the art.

Identiying Candidate Antifungal Agents

There are a variety of assay formats for testing compounds for appropriate fungal GGPTase inhibitory activity, whether they be peptide or non-peptide. In general, the GGPTase inhibitor(s) selected for use in the subject method will be orders of magnitude better inhibitors of a fungal GGPTase than a mammalian GGPTase, and/or have greater membrane permeance through a fungal cell wall than a mammalian cell membrane.

In general, candidate inhibitors of GGPTase will be screened for activity in appropriate fungal assays. Compounds that display desired characteristics in a given assay may serve as lead compounds for the discovery of more potent inhibitors. Additionally, compounds active against fungal GGPTase will be screened independently against mammalian GGPTases. The present invention is not limited in terms of the methods relied upon for pinpointing potent inhibitors. Compounds selected based on their activity in vitro will be screened subsequently in vivo.

In one embodiment, a candidate GGPTase inhibitor can be tested in an assay comprising a prenylation reaction system that includes a fungal geranylgeranyl protein transferase (GGPTase), a fungal GTPase protein, or a portion thereof, which serves as a prenylation target substrate, and an activated geranylgeranyl moiety which can be covalent attached to the prenylation substrate by the GGPTase. The level of prenylation of the target substrate brought about by the system is measured in the presence and absence of a candidate agent, and a statistically significant decrease in the level prenylation is indicative of a potential anti-fungal activity for the candidate agent.

As described below, the level of prenylation of the GTPase target protein can be measured by determining the actual concentration of substrate:geranylgeranyl conjugates formed; or inferred by detecting some other quality of the target substrate affected by prenylation, including membrane localization of the target. In certain embodiments, the present assay comprises an in vivo prenylation system, such as a cell able to conduct the target substrate through at least a portion of a geranylgeranyl conjugation pathway. In other embodiments, the present assay comprises an in vitro prenylation system in which at least the ability to transfer isoprenoids to the GTPase target protein is constituted. Still other embodiments provide assay formats which detect protein-protein interaction between the GGPTase and a target protein, rather than enzymatic activity per se.

Cell-free Assay Formats

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins or cell-lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, a reaction mixture is generated to include a fungal GTPase polypeptide, compound(s) of interest, and a "target polypeptide", e.g., which includes GGPTase activities such as GGPTase I. Detection and quantification of the enzymatic conversion of the fungal GTPase, or the formation of complexes containing the fungal GTPase protein, provide a means for determining a compound's efficacy at inhibiting (or potentiating) the complex bioactivity of the GTPase. The efficacy of the compound can be assessed by generating dose response curves from data obtained using various concentrations of the test compound. Moreover, a control assay can also be performed to provide a baseline for comparison.

In one embodiment, the subject drug screening assay comprises a prenylation system, e.g. a reaction mixture which enzymatically conjugates isoprenoids to a target protein, which is arranged to detect inhibitors of the prenylation of a Rho-like GTPase with a geranylgeranyl group. For instance, in one embodiment of a cell-free prenylation system, one or more cell lysates including a fungal GGPTase, a fungal Rho-like GTPase (or substrate analog thereof), and an activated geranylgeranyl group are incubated with the test compound and the level of prenylation of the Rho-like GTPase substrate is detected. Lysates can be derived from cells expressing one or more of the relevant proteins, and mixed appropriately (or split) where no single lysate contains all the components necessary for generating the prenylation system. In preferred embodiments, one or more of the components, especially the substrate target, are recombinantly produced in a cell used to generate a lysate, or added by spiking a lysate mixture with a purified or semi-purified preparation of the substrate. These embodiments have several advantages including: the ability to use a labeled substrate, e.g. a dansylated peptide, or fusion protein for facilitating purification e.g. a Rho1-GST fusion protein; the ability to carefully control reaction conditions with respect to concentrations of reactants; and where targets are derived from fungal pathogens, the ability to work in a non-pathogenic system by recombinantly or synthetically by producing components from the pathogen for constituting the prenylation system.

The prenylates can be derived from any number of cell types, ranging from bacterial cells to yeast cells to cells from metazoan organisms including insects and mammalian cells. To illustrate, a fungal prenylation system can be reconstituted by mixing cell lysates derived from insect cells expressing fungal GGPTase subunits cloned into baculoviral expression vectors. For example, the exemplary GGPTase-I expression vectors described below can be recloned into baculoviral vectors (e.g. pVL vectors), and recombinant GGPTase-I produced in transfected *Spodoptera fungiperda* cells. The level of activity can be assessed by enzymatic activity, or by quantitating the level of expression by detecting, e.g., an exogenous tag added to the recombinant protein. Substrate and activated geranylgeranyl diphosphate can be added to the lysate mixtures. As appropriate, the transfected cells can be cells which lack an endogenous GGPTase activity, or the substrate can be chosen to be particularly sensitive to prenylation by the exogenous fungal GGPTase relative to any endogenous activity of the cells.

In other cell-free embodiments of the present assay, the prenylation system comprises a reconstituted protein mixture of at least semi-purified proteins. By semi-purified, it is meant that the proteins utilized in the reconstituted mixture have been previously separated from other cellular proteins. For instance, in contrast to cell lysates, the proteins involved in conjugation of geranylgeranyl moieties to a target protein, together with the target protein, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins which might interfere with or otherwise alter the ability to measure specific prenylation rates of the target GTPase substrate.

In the subject method, prenylation systems derived from purified proteins may have certain advantages over cell lysate based assays. Unlike the reconstituted protein system, the prenylation activity of a cell-lysate may not be readily controlled. Measuring kinetic parameters is made tedious by the fact that cell lysates may be inconsistent from batch to batch, with potentially significant variation between preparations. In vitro evidence indicates that prenyltransferases have the ability to cross-prenylate CAAX-related sequences, so that farnesyl transferase present in a lysate may provide an unwanted kinetic parameter. Moreover, cycling of prenylated proteins by guanine nucleotide dissociation inhibitor (GDI)-like proteins in the lysate could further complicate kinetics of the reaction mixture. Evaluation of a potential inhibitor using a lysate system is also complicated in those circumstances where the lysate is charged with mRNA encoding the GTPase substrate polypeptide or GGPTase activity, as such lysates may continue to synthesize proteins active in the assay during the development period of the assay, and can do so at unpredictable rates. Knowledge of the concentration of each component of the prenylation system can be required for each lysate batch, along with the overall kinetic data, in order to determine the necessary time course and calculate the sensitivity of experiments performed from one lysate preparation to the next. The use of reconstituted protein mixtures can allow more careful control of the reaction conditions in the prenylation reaction.

The purified protein mixture includes a purified preparation of the substrate polypeptide and a geranylgeranyl isoprenoid (or analog thereof) under conditions which drive the conjugation of the two molecules. For instance, the mixture can include a fungal GGPTase I complex including RAM2 and CDC43 subunits, a geranylgeranyl diphosphate, a divalent cation, and a substrate polypeptide, such as may be derived from Rho1.

Prenylation of the target regulatory protein via an in vitro prenylation system, in the presence and absence of a candidate inhibitor, can be accomplished in any vessel suitable for containing the reactants. Examples include microtitre plates, test tubes, and micro-centrifuge tubes. In such embodiments, a wide range of detection means can be practiced to score for the presence of the prenylated protein.

In one embodiment of the present assay, the products of a prenylation system are separated by gel electrophoresis, and the level of prenylated substrate polypeptide assessed, using standard electrophoresis protocols, by measuring an increase in molecular weight of the target substrate that corresponds to the addition of one or more geranylgeranyl moieties. For example, one or both of the target substrate and geranylgeranyl group can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to prenylation or degradation under the conditions which the assay is performed. Similarly, other means of detecting electrophoretically separated proteins can be employed to quantify the level of prenylation of the target substrate, including immunoblot analysis using antibodies specific for either the target substrate or geranylgeranyl epitopes.

As described below, the antibody can be replaced with another molecule able to bind one of either the target substrate or the isoprenoid. By way of illustration, one embodiment of the present assay comprises the use of a biotinylated target substrate in the conjugating system. Indeed, biotinylated GGPTase substrates have been described in the art (c.f. Yokoyama et al. (1995) *Biochemistry* 34:1344–1354). The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the target substrate and geranylgeranyl conjugates in the gel by standard staining protocols, including coomassie blue and silver staining.

In a similar fashion, prenylated and unprenylated substrate can be separated by other chromatographic techniques, and the relative quantities of each determined. For example, HPLC can be used to quantitate prenylated and unprenylated substrate (Pickett et al. (1995) *Analytical Biochem* 225:60–63), and the effect of a test compound on that ratio determined.

In another embodiment, an immunoassay or similar binding assay, is used to detect and quantify the level of prenylated target substrate produced in the prenylation system. Many different immunoassay techniques are amenable for such use and can be employed to detect and quantitate the conjugates. For example, the wells of a microtitre plate (or other suitable solid phase) can be coated with an antibody which specifically binds one of either the target substrate or geranylgeranyl groups. After incubation of the prenylation system with and without the candidate agent, the products are contacted with the matrix bound antibody, unbound material removed by washing, and prenylated conjugates of the target substrate specifically detected. To illustrate, if an antibody which binds the target substrate is used to sequester the protein on the matrix, then a detectable anti-geranylgeranyl antibody can be used to score for the presence of prenylated target substrate on the matrix.

Still a variety of other formats exist which are amenable to high through put analysis on microtitre plates or the like. The prenylation substrate can be immobilized throughout the reaction, such as by cross-linking to activated polymer, or sequestered to the well walls after the development of the prenylation reaction. In one illustrative embodiment, a Rho-like GTPase, e.g. a fungal Rho1, Rho2, Cdc42 or Rsr1/Bud1, is cross-linked to the polymeric support of the well, the prenylation system set up in that well, and after completion, the well washed and the amount of geranylgeranyl sidechains attached to the immobilized GTPase detected. In another illustrative embodiment, wells of a microtitre plate are coated with streptavidin and contacted with the developed prenylation system under conditions wherein a biotinylated substrate binds to and is sequestered in the wells. Unbound material is washed from the wells, and the level of prenylated target substrate is detected in each well. There are, as evidenced by this specification, a variety of techniques for detecting the level of prenylation of the immobilized substrate. For example, by the use of dansylated (described infra) or radiolabelled geranylgeranyl diphosphate in the reaction mixture, addition of appropriate scintillant to the wells will permit detection of the label directly in the microtitre wells. Alternatively, the substrate can be released and detected, for example, by any of those means described above, e.g. by radiolabel, gel electrophoresis, etc. Reversibly bound substrate, such as the biotin-conjugated substrate set out above, is particularly amenable to the latter approach. In other embodiments, only the geranylgeranyl moiety is released for detection. For instance, the thioether linkage of the isoprenoid with the substrate peptide sequence can be cleaved by treatment with methyl iodide. The released geranylgeranyl products can be detected, e.g., by radioactivity, HPLC, or other convenient format.

Other geranylgeranyl derivatives include detectable labels which do not interfere greatly with the conjugation of that group to the target substrate. For example, in an illustrative embodiment, the assay format provides fluorescence assay which relies on a change in fluorescent activity of a group associated with a GGPTase substrate to assess test compounds against a fungal GGPTase. To illustrate, GGPTase-I activity can be measured by a modified version of the continuous fluorescence assay described for farnesyl transferases (Cassidy et al., (1985) *Methods Enzymol.* 250: 30–43; Pickett et al. (1995) *Analytical Biochem* 225:60–63; and Stirtan et al. (1995) *Arch Biochem Biophys* 321:182–190). In an illustrative embodiment, dansyl-Gly-Cys-Ile-Ile-Leu (d-GCIIL) and the geranylgeranyl diphosphate are added to assay buffer, along with the test agent or control. This mixture is preincubated at 30° C. for a few minutes before the reaction is initiated with the addition of GGPTase enzyme. The sample is vigorously mixed, and an aliquot of the reaction mixture immediately transferred to a prewarmed cuvette, and the fluorescence intensity measured for 5 minutes. Useful excitation and emission wavelengths are 340 and 486 nm, respectively, with a bandpass of 5.1 nm for both excitation and emission monochromators. Generally, fluorescence data are collected with a selected time increment, and the inhibitory activity of the test agent is determined by detecting a decrease in the initial velocity of the reaction relative to samples which lack a test agent.

In yet another embodiment, the geranylgeranyl transferase activity against a particular substrate can be detected in the subject assay by using a phosphocellulose paper absorption system (Roskoski et al. (1994) *Analytical Biochem* 222:275–280), or the like. To effect binding of a peptidyl substrate to phosphocellulose at low pH, several basic residues can be added, preferably to the amino-terminal side of the CAAX target sequence of the peptide, to produce a peptide with a minimal minimum charge of +2 or +3 at pH less than 2. This follows the strategy used for the phosphocellulose absorption assay for protein kinases. In an illustrative embodiment; the transfer of the [$H^3$] geranylgeranyl group from [$H^3$]-geranylgeranyl pyrophosphate to KLKCAIL or other acceptor peptides can be measured under conditions similar to the farnesyl transferase reactions described by Reiss et al. (Reiss et al., (1990) *Cell* 62: 81–88) In an illustrative embodiment, reaction mixtures can be generated to contain 50 mM Tris-HCL (pH 7.5), 50 µM $ZnCl_2$, 20 mM KCl, 1 mM dithiothreitol, 250 µM KLKCAIL, 0.4 gM [$H^3$] geranylgeranyl pyrophosphate, and 10–1000 µg/ml of purified fungal GGPTase protein. After incubation, e.g., for 30 minutes at 37° C., samples are applied to Whatman P81 phosphocellulose paper strips. After the liquid permeates the paper (a few seconds), the strips are washed in ethanol/phosphoric acid (prepared by mixing equal volumes of 95% ethanol and 75 mM phosphoric acid) to remove unbound isoprenoids. The samples are air dried, and radioactivity can be measured by liquid scintillation spectrometry. Background values are obtained by using reaction mixture with buffer in place of enzyme.

An added feature of this strategy is that it produces hydrophilic peptides that are more readily dissolved in water. Moreover, the procedure outlined above works equally well for protein substrates (most proteins bind to phosphocellulose at acidic pH), so should be useful where full length protein, e.g., Rho1 or Cdc42, are utilized as the GGPTase substrate.

Cell-based Assay Formats

In other embodiments, compounds for use in the subject method can be detected using a screening assay derived to include a whole cell expressing a fungal GTPase protein, along with a GGPTase. In preferred embodiments, the reagent cell is a non-pathogenic cell which has been engineered to express one or more of these proteins from recombinant genes cloned from a pathogenic fungus. For example, non-pathogenic fungal cells, such as *S. cerevisae*, can be derived to express a Rho-like GTPase from a fungal pathogen such as *Candida albicans*. Furthermore, the reagent cell can be manipulated, particularly if it is a yeast cell, such that the recombinant gene(s) complement a loss-of-function mutation to the homologous gene in the reagent cell. In an exemplary embodiment, a non-pathogenic yeast cell is engineered to express a Rho-like GTPase, e.g. Rho1, and at least one of the subunits of a GGPTase, e.g. RAM2 and/or Cdc43, derived from a fungal protein. One salient feature to such reagent cells is the ability of the practitioner to work with a non-pathogenic strain rather than the pathogen itself. Another advantage derives from the level of knowledge, and available strains, when working with such reagent cells as *S. cerevisae*.

The ability of a test agent to alter the activity of the GTPase protein can be detected by analysis of the cell or products produced by the cell. For example, agonists and antagonists of the GTPase biological activity can be detected by scoring for alterations in growth or viability of the cell. Other embodiments will permit inference of the level of GTPase activity based on, for example, detecting expression of a reporter, the induction of which is directly or indirectly dependent on the activity of a Rho-like GTPase. General techniques for detecting each are well known, and will vary with respect to the source of the particular reagent cell utilized in any given assay.

For example, quantification of proliferation of cells in the presence and absence of a candidate agent can be measured with a number of techniques well known in the art, including simple measurement of population growth curves. For instance, where the assay involves proliferation in a liquid medium, turbidimetric techniques (i.e. absorption/transmission of light of a given wavelength through the sample) can be utilized. For example, in the instance where the reagent cell is a yeast cell, measurement of absorption of light at a wavelength between 540 and 600 nm can provide a conveniently fast measure of cell growth. Likewise, ability to form colonies in solid medium (e.g. agar) can be used to readily score for proliferation. In other embodiments, a GTPase substrate protein, such as a histone, can be provided as a fusion protein which permits the substrate to be isolated from cell lysates and the degree of acetylation detected. Each of these techniques are suitable for high through-put analysis necessary for rapid screening of large numbers of candidate agents.

Additionally, visual inspection of the morphology of the reagent cell can be used to determine whether the biological activity of the targeted GTPase protein has been affected by the added agent. To illustrate, the ability of an agent to create a lytic phenotype which is mediated in some way by a recombinant GTPase protein can be assessed by visual microscopy.

The nature of the effect of test agent on reagent cell can be assessed by measuring levels of expression of specific genes, e.g., by reverse transcription-PCR. Another method of scoring for effect on GTPase activity is by detecting cell-type specific marker expression through immunofluorescent staining. Many such markers are known in the art, and antibodies are readily available.

In yet another embodiment, in order to enhance detection of cell lysis, the target cell can be provided with a cytoplasmic reporter which is readily detectable, either because it has "leaked" outside the cell, or substrate has "leaked" into the cell, by perturbations in the cell wall. Preferred reporters are proteins which can be recombinantly expressed by the target cell, do not interfere with cell wall integrity, and which have an enzymatic activity for which chromogenic or fluorogenic substrates are available. In one example, a fungal cell can be constructed to recombinantly express the β-galactosidase gene from a construct (optionally) including an inducible promoter. At some time prior to contacting the cell with a test agent, expression of the reporter protein is induced. Agents which inhibit prenylation of a Rho-like GTPase in the cell, or the subsequent involvement of a Rho-like GTPase in cell wall integrity, can be detected by an increase in the reporter protein activity in the culture supernatant or from permeation of a substrate in the cell. Thus, for example, β-galactosidase activity can be scored using such colorimetric substrates as 5-bromo-4-chloro-3-indolyl-β-D-galactopyranoside or fluorescent substrates such as methylumbelliferyl-β-D-galactopyranoside. Permeation of the substrate into the cell, or leakage of the reporter into the culture media, is thus readily detectable.

In still another embodiment, the membrane localization resulting from prenylation of the fungal GTPase can be exploited to generate the cell-based assay. For instance, the subject assay can be derived with a reagent cell having: (i) a reporter gene construct including a transcriptional regulatory element which can induce expression of the reporter upon interaction of the transcriptional regulatory protein portion of the above fusion protein. For example, a gal4 protein can be fused with a Rho1 polypeptide sequence which includes the CAAX prenylation target. In the absence of inhibitors of GGPTase activity in the reagent cell, prenylation of the fusion protein will result in partitioning of the fusion protein at the cell surface membrane. This provides a basal level of expression of the reporter gene construct. When contacted with an agent that inhibits prenylation of the fusion protein, partitioning is lost and, with the concomitant increase in nuclear concentration of the protein, expression from the reporter construct is increased.

In a preferred embodiment, the cell is engineered such that inhibition of the GGPTase activity does not result in cell lysis. For example, as described in Ohya et al. (1993) *Mol Cell Biol* 4:1017–1025, mutation of the C-terminus of Rho1 and cdc42 can provide proteins which are targets of farsenyl transferase rather than geranylgeranyl transferase. As Ohya et al. describe, such mutants can be used to render the GGPTase I activity dispensable. Accordingly, providing a reporter gene construct and an expression vector for the GGPTase substrate/transcription factor fusion protein in such cells as YOT35953 cells (Ohya et al., supra) generates a cell whose viability vis-a-vis the GGPTase activity is determined by the reporter construct, if at all, rather than by prenylation of an endogenous Rho-like GTPase by the GGPTase. Of course, the reporter gene product can be derived to have no effect on cell viability, providing for example another type of detectable marker (described, infra). Such cells can be engineered to express an exogenous GGPTase activity in place of an endogenous activity, or can rely on the endogenous activity. To further illustrate, the Call mutant YOT35953 cell can be further manipulated to express a Call homolog from, e.g., a fungal pathogen or a mammalian cell.

Alternatively, where inhibition of a GGPTase activity causes cell lysis and reporter gene expression, the leakage assay provided above can be utilized to detect expression of the reporter protein. For instance, the reporter gene can encode β-galactosidase, and inhibition of the GGPTases activity scored for by the presence of cells which take up substrate due to loss of cell wall integrity, and convert substrate due to the expression of the reporter gene.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not.

The marker gene is coupled to GTPase-dependent activity, be it membrane association, or a downstream signaling pathway induced by a GTPase complex, so that expression of the marker gene is dependent on the activity of the GTPase. This coupling may be achieved by operably linking the marker gene to a promoter responsive to the therapeutically targeted event. The term "GTPase-responsive promoter" indicates a promoter which is regulated by some product or activity of the fungal GTPase. By this manner, the activity of a GGPTase can be detected by its effects on prenylation of GTPase and, accordingly, the downstream targets of the prenylated protein. Thus, transcriptional regulatory sequences responsive to signals generated by PKC/GTPase, GS/GTPase and/or other GTPase complexes, or to signals by other proteins in such complexes which are interrupted by GTPase binding, can be used to detect function of Rho-like GTPases such as Rho1 and cdc42.

In the case of yeast, suitable positively selectable (beneficial) genes include the following: URA3, LYS2, HIS3, LEU2, TRP1; ADE1, 2, 3, 4, 5, 7, 8; ARG1, 3, 4, 5, 6, 8; HIS1, 4, 5; ILV1, 2, 5; THR1, 4; TRP2, 3, 4, 5; LEU1, 4; MET2, 3, 4, 8, 9, 14, 16, 19; URA1, 2, 4, 5, 10; HOM3, 6; ASP3; CHO1; ARO 2, 7; CYS3; OLE1; INO1, 2, 4; PRO1, 3. Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation of the gene leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

The marker gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exbl gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). a preferred screenable marker gene is β-galactosidase; yeast cells expressing the enzyme convert the colorless substrate Xgal into a blue pigment.

It has also been observed in the art that mutations to Gsc1 (Fks1) confer hypersensitivity to the immunosuppressants FK506 and cyclosporin A (Douglas et al. (1994) *PNAS* 91:12907). The mechanism of action of such agents is understood to involve inhibition of expression of the Fks2 gene (Mazur et al. (1995) *Mol Cell Biol* 15:5671). Similar to the echinocandin-sensitivity assay embodiments provided above, another assay format provides a cell in which Fks2 activity is compromised. Synergism of the Fks2 impairment with a test compound can be used to identify inhibitors of, for example, the glucan synthase subunit Gsc1. For instance, FK506 or cyclosporin A can be used to impair Fks2 activity, as can mutations to calcineurin or to the Fks2 gene.

These observations also suggest that Call-1 cells or the like, e.g., impaired for certain GGPTase activities, are suitable for use in assay to detect GS inhibitors, as such cells are more sensitive to the effects of GS inhibitors. The benefits to enhanced sensitivity include speedier development of assay readouts, and the further prejudicing of the assay towards GS inhibitors rather than other targets which may not provide cytotoxicity. The latter can provide the ability to identify potential hits which may not themselves be potent GS inhibitors, but which can be manipulated, e.g., by combinatorial chemistry approaches, to provide potent and specific GS inhibitors.

Returning to the teachings of Ohya et al. (1993) supra, it is noted that there are only two essential targets of GGPTase in *S. cerevisae*, the Rho-like GTPases Rho1 and cdc42. With such observations in mind, yet another embodiment of the subject assay utilizes a side-by-side comparison of the effect of a test agent on (i) a cell which prenylates a Rho-like GTPase by adding geranylgeranyl moieties, and (ii) a cell which prenylates an equivalent Rho-like GTPase by adding farnesyl moieties. In particular, the assay makes use of the ability to suppress GGPTase I defects in yeast by altering the C-terminal tail of Rho1 and cdc42 to become substrate targets of famesyl transferase (see Ohya et al., supra). According to the present embodiment, the assay is arranged by providing a yeast cell in which the target Rho-like GTPases is prenylated by a GGPTase activity of the cell. Both the GGPTase and GTPase can be endogenous to the "test" cell, or one or both can be recombinantly expressed in the cell. The level of prenylation of the GTPase is detected, e.g., cell lysis or other means described above. The ability of the test compound to inhibit the addition of geranylgeranyl groups to the GTPase in the first cell is compared against the ability of test compound to inhibit the farnesylation of the GTPase in a control cell. The "control" cell is preferably identical to the test cell, with the exception that the targeted GTPase(s) are mutated at their CAAX sequence to become substrates for FPTases rather than GGPTases. Agents which inhibit prenylation in the test cell but not the control cell are selected as potential antifungal agents. Such differential screens can be exquisitely sensitive to inhibitors of GGPTase I prenylation of Rho-like GTPases. In a preferred embodiment, the test cell is derived from the *S. cerivisae* cell YOT35953 (Ohya et al., supra) or the like which is defective in GGPTase subunit cdc43. The cell is then engineered with a cdc43 subunit from a fungal pathogen such as *Candida albicans* to generate the test cell, and additionally with the mutated Rho-like GTPases to generate the control cell.

Differential Screening Formats

In a preferred embodiment, assays can be used to identify compounds that have therapeutic indexes more favorable than such antifungal. For instance, antifungal agents can be identified by the present assays which inhibit proliferation of yeast cells or other lower eukaryotes, but which have a substantially reduced effect on mammalian cells, thereby improving therapeutic index of the drug as an anti-mycotic agent.

Accordingly, differential screening assays can be used to exploit the difference in protein interactions and/or catalytic mechanism of mammalian and fungal GGPTases in order to identify agents which display a statistically significant increase in specificity for inhibiting the fungal prenylation reaction relative to the mammalian prenylation reaction. Thus, lead compounds which act specifically on the prenylation reaction in pathogens, such as fungus involved in mycotic infections, can be developed. By way of illustration, the present assays can be used to screen for agents which may ultimately be useful for inhibiting the growth of at least one fungus implicated in such mycosis as *candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis,* or *sporotrichosis.* For example, if the mycotic infection to which treatment is desired is candidiasis, the present assay can comprise comparing the relative effectiveness of a test compound on inhibiting the prenylation of a mammalian GTPase protein with its effectiveness towards inhibiting the prenylation of a GTPase from a yeast selected from the group consisting of *Candida albicans, Candida stellatoidea, Candida glabrata, Candida tropicalis, Candida parapsilosis, Candida krusei, Candida pseudotropicalis, Candida guilliermondii,* or *Candida rugosa.* Likewise, the present assay can be used to identify antifungal agents which may have therapeutic value in the treatment of aspergillosis by selectively targeting, relative to human cells, GTPase homologs from yeast such as *Aspergillus fumigatus, Aspergillus flavus, Aspergillus niger, Aspergillus nidulans,* or *Aspergillus terreus.* Where the mycotic infection is mucormycosis, the GTPase system to be screened can be derived from yeast such as *Rhizopus arrhizus, Rhizopus oryzae, Absidia corymbifera, Absidia ramosa,* or *Mucor pusillus.* Sources of other assay reagents for includes the pathogen *Pneumocystis carinii.*

III. Exemplification

The invention now being generally described, it will be more readily understood by reference to the following examples which are included merely for purposes of illustration of certain aspects and embodiments of the present invention, and are not intended to limit the invention.

a. Synthesis of Prenylation Inhibitors

Figure 56:
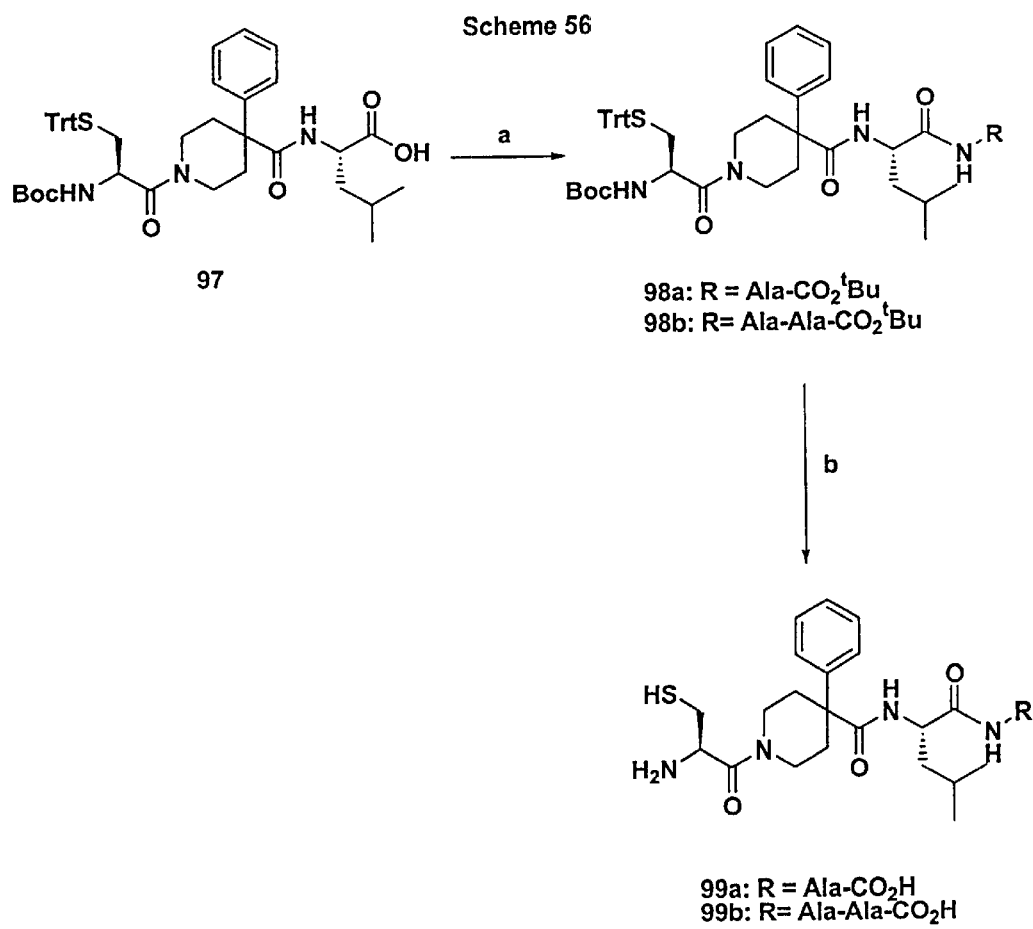

As described below, a variety of different compounds were synthesized and tested for inhibitory activity against human and Candida GGTase. Exemplary synthesis schemes for generating prenyltransferase inhibitors useful in the methods and compositions of the present invention are shown in FIGS. 1–56. Tables 1–5 provide Structure-Activity relationship (SAR) data for several different classes of prenyltransferase inhibitors.

The reaction conditions in the illustrated schemes of FIGS. 1–56 are as follows:
1) $R_1CH_2CN$, $NaNH_2$, toluene (Arzneim-Forsch, 1990, 40, 11, 1242)
2) $H_2SO_4$, $H_2O$, reflux (Arzneim-Forsch, 1990, 40, 11, 1242)
3) $H_2SO_4$, EtOH, reflux (Arzneim-Forsch, 1990, 40, 11, 1242)
4) NaOH, EtOH, reflux
5) $(Boc)_2O$, 2M NaOH, THF
6) LiHDMS, $R_1X$, THF (Merck Patent Applic # WO 96/06609)
7) Pd—C, $H_2$, MeOH
8) t-BuONO, CuBr, HBr, $H_2O$ (J. Org. Chem. 1977, 42, 2426)
9) $ArB(OH)_2$, $Pd(PPh_3)_4$, Dioxane (J. Med. Chem. 1996, 39, 217–223)
10) $R_{12}(H)C=CR_{13}R_{14}$, $Pd(OAc)_2$, $Et_3N$, DMF (Org. React. 1982, 27, 345)
11) $Tf_2O$, THF (J. Am. Chem. Soc. 1987, 109, 5478–5486)
12) $ArSnBu_3$, $Pd(PPh_3)_4$, Dioxane (J. Am. Chem. Soc. 1987, 109, 5478–5486)
13) $KMnO_4$, Py, $H_2O$ (J. Med. Chem. 1996, 39, 217–223)
14) $NaOR_1$, THF
15) $NaSR_1$, THF
16) $HNR_1R_{13}$, THF
17) HONO, $NaBF_4$ (Adv. Fluorine Chem. 1965, 4, 1–30)
18) $Pd(OAc)_2$, NaH, DPPF, $PhCH_3$, $R_1OH$ (J. Org. Chem. 1997, 62, 5413–5418)
19) i. $R_1X$, $Et_3N$, $CH_2Cl_2$, ii. $R_{13}X$
20) $SOCl_2$, cat DMF
21) $CH_2N_2$, $Et_2O$
22) $Ag_2O$, $Na_2CO_3$, $Na_2S_2O_3$, $H_2O$ (Tetrahedron Lett. 1979, 2667)
23) $AgO_2CPh$, $Et_3N$, MeOH (Org. Syn., 1970, 50, 77; J. Am. Chem. Soc. 1987, 109, 5432)
24) LiOH, THF-MeOH
25) $(EtO)_2P(O)CH_2CO_2R$, BuLi, THF
26) $MeO_2CCH(Br)=P(Ph)_3$, benzene
27) KOH or KOtBu
28) Base, $X(CH_2)_nCO_2R$
29) DPPA, $Et_3N$, toluene (Synthesis 1985, 220)
30) HONO, $H_2O$
31) $SO_2$, CuCl, HCl, $H_2O$ (Synthesis 1969, 1–10, 6)
32) Lawesson's reagent, toluene (Tetrahedron Asym. 1996, 7, 12, 3553)
33) $R_2M$, solvent
34) 30% $H_2O$, glacial $CH_3CO_2H$ (Helv. Chim. Acta. 1968, 349, 323)
35) triphosgene, $CH_2Cl_2$ (Tetrahedron Lett., 1996, 37, 8589)
36) i. $(EtO)_2P(O)CHLiSO_2Oi$-Pr, THF, ii. NaI
37) $Ph3PCH_3I$, $NaCH_2S(O)CH_3$, DMSO (Synthesis 1987, 498)
38) $Br_2$, $CHCl_3$ or other solvent (Synthesis 1987, 498)
39) BuLi, $Bu_3SnCl$
40) $ClSO_2OTMS$, $CCL_4$ (Chem. Ber. 1995, 128, 575–580)
41) MeOH—HCl, reflux
42) LAH, $Et_2O$ or $LiBH_4$, EtOH or $BH_3$-THF (Tetrahedron Lett., 1996, 37, 8589)

43) MsCl, Et$_3$N, CH$_2$Cl$_2$ (Tetrahedron Lett., 1996, 37, 8589)
44) Na$_2$SO$_3$, H$_2$O (Tetrahedron Lett., 1996, 37, 8589)
45) R$_2$R$_4$NH, Et$_3$N, CH$_2$Cl$_2$
46) R$_2$M, solvent
47) CH$_3$NH(OCH$_3$), EDC, HOBt, DIEA, CH$_2$Cl$_2$ or DMF (Tetrahedron Lett, 1981, 22, 3815)
48) MeLi, THF
49) mCPBA, CH$_2$Cl$_2$
50) HONO, Cu$_2$O, Cu(NO$_3$)$_2$, H$_2$O (J. Org. Chem. 1977, 42, 2053)
51) R$_1$M, solvent
52) HONO, NaS(S)COEt, H$_2$O (Org. Synth. 1947, 27, 81)
53) HSR$_2$ or HSR$_4$, CH$_2$Cl$_2$
54) i-BuOC(O)Cl, Et$_3$N, NH$_3$, THF
55) R$_2$R$_4$NH, CH$_2$Cl$_2$, NaBH(OAc)$_3$
56) R$_2$R$_4$NH, MeOH/CH$_3$CO$_2$H, NaBH$_3$CN
57) R$_2$OH, EDC, HOBt, DIEA, CH$_2$Cl$_2$ or DMF
58) R$_2$OH, HBTU, HOBt, DIEA, CH$_2$Cl$_2$ or DMF
59) R$_2$R$_4$NH, EDC, HOBt, DIEA, CH$_2$Cl$_2$ or DMF
60) R$_2$R$_4$NH, HBTU, HOBt, DIEA, CH$_2$Cl$_2$ or DMF
61) POCl$_3$, Py, CH$_2$Cl$_2$
62) R$_2$R$_4$NCO, solvent
63) R$_2$OC(O)Cl, Et$_3$N, solvent
64) R$_2$CO$_2$H, EDC or HBTU, HOBt, DIEA, CH$_2$Cl$_2$ or DMF
65) R$_2$X, Et$_3$N, solvent
66) (CH$_3$S)$_2$C=N(CN), DMF, EtOH (J. Med. Chem. 1994, 37, 57–66)
67) R$_2$SO$_2$Cl, Et$_3$N, CH$_2$Cl$_2$
68) R$_2$— or R$_3$— or R$_4$CHO, MeOH/CH$_3$CO$_2$H, NaBH$_3$CN (Synthesis 1975, 135–146)
69) Boc(Tr)-D or L-CysOH, HBTU, HOBt, DIEA, CH$_2$Cl$_2$ or DMF
70) Boc(Tr)-D or L-CysH, NaBH$_3$CN, MeOH/CH$_3$CO$_2$H (Synthesis 1975, 135–146)
71) S-Tr-N-Boc cysteinal, ClCH$_2$CH$_2$Cl or THF, NaBH(OAc)$_3$ (J. Org. Chem. 1996, 61, 3849–3862)
72) TFA, CH$_2$Cl$_2$, Et$_3$SiH or (3:1:1) thioanisole/ethanedithiol/DMS
73) TFA, CH$_2$Cl$_2$
74) DPPA, Et$_3$N, toluene, HOCH$_2$CH$_2$SiCH$_3$ (Tetrahedron Lett. 1984, 25, 3515)
75) TBAF, THF
76) Base, TrSH or BnSH
77) Base, R$_2$X or R$_4$X
78) R$_3$NH$_2$, MeOHWCH$_3$CO$_2$H, NaBH$_3$CN
79) N$_2$H$_4$, KOH
80) Pd2(dba)$_3$, P(o-tol)$_3$, RNH$_2$, NaOtBu, Dioxane, R$_1$NH$_2$ (Tetrahedron Lett. 1996, 37, 7181–7184).
81) Cyanamide.
82) Fmoc-Cl, sodium bicarbonate.
83) BnCOCl, sodium carbonate.
84) AllylOCOCl, pyridine.
85) Benzyl bromide, base.
86) Oxalyl chloride, DMSO.
87) RCONH$_2$.
88) Carbonyldiimidazole, neutral solvents (e.g. DCM, DMF, THF, toluene).
89) Thiocarbonyldiimidazole, neutral solvents (e.g. DCM, DMF, THF, toluene).
90) Cyanogen bromide, neutral solvents (e.g. DCM, DMF, THF, toluene).
91) RCOCl, Triethylamine
92) RNHNH$_2$, EDC.
93) RO$_2$CCOCl, Et$_3$N, DCM.
94) MsOH, Pyridine (J. Het. Chem., 1980, 607.)
95) Base, neutral solvents (e.g. DCM, toluene, THF).
96) H$_2$NOR, EDC.
97) RCSNH$_2$.
98) RCOCHBrR, neutral solvents (e.g. DCM, DMF, THF, toluene), (Org. Proc. Prep. Intl., 1992, 24, 127).
99) CH$_2$N$_2$, HCl. (Synthesis, 1993, 197).
100) NH2NHR, neutral solvents (e.g. DCM, DMF, THF, toluene).
101) RSO$_2$Cl, DMAP. (Tetrahedron Lett., 1993, 34, 2749).
102) Et$_3$N, RX. (J. Org. Chem., 1990, 55, 6037).
103) NOCl or Cl$_2$ (J. Org. Chem., 1990, 55, 3916).
104) H$_2$NOH, neutral solvents (e.g. DCM, DMF, THF, toluene).
105) RCCR, neutral solventss (DCM, THF, Toluene).
106) RCHCHR, neutral solventss (DCM, THF, Toluene).
107) H$_2$NOH, HCl.
108) Thiocarbonyldiimidazole, SiO$_2$ or BF$_3$OEt$_2$. (J. Med. Chem., 1996, 39, 5228).
109) Thiocarbonyldiimidazole, DBU or DBN. (J. Med. Chem., 1996, 39, 5228).
110) HNO$_2$, HCl.
111) ClCH$_2$CO$_2$Et (Org. Reactions, 1959, 10,143).
112) Morpholine enamine (Eur. J. Med. Chem., 1982, 17, 27).
113) RCOCHR'CN
114) RCOCHR'CO$_2$Et
115) Na$_2$SO$_3$
116) H$_2$NCHRCO$_2$Et
117) EtO$_2$CCHRNCO
118) RCNHNH$_2$.
119) RCOCO$_2$H, (J. Med. Chem., 1995, 38, 3741).
120) RCHO, KOAc.
121) 2-Fluoronitrobenzene.
122) SnCl$_2$, EtOH, DMF.
123) RCHO, NaBH$_3$CN, HOAc.
124) NH$_3$, MeOH.
125) 2,4,6-Me$_3$PhSO$_2$NH$_2$.
126) Et$_2$NH, CH$_2$Cl$_2$
127) MeOC(O)Cl, Et$_3$N, CH$_2$Cl$_2$
128) R$_2$NH$_2$, EDC, HOBT, Et$_3$N, CH$_2$Cl$_2$
129) DBU, PhCH$_3$
130) BocNHCH(CH$_2$STr)CH$_2$NH$_2$, EDC, HOBT, Et$_3$N, CH$_2$Cl$_2$
131) R$_2$NHCH$_2$CO$_2$Me, HBTU, HOBT, Et$_3$N, CH$_2$Cl$_2$
132) BocNHCH(CH$_2$STr)CH$_2$OMs, LiHMDS, THF
133) R$_2$NHCH$_2$CO$_2$Me, NaBH(OAc)$_3$, ClCH$_2$CH$_2$Cl or THF
134) R$_2$NHCH$_2$CH(OEt)$_2$, HBTU, HOBT, Et$_3$N, CH$_2$Cl$_2$
135) NaBH(OAc)$_3$, ClCH$_2$CH$_2$Cl or THF, AcOH.
136) Piperidine, DMF.
137) Pd(Ph$_3$P)$_4$, Bu$_3$SnH.
138) RCO$_2$H, EDC, HOBT, Et$_3$N, DCM.

Fmoc-1-Nal-Leu-O-Wang Resin (2): 300 mg (0.72 mmol/g) of Fmoc-Leu-O-Wang resin in an Irori MacroKan was treated with 20% piperidine/DMF solution for 35 min. The mixture was removed via filtration, and the resin was again treated with 20% piperidine/DMF solution for 35 min. The mixture was removed and the resin washed twice with DMF, three times with 1:1 methanol/dichloromethane, three times with dichloromethane, and then dried under vacuum. The resin was treated with 2.5 eq of Fmoc-1-Nal-OH, 3.0 eq of EDC, 3.0 eq of HOBT, 3.0 eq of DIEA and 20 mL of DMF overnight. The mixture was removed and the resin washed twice with DMF, three times with 1:1 methanol/dichloromethane, three times with dichloromethane, and then dried under vacuum.

Fmoc-AA-1-Nal-Leu-O-Wang Resin (3): The resin was treated with 20% piperidine/DMF solution for 35 min. The mixture was removed via filtration, and the resin was again treated with 20% piperidine/DMF solution for 35 min. The mixture was removed and the resin washed twice with DMF, three times with 1:1 methanol/dichloromethane, three times with dichloromethane, and then dried under vacuum. The resin was treated with 2.5 eq of Fmoc-AA-OH, 3.0 eq of EDC, 3.0 eq of HOBT, 3.0 eq of DIEA and 20 mL of DMF overnight. The mixture was removed and the resin washed twice with DMF, three times with 1:1 methanol/dichloromethane, three times with dichloromethane, and then dried under vacuum.

Boc(Tr)Cys-AA-1-Nal-Leu-O-Wang Resin (4): The resin was treated with 20% piperidine/DMF solution for 35 min. The mixture was removed via filtration, and the resin was again treated with 20% piperidine/DMF solution for 35 min. The mixture was removed and the resin washed twice with DMF, three times with 1:1 methanol/dichloromethane, three times with dichloromethane, and then dried under vacuum. The resin was treated with 2.5 eq of Boc(Tr)Cys-OH, 3.0 eq of EDC, 3.0 eq of HOBT, 3.0 eq of DIEA and 20 mL of DMF overnight. The mixture was removed and the resin washed twice with DMF, three times with 1:1 methanol/dichloromethane, three times with dichloromethane, and then dried under vacuum.

Cys-AA-1-Nal-Leu (5): The resin was treated with 13.5 mL of 1:1:0.1 mixture of TFA, dichloromethane and triethylsilane for 35 min. The mixture was removed via filtration and the resin treated again treated with 13.5 mL of 1:1:0.1 mixture of TFA, dichloromethane and triethylsilane for 35 min. The mixture was removed via filtration and the combined deprotection mixtures were evaporated under vacuum. The resulting residue was triturated with ether and dried to a fine powder under vacuum.

Compound 6: To a solution of Boc-2-napthylalanine (870 mg, 2.7 mmol) in $CH_2Cl_2$ (10 mL) was added the L-leucine methyl ester (500 mg, 2.7 mmol) followed by $Et_3N$ (0.4 mL, 2.7 mmol), EDC (530 mg, 2.7 mmol) and HOBt (370 mg, 2.7 mmol). The reaction mixture was stirred at room temperature for 2 h and poured into saturated sodium bicarbonate solution. The aqueous layer was extracted with methylene chloride. The organic extracts were dried and concentrated. The crude product was purified by silica gel chromatography (30% ethyl acetate/hexane) to give 6 (1.2 g).

Compound 7: To a solution of 6 (1.2 g) in $CH_2Cl_2$ (10 mL), was added TFA (10 mL). The reaction mixture was stirred at room temperature for 1 h. The solvents were removed under reduced pressure and the residue was dried under vacumn. The crude amine (720 mg, 1.6 mmol) was dissolved in methanol (10 mL). To this solution was added KOAc (470 mg, 4.8 mmol), followed by Boc valinal (900 mg, 4.8 mmol). Sodium cyanoborohydride (300 mg, 4 mmol) was added to this solution and reaction mixture was stirred at room temperature for 14 h. The reaction mixture was poured into saturated sodium bicarbonate solution. The aqueous layer was extracted with methylene chloride. The organic extracts were dried and concentrated. The crude product was purified by silica gel chromatography (30%–40% ethyl acetate/hexane) to give 7 (0.74 g).

Compound 8: To a solution of 7 (0.74 g) in $CH_2Cl_2$ (10 mL), was added TFA (10 mL). The reaction mixture was stirred at room temperature for 1 h. The solvents were removed under reduced pressure and the residue was dried under vacumn. The crude amine was dissolved in methanol (10 mL). To this solution was added KOAc (440 mg, 4.5 mmol), followed by S-Tr-N-Boc cysteinal (2 g, 4.5 mmol). Sodium cyanoborohydride (280 mg, 4.5 mmol) was added to this solution and reaction mixture was stirred at room temperature for 14 h. The reaction mixture was poured into saturated sodium bicarbonate solution. The aqueous layer was extracted with methylene chloride. The organic extracts were dried and concentrated. The crude product was purified by silica gel chromatography (30%–50% ethyl acetate/hexane) to give 8 (0.41 g).

Compound 9: To a solution of methyl ester 8 (200 mg, 0.23 mmol) in THF/MeOH (1:1, 8 mL) was added 1M LiOH solution (1.2 mL). The reaction mixture was stirred at room temperature for 15 h and poured into 10% citric acid solution. The aqueous layer was extracted with methylene chloride. The organic extracts were washed with water, dried and concentrated to give the acid. The acid was dissolved in $CH_2Cl_2$ (5 mL). To this solution was added TFA (5 mL) followed by $Et_3SiH$ (0.2 mL). The reaction mixture was stirred at room temperature for 2 h. The solvents were removed under reduced pressure. The residue was triturated with diethylether. The resulting solid was filtered, washed with ether and dried under vacuum to give 9 (67 mg).

Compound 10: Methyl ester 8 (200 mg) was dissolved in $CH_2Cl_2$ (5 mL). To this solution was added TFA (5 mL) followed by $Et_3SiH$ (0.1 mL). The reaction mixture was stirred at room temperature for 2 h. The solvents were removed under reduced pressure. The residue was triturated with diethyl ether/hexanes. The resulting solid was filtered, washed with ether and dried under vacuum to give 10 (90 mg).

Compound 11: A solution of 2-bromo-4-nitrotoluene (5 g, 23 mmol) and $Pd(PPh_3)_4$ (0.5 g, 0.45 mol) in DME (100 mL) was stirred at room temperature. Phenyl boronic acid (4 g, 32 mmol) was added to the reaction mixture, followed by 2M $Na_2CO_3$ solution (20 mL). The reaction mixture was heated at reflux for 15 h, cooled to room temperature and poured into saturated sodium bicarbonate solution. The aqueous layer was extracted with methylene chloride. The organic extracts were dried and concentrated. The crude product was purified by silica gel chromatography to give 11 (4.8 g).

Compound 12: A suspension of 2-phenyl-4-nitrotoluene 11 (1 g, 4.7 mmol) in pyridine (5 mL) and water (10 mL) was heated to reflux. Solid $KMnO_4$ was added to the reaction mixture and heating was continued at reflux for 3 h. The hot reaction mixture was filtered through a bed of celite and washed with hot water. The filtrate was acidified with concentrated HCl. The precipitated solid was filtered and dried under vacuum to give 12 (0.83 g).

Compound 13: To a solution of biphenyl acid 12 in $CH_2Cl_2$ was added the appropriate amine $R_1R_2R_3N$ (1.2 equiv) followed by DIEA (1.2 equiv), EDC (1.2 equiv) or HBTU (1.2 equiv) and HOBt (1.2 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 13.

Compound 14: To a solution of nitro compound 13 in DMF was added $SnCl_2.2H_2O$ (8 equiv). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (ethyl acetate/hexane) to give aniline 14.

Compound 15: To a solution of aniline 14 in 10% acetic acid/MeOH was added S-Tr-N-Boc cysteinal (1.5 equiv). To this solution was added sodium cyanoborohydride (2 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 15.

Compound 16: To a solution of 14 in THF/MeOH (1:1) was added 1M LiOH solution (5 equiv). The reaction mixture was stirred at room temperature for 15 h and poured into 10% citric acid solution. The aqueous layer was extracted with methylene chloride. The organic extracts were washed with water, dried and concentrated to give the corresponding acid 16.

Compounds 17–28: To a solution of compound 15 or 16 in $CH_2Cl_2$/TFA (1:1) was added $Et_3SiH$ (5% vol/vol). The reaction mixture was stirred at room temperature for 2 h. The solvents were removed under reduced pressure. The residue was triturated with diethylether or diethyl ether/hexanes. The resulting solid was filtered, washed with ether and dried under vacuum to give compounds 17–28.

Compound 29: A solution of 2-phenyl-4-nitrobenzoic acid 12 (2.5 g, 10 mmol), EDC (3.8 g, 20 mmol), dimethylaminopyridine (0.1 mmol), triethylamine (5.6 mL, 40 mmol) in dichloromethane (100 mL) was stirred at room temperature. Dimethylhydroxylamine hydrochloride was added and the mixture was stirred overnight at room temperature. Dichloromethane was added and washed with 10% citric acid (three times), saturated sodium bicarbonate (twice) and with brine (once). The organic layer was dried and concentrated to give 29 (1.3 g).

Compound 30: Lithium aluminum hydride (190 mg, 5.0 mmol) was added to a solution of 29 (1.3 g) in ether at 0° C. The mixture was allowed to return to room temperature and stirred for 6 hrs. Ehtyl acetate was added, followed by 1M HCl. The aqueous layer was extracted with ethyl acetate. The organic extracts were dried and concentrated to give 30 (0.9 g).

Compound 31: To a solution of aldehyde 30 (0.9 g, 4 mmol) in 10% acetic acid/MeOH (10 mL) was added leucine methyl ester (1.2 g, 6.5 mmol). To this solution was added sodium cyanoborohydride (1.2 g, 18 mmol). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (25%–50% ethyl acetate/hexane) to give 31 (0.84 g).

Compound 32: To a solution of nitro compound 31 (0.84 g, 2.5 mmol) in DMF (20 mL) was added $SnCl_2.2H_2O$ (4.6 g, 24 mmol). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (ethyl acetate/hexane) to give aniline 32 (0.69 g).

Compound 33: To a solution of aniline 32 (0.69 g, 2.1 mmol) in 10% acetic acid/MeOH (10 mL) was added S-Tr-N-Boc cysteinal (1.4 g, 3.1 mmol). To this solution was added sodium cyanoborohydride (0.66 g, 10 mmol). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (25%–50% ethyl acetate/hexane) to give 33 (1 g).

Compound 34: To a solution of methyl ester 8 (400 mg, 0.52 mmol) in THF/MeOH (1:1, 2 mL) was added 1M LiOH solution (2 mL). The reaction mixture was stirred at room temperature for 15 h and poured into 10% citric acid solution. The aqueous layer was extracted with methylene chloride. The organic extracts were washed with water, dried and concentrated to give the acid. The acid was dissolved in $CH_2Cl_2$ (3 mL). To this solution was added TFA (3 mL) followed by $Et_3SiH$ (0.2 mL). The reaction mixture was stirred at room temperature for 1 h. The solvents were removed under reduced pressure. The residue was triturated with diethylether. The resulting solid was filtered, washed with ether and dried under vacuum to give 34 (114 mg).

Compound 35: Methyl ester 32 (80 mg) was dissolved in $CH_2Cl_2$ (5 mL). To this solution was added TFA (5 mL) followed by $Et_3SiH$ (0.1 mL). The reaction mixture was stirred at room temperature for 2 h. The solvents were removed under reduced pressure. The residue was triturated with diethyl ether/hexanes. The resulting solid was filtered, washed with ether and dried under vacuum to give 35 (56 mg).

Compound 37: N-butyl lithium (0.8 mL, 2.5M, 2.0 mmol) was added to a solution of triethyl phosphonoacetate (386 µL, 2.0 mmol) in THF (20 mL) stirred at 0° C. The aldehyde 36 (389 mg, 1.4 mmol) was added after 20 min. and the mixture was stirred for 3 hrs at 0° C. and poured into saturated sodium bicarbonate solution. The aqueous layer was extracted with ethyl acetate. The organic extracts were dried and concentrated to give 37 (450 mg).

Compound 38: A solution of 37 (450 mg, 1.3 mmol) in ethanol (0.5 mL) was added to a solution of phenyl boronic acid (225 mg, 1.4 mmol) and $Pd(PPh_3)_4$ (30 mg, 0.026 mmol) in DME (10 mL) stirred at room temperature, followed by 2M $Na_2CO_3$ solution (2 mL). The reaction mixture was heated at reflux for 15 h, cooled to room temperature and poured into saturated sodium bicarbonate solution. The aqueous layer was extracted with ether. The aqueous layer was acidified and extracted with ethyl acetate. The ethyl acetate extracts were dried and concentrated. The crude product was purified by silica gel chromatography to give 38 (120 mg).

Compound 39: To a solution of 38 (120 mg, 0.45 mmol) in $CH_2Cl_2$ was added leucine methyl ester hydrochloride (97 mg, 0.53 mmol) followed by $Et_3N$ (138 µL, 0.99 mmol), EDC (102 mg, 0.53 mmol) and HOBt (61 mg, 0.45 mmol). The reaction mixture was stirred at room temperature for 15 h. Poured into ethyl acetate, washed with 1M HCl, 10% citric acid, saturated sodium bicarbonate solution (twice) and brine. The organic extracts were dried and concentrated to give 39 (120 mg).

Compound 40: To a solution of nitro compound 39 (120 mg, 0.3 mmol) in DMF was added $SnCl_2.2H_2O$ (342 mg, 1.5 mmol). The reaction mixture was stirred at room temperature for 15 h and poured into saturated sodium bicarbonate solution. The aqueous layer was extracted with ethyl acetate. The organic extracts were dried and concentrated to give the aniline 40.

Compound 41: To a solution of aniline 40 (120 mg, 0.33 mmol) in 5% acetic acid/MeOH was added S-Tr-N-Boc cysteinal (193 mg, 0.43 mmol). To this solution was added sodium cyanoborohydride (42 mg, 0.66 mmol). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (ethyl acetate/hexane) to give 41 (179 mg).

Compound 42: To a solution of 41 (80 mg, 0.1 mmol) in MeOH (3 mL) was added 1M LiOH solution (0.5 mL, 5 mmol). The reaction mixture was stirred at room temperature for 15 h, the solvent was stripped down to 1 ml and poured into 10% citric acid solution. A white solid separated which was filtered, washed with water and dried under vacuum. The solid (29 mg) was dissolved in $CH_2Cl_2$/TFA (1:1, 10 mL) and $Et_3SiH$ (0.5 mL) was added. The reaction mixture was stirred at room temperature for 2 h. The solvents were removed under reduced pressure. The residue was triturated with diethylether. The resulting solid was filtered, washed with ether, dissolved in methanol and dried under vacumn to give 42 (14 mg).

Compound 43: To a solution of 4-nitro aniline (15 g, 108 mmol) in THF (300 mL) was added 10% aqueous HCl solution (150 mL). To this solution was added pyridinium tribromide (42 g, 130 mmol). The reaction mixture was stirred at room temperature for 5 h and poured into excess 10% sodium hydroxide solution. The aqueous layer was extracted with dichloromethane. The organic extracts were dried and concentrated to give 43 (21 g).

Compound 44: A solution of 43 (1.5 g, 7 mmol) and $Pd(PPh_3)_4$ (0.4 g, 0.35 mmol) in dioxane (60 mL) was stirred at room temperature. Phenyl boronic acid (1.2 g, 10 mmol) was added to the reaction mixture, followed by 2M $Na_2CO_3$ solution (20 mL). The reaction mixture was heated at reflux for 15 h, cooled to room temperature and poured into water. The aqueous layer was extracted with methylene chloride. The organic extracts were dried and concentrated. The crude product was purified by silica gel chromatography (15%–25% EA/hexanes) to give 44 (1.1 g).

Compound 45: A solution of aniline 44 (500 mg, 2.3 mmol) and leucine isocyanate 430 mg, 2.5 mmol) in pyridine (10 mL) was heated at reflux for 18 h. The reaction mixture was cooled to room temperature and poured into sodium bicarbonate solution. The aqueous layer was extracted with dichloromethane. The organic extracts were dried and concentrated. The crude product was purified by silica gel chromatography (30% EA/hexanes) to give urea 45 (480 mg)

Compound 46: To a solution of urea 45 (0.46 g, 1.2 mmol) in DMF (10 mL) was added $SnCl_2.2H_2O$ (2.3 g, 10 mmol). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (50% ethyl acetate/hexane) to give aniline 46 (0.36 g).

Compound 47: To a solution of aniline 46 (0.36 g, 1.1 mmol) in 10% acetic acid/MeOH (10 mL) was added S-Tr-N-Boc cysteinal (0.72 g, 1.6 mmol). To this solution was added sodium cyanoborohydride (0.1 g, 1.6 mmol). The reaction mixture was stirred at room temperature for 15 h and poured into saturated sodium bicarbonate solution. The aqueous layer was extracted with dichloromethane. The organic extracts were dried and concentrated. The crude product was purified by silica gel chromatography (25%–50% ethyl acetatelhexane) to give 47 (0.52 g).

Compound 48: To a solution of 47 (200 mg, 0.26 mmol) in THF (5 mL) was added 1M LiOH solution (1 mL). The reaction mixture was stirred at room temperature for 2 h and poured into 10% citric acid solution. The aqueous layer was extracted with methylene chloride. The organic extracts were washed with water, dried and concentrated to give hydantoin 48 (130 mg).

Compound 49: Hydantoin 48 (120 mg) was dissolved in $CH_2Cl_2$ (4 mL). To this solution was added TFA (4 mL) followed by $Et_3SiH$ (0.1 mL). The reaction mixture was stirred at room temperature for 2 h. The solvents were removed under reduced pressure. The residue was triturated with diethyl ether. The resulting solid was filtered, washed with ether and dried under vacuum to give 49 (59 mg).

Compound 51: 10.1 g (26.9 mmol) of 4-phenylpiperidine-4-carboxylic acid (50), 12.5 g (26.9 mmol) of (Boc)(Tr)Cys-OH, 16.4 g (85.6 mmol) of EDC, 10.17 g (66.4 mmol) of HOBT, 30.0 mL (173 mmol) of DIEA, and 250 mL of dichloromethane were combined at room temperature and stirred 16 h. The mixture was partitioned between EtOAc and 10% citric acid solution and the organic phase washed with brine. The solution was dried over $MgSO_4$, filtered and evaporated to dryness in vacuo. 7.98 g of a foam was recovered and used without further purification.

Compound 52: 0.30 g (0.46 mmol) of (Boc)(Tr)Cys-4-phenylpiperidine-4-carboxylic acid (51), (1.2 mmol) of amine, 0.45 g (2.3 mmol) of EDC, 0.35 g (2.3 mmol) of HOBT, 0.80 mL (4.6 mmol) of DIEA, and 6.0 mL of dichloromethane were combined at room temperature and stirred 16 h. The mixture was partitioned between EtOAc and 10% citric acid solution and the organic phase washed with brine. The solution was dried over $MgSO_4$, filtered and evaporated to dryness in vacuo. The residue was purified via silica gel chromatography using MeOH/EtOAc/hexanes as eluent.

Compound 53: When appropriate, to a solution of methyl ester (52a only) (~0.46 mmol) in THF/MeOH (1:1, 8 mL) was added 1M LiOH solution (1.2 mL). The reaction mixture was stirred at room temperature for 15 h and poured into 10% citric acid solution. The aqueous layer was extracted with methylene chloride. The organic extracts were washed with water, dried and concentrated to give the acid. (Boc)(Tr)Cys-4-phenylpiperidine-NHR (52) (~0.46 mmol) was dissolved in 4.0 mL of a 1:1:0.1 mixture of TFA/$CH_2Cl_2$/$Et_3SiH$ and stirred at room temperature for 3 h. The mixture was evaporated to dryness and the residue triturated with 1:1 ether/hexanes to obtain a fine powder.

Compound 56: To a solution of piperidine acid 54 in methylene chloride was added amine $R_2$(Bn)NH (1.1 equiv), followed by DIEA (1.1 equiv), HBTU (1.1 equiv) and HOBt (1.1 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give amide 56.

Compound 55: To a solution of piperidine acid 54 (2 g, 9.4 mmol) in methylene chloride (30 mL) was added aniline (0.94 g, 10 mmol), followed by DIEA (1.9 mL, 10 mmol), EDC (1.92 g 10 mmol) and HOBt (1.5 g, 10 mmol). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 55 (1.9 g).

Compound 56: To a solution of amide 55 (1.9 g, 6.6 mmol) in THF (50 mL) at 0° C. was added KHDMS (26 mL, 0.5M in toluene, 13 mmol). The reaction mixture was warmed to room temperature and stirred for 14 h. The reaction mixture was poured into saturated $NaHCO_3$ solution and extracted with methylene chloride. The organic extracts were dried and concentrated. The crude product was purified by silica gel chromatography (30–50% ethyl acetate/hexane) to give 56 (1.8 g).

Compound 57: A solution of Boc-piperidine 56 in (1:1) $CH_2Cl_2$/TFA was stirred at room temperature for 1 h. The solvents were removed under reduced pressure. The residue was dissolved in methylene chloride and poured into 2M sodium carbonate solution. The aqueous layer was extracted with methylene chloride. The organic extracts were dried and concentrated to give amine 57.

Compound 58: To a solution of amine 57 in methylene chloride was added S-Tr-N-Boc cysteine (1.2 equiv), followed by DIEA (1.5 equiv), HBTU (1.5 equiv) and HOBt (1.5 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (30–50% ethyl acetate/hexane) to give 58.

Compounds 59–64: To a solution of 58 in (1:1) $CH_2Cl_2$/TFA was added $Et_3SiH$ (10% vol/vol). The reaction mixture was stirred at room temperature for 2 h. The solvents were removed under reduced pressure. The residue was triturated with diethylether or 50% diethylether/hexanes. The resulting solid was filtered, washed with ether/hexanes and dried under vacuum to give 59–64.

Compound 66: To a solution of acid 65 (1 g, 3.3 mmol) in toluene (10 mL) was added $Et_3N$ (1.1 mL, 8 mmol), followed by DPPA (0.74 mL, 3.4 mmol). The reaction mixture was heated at 80° C. for 3 h. To this solution was added leucine methyl ester (900 mg, 5 mmol) and heating at 80° C. was continued for another 3 h. The reaction mixture was cooled to room temperature, poured into saturated $NaHCO_3$ solution and extracted with methylene chloride. The organic extracts were dried and concentrated. The crude product was purified by silica gel chromatography (30–50% ethyl acetate/hexane) to give urea 66 (700 mg).

Compound 67: To a solution of urea 66 (700 mg, 1.2 mmol) in THF (10 mL) at 0° C. was added KHDMS (8 mL, 0.5M in toluene, 4 mmol). The reaction mixture was warmed to room temperature and stirred for 3 h. The reaction mixture was poured into saturated $NaHCO_3$ solution and extracted with methylene chloride. The organic extracts were dried and concentrated. The crude product was purified by silica gel chromatography (40% ethyl acetate/hexane) to give hydantoin 67 (380 mg).

Compound 69: A solution of Boc-piperidine 67 (370 mg) in (1:1) $CH_2Cl_2$/TFA (5 mL) was stirred at room temperature for 1 h. The solvents were removed under reduced pressure. The residue was dissolved in methylene chloride and poured into 2M sodium carbonate solution. The aqueous layer was extracted with methylene chloride. The organic extracts were dried and concentrated to give amine 68. To a solution of amine 68 (150 mg, 0.48 mmol) in methylene chloride (5 mL) was added S-Tr-N-Boc cysteine (265 mg, 0.57 mmol), followed by DIEA (0.13 mL, 0.72 mmol), HBTU (272 mg, 0.72 mmol) and HOBt (110 mg, 0.72 mmol). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (30–50% ethyl acetate/hexane) to give 69 (160 mg).

Compound 70: To a solution of 69 (160 mg) in (1:1) $CH_2Cl_2$/TFA (3 mL) was added $Et_3SiH$ (0.1 mL). The reaction mixture was stirred at room temperature for 2 h. The solvents were removed under reduced pressure. The residue was triturated with diethylether. The resulting solid was filtered, washed with ether and dried under vacuum to give 70 (94 mg).

Compound 72: A solution of 2-bromo-5-nitrotoluene (5.5 g, 25 mmol) and $Pd(PPh_3)_4$ (0.17 g, 0.15 mmol) in dioxane (150 mL) was stirred at room temperature. Phenyl boronic acid (3.3 g, 27 mmol) dissolved in 6 mL of EtOH was added to the reaction mixture, followed by 2M $Na_2CO_3$ solution (26 mL). The reaction mixture was heated at reflux for 15 h, cooled to room temperature and poured into saturated sodium bicarbonate solution. The aqueous layer was extracted with methylene chloride. The organic extracts were dried and concentrated to give 72 (5.8 g).

Compound 73: A suspension of 2-phenyl-5-nitrotoluene 72 (5.82 g, 27 mmol) in pyridine (30 mL) and water (60 mL) was heated to reflux. Solid $KMnO_4$ (18.44 g, 117 mmol) was added to the reaction mixture and heating was continued at reflux for 3 h. The hot reaction mixture was filtered through a bed of celite and washed with hot water. The filtrate was acidified with concentrated HCl. The precipitated solid was filtered and dried under vacuum to give 73 (2.9 g).

Compound 74: To a solution of biphenyl acid 73 in $CH_2Cl_2$ was added the appropriate amine $R_1R_2NH$ (1.2 equiv) followed by DIEA (1.2 equiv), EDC (1.2 equiv) or HBTU (1.2 equiv) and HOBt (1.2 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 74.

Compound 75: To a solution of nitro compound 74 in MeOH was added 10% Pd/C. The reaction mixture was shaken under 40 psi of $H_2$ at room temperature for 3 h and filtered through Celite. The solvent was evaporated to give aniline 75.

Compound 76: To a solution of aniline 75 in 10% acetic acid/MeOH was added S-Tr-N-Boc cysteinal (1.5 equiv). To this solution was added sodium cyanoborohydride (2 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 76a–b.

Compound 77: To a solution of 76 in THF/MeOH (1:1) was added 1M LiOH solution (5 equiv). The reaction mixture was stirred at room temperature for 15 h and poured into 10% citric acid solution. The aqueous layer was extracted with methylene chloride. The organic extracts were washed with water, dried and concentrated to give the corresponding acid. To a solution of the resulting acid or non-carboxyl compound in $CH_2Cl_2$/TFA (1:1) was added $Et_3SiH$ (5% vol/vol). The reaction mixture was stirred at room temperature for 2 h. The solvents were removed under reduced pressure. The residue was triturated with diethylether or diethyl ether/hexanes. The resulting solid was filtered, washed with ether and dried under vacuum to give compounds 77a–b.

Compound 78: To a solution of acid 73 (500 mg, 2.1 mmol) in toluene (10 mL) was added $Et_3N$ (0.84 mL, 6 mmol), followed by DPPA(0.5 mL, 2.3 mmol). The reaction mixture was heated at 80° C. for 3 h. To this solution was added leucine methyl ester (540 mg, 3 mmol) and heating at 80° C. was continued for another 3 h. The reaction mixture was cooled to room temperature, poured into saturated $NaHCO_3$ solution and extracted with methylene chloride. The organic extracts were dried and concentrated. The crude product was purified by silica gel chromatography (30–50% ethyl acetate/hexane) to give urea 78 (480 mg).

Compound 79: To a solution of urea 78 (480 mg, 1.2 mmol) in methylene chloride (10 mL) was added DBU (0.6 mL, 4 mmol). The reaction mixture was stirred at room temperature for 3 h. The reaction mixture was poured into saturated NaHCO$_3$ solution and extracted with methylene chloride. The organic extracts were dried and concentrated. The crude product was purified by silica gel chromatography (40% ethyl acetate/hexane) to give hydantoin 79 (400 mg).

Compound 80: To a solution of nitro hydantoin 79 (400 mg, 1.1 mmol) in DMF (20 mL) was added SnCl$_2$.2H$_2$O (2 g, 9 mmol). The reaction mixture was stirred at room temperature for 15 h and poured into saturated sodium bicarbonate solution. The aqueous layer was extracted with ethyl acetate. The organic extracts were dried and concentrated. The crude product was purified by silica gel chromatography (60% ethyl acetate/hexane) to give aniline 80 (240 mg).

Compound 81: To a solution of aniline 80 (240 mg, 0.75 mmol) in 10% acetic acid/MeOH (5 mL) was added S-Tr-N-Boc cysteinal (500 mg, 1.1 mmol). To this solution was added sodium cyanoborohydride (128 mg, 2 mmol). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (30–50% ethyl acetate/hexane) to give 81 (230 mg).

Compound 82: To a solution of 81 (230 mg) in (1:1) CH$_2$Cl$_2$/TFA (5 mL) was added Et$_3$SiH (0.2 mL). The reaction mixture was stirred at room temperature for 2 h. The solvents were removed under reduced pressure. The residue was triturated with diethylether. The resulting solid was filtered, washed with ether and dried under vacuum to give 82 (80 mg).

Compound 84: To a solution of N-Cbz-Dpr (83) (10 g, 42 mmol) in 50 mL of THF (50 mL) was added di-t-butyldicarbonate (12.5 g, 57 mmol), and 10% NaOH/H$_2$O (50 mL). The mixture was stirred vigorously overnight at room temperature. The mixture was partitioned between EtOAc and 10% citric acid and washed with brine. The organic fraction was dried and concentrated to give 16.7 g of crude 84.

Compound 85: To a solution of 84 (16.7 g, 49 mmol) in CH$_2$Cl$_2$ (100 mL) was added MeI (5.0 mL, 80 mmol) and Cs$_2$CO$_3$ (16 g, 49 mmol). The mixture was stirred overnight and then diluted with EtOAc and washed with brine. The organic fractions were dried and evaporated to give 12.6 g of 85.

Compound 86: To a solution of compound 85 (12.6 g, 36 mmol) in MeOH was added 10% Pd/C. The reaction mixture was shaken under 40 psi of H$_2$ at room temperature for 3 h and filtered through Celite. The solvent was evaporated to give 8.1 g of an oil. To a solution of compound of this oil (9.3 g, 43 mmol) in 430 mL of CH$_2$Cl$_2$ was added Boc(Tr)Cys-OH (23.92 g, 52 mmol), EDC (9.89 g, 52 mmol), HOBT (7.96 g, 52 mmol), and DIEA (15 mL, 86 mmol), and the mixture was stirred overnight at room temperature. The mixture was washed with saturated NaHCO$_3$ and brine, dried, and concentrated. The crude product was purified by flash silica gel chromatography with 25–50% EtOAc/hexanes as eluent to give 23.55 g of 86.

Compound 87: To a solution of 86 (10 g, 15 mmol) in THF (25 mL) and MeOH (25 mL) was added 1M LiOH (76 mL, 75 mmol). The mixture was stirred overnight and poured into 10% citric acid. The aqueous fraction was extracted with EtOAc, and the combined organic fractions were washed with brine, dried, and concentrated to give 8.7 g of 87.

Compound 88a–g: To a solution of compound 87 in CH$_2$Cl$_2$ was added the appropriate amine R$_{302}$R$_{304}$NH (1.2 equiv) followed by DIEA (1.2 equiv), EDC (1.2 equiv) or HBTU (1.2 equiv) and HOBt (1.2 equiv). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 88a–g.

Compounds 89a–g: To a solution of compound 88 in CH$_2$Cl$_2$/TFA (1:1) was added Et$_3$SiH (5% vol/vol). The reaction mixture was stirred at room temperature for 2 h. The solvents were removed under reduced pressure. The residue was triturated with diethylether or diethyl ether/hexanes. The resulting solid was filtered, washed with ether and dried under vacuum to give compounds 89a–g.

Compound 91: To a solution of acid 90 in CH$_2$Cl$_2$ was added leucine methyl ester (0.51 g, 1.0 mmol) followed by DIEA (0.5 mL, 2.9 mmol), HBTU (0.71 g, 1.9 mmol) and HOBt (0.16 g, 1.1 mmol). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 0.47 g of 91.

Compound 92: To a solution of compound 91 (0.47 g, 0.73 mmol) in CH$_2$Cl$_2$ (5 mL) was added diethylamine (1 mL) and the mixture stirred for 3 h. The solution was concentrated and redissolved in CH$_2$Cl$_2$ (5 mL). To this was added Boc(Tr)Cys-OH (0.47 g, 1.0 mmol), HBTU (0.41 g, 1.1 mmol), HOBT (0.12 g, 0.79 mmol), DIEA (1 mL, 5.8 mmol). The reaction mixture was stirred at room temperature for 15 h and poured into saturated sodium bicarbonate solution. The aqueous layer was extracted with methylene chloride. The organic extracts were dried and concentrated. The crude product was purified by silica gel chromatography (ethyl acetate/hexane) to give 0.50 g of 92.

Compound 93: To a solution of 92 (0.15 g, 0.18 mmol) in THF (1 mL) and MeOH (1 mL) was added 1M LiOH (2 mL, 2 mmol). The mixture was stirred overnight and poured into 10% citric acid. The aqueous fraction was extracted with EtOAc, and the combined organic fractions were washed with brine, dried, and concentrated to give an oil. To a solution of compound this oil in CH$_2$Cl$_2$/TFA (1:1) (4 mL) was added Et$_3$SiH (0.2 mL). The reaction mixture was stirred at room temperature for 2 h. The solvents were removed under reduced pressure. The residue was triturated with diethylether or diethyl ether/hexanes. The resulting solid was filtered, washed with ether and dried under vacuum to give compounds 0.058 g of 93.

Compound 95: To a solution of 94 (3.015 g) in CH$_2$Cl$_2$ (15 ml) was added diethylamine (15 mL). The reaction mixture was stirred at room temperature for 15 h. The solvents were removed under reduced pressure, toluene was added and the solvents were removed under reduced pressure one more time to remove all traces of diethylamine. Compound 95 was obtained as a foamy solid.

Compound 96b: To a solution of 95 (1.03 g, 1.6 mmol) in CH$_2$Cl$_2$ (10 mL) was added Boc-Ala-Ala-OH (500 mg, 1.9 mmol) followed by DIEA (836 μL, 4.8 mmol), EDC (368 mg, 1.9 mmol) and HOBt (291 mg, 1.9 mmol). The reaction mixture was stirred at room temperature for 15 h. Poured into ethyl acetate, washed with 10% citric acid (twice), saturated sodium bicarbonate solution (thrice) and brime. The organic extract was dried, concentrated to give an oil that was purified by silica gel chromatography (0 to 6% MeOH/CH$_2$Cl$_2$). The resulting solid (420 mg) was dissolved in CH₂Cl₂/TFA (1:1, 10 mL) and Et₃SiH (0.5 mL) was added. The reaction mixture was stirred at room temperature for 2 h. The solvents were removed under reduced pressure. The residue was triturated with diethyl ether. The resulting solid was filtered, washed with ether and dried under vacuum to give c. The product 96b was then purified by preparative HPLC (C8 reverse phase, acetonitrile/water/ 0.1% TFA).

Compound 96a: To a solution of 95 (1.03 g, 1.6 mmol) in CH₂Cl₂ (10 mL) was added Boc-Ala-OH (363 mg, 1.9 mmol) followed by DIEA (836 μL, 4.8 mmol), EDC (368 mg, 1.9 mmol) and HOBt (291 mg, 1.9 mmol). The reaction mixture was stirred at room temperature for 15 h. Poured into ethyl acetate, washed with 10% citric acid (twice), saturated sodium bicarbonate solution (thrice) and brine. The organic extract was dried, concentrated to give an oil that was purified by silica gel chromatography (0 to 6% MeOH/CH₂Cl₂). The resulting solid (420 mg) was dissolved in CH₂Cl₂/TFA (1:1, 10 mL) and Et₃SiH (0.5 mL) was added. The reaction mixture was stirred at room temperature for 2 h. The solvents were removed under reduced pressure. The residue was triturated with diethyl ether. The resulting solid was filtered, washed with ether and dried under vacuum to give 96a.

Compound 98a or 98b: To a solution of 97 (2 mmol) in DMF (5 mL) was added H₂N-Ala-CO₂-t-Bu or H₂N-Ala-Ala-CO₂-t-Bu (2.3 mmol) followed by DIEA (6 mmol), EDC (2.3 mmol) and HOBt (2.3 mmol). The reaction mixture was stirred at room temperature for 15 h. Poured into ethyl acetate, washed with 10% citric acid (twice), saturated sodium bicarbonate solution and brime. The organic extract was dried, concentrated to give an oil that was purified by silica gel chromatography to give a foamy solid 98a or 98b.

Compound 99a or 99b: 98a or 98b was dissolved in CH₂Cl₂/TFA (1:1, 5 mL) and Et₃SiH (0.25 mL) was added. The reaction mixture was stirred at room temperature for 2 h. The solvents were removed under reduced pressure. The residue was triturated with diethyl ether. The resulting solid was filtered, washed with ether and dried under vacuum to give 99a or 99b.

5a: $^1$H NMR (300 MHz, CD₃OD) δ (ppm) 8.2 (d, 1H), 7.8 (d, 1H), 7.7 (d, 1H), 7.3–7.5 (m, 4H), 4.3–4.5 (m, 3H), 3.9 (t, 1H), 3.2–3.7 (m, 3H), 3.0 (t, 1H), 2.9 (d, 2H), 1.5–2.0 (m, 5H), 0.9 (dd, 6H).

5b: $^1$H NMR (300 MHz, CD₃OD) δ (ppm) 8.2 (d, 1H), 7.8 (d, 1H), 7.7 (d, 1H), 7.3–7.5 (m, 4H), 4.7 (t, 1H), 4.4 (t, 1H), 3.9 (t, 1H), 3.7 (m, 1H), 3.1–3.5 (m, 4H), 2.8 (d, 2H), 1.5–1.7 (m, 3H), 0.9 (dd, 6H).

5c: $^1$H NMR (300 MHz, CD₃OD) δ (ppm) 8.2 (d, 1H), 7.8 (d, 1H), 7.7 (d, 1H), 7.4–7.6 (m, 4H), 4.4 (t, 1H), 4.2 (t, 1H), 4.0 (t, 1H), 3.6–3.8 (m, 3H), 3.3–3.5 (m, 2H), 3.0 (d, 2H), 1.6–1.8 (m, 3H), 0.9 (dd, 6H).

5d: $^1$H NMR (300 MHz, CD₃OD) δ (ppm) 8.2 (d, 1H), 7.8 (d, 1H), 7.7 (d, 1H), 7.3–7.6 (m, 4H), 4.3–4.5 (m, 2H), 3.9 (t, 1H), 3.6 (dd, 1H), 3.2–3.5 (m, 1H), 3.0 (dd, 1H), 2.9 (d, 2H), 2.2 (q, 2H), 1.8–2.0 (m, 2H), 1.6–1.7 (m, 3H), 0.9 (dd, 6H).

5e: $^1$H NMR (300 MHz, CD₃OD) δ (ppm) 8.2 (d, 1H), 7.8 (d, 1H), 7.7 (d, 1H), 7.4–7.6 (m, 4H), 4.4 (t, 1H), 4.3 (t, 1H), 4.0 (t, 1H), 3.6 (dd, 1H), 3.3–3.5 (m, 1H), 3.0 (m, 1H), 2.9 (m, 4H), 1.5–1.8 (m, 7H), 1.3–1.4 (m, 2H), 0.9 (dd, 6H).

5f: $^1$H NMR (300 MHz, CD₃OD) δ (ppm) 8.2 (d, 1H), 7.8 (d, 1H), 7.7 (d, 1H), 7.3–7.6 (m, 4H), 4.3–4.5 (m, 2H), 4.0 (t, 1H), 3.7 (dd, 1H), 3.3–3.4 (m, 1H), 3.0 (m, 1H), 2.7–2.9 (m, 4H), 1.6–1.8 (m, 3H), 0.9 (dd, 6H).

5g: $^1$H NMR (300 MHz, CD₃OD) δ (ppm) 8.2 (d, 1H), 7.8 (d, 1H), 7.7 (d, 1H), 7.3–7.6 (m, 4H), 4.4–4.5 (m, 2H), 3.9 (t, 1H), 3.7 (dd, 1H), 3.3–3.5 (m, 2H), 3.0 (m, 1H), 2.8–2.9 (m, 2H), 2.2–2.5 (m, 2H), 1.6–1.8 (m, 3H), 0.9 (dd, 6H).

5 h: $^1$H NMR (300 MHz, CD₃OD) δ (ppm) 8.2 (d, 1H), 7.8 (d, 1H), 7.7 (d, 1H), 7.4–7.6 (m, 4H), 4.4–4.5 (m, 2H), 3.9 (dd, 1H), 3.6–3.8 (m, 2H), 2.9–3.1 (m, 2H), 2.5–2.9 (m, 3H), 1.6–1.8 (m, 3H), 0.9 (dd, 6H).

5i: $^1$H NMR (300 MHz, CD₃OD) δ (ppm) 8.2 (d, 1H), 7.8 (d, 1H), 7.7 (d, 1H), 7.4–7.6 (m, 4H), 7.3–7.4 (m, 2H), 4.4 (t, 1H), 3.9 (t, 1H), 3.8 (d, 2H), 3.7 (dd, 1H), 3.3–3.4 (m, 2H), 2.9 (d, 2H), 1.6–1.8 (m, 3H), 0.9 (dd, 6H).

9: $^1$H NMR (300 MHz, CD₃OD) δ (ppm) 7.7–7.9 (m, 4H), 7.45 (m, 3H), 4.3 (dd, 1H), 4.1 (br t, 1H), 2.5–3.3 (m, 12H), 1.9 (m, 1H), 1.6 (m, 2H), 1.35 (m, 1H), 0.95 (d, 3H), 0.85 (d, 3H), 0.8 (d, 6H).

10: $^1$H NMR (300 MHz, CD₃OD) δ (ppm) 7.84 (m, 3H), 7.75 (s, 1H), 7.5 (m, 2H), 7.41 (d, 1H), 4.35 (dd, 1H), 4.26 (dd, 1H), 3.36 (s, 3H), 2.5–3.3 (m, 12H), 2.0 (m, 1H), 1.52 (m, 2H), 1.28 (m, 1H), 0.95 (d, 3H), 0.86 (d, 3H), 0.81 (d, 6H).

17: $^1$H NMR (300 MHz, CD₃OD) δ (ppm) 7.42 (d, 1H), 7.35 (m, 5H), 6.73 (d, 1H), 6.66 (s, 1H), 4.31 (dd, 1H), 3.49 (m, 3H), 2.83 (dd, 2H), 1.42 (t, 2H), 1.19 (m, 1H), 0.81 (s, 3H), 0.78 (d, 3H).

18: $^1$H NMR (300 MHz, CD₃OD) δ (ppm) 7.87 (d, 1H), 7.36 (m, 5H), 6.67 (d, 1H), 6.66 (s, 1H), 4.32 (dd, 1H), 3.66 (s, 3H), 3.47 (m, 3H), 2.84 (dd, 2H), 1.39 (t, 2H), 1.19 (m, 1H), 0.80 (d, 3H), 0.77 (d, 3H).

19: $^1$H NMR (300 MHz, CD₃OD) δ (ppm) 7.4 (s, 5H), 7.1–7.2 (m, 1H), 6.7 (d, 1H), 6.6 (s, 1H), 5.0–5.1 (m, 1H), 3.4–3.6 (m, 3H), 3.3 (s, 3H), 2.8–2.9 (m, 2H), 2.4–2.6 (m, 2H), 1,2–1.6 (M, 3H), 0.6–0.9 (m, 6H).

20: $^1$H NMR (300 MHz, CD₃OD) δ (ppm) 7.4 (s, 5H), 7.1 (d, 1H), 6.8 (d, 1H), 6.7 (s, 1H), 5,0–5.1 (m, 1H), 5.1 (m, 1H), 3.4–3.8 (m, 4H), 3.3 (s, 3H), 2.8–3.0 (m, 2H), 2.4–2.6 (m, 2H), 1.3–1.6 (m, 3H), 0.6–0.9 (m, 6H).

21: $^1$H NMR (300 MHz, CD₃OD) δ (ppm) 7.1–7.5 (m, 6H), 6.8 (d, 1H), 6.7 (s, 1H), 4.1–4.2 (m, 1H), 3.3–3.6(m, 6H), 2.85 (dd, 2H), 1.2–1.6 (br m, 3H), 0.8 (br s, 6H), 0.6 (t, 3H).

22: $^1$H NMR (300 MHz, CD₃OD) δ (ppm) 7.4 (m, 5H), 7.15 (m, 1H), 6.8 (d, 1H), 6.7 (s, 1H), 3.9 (br m, 1H), 3.7 (s, 3H), 3.2–3.6 (m, 6H), 2.8 (dd, 2H), 1.1–1.8 (br m, 3H), 0.8 (br s, 6H), 0.6 (m, 3H).

23: $^1$H NMR (300 MHz, CD₃OD) d ppm 7.3 (m, 6H), 6.7 (d, 1H), 6.6 (s, 1H), 3.6–3.8 (m, 1H), 3.4–3.6 (m, 2H), 3.1 (t, 2H), 2.7–2.9 (m, 2H), 1.3 (m, 1H), 1.1 (q, 2H), 0.8 (d, 6H).

24: $^1$H NMR (300 MHz, CD₃OD) δ (ppm) 7.38 (m, 5H), 7.16 (d, 1H), 6.76 (m, 1H), 6.72 (s, 1H), 3.5 (m, 4H), 2.91 (dd, 3H), 2.77 (s, 1.5H), 2.47 (s, 1.5H), 1.18 (m, 3H), 0.83 (d, 3H), 0.65 (br s, 3H).

25: $^1$H NMR (300 MHz, CD₃OD) δ (ppm) 7.4 (d, 1H), 7.35 (m, 5H), 6.7 (d, 1H), 6.65 (s, 1H), 4.3 (dd, 1H), 3.5 (m, 3H), 2.85 (dd, 2H), 1.45 (t, 2H), 1.2 (m, 1H), 0.8 (m, 6H).

26: $^1$H NMR (300 MHz, CD₃OD) δ (ppm) 7.75 (d, 1H), 7.36 (m, 5H), 6.74 (d, 1H), 6.66 (s, 1H), 4.3 (dd, 1H), 3.66 (s, 3H), 3.47 (m, 3H), 2.84 (dd, 2H), 1.41 (t, 2H), 1.3 (m, 1H), 0.8 (d, 3H), 0.77 (d, 3H).

27: $^1$H NMR (300 MHz, CD₃OD) δ (ppm) 7.4 (m, 5H), 7.2 (d, 0.35H), 7.1 (d, 0.65H), 6.65–6.8 (m, 2H), 3.6–3.8 (m, 2H), 3.3–3.6 (m, 4H), 2.5–3.0 (m, 4H), 1.3 (m, 1H), 0.5–0.7 (br, 6H).

28: $^1$H NMR (300 MHz, CD₃OD) δ (ppm) 7.39 (m, 5H), 7.2 (d, 0.5H), 7.08 (d, 0.5H), 6.69–6.76 (m, 2H), 4.14 (q, 1H), 4.01 (q, 1H), 3.5–3.8 (m, 5H), 2.79–2.9 (m, 3H), 1.3 (m, 1H), 1.15–1.22 (m, 3H), 0.53–0.64 (br, 6H).

34: $^1$H NMR (300 MHz, CD₃OD) δ (ppm) 7.44 (m, 5H), 7.34 (d, 1H), 6.79 (dd, 1H0, 6.65 (d, 1H), 4.1 (s, 2H), 3.36–3.53 (m, 5H0, 2.82 (dd, 2H), 1.60 (m, 2H), 1.4 (m, 1H), 0.82 (d, 3H), 0.79 (d, 3H).

35: $^1$H NMR (300 MHz, CD$_3$OD) δ (ppm) 7.5 (d, 2H), 7.4 (d, 2H), 7.3 (d, 1H), 6.8 (d, 1H), 6.6 (s, 1H), 4.1 (d, 2H), 3.6 (t, 1H), 3.6 (s, 3H), 3.4–3.6 (m, 3H), 2.7–2.9 (m, 2H), 1.6–1.7 (m, 1H), 1.4–1.6 (m, 2H), 0.8 (dd, 6H).

42: $^1$H NMR (300 MHz, acetone-d$_6$) δ (ppm) 7.3 (m, 6H), 6.6 (m, 2H), 4.5 (m, 1H), 3.6 (m, 2H), 3.4 (m, 1H), 2.8 (m, 2H), 2.4 (m, 2H), 1.9 (m, 2H), 1.6 (m, 3H), 0.9 (m, 6H).

49: $^1$H NMR (300 MHz, CD$_3$OD) δ (ppm) 7.35 (m, 3H), 7.25 (m, 2H), 7.1 (d, 0.65H), 7.0 (d, 0.35H), 6.8 (d, 1H), 6.7 (s, 1H), 4.05 (m, 0.65H), 3.8 (m, 0.35H), 3.3–3.6 (m, 4H), 2.9 (dd, 2H), 1.6 (m, 2H), 1.2 (m, 1H), 0.95 (d, 2H), 0.85 (d, 4H).

53a: $^1$H NMR (300 MHz, CD$_3$OD) δ (ppm) 7.2–7.5 (m, 5H), 4.4–4.6 (m, 2H), 3.8 (dd, 1H), 3.5 (dd, 1H), 3.1–3.4 (m, 1H), 2.9 (abq, 2H), 2.5–2.7 (m, 2H), 2.0–2.2 (m, 1H), 1.5–1.7 (m, 1H), 0.7–0.9 (m, 6H).

53b: $^1$H NMR (300 MHz, CD$_3$OD) δ (ppm) 7.8 (m, 1H), 7.1–7.5 (m, 12H), 6.9 (d, 1H), 4.5 (dd, 1H), 4.3 (m, 3H), 3.7 (t, 1H), 3.5 (m, 1H), 2.9–3.3 (m, 4H), 2.8 (m, 1H), 2.5 (m, 2H), 2.0 (m, 2H).

53c: $^1$H NMR (300 MHz, CD$_3$OD) δ (ppm) 7.2–7.6 (br, 1H), 4.5 (m, 1H), 4.3 (d, 0.5H), 4.1 (d, 0.5H), 3.8 (t, 0.5H), 3.5 (t, 0.5H), 3.2 (m, 3H), 3.0 (m, 1H), 2.8 (m, 1H), 2.5 (abq, 2H), 2.0 (m, 2H), 1.3 (m, 3H), 0.8 (d, 6H).

53d: $^1$H NMR (300 MHz, CD$_3$OD) δ (ppm) 7.2–7.5 (m, 5H), 7.1 (d, 1H), 6.8 (d, 1H), 6.6 (d, 1H), 4.1 (d, 1H), 3.9 (m, 1H), 3.8 (br t, 1H), 3.3–3.5 (m, 3H), 2.4–3.1 (m, 7H), 1.9 (m, 2H).

53e: $^1$H NMR (300 MHz, CD$_3$OD) δ (ppm) 7.1–7.5 (m, 13H), 6.9–7.1 (m, 1H), 4.3–4.5 (m, 3H), 4.0–4.3 (m, 1H), 3.8 (dd, 1H), 3.5 (dd, 1H), 3.1–3.3 (m, 1H), 2.9 (abq, 2H), 2.5–2.7 (m, 2H), 1.9–2.1 (m, 2H).

53f: $^1$H NMR (300 MHz, CD$_3$OD) δ (ppm) 7.9–8.0 (m, 0.5H), 7.2–7.5 (m, 4.5H), 4.5–4.6 (m, 1H), 4.1–4.2 (m, 1H), 3.9–4.1 (m, 3H), 3.6–3.9 (m, 3H), 3.4–3.6 (m, 4H), 2.7–3.1 (m, 6H), 2.4–2.7 (m, 2H), 1.9–2.2 (m, 2H), 1.8–1.9 (m, 2H).

53g: $^1$H NMR (300 MHz, CD$_3$OD) δ (ppm) 7.6–7.7 (m, 0.5H), 7.0–7.5 (m, 4.5H), 4.5 (dd, 1H), 4.2 (d, 0.5H), 4.0 (d, 0.5H), 3.8 (dd, 1H), 3.5 (dd, 1H), 3.0–3.4 (m, 8H), 2.8–2.9 (m, 1H), 2.6 (dd, 2H), 2.3 (t, 2H), 1.9–2.1 (m, 4H), 1.5–1.7 (m, 2H).

53h: $^1$H NMR (300 MHz, CD$_3$OD) δ (ppm) 7.7 (d, 2H), 7.5 (d, 2H), 7.1–7.4 (m, 5H), 4.8 (d, 2H), 4.5 (dd, 1H), 4.1 (d, 0.5H), 4.0 (d, 0.5H), 3.7 (dd, 1H), 3.5 (dd, 1H), 3.3–3.4 (m, 1H), 2.9 (abq, 2H), 2.5 (dd, 2H), 2.0–2.2 (m, 2H).

53i: $^1$H NMR (300 MHz, CD$_3$OD) δ (ppm) 7.1–7.5 (m, 5H), 4.3–4.6 (m, 1H), 4.2 (dd, 1H), 3.7–3.9 (m, 1H), 3.5 (dd, 1H), 3.1–3.4 (m, 1H), 2.9 (abq, 2H), 2.5–2.7 (m, 2H), 1.8–2.2 (m, 2H), 1.2–1.6 (m, 3H), 0.7–0.8 (m, 6H).

53j: $^1$H NMR (300 MHz, CD$_3$OD) δ (ppm) 8.8 (s, 1H), 7.8 (bd, 1H), 7.2–7.6 (m, 6H), 4.5–4.6 (m, 1H), 4.2 (d, 1H), 3.9–4.1 (m, 3H), 3.8 (dd, 1H), 3.4–3.6 (m, 1H), 3.1–3.3 (m, 2H), 2.9 (abq, 2H), 2.4–2.7 (m, 2H), 1.8–2.2 (m, 4H).

53k: $^1$H NMR (300 MHz, CD$_3$OD) δ (ppm) 8.6 (dd, 2H), 8.4 (dd, 2H), 7.3–7.6 (m, 5H), 4.49–4.6 (m, 3H), 4.2 (d, 0.5H), 4.0 (d, 0.5H), 3.8 (dd, 1H), 3.5 (dd,1H), 3.4 (dd, 0.5H), 3.3 (dd, 0.5H), 2.9 (abq, 2H), 2.6 (dd, 2H), 2.0–2.2 (m, 2H).

53l: $^1$H NMR (300 MHz, CD$_3$OD) δ (ppm) 7.1–7.5 (m, 5H), 4.5 (dd, 1H), 4.3 (d, 0.5H), 4.1 (d, 0.5H), 4.0–4.1 (m, 4H), 3.7–3.9 (m, 2H), 3.5 (dd, 1H), 2.9–3.3 (m, 2H), 2.8–2.9 (m, 3H), 2.5 (dd, 2H), 1.8–2.1 (m, 2H), 1.6–1.8 (m, 2H), 1.3–1.5 (m, 2H), 1.2 (t, 3H).

53m: $^1$H NMR (300 MHz, CD$_3$OD) δ (ppm) 7.7 (d, 2H), 7.6 (d, 2H), 7.1–7.4 (m, 5H), 4.5 (dd, 1H), 4.1 (d, 0.5H), 4.0 (d, 0.5H), 3.7 (d, 0.5H), 3.6 (d, 0.5H), 3.4–3.5 (m, 2.5H), 3.2–3.4 (m, 0.5H), 2.9–3.1 (m, 2H), 2.7–2.9 (m, 3H), 2.4–2.6 (m, 2H), 1.7–2.0 (m, 2H).

53n: $^1$H NMR (300 MHz, CD$_3$OD) δ (ppm) 7.5–7.7 (m, 0.5H), 7.1–7.5 (m, 0.5H), 4.5 (dd, 1H), 4.3 (d, 0.5H), 4.1 (d, 0.5H), 3.8 (dd, 1H), 3.5 (dd, 1H), 2.9–3.3 (m, 4H), 2.8–2.9 (m, 1H), 2.4–2.7 (m, 3H), 1.8–2.2 (m, 4H), 1.1–1.6 (m, 7H).

53o: $^1$H NMR (300 MHz, CD$_3$OD) δ (ppm) 8.0–8.2 (m, 2H), 7.9–8.0 (m, 1H), 7.7–7.8 (m, 3H), 7.1–7.6 (m, 6H), 4.5 (dd, 1H), 4.4 (d, 0.5H), 4.2 (d, 0.5H), 4.0 (d, 2H), 3.8 (dd, 1H), 3.7 (dd, 1H), 3.5 (dd, 0.5H), 3.4 (dd, 0.5H), 2.9 (abq, 2H), 2.7 (dd, 2H), 1.9–2.1 (m, 2H).

53p: $^1$H NMR (300 MHz, CD$_3$OD) δ (ppm) 8.2–8.3 (m, 1H), 7.2–7.4 (m, 6H), 6.9–7.1 (m, 2H), 4.5 (dd, 1H), 4.3 (d, 2H), 4.3 (d, 0.5H), 4.1 (d, 0.5H), 3.8 (dd, 1H), 3.5 (dd, 1H), 3.1–3.4 (m, 1H), 2.9 (abq, 2H), 2.6 (dd, 2H), 1.9–2.2 (m, 2H).

53q: $^1$H NMR (300 MHz, CD$_3$OD) δ (ppm) 8.0–8.1 (m, 1H), 7.2–7.4 (m, 5H), 7.1 (d, 1H), 6.5 (s, 1H), 5.9 (s, 2H), 4.5 (dd, 1H), 4.2–4.3 (m, 2.5H), 4.1 (d, 0.5H), 3.8 (dd, 1H), 3.5 (dd, 1H), 3.1–3.4 (m, 1H), 2.9 (abq, 2H), 2.6 (dd, 2H), 1.9–2.2 (m, 2H).

53r: $^1$H NMR (300 MHz, CD$_3$OD) δ (ppm) 8.1–8.2 (m, 1H), 7.2–7.4 (m, 5H), 6.7–7.0 (m, 2H), 4.5 (dd, 1H), 4.3 (s, 2H), 4.3 (d, 0.5H), 4.1 (d, 0.5H), 3.8 (dd, 1H), 3.5 (dd, 1H), 3.3 (dd, 0.5H), 3.1 (dd, 0.5H), 2.9 (abq, 2H), 2.6 (dd, 2H), 1.9–2.1 (m, 2H).

53s: $^1$H NMR (300 MHz, CD$_3$OD) δ (ppm) 7.2–7.4 (m, 5H), 4.5 (dd, 1H), 4.3 (d, 0.5H), 4.1 (d, 0.5H), 3.8 (dd, 1H), 3.6–3.7 (m, 1H), 3.5 (dd, 1H), 3.3 (dd, 0.5H), 3.1 (dd, 0.5H), 2.9 (abq, 2H), 2.6 (dd, 2H), 1.8–2.1 (m, 2H), 1.6–1.8 (m, 5H), 1.0–1.4 (m, 5H).

53t: $^1$H NMR (300 MHz, CD$_3$OD) δ (ppm) 7.2–7.6 (m, 5H), 4.5 (dd, 1H), 4.2 (dd, 0.5H), 4.1 (dd, 0.5H), 3.8–3.9 (m, 1H), 3.5–3.8 (m, 4H), 3.1–3.4 (m, 5H), 2.9 (abq, 2H), 2.6 (dd, 2H), 1.9–2.2 (m, 2H), 1.7–1.9 (m, 2H).

53u: $^1$H NMR (300 MHz, CD$_3$OD) δ (ppm) 7.6–7.8 (m, 1H), 7.1–7.5 (m, 6H), 6.7–6.9 (m, 2H), 4.5 (dd, 1H), 4.3–4.4 (m, 2H), 4.2 (d, 0.5H), 4.0 (d, 0.5H), 3.6–3.8 (m, 4H), 3.5 (dd, 1H), 3.2–3.4 (m, 1H), 2.9 (abq, 2H), 2.6 (dd, 2H), 1.9–2.2 (m, 2H).

53v: $^1$H NMR (300 MHz, CD$_3$OD) δ (ppm) 7.8–7.9 (m, 1H), 7.0–7.4 (m, 9H), 4.5 (dd, 1H), 4.3 (d, 0.5H), 4.2 (d, 0.5H), 3.8 (dd, 1H), 3.5 (dd, 1H), 3.0–3.3 (m, 3H), 2.7–2.9 (m, 2H), 2.6 (dd, 2H), 1.8–2.1 (m, 4H).

53w: $^1$H NMR (300 MHz, CD$_3$OD) δ (ppm) 8.1 (dd, 1H), 7.9 (dd, 1H), 7.8 (d, 1H), 7.7 (d, 1H), 7.0–7.5 (m, 8H), 4.8 (s, 2H), 4.5 (dd, 1H), 4.2 (d, 0.5H), 4.0 (d, 0.5), 3.7 (dd, 1H), 3.5 (dd, 1H), 3.3 (dd, 0.5H), 3.1 (dd, 0.5H), 2.9 (abq, 2H), 2.6 (dd, 2H), 1.9–2.1 (m, 2H).

53x: $^1$H NMR (300 MHz, CD$_3$OD) δ (ppm) 7.7–7.8 (m, 1H), 7.1–7.4 (m, 7H), 7.1 (d, 1H), 4.5 (dd, 1H), 4.3 (d, 0.5H), 4.1 (d, 0.5H), 3.7–3.9 (m, 3H), 3.6 (dd, 1H), 3.3–3.5 (m, 2.5H), 3.2 (dd, 0.5H), 2.9 (abq, 2H), 2.5–2.7 (m, 4H), 1.8–2.1 (m, 2H).

53y: $^1$H NMR (300 MHz, CD$_3$OD) δ (ppm) 7.2 (m, 15H), 4.3 (m, 1H), 4.0 (m, 1H), 3.7 (m, 3H), 2.3–3.1 (m, 7H), 1.8 (m, 3H).

53z: $^1$H NMR (300 MHz, CD$_3$OD) δ (ppm) 8.1 (t, 1H), 7.7 (m, 2H), 7.0–7.5 (m, 10H), 6.1 (m, 1H), 4.6 (m, 1H), 4.3 (d, 0.5H), 4.2 (d, 0.5H), 3.8 (t, 1H), 3.6 (t, 1H), 2.5–3.2 (m, 5H), 2.0 (m, 2H).

53aa: $^1$H NMR (300 MHz, CD$_3$OD) δ (ppm) 7.6 (t, 1H), 7.0–7.5 (m, 9H), 4.7 (br t, 1H), 4.2 (br, 1H), 3.7 (br t, 1H), 3.5 (br m, 1H), 3.2 (m, 4H), 2.5 (m, 4H), 2.0 (m, 3H), 1.4 (m, 4H).

53bb: $^1$H NMR (300 MHz, CD$_3$OD) δ (ppm) 8.1–8.2 (m, 1H), 7.0–7.5 (m, 10H), 4.5 (dd, 1H), 4.2–4.4 (m, 3H), 4.0–4.1 (m, 1H), 3.7–3.9 (m, 1H), 3.4–3.6 (m, 1H), 2.8–3.1 (m, 2H), 2.5–2.7 (m, 2H), 1.9–2.2 (m, 2H).

59: $^1$H NMR (300 MHz, CD$_3$OD) δ (ppm) 7.2–7.4 (m, 4H), 7.05 (d, 1H), 4.5 (m, 2H), 4.3 (s, 2H), 3.9 (d, 1H), 3.2 (m, 1H), 3.0 (m, 1H), 2.75 (m, 2H), 2.5 (m, 1H), 1.8 (m, 2H), 1.5–1.8 (m, 2H).

60: $^1$H NMR (300 MHz, CD$_3$OD) δ (ppm) 7.0–7.5 (m, 101H), 4.4 (m, 2H), 3.9 (m, 1H), 2.5–3.1 (m, 6H), 1.7 (m, 5H).

61: $^1$H NMR (300 MHz, CD$_3$OD) δ (ppm) 7.0–7.5 (m, 101H), 4.2–4.6 (m, 5H), 3.9 (d, 1H), 2.6–3.2 (m, 6H), 1.7 (m, 5H).

62: $^1$H NMR (300 MHz, CD$_3$OD) δ (ppm) 7.0–7.5 (m, 10H), 4.3–4.7 (m, 4H), 3.5–3.9 (d, 3H), 2.5–3.2 (m, 6H), 1.3–1.7 (m, 5H).

63: $^1$H NMR (300 MHz, CD$_3$OD) δ (ppm) 7.1–7.3 (m, 5H), 4.3–4.4 (bs, 2H), 3.8–4.1 (m, 1H), 3.8–3.6–3.7 (m, 1H), 3.2–3.3 (m, 2H), 2.8–3.2 (m, 2H), 2.0–2.2 (m, 2H), 1.4–1.6 (dd, 2H), 1.2–1.3 (bs, 3H).

64: $^1$H NMR (300 MHz, CD$_3$OD) δ (ppm) 8.3 (d, 1H), 7.2–7.4 (m, 5H), 7.1–7.2 (m, 3H), 6.9–7.0 (m, 2H), 4.4–4.5 (m, 1H), 4.2–4.4 (m, 3H), 3.7–3.8 (m, 1H), 3.2–3.3 (m, 1H), 2.7–3.1 (m, 6H), 2.1–2.3 (m, 2H), 1.4–1.7 (m, 2H).

70: $^1$H NMR (300 MHz, CD$_3$OD) δ (ppm) 7.2–7.5 (m, 5H), 5.55 (d, 1H), 4.2–4.6 (m, 3H), 3.9 (d, 1H), 3.1–3.4 (m, 1H), 3.4–3.7 (m, 5H), 3.05 (dd, 3H), 2.85 (m, 1H), 2.6 (m, 1H), 1.9–2.2 (m, 3H), 1.1 (d, 6H).

77a: $^1$H NMR (300 MHz, CD$_3$OD) δ (ppm) 8.6 (d, 2H), 7.4 (d, 2H), 7.3 (s, 5H), 7.2 (d, 1H), 6.9 (d, 1H), 6.8 (s, 1H), 4.5 (s, 2H), 3.4–3.6 (m, 3H), 2.8–3.0 (m, 2H).

77b: $^1$H NMR (300 MHz, CD$_3$OD) δ (ppm) 7.1–7.4 (m, 6H), 6.7–6.9 (m, 2H), 4.3–4.4 (m, 1H), 3.4–3.8 (m, 3H), 2.7–2.9 (m, 2H), 1.3–1.5 (m, 3H), 1.8 (dd, 6H).

82: $^1$H NMR (300 MHz, CD$_3$OD) δ ppm 7.1–7.5 (m, 6H), 6.9 (dd, 1H), 6.6 (s, 1H), 6.8 (d, 1H), 6.7 (s, 1H), 4.05 (m, 0.65H), 3.85 (m, 0.35H), 3.35–3.6 (m, 4H), 2.9 (dd, 3H), 1.6 (m, 2H), 1.2 (m, 1H), 0.95 (d, 2H), 0.85 (d, 4H).

89a: $^1$H NMR (300 MHz, CD$_3$OD) δ (ppm) 8.0–8.1 (m, 1H), 7.9 (d, 1H), 7.8 (d, 1H), 7.4–7.6 (m, 4H), 4.7–5.0 (m, 3H), 4.0–4.1 (dd, 1H), 3.2–3.5 (m, 2H), 2.9–3.1 (m, 2H).

89b: $^1$H NMR (300 MHz, CD$_3$OD) δ (ppm) 7.5–7.6 (m, 4H), 7.2–7.5 (m, 5H), 4.7–4.8 (m, 1H), 4.4–4.6 (m, 2H), 4.0–4.1 (m, 1H), 3.2–3.5 (m, 2H), 2.9–3.1 (m, 2H).

89c: $^1$H NMR (300 MHz, CD$_3$OD) δ (ppm) 8.6 (d, 2H), 8.5 (bs, 1H), 7.5 (d, 2H), 7.3–7.5 (m, 5H), 5.1–5.3 (m, 1H), 4.6 (s, 2H), 4.0–4.2 (m, 2H), 3.8 (dd, 1H), 3.4–3.6 (m, 2H), 3.2–3.4 (m, 2H), 3.0–3.1 (m, 2H), 2.5–2.7 (m, 2H), 2.0–2.2 (m, 2H).

89d: $^1$H NMR (300 MHz, CD$_3$OD) δ (ppm) 6.7–6.8 (m, 3H), 5.9 (s, 2H), 4.7–4.8 (m, 1H), 4.2–4.4 (m, 2H), 4.1–4.2 (m, 1H), 3.2–3.6 (m, 2H), 2.9–3.1 (m, 2H).

89e: $^1$H NMR (300 MHz, CD$_3$OD) δ (ppm) 8.2 (s, 1H), 7.7–7.9 (m, 3H), 7.5 (d, 1H), 7.3–7.5 (m, 2H), 4.8–4.9 (m, 1H), 4.0–4.3 (m, 3H), 3.3–3.5 (m, 2H), 3.0–3.2 (m, 2H).

89f: $^1$H NMR (300 MHz, CD$_3$OD) δ (ppm) 7.1–7.3 (m, 5H), 5.1–5.2 (m, 1H), 4.8–5.0 (m, 1H), 4.4–4.5 (m, 1H), 4.0–4.2 (m, 1H), 3.7–3.9 (m, 1H), 2.9–3.2 (m, 4H), 2.5–2.7 (m, 3H), 1.6–1.9 (m, 3H), 1.0–1.3 (m, 2H).

89g: $^1$H NMR (300 MHz, CD$_3$OD) δ (ppm) 7.5–7.7 (m, 4H), 7.0–7.2 (m, 4H), 5.0–5.2 (m, 2H), 4.1 (m, 1H), 3.6–3.9 (m, 4H), 3.1–3.4 (m, 2H), 2.6–3.1 (m, 6H).

93: $^1$H NMR (300 MHz, CD$_3$OD) δ (ppm) 7.2–7.3 (m, 1H), 7.0–7.2 (m, 3H), 5.1 (dd, 1H), 4.7–4.8 (m, 1H), 4.5–4.6 (m, 1H), 4.0–4.2 (m, 1H), 3.3–3.4 (m, 1H), 2.8–3.1 (m, 5H), 2.3–2.6 (m, 2H), 1.5–2.1 (m, 6H), 0.9 (dd, 6H).

96b: $^1$H NMR (300 MHz, CD$_3$OD) δ (ppm) 8.6 (d, 2H), 8.4 (m, 1H), 7.4 (m, 7H), 4.5 (m, 2H), 4.4 (t, 1H), 4.2 (m, 1H), 3.9 (m, 3H), 3.6 (m, 1H), 3.3 (m, 1H), 2.9 (m, 1H), 2.6 (m, 3H), 2.1 (m, 2H), 1.5 (t, 3H), 1.3 (dd, 3H).

96a: $^1$H NMR (300 MHz, CD$_3$OD) δ (ppm) 8.6 (d, 2H), 8.5 (m, 1H), 7.4 (m, 7H), 4.5 (m, 2H), 4.2 (m, 1H), 3.9 (m, 3H), 3.6 (m, 1H), 3.3 (m, 1H), 2.9 (m, 1H), 2.6 (m, 3H), 2.1 (m, 2H), 1.5 (dd, 3H).

99a: $^1$H NMR (300 MHz, CD$_3$OD) δ (ppm) 7.4 (m, 6H), 4.5 (m, 2H), 4.3 (m, 2H), 3.8 (m, 1H), 3.5 (m, 1H), 3.2 (m, 1H), 3.0 (m, 1H), 2.8 (m, 1H), 2.6 (m, 2H), 2.1 (m, 1H), 1.8 (m, 1H), 1.5 (m, 2H), 1.4 (d, 3H), 1.3 (m, 1H), 0.8 (m, 6H).

99b: $^1$H NMR (300 MHz, CD$_3$OD) δ (ppm) 8.2 (m, 1H), 7.9 (dd, 1H), 7.4 (m, 6H), 4.6 (m, 1H), 4.3 (m, 5H), 3.8 (m, 1H), 3.5 (m, 1H), 3.2 (m, 1H), 3.0 (m, 1H), 2.8 (m, 1H), 2.6 (m, 2H), 2.1 (m, 1H), 1.8 (m, 1H), 1.5 (m, 2H), 1.4 (d, 3H), 1.3 (d, 3H), 1.2 (m, 1H), 0.8 (m, 6H), b. Demonstration of the Effect of GGPTase Inhibitors on the Prenylation State of Newly Synthesized Candida RHO1 (CaRHO1)

(i) Methodology.

To look at the effect of GGPTase I inhibitors in vivo a recombinant *C. albicans* strain engineered to express a Myc tagged CaRHO1 under the control of the *C. albicans* phosphoenolpyruvate carboxykinase 1 (PCK1) promoter is used. This promoter is repressed by glucose and derepressed by gluconeogenic carbon sources such as succinate. It should also be possible to be look at the endogenous substrates of the GGPTase I. Cells are treated with a sublethal dose of compound for a period of time which has been established from a kill curve analysis in the appropriate media. After the treatment time, cells are harvested and whole cell extracts (WCE) made, these extracts are then resolved by high speed centrifugation into cytosolic and membrane fractions. Visualisation of the localisation of the MycCaRHO1 is achieved by sodium dodecyl sulfate-polyacrylamide gel electrophoresis (SDS-PAGE) and Western blotting. MycCaRHO1 that has been geranylgeranylated will be localised to the membrane whereas ungeranylgeranylated protein should be found in the cytosolic fraction. Treatment of cells with DMSO (mock) and GGPTase I inhibitor MycCaRHO1 will be apparent in the WCE and pellet fractions. In mock treated cells MycCaRHO1 should be absent from the cytosolic fraction whereas in GGPTase I inhibitor treated cells some MycCaRHO1 should be apparent in the cytosolic fraction indicating that a proportion of the newly synthesised Myc-CaRHO1 has not been geranylgeranylated. FIG. 1 shows that this prediction is borne out.

(ii) Generation of the CaRHO1 Replacement Construct.

The 5' and 3' non-coding regions of CaRHO1 were generated by polymerase chain reaction (PCR) and cloned into pBluescript KS- in which the CaRHO1 open reading frame (ORF) has been exactly replaced with a BamHI site. Into this vector (pSCaRHO1.5c23) a PCK1.CaURA3 cassette was inserted from pSCaPCK1.3c1 to generate pSCaRHO1.19c1. This vector was mutagenised to destroy one of the two BamHI sites (pSCaRHO1.22c22) into which the Myc tagged CaRHO1 ORF (from pSCaRHO1.20c58) was inserted. The sequence of the oligos used to generate the Myc tagged CaRHO1 ORF are:

CaRHO1.13: 5' CCCGGGATCCTTACAAGACAACA-CATTTCTT 3'

CaRHO1.13: 5' CCGGGATCCTTACATAATGTCT-GAACAAAAATT GATATCAGAAGAAGATTTGGTTAACGG 3' the sequence of the Myc tag is underlined and corresponds to the amino acid sequence EQKLISEEDL. This epitope is recognised by the commercially available 9E10 monoclonal antibody. The final vector designated pSCaRHO1.23c21, harbours of the 5' non-coding region of CaRHO1, the CaURA3 selectable marker, the *C. albicans* PCK1 promoter directing the expression of the Myctagged CaRHO1 and the 3' untranslated region of CaRHO1. The presence of the CaRHO1 5' and 3' regions should direct this cassette to one of the 2 WT alleles of CaRHO1 by homologous recombination.

(iii) Generation of the *C. Albicans* PCK1-MycCaRHO1 Strain

The PCK1-MycCaRHO1 replacement construct was excised by a BssHII digest from the parent plasmid pSCaRHO1.23c21. The desired fragment was gel purified prior to being transformed into the *C. albicans* strain CAF3-1. The method used for CAF3-1 transformation is a lithium acetate protocol (from U. of Minnesota *C. ablicans* web site: http://alces.med.umn.edu/candida/liac.html). The transformation mixture is then plated onto selective (-Ura glucose) plates and incubated at 30° C. for 3days. Individual transformants that appear are restreaked for singles and then preserved as a glycerol stock. To ensure that the correct integrative event has occurred, southern analysis was carried out on several colonies. Those colonies that exhibited the correct genotype were retained.

The strain used for the work described here is referred to as DIY-BL2-058.

(iv) Growth and Treatment of Cells

Cells of strain DIY-BL2-058 were grown overnight in YNB supplemented with 1 µg/ml histidine, 2 µg/ml methionine, 2 µg/ml tryptophan, 200 µg/ml glutamine and 2% glucose at 220 rpm at 31° C. The cell number was then determined, cells were pelleted by centrifugation and resuspended in fresh media at a density of $1\times10^7$ cells/ml and incubated as above. Cells were either treated with 14 µl DMSO alone or 14 µl of a 25.6 mg/ml stock of 99a in DMSO (3 µg/ml final concentration). After 3 hrs incubation cells were pelleted, washed twice and resuspended to the original volume with the following media: YNB supplemented with 1 µg/ml histidine, 2µg/ml methionine, 2 µg/ml tryptophan, 200 µg/ml glutamine, 2% succinate and 0.05% glucose. The PCK1 promoter is repressed in the media containing 2% glucose. The switch in media to 2% succinate, 0.05% glucose partially derepresses the PCK1 promoter such that the MycCaRHO1 protein is not overproduced. DMSO or 99a are then again added to this new media and the cells incubated for a further 5 hrs. After the required incubation the cells are pelleted and frozen at −80° C.

(v) Generation and Fractionation of Cellular Extracts

To generate cellular extracts, 10×TE supplemented with a protease inhibitors cocktail was added at 3–4 volumes of the pellet size (about 200 µl) and glass beads (425–600 microns; Sigma) were added to the meniscus. This mixture was then subjected to 5 1'pulses in a bead beater with 2' on ice between pulses. The mixture was then centrifuged at 300 rpm to pellet cellular debris and the supernatent removed. The beads were washed with an equal volume of buffer and the supernatent added to the initial sample. This whole cell extract (WCE) was again centrifuged at 300 rpm and the supernatent removed into a fresh tube. 50 µl of this WCE was subjected to high speed centrifugation (54000 rpm for 1 hr in a T1120.1 rotor) to resolve the membrane and cytosolic fractions. The cytosolic fraction was carefully removed. The membrane pellet fraction was washed with buffer and resuspended in 1×loading buffer. All fractions were frozen at −80° C.

(vi) SDS.PAGE and Western Blotting

Fractions were thawed on ice. The protein concentration was determined using the standard Bradford method for the WCEs and cytosolic fraction. 30 µg of protein were loaded for both the WCE and cytosolic fractions. For the membrane fraction, a volume equal to that loaded for the cytosolic fraction was loaded. Prior to loading, all fractions were boiled for 3' with loading dye. Standard procedures were employed for the SDS.PAGE and Western blotting.

To analyse the western blot, the blot was pre-blocked with 4% fat free milk in PBST. The 9E10 monoclonal anti-myc epitope antibody (available from Calbiochem) was incubated with the blot overnight at 4° C. at a concentration recommended by the manufacturers. The primary antibody was removed and the blot was washed 3×15' with PBST. The blot is then incubated with 2° antibody which was goat anti-mouse HRP conjugated antibody for 1 hr at room temperature. The 2° antibody is removed and the blot washed again with 3×15' with PBST and developed using the Pierce luminescent kit according to the manufacturers instructions.

Figure 57:
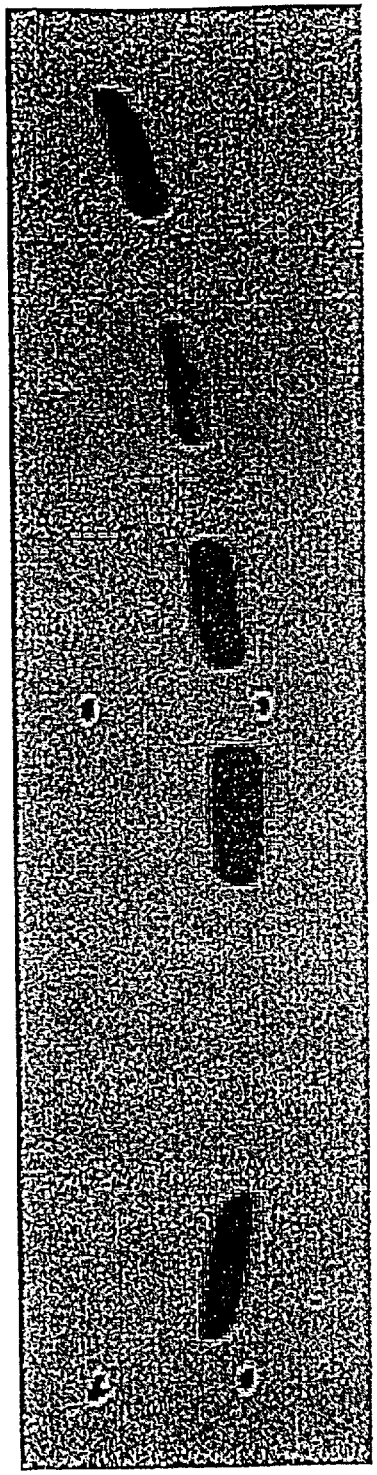
FIG. 57 shows a gel which illustrates the effect of 99a on localisation of MycCaRHO1.

As shown in FIG. 57, exposure of cells to a GGPTase I inhibitor increases the abundance of MycCaRHO1 in the cytosolic fraction (99a treated cells) but not of mock (DMSO) treated cells. Numbers 1–6 indicate the lanes of the gel which are denoted as W, whole cell extract, C, cytosolic fraction and P, pellet fraction. Protein molecular weight markers are indicated.

c. In Vitro Assays of Fungal GGPTase Inhibitors (i) Assay Protocol for Determining IC50

Plate test compounds (10 µL per well) at predetermined concentration in 50% DMSO. For background control (blank) and reaction control (negative), add 10 µL of 200 µM GGPP and 10 µL 50% DMSO, respectively. Prepare assay buffer: 50 mM Tris, pH7.5, 20 mM KCL, 5 mM $MgCl_2$, 5 µM $ZnCl_2$, 0.5 mM Zw(3–14), 2 mM DTT and 0.1 mg/mL BSA.

Add 20 µL of *C. albicans* GGPTase and $^3$H-GGPP in assay buffer to test compound. Preincubate enzyme and $^3$H-GGPP with test compound for 15 minutes at room temperature. Add 20 µL *C. albicans* Rho in assay buffer. Incubate for 30 minutes at room temperature. Final assay conditions are 2 nM *C. albicans* GGPTase, 250 nM $^3$H-GGPP and 250 nM *C. albicans* Rho.

Add 100 µL 15 mM GGPP, 50 mM Tris, pH7.0 and 2% BSA to quench reaction. Transfer reaction to Nickel chelate FlashPlate. Allow his-tagged *C. albcians* Rho to capture onto plate. Rinse plate 1× with 200 µL 20 mM Tris, pH7.0. Read in TOPCOUNT.

(ii) In Vitro Susceptibility Testing of Compounds in *C. Albicans*

1: Innoculate strain *C. albicans* strain such as SC5314 into 20 mL of the appropriate medium and incubate at 35° C. with shaking (220 rpm) overnight 2: Count the *C. albicans* cells in a 1:10 dilution of the overnight culture using a haemocytometer.

3: Work out the dilution factor required to bring the cell number to $1\times10^3$ cells/100 µL (equivalent to $1\times10^4$ cells/mL) then add the required volume of the overnight culture to 25 mL media in a falcon tube.

4: Vortex the diluted cells and immediately pipette 100 µL of the cell suspension to each of the required rows of a 96 well plate using the multipipettor.

5: Prepare each of the 100×stock solutions for the compounds to be tested in DMSO in the required concentration range in Eppendorf tubes.

6: The dilution series for each of the compounds may now be prepared in sequence:

For each compound—start with highest dilution. Add 10 µL compound in DMSO to the 490 µL of appropriate media.

Immediately vortex and add 100 μL to the appropraite row of cells on the 96-well plate. Repeat this process for the next and subsequent concentrations of this compound before starting on the dilution series for additional compounds.

7: When complete cover the 96-well plate with an acetate sheet and incubate at 35° C. Inspect visually and record results for both plates at the 24 hr and 48 hr. The MIC corresponds to the concentration of compound where no visible growth is observed.

(iii) Determination of Minimum Fungicidal Concentrations (MFC)

After the required time course for the MIC determination, the minimum fungicidal concentration can then be determined by plating out the entire contents of the well of the microtitre plates onto YPD or Sabourand plates. These plates are then incubated at 35° C. for 24–48 hrs. The MFC corresponds to the concentration of compound where no cellular growth is observed on the plate. For compound 99a, and MFC was calculated of 2 μg/ml.

(iv) Assay Protocol for Determining Cytotoxicity of GGPTase Inhibitors in Human Cells (A) Plate out cells at predetermined concentration in a volume of 150 μl.

(B) Allow cells to adhere to plate for twenty four hours (C) Add compounds to cells at predetermined concentration (62.5 μg/mL down four-fold, 8 dilutions) n=2

(D) Cells are exposed to drug for 7 days for the IMR90 Cell Line, and a period of 3 days for the H460 Cell Line.

(E) 1. H460 Cells are fixed in TCA, rinsed, stained with Sulforhodamine B stain, and the stain is solubilized for a final OD read.

2. IMR90 Cells have 3-{4,5-Dimethylthiazol-2-yl}-2, 5-diphenyltetrazolium bromide (MTT) added to them for three hours prior to final read out. After the three hours, media and MTT are removed and MTT crystals are solubilized in 100% DMSO for final OD read.

TABLE 1

Peptide Analogs

| Compound | IC50 (nM) Ca GG | IC50 (nM) Hu GG | IC50 (nM) Asp GG | IC50 (nM) Cryp GG | MIC (μg/mL) C alb |
|---|---|---|---|---|---|
| 5a | <500 | <500 | | | |
| 5b | <10 | <500 | | | |
| 5c | <1000 | >1000 | | | |
| 5d | >1000 | >1000 | | | |
| 5e | <1000 | >1000 | | | |
| 5f | <10 | >100 | | | |
| 5g | <1000 | <500 | | | |
| 5h | <1000 | <500 | | | |
| 5i | <500 | <500 | | | |
| 9 | <1000 | <100 | | | <10 (Me ester of 9) |
| 89a | <1000 | >1000 | | >1000 | >200 |
| 89b | <500 | >1000 | | | >200 |
| 89c | <1000 | >1000 | >1000 | >1000 | |
| 89d | >1000 | >1000 | | | |
| 89e | >1000 | >1000 | | | |
| 89f | <1000 | >1000 | | | |
| 89g | <500 | >1000 | | | |

TABLE 2

Biphenyl Analogs

| Compound # | IC50 (nM) Ca GG | IC50 (nM) Hu GG | IC50 (nM) Asp GG | IC50 (nM) Cryp GG | MIC (μg/mL) C alb |
|---|---|---|---|---|---|
| 17 | <10 | <10 | >1000 | <100 | <50 (Me ester of 17) |
| 19 | <10 | <10 | | >100 | <25 (Me ester of 19) |
| 21 | <100 | <100 | | | <100 (Me ester of 21) |
| 23 | <500 | <100 | | | <100 |
| 24 | <500 | <500 | | | <100 |
| 25 | <500 | <100 | | | <100 (Me ester of 25) |
| 27 | <1000 | <500 | | | <100 (Me ester of 27) |
| 34 | >1000 | >1000 | | | <100 (Me ester of 34) |
| 42 | <100 | <100 | | | |
| 49 | <50 | <100 | <1000 | <100 | <200 |
| 77a | <500 | >1000 | >1000 | >1000 | >200 |
| 77b | <10 | <100 | | | |
| 82 | <50 | >500 | | | |

TABLE 3

Piperidine Analogs

| Compound # | IC50 (nM) Ca GG | IC50 (nM) Hu GG | IC50 (nM) Hu FT | IC50 (nM) Asp GG | IC50 (nM) Cryp GG | MIC #g/mL C alb |
|---|---|---|---|---|---|---|
| 53a | <100 | <100 | | | | >200 |
| 53b | <100 | <1000 | | | | >200 |
| 53c | <100 | <100 | | | | >200 |
| 53d | <500 | >1000 | | | | >200 |
| 53e | <100 | >1000 | >1000 | | | >200 |
| 53f | <500 | >1000 | >1000 | >1000 | >1000 | >200 |
| 53g | <100 | >1000 | >1000 | | | >200 |
| 53h | <100 | >1000 | >1000 | | | >200 |
| 53i | <100 | <100 | >1000 | | | >200 |
| 53j | <100 | >1000 | >1000 | | | >200 |
| 53k | <10 | >1000 | >1000 | >1000 | >1000 | >200 |
| 53l | >1000 | >1000 | | | | >200 |
| 53m | >1000 | >1000 | | | | >200 |
| 53n | <100 | >1000 | >1000 | | | >200 |
| 53o | <1000 | >1000 | | >1000 | >1000 | >200 |
| 53p | <100 | <1000 | >1000 | | | >200 |
| 53q | <100 | >1000 | >1000 | | | >200 |
| 53r | <100 | >1000 | >1000 | | | >200 |
| 53s | <500 | >1000 | | | | >200 |
| 53t | <100 | >1000 | | | | >200 |
| 53u | <100 | >500 | >1000 | | | >200 |
| 53v | <10 | >1000 | >1000 | | | >200 |
| 53w | <100 | >500 | >1000 | | | >200 |
| 53x | <100 | >1000 | >1000 | | | >200 |
| 53y | <100 | <500 | | | | >200 |
| 53z | <100 | >1000 | >1000 | >1000 | >1000 | >200 |
| 53aa | <100 | >1000 | | | | >200 |
| 53bb | <100 | >1000 | | | | >200 |
| 59 | >1000 | >1000 | | | | |
| 60 | >1000 | >1000 | | | | |
| 61 | >1000 | >1000 | | | | |
| 62 | <200 | >1000 | | | | |
| 63 | <500 | >1000 | | | | |
| 64 | <100 | >1000 | | | | |
| 70 | <50 | >1000 | | | | |
| 93 | >1000 | >1000 | | | | >200 |
| 96a | >1000 | >1000 | | | | >200 |
| 96b | <1000 | >1000 | | | | >200 |
| 99a | <50 | >500 | | | | <10 |
| 99b | <200 | >500 | | | | <100 |

TABLE 4

| Compound # | Human Cell Data | |
|---|---|---|
| | IC50 (nM) H460 | IC50 (nM) IMR90 |
| 9 | >1000 (Me ester of 9) | >1000 (Me ester of 9) |
| 17 | >1000 (Me ester of 17) | >1000 (Me ester of 17) |
| 19 | >1000 (Me ester of 19) | >1000 (Me ester of 19) |
| 23 | >1000 | >1000 |
| 24 | >1000 | >1000 |
| 34 | >1000 (Me ester of 34) | >1000 (Me ester of 34) |
| 52i | >1000 | >1000 |
| 52k | >1000 | >1000 |
| 52n | >1000 | >1000 |
| 52o | >1000 | >1000 |
| 52v | >1000 | >1000 |
| 52z | >1000 | >1000 |
| 96a | >1000 | >1000 |
| 96b | >1000 | >1000 |

TABLE 5

| Compound | IC50 (nM) | | Candida | | Human cell IC50 (nM) | |
|---|---|---|---|---|---|---|
| | Candida | Human | MIC (g/mL) | MFC (g/mL) | H460 | IMR90 |
| 99a | <50 | >500 | <10 | 2 | >10,000 | >10,000 |
| 10 | | | <10 | | 10,000 | >10,000 |
| 9 | <1000 | <100 | | | | |
| 20 | | | <25 | | >1000 | >10,000 |
| 19 | <10 | <10 | | | | |
| 18 | | | <50 | | | |
| 17 | <10 | <10 | | | | | d. In Vivo Animal Study of GGPTase Inhibitor

Mice were infected with *Candida albicans* (one million cells) intravenously. Treatment began 24 hr later. Mice are treated ip daily for 10 days and survival was monitored for 30 days. There were 10 animals per experimental group which included 1. untreated control
2. Fluconazole (40 mg/kg/day)
3. Compound 18 (50 mg/kg/day)
4. Compound 18 (100 mg/kg/day)

Figure 58:
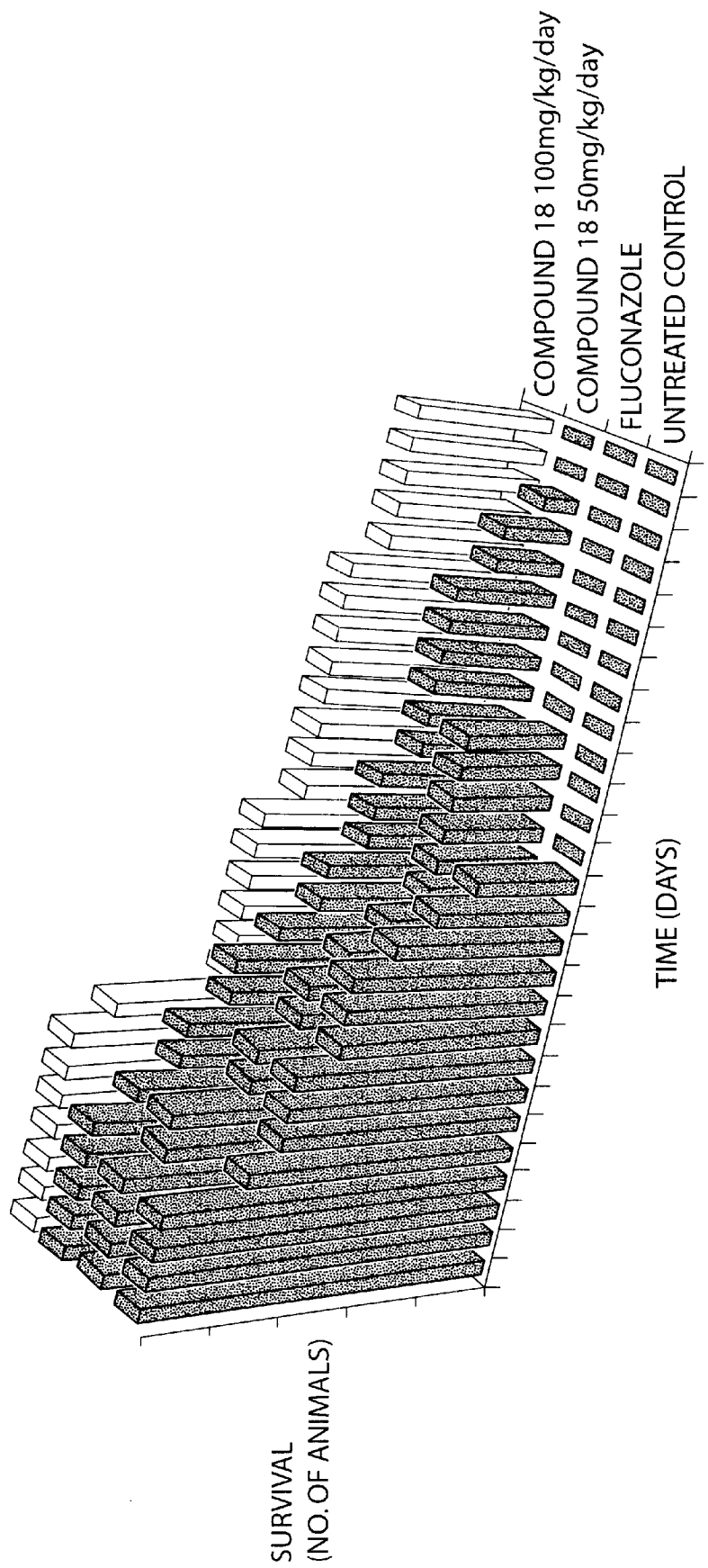
FIG. 58 is a graph demonstrating that a fungal GGPTase inhibitor increases animal survival.

FIG. 58 is a graph demonstrating that a fungal GGPTase inhibitor increases animal survival All of the references and publications cited herein are hereby incorporated by reference.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

---

We claim:

1. A method for inhibiting growth of a fungal cell comprising contacting the fungal cell with a compound which inhibits a prenyltransferase activity of the fungal cell, which compound includes a permease tag which facilitates permease-mediated transport of the compound into the fungal cell.

2. A method of claim 1, comprising contacting the fungal cell with a compound which inhibits a geranylgeranylproteintransferase (GGPTase) activity of the pathogen with a MIC of less than 25 mg/mL.

3. The method of claim 2, wherein the compound inhibits the GGPTase activity with a Ki of 1 $\mu$M or less.

4. The method of claim 2, wherein the compound inhibits the GGPTase activity with a Ki of 100 nM or less.

5. The method of claim 2, wherein the compound inhibits the GGPTase activity of the fungal cell with a Ki at least 1 order of magnitude lower than a GGPTase activity of a human.

6. The method of claim 2, wherein the compound inhibits the GGPTase activity of the fungal cell with a Ki at least 2 orders of magnitude lower than a GGPTase activity of a human.

7. The method of claim 2, wherein the compound inhibits growth of the fungal cell with a MIC of less than 7 $\mu$g/mL.

8. The method of claim 2, wherein the compound inhibits growth of the fungal cell with a MIC of less than 1 $\mu$g/mL.

9. The method of claim 2, wherein the compound also inhibits a farnesylproteintransferase (FPTase) activity of the fungal cell.

10. The method of claim 2, wherein the method is used to treat an animal with fungal infection or prevent a fungal infection of the animal.

11. The method of claim 10, wherein the animal is a human.

12. The method of claim 10, wherein the compound is administered topically to the animal.

13. The method of claim 10, wherein the compound is administered as a suppository to the animal.

14. The method of claim 10, wherein the compound is administered systemically to the animal.

15. The method of claim 14, wherein the animal is an immunocompromised animal.

16. The method of claim 10, wherein the compound has a therapeutic index in the animal being treated of at least 10.

17. The method of claim 10, wherein the compound has an $ED_{50}$ for inhibition of growth of the fungal cell at least one order of magnitude less than its $ED_{50}$ for modulation of signal transduction by geranylgeranylproteintransferase in the cells of the animal.

18. The method of claim 10, wherein the method is used to treat or prevent *candidiasis, aspergillosis* or *mucormycosis*.

19. The method of claim 2, wherein the method is used to treat a plant with fungal infection or prevent a fungal infection of the plant.

20. The method of claim 2, wherein the method is used to disinfect an inanimate surface.

21. The method of claim 2, wherein the fungal cell is a Candida strain.

22. The method of claim 21, wherein fungal cell is selected from *Candida albicans, Candida stellatoidea, Candida glabrata, Candida tropicalis, Candida parapsilosis, Candida krusei, Candida pseudotropicalis, Candida guilliermondii,* and *Candida rugosa*.

23. The method of claim 2, wherein the fungal cell is an Aspergillus strain.

24. The method of claim 23, wherein fungal cell is selected from *Aspergillus fumigatus*, *Aspergillus flavus*, *Aspergillus niger*, *Aspergillus nidulans*, and *Aspergillus terreus*.

25. The method of claim 2, wherein fungal cell is *Pneumocystis carinii*.

26. The method of claim 2, wherein fungal cell is a Cryptococcus strain.

27. The method of claim 2, wherein the compound is an organic molecule having a molecular weight of 1000 amu or less.

28. The method of claim 2, wherein the compound is a peptide or peptide-like inhibitor of the fungal GGPTase activity.

29. The method of claim 28, wherein the compound is represented in the general formula:

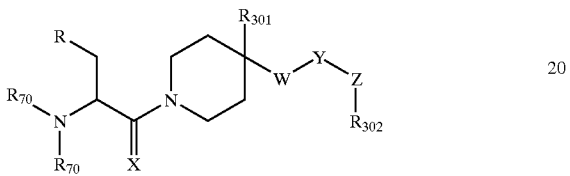

wherein,

X represents, independently for each occurrence, O, S or $H_2$;

$X_2$ represents O or S;

R represents

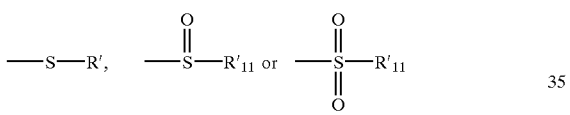

R' represents a hydrogen, a lower alkyl, a lower alkenyl, or an aryl;

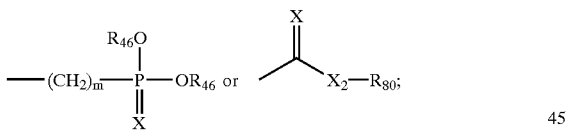

$R_7$ represents an aryl, a cycloalkyl, a cycloalkenyl, or a heterocycle;

$R'_{11}$ represents an alkyl, an alkenyl or —$(CH_2)_m$—$R_7$;

$R_{46}$, independently for each occurrence, represents a hydrogen, a lower alkyl or an aryl;

$R_{70}$, independently for each occurrence, represents a hydrogen,

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or $R_{70}$ and R taken together, or $R_{70}$ and $R_{70}$ taken together, form a 4–8 membered heterocycle;

$R_{80}$ represents a hydrogen, a lower alkyl, a lower alkenyl, a lower alkynyl, or —$(CH_2)_m$—$R_7$;

$R_{301}$, independently for each occurrence, represents a hydrogen, lower alkyl, —$(CH_2)_n$aryl, —$(CH_2)_n$heteroaryl, $R_{302}$, independently for each occurrence, represents a hydrogen, lower alkyl, —$(CH_2)_n$aryl, —$(CH_2)_n$heteroaryl, —$(CR_{309}R_{310})_n CO_2 R_7$, —$(CR_{309}R_{310})_n C(=O)N(R_{308})_2$, —$C(R_{309}R_{310})$—$C(=O)$—$[N(R_{308})$—$CR'_{310}$—$C(=O)]_p$—OH, —$(CR_{309}R_{310})_n COR_{311}$;

$R_{303}$ and $R_{304}$, independently for each occurrence, represents a hydrogen, lower alkyl, —$(CH_2)_n$aryl, —$(CH_2)_n$heteroaryl;

$R_{308}$, independently for each occurrence, represents a hydrogen, lower alkyl, —$(CH_2)_n$aryl, —$(CH_2)_n$heteroaryl, or, taken together along with the N form a 4–8 membered heterocycle;

$R_{309}$ and $R_{310}$ represent, independently for each occurrence, H, lower alkyl, —$(CH_2)_n$aryl, —$(CH_2)_n$heteroaryl, or a sidechain of a naturally occurring amino acid;

$R'_{310}$ represents, individually for each occurrence, a natural or unnatural amino acid sidechain, such as a lower alkyl;

$R_{311}$ is a naturally occurring amino acid or dipeptide or tripeptide connected through an amide linkage;

W represents $(CH_2)_n$, vinyl, acetylenyl, —$O(CH_2)_n$, —$N(R_{303})(CH_2)_n$—, —$S(CH_2)_n$, —$(CH_2)_n$—O—, —$(CH_2)_n$—$N(R_{303})$—, —$(CH_2)_n$—S—; n is an integer from 0–3;

Y represents —$C(=O)$—, —$S(O_2)$—, —$C(=NCN)$— or a direct bond between W and Z;

Z represents —$N(R_{304})$—, —O—, —S— or a direct bond between Y and $R_{302}$ with the following provisions:

when W is $(CH_2)_n$ and Y is C=O, then Z is $NR_{304}$, O, or a direct bond between Y and $R_{302}$;

when W is $(CH_2)_n$ and Y is $SO_2$ then Z is $NR_{304}$ or a direct bond between Y and $R_{302}$;

when W is $(CH_2)_n$ and Y is a direct bond between W and Z, then Z is $NR_{304}$, O, S or a direct bond between Y and $R_{302}$;

when W is vinyl or acetylenyl and Y is C=O, then Z is $NR_{304}$, O, or a direct bond between Y and $R_{302}$;

when W is vinyl or acetylenyl and Y is $SO_2$, then Z is $NR_{304}$ or a direct bond between Y and $R_{302}$;

when W is vinyl or acetylenyl and Y is a direct bond between W and Z, then Z is a direct bond between Y and $R_{302}$;

when W is O—$(CH_2)_n$ and Y is C=O, then Z is $NR_{304}$, O, or a direct bond between Y and $R_{302}$ and $R_{301}$ is H;

when W is O—$(CH_2)$, and Y is $SO_2$, then Z is $NR_{304}$, or a direct bond between Y and $R_{302}$ if n is an integer from 1–3 and $R_{301}$ is H;

when W is O—$(CH_2)_n$ and Y is a direct bond between W and Z, then Z is a direct bond between Y and $R_{302}$ if n is an integer from 0–1 and $R_{301}$ is H;

when W is O—$(CH_2)_n$ and Y is a direct bond between W and Z, then Z is $NR_{304}$, O, S, or a direct bond between Y and $R_{302}$ if n is an integer from 2–4 and $R_{301}$ is H;

when W is S—(CH$_2$)$_n$ and Y is C=O, then Z is NR$_{304}$, O, or a direct bond between Y and R$_{302}$ if n is an integer from 1–3 and R$_{301}$ is H;

when W is S—(CH$_2$)$_n$ and Y is SO$_2$, then Z is NR$_{304}$ or a direct bond between Y and R$_{302}$ if n is an integer from 1–3 and R$_{301}$ is H;

when W is S—(CH$_2$)$_n$ and Y is a direct bond between W and Z, then Z is a direct bond between Y and R$_{302}$ if n is an integer from 0–1 and R$_{301}$ is H;

when W is NR$_{303}$—(CH$_2$)$_n$ and Y is C=O, then Z is NR$_{304}$, O, or a direct bond between Y and R$_{302}$;

when W is NR$_{303}$—(CH$_2$)$_n$ and Y is SO$_2$, then Z is NR$_{304}$ or a direct bond between Y and R$_{302}$;

when W is NR$_{303}$—(CH$_2$)$_n$ and Y is a direct bond between W and Z, then Z is a direct bond between Y and R$_{302}$ if n is an integer from 0–1;

when W is NR$_{303}$—(CH$_2$)$_n$ and Y is a direct bond between W and Z, then Z is NR$_{304}$, O, S or a direct bond between Y and R$_{302}$ if n is an integer from 2–4;

when W is NR$_{303}$—(CH$_2$)$_n$ and Y is C=NCN, then Z is NR$_{304}$ if n=0;

when W is (CH$_2$)$_n$—O and Y is C=O, then Z is NR$_{304}$, O, or a direct bond between Y and R$_{302}$;

when W is (CH$_2$)$_n$—O and Y is a direct bond between W and Z, then Z is a direct bond between Y and R$_{302}$;

when W is (CH$_2$)$_n$—S and Y is a direct bond between W and Z, then Z is a direct bond between Y and R$_{302}$;

when W is (CH$_2$)$_n$NR$_{303}$ and Y is C=O, then Z is NR$_{304}$, O, or a direct bond between Y and R$_{302}$;

when W is (CH$_2$)$_n$NR$_{303}$ and Y is SO$_2$, then Z is NR$_{304}$ or a direct bond between Y and R$_{302}$;

when W is (CH$_2$)$_n$NR$_{303}$ and Y is a direct bond between W and Z, then Z is a direct bond between Y and R$_{302}$;

when W is (CH$_2$)$_n$NR$_{303}$ and Y is C=NCN, then Z is NR$_{304}$;

m, independently for each occurrence, represents 0 or an integer from 1–3; and n, individually for each occurrence, represents 0 or an integer from 1–5.

30. The method of claim 1, wherein the permease tag includes an amino acid residue, dipeptide or tripeptide which facilitates permease-mediated transport of the compound into the fungal cell.

31. The method of claim 1, wherein the permease tag is removed from the compound after permease-mediated transport into the fungal cell.

32. The method of claim 1, wherein the permease tag facilitates permease-mediated transport by an alanine transporter fungal cell.

33. The method of claim 32, wherein the permease tag includes L-alanine, or a dipeptide or tripeptide including L-alanine.

34. The method of claim 1, wherein the permease tag includes a moiety resented in the general formula —C(R$_{309}$R$_{310}$)—C(=O)—[N(R$_{308}$)—CHR'$_{310}$—C(=O)]$_p$—OH wherein R$_{308}$ represents a hydrogen, lower alkyl, —(CH$_2$)$_n$aryl or —(CH$_2$)$_n$heteroaryl;

R$_{309}$ and R$_{310}$ represent H, lower alkyl, —(CH$_2$)$_n$aryl, —(CH$_2$)$_n$heteroaryl, or a sidechain of an amino acid;

R'$_{310}$ represents, individually for each occurrence, a natural or unnatural amino acid sidechain, such as a lower alkyl; and p is 1, 2 or 3.

35. The method of claim 1, wherein the permease tag includes a moiety represented in the general formula NH$_2$—[CHR'$_{310}$—C(=O)—N(R$_{308}$)]$_p$—C(R$_{309}$R$_{310}$)—C(=O)— wherein

R$_{308}$ represents a hydrogen, lower alkyl —(CH$_2$)$_n$aryl or —(CH$_2$)$_n$heteroaryl;

R$_{309}$ and R$_{310}$ represent H, lower alkyl, —(CH$_2$)$_n$aryl, —(CH$_2$)$_n$heteroaryl, or a sidechain of an amino acid;

R'$_{310}$ represents, individually for each occurrence, a natural or unnatural amino acid sidechain, such as a lower alkyl; and p is 1, 2 or 3.

36. The method of claim 1, wherein the compound inhibits a geranylgeranylproteininsferase activity of the fungal cell with an IC$_{50}$ less than 1 μM.

37. The method of claim 1, wherein the compound is cytotoxic to the fungal cell.

38. The method of claim 1, wherein the compound inhibits a GGPTase-I activity of the fungal cell.

39. A method for inhibiting growth of a fungal cell comprising contacting the fungal cell with a compound which inhibits a prenyltransferase activity of the fungal cell with an IC$_{50}$ less than 1 μM, which compound includes a permease tag that facilitates permease-mediated transport of the compound into the fungal cell, wherein the compounds are represented in the general formulae

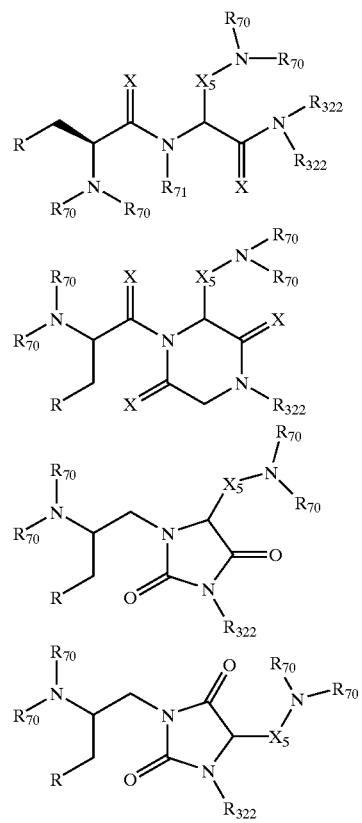

wherein,
R represents

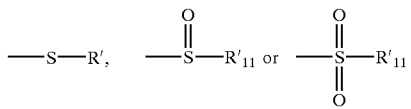

R' represents a hydrogen, a lower alkyl, a lower alkenyl, or an aryl;

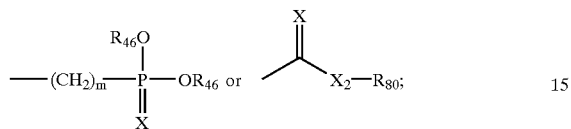

$R_7$ represents an aryl, a cycloalkyl, a cycloalkenyl, or a heterocycle;
$R'_{11}$ represents an alkyl, an alkenyl or —$(CH_2)_m$—$R_7$;
$R_{46}$, independently for each occurrence, represents a hydrogen, a lower alkyl or an aryl;
$R_{70}$, independently for each occurrence, represents a hydrogen,

a lower alkyl, lower alkenyl, lower alkynyl, aryl, alkylaryl, cycloalkyl, alkoxyalkyl, alkylthioalkyl, hydroxyalkyl, aminoalkyl, carboxyalkyl, alkoxycarbonylalkyl, arylalkyl, alkylsulfonylalkyl, and an alpha-carbon sidechain of an amino acid residue or analog or other amino-protecting group, or a pharmaceutically acceptable salt or
$R_{70}$ and R taken together, or $R_{70}$ and $R_{70}$ taken together, form a 4–8 membered heterocycle;
$R_{80}$ represents a hydrogen, a lower alkyl, a lower alkenyl, a lower alkynyl, or —$(CH_2)_m$—$R_7$;
X represents, independently for each occurrence, O, S or $H_2$;
$X_2$ represents O or S;
$X_5$ represents $(CH_2)_n$ or $(CH_2)_n CO$
$R_{322}$, independently for each occurrence, represents a hydrogen, lower alkyl, —$(CH_2)_n$aryl, —$(CH_2)_n$heteroaryl, —$(CR_{309}R_{310})_n CO_2 R_7$, —$(CR_{309}R_{310})_n CON(R_{308})_2$, —$(CR_{309}R_{310})_n COR_{311}$, or
$R_{322}$ and $R_{322}$ taken together can be a 5–8 membered heterocycle;
$R_{308}$ independently for each occurrence, represents a hydrogen, lower alkyl, —$(CH_2)_n$aryl, —$(CH_2)_n$heteroaryl;
$R_{308}$ and $R_{308}$ taken together form a 4–8 membered heterocycle;
$R_{309}$ and $R_{310}$ represent independently for each occurrence, H, lower alkyl, —$(CH_2)_n$aryl, —$(CH_2)_n$heteroaryl, or a sidechain of a natural or unnatural amino acid;
$R_{311}$ is a naturally occurring amino acid; and
n and m are, independently for each occurrence, 0 or an integer from 1–5.

* * * * *

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      Illustrative Peptide

<400> SEQUENCE: 1

Gly Cys Ile Ile Leu
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:
      Illustrative Peptide

<400> SEQUENCE: 2

Lys Leu Lys Cys Ala Ile Leu
 1               5

<210> SEQ ID NO 3

```
<211> LENGTH: 31
<212> TYPE: DNA
<213> ORGANISM: Artificial Sequence
<220> FEATURE:
<223> OTHER INFORMATION: Description of Artificial  Sequence:
      Oligonucleotide

<400> SEQUENCE: 3
cccgggatcc ttacaagaca acacatttct t                               31

<210> SEQ ID NO 4
<211> LENGTH: 60
<212> TYPE: DNA
<213> ORGANISM: Artificial Sequence
<220> FEATURE:
<223> OTHER INFORMATION: Description of Artificial  Sequence:
      Oligonucleotide

<400> SEQUENCE: 4
ccgggatcct tacataatgt ctgaacaaaa attgatatca gaagaagatt t ggttaacgg    60

<210> SEQ ID NO 5
<211> LENGTH: 10
<212> TYPE: PRT
<213> ORGANISM: Artificial Sequence
<220> FEATURE:
<223> OTHER INFORMATION: Description of Artificial  Sequence:
      Illustrative Peptide

<400> SEQUENCE: 5

Glu Gln Lys Leu Ile Ser Glu Glu Asp Leu
 1               5                  10
```